US012569308B2

(12) United States Patent
Berry et al.

(10) Patent No.: US 12,569,308 B2
(45) Date of Patent: Mar. 10, 2026

(54) USER INTERFACE FOR ROTATIONAL DEVICE MOVEMENT

(71) Applicant: Imperative Care, Inc., Campbell, CA (US)

(72) Inventors: Julie Leigh Berry, Portland, OR (US); Kyle Bartholomew, Campbell, CA (US); David Gonzalez, Campbell, CA (US); Monica Metzger, Monte Sereno, CA (US)

(73) Assignee: Imperative Care, Inc., Campbell, CA (US)

( * ) Notice: Subject to any disclaimer, the term of this patent is extended or adjusted under 35 U.S.C. 154(b) by 115 days.

(21) Appl. No.: 18/525,278

(22) Filed: Nov. 30, 2023

(65) Prior Publication Data

US 2024/0180651 A1     Jun. 6, 2024

Related U.S. Application Data

(60) Provisional application No. 63/429,502, filed on Dec. 1, 2022.

(51) Int. Cl.
      *A61B 34/37*          (2016.01)
      *A61B 17/22*          (2006.01)
      (Continued)

(52) U.S. Cl.
      CPC .............. *A61B 34/37* (2016.02); *A61B 17/22* (2013.01); *A61B 34/20* (2016.02); *A61B 34/25* (2016.02);
      (Continued)

(58) Field of Classification Search
      CPC ......... A61B 34/37; A61B 17/22; A61B 34/20; A61B 34/25; A61B 34/30; A61B 34/74;
      (Continued)

(56) References Cited

U.S. PATENT DOCUMENTS 1,286,033 A     11/1918   Lambeth
4,819,653 A      4/1989   Marks
              (Continued)

FOREIGN PATENT DOCUMENTS

AU     2006268156      4/2012
CN     102462533       5/2012
              (Continued)

OTHER PUBLICATIONS

US 12,076,032 B1, 09/2024, Teigen et al. (withdrawn)
              (Continued)

*Primary Examiner* — Bao Long T Nguyen
(74) *Attorney, Agent, or Firm* — Knobbe, Martens, Olson & Bear, LLP

(57)          ABSTRACT

A robotic interventional device control system includes an interventional device comprising a longitudinal axis and configured to rotate about the longitudinal axis; a controller configured to control rotational movement of the interventional device about the longitudinal axis; at least one sensor configured to detect rotational movement of the interventional device about the longitudinal axis; and one or more hardware processors configured to receive motion data from the at least one sensor, the motion data indicative of whether the interventional device is rotating. The one or more hardware processors are further configured to generate a user interface comprising an instrument window having a representation of the interventional device and an interventional device marker associated with the representation of the interventional device. The interventional device marker includes a radial progress indicator configured to provide a visual indication of a degree of rotation relative of the interventional device about the longitudinal axis.

20 Claims, 91 Drawing Sheets

(51) Int. Cl.

| | | |
|---|---|---|
| *A61B 34/00* | (2016.01) |
| *A61B 34/20* | (2016.01) |
| *A61B 34/30* | (2016.01) |
| *A61B 90/00* | (2016.01) |
| *A61M 25/01* | (2006.01) |
| *B25J 13/06* | (2006.01) |
| *A61B 6/50* | (2024.01) |
| *A61M 25/00* | (2006.01) |
| *A61M 25/09* | (2006.01) |

(52) U.S. Cl.

CPC .............. *A61B 34/30* (2016.02); *A61B 34/74* (2016.02); *A61B 90/37* (2016.02); *A61B 90/39* (2016.02); *A61M 25/01* (2013.01); *B25J 13/065* (2013.01); *A61B 6/504* (2013.01); *A61B 2017/22079* (2013.01); *A61B 2034/2048* (2016.02); *A61B 2034/2059* (2016.02); *A61B 2034/2065* (2016.02); *A61B 2034/2068* (2016.02); *A61B 2034/2074* (2016.02); *A61B 2034/254* (2016.02); *A61B 2034/256* (2016.02); *A61B 2034/301* (2016.02); *A61B 2034/303* (2016.02); *A61B 34/73* (2016.02); *A61B 2034/742* (2016.02); *A61B 2090/3983* (2016.02); *A61B 2217/005* (2013.01); *A61M 25/0097* (2013.01); *A61M 25/0113* (2013.01); *A61M 25/0127* (2013.01); *A61M 2025/0175* (2013.01); *A61M 25/09041* (2013.01); *A61M 2205/502* (2013.01)

(58) Field of Classification Search

CPC ......... A61B 90/37; A61B 90/39; A61B 6/504; A61B 34/73; A61B 2017/22079; A61B 2034/2048; A61B 2034/2059; A61B 2034/2065; A61B 2034/2068; A61B 2034/2074; A61B 2034/254; A61B 2034/256; A61B 2034/301; A61B 2034/303; A61B 2034/742; A61B 2090/3983; A61B 2217/005; A61B 2034/107; A61B 2034/2061; A61B 2090/376; A61B 34/35; A61B 2034/2051; A61M 25/01; A61M 25/0097; A61M 25/0113; A61M 25/0127; A61M 25/09041; A61M 2025/0175; A61M 2205/502; B25J 13/065; B25J 9/1689

See application file for complete search history.

(56) References Cited

U.S. PATENT DOCUMENTS

| | | | |
|---|---|---|---|
| 4,925,444 | A | 5/1990 | Orkin |
| 5,037,404 | A | 8/1991 | Gold et al. |
| 5,131,391 | A | 7/1992 | Sakai et al. |
| 5,380,268 | A | 1/1995 | Wheeler |
| 5,638,818 | A | 6/1997 | Diab et al. |
| 5,882,333 | A | 3/1999 | Schaer et al. |
| 5,989,208 | A | 11/1999 | Nita |
| 6,096,004 | A | 8/2000 | Meglan et al. |
| 6,375,471 | B1 | 4/2002 | Wendlandt et al. |
| 6,400,971 | B1 | 6/2002 | Firanov et al. |
| 7,192,433 | B2 | 3/2007 | Osypka et al. |
| 7,214,230 | B2 | 5/2007 | Brock et al. |
| 7,331,967 | B2 | 2/2008 | Lee et al. |
| 7,379,790 | B2 | 5/2008 | Toth et al. |
| 7,556,611 | B2 | 7/2009 | Kolenbrander et al. |
| 7,567,233 | B2 | 7/2009 | Garibaldi et al. |
| 7,608,083 | B2 | 10/2009 | Lee et al. |
| 7,615,042 | B2 | 11/2009 | Beyar et al. |
| 7,727,185 | B2 | 6/2010 | Weitzner |
| 7,747,960 | B2 | 6/2010 | Garibaldi et al. |
| 7,756,308 | B2 | 7/2010 | Viswanathan |
| 7,761,133 | B2 | 7/2010 | Viswanathan et al. |
| 7,789,874 | B2 | 9/2010 | Yu et al. |
| D626,250 | S | 10/2010 | Wenderow et al. |
| 7,818,076 | B2 | 10/2010 | Viswanathan |
| 7,831,294 | B2 | 11/2010 | Viswanathan |
| 7,850,640 | B2 | 12/2010 | Williams et al. |
| 7,850,642 | B2 | 12/2010 | Moll et al. |
| 7,853,306 | B2 | 12/2010 | Viswanathan et al. |
| 7,884,727 | B2 | 2/2011 | Tran |
| 7,886,743 | B2 | 2/2011 | Cooper et al. |
| 7,887,549 | B2 | 2/2011 | Wenderow et al. |
| 7,909,798 | B2 | 3/2011 | Osypka |
| 7,951,243 | B2 | 5/2011 | Boyle, Jr. et al. |
| 7,955,316 | B2 | 6/2011 | Weitzner et al. |
| 7,963,288 | B2 | 6/2011 | Rosenberg et al. |
| 8,004,229 | B2 | 8/2011 | Nowlin et al. |
| 8,021,326 | B2 | 9/2011 | Moll et al. |
| RE42,804 | E | 10/2011 | Dedig et al. |
| 8,052,636 | B2 | 11/2011 | Moll et al. |
| 8,083,753 | B2 | 12/2011 | Solar et al. |
| 8,108,069 | B2 | 1/2012 | Stahler et al. |
| 8,114,032 | B2 | 2/2012 | Ferry et al. |
| 8,123,726 | B2 | 2/2012 | Searfoss et al. |
| 8,131,379 | B2 | 3/2012 | Hauck |
| 8,137,317 | B2 | 3/2012 | Osypka |
| 8,146,874 | B2 | 4/2012 | Yu |
| 8,165,684 | B2 | 4/2012 | Putz et al. |
| 8,190,238 | B2 | 5/2012 | Moll et al. |
| 8,220,468 | B2 | 7/2012 | Cooper et al. |
| 8,242,972 | B2 | 8/2012 | Garibaldi et al. |
| 8,244,824 | B2 | 8/2012 | Garibaldi et al. |
| 8,257,302 | B2 | 9/2012 | Beyar et al. |
| 8,262,671 | B2 | 9/2012 | Osypka |
| 8,281,807 | B2 | 10/2012 | Trombley et al. |
| 8,307,693 | B2 | 11/2012 | Uram et al. |
| D674,484 | S | 1/2013 | Murphy et al. |
| 8,343,096 | B2 | 1/2013 | Kirschenman et al. |
| 8,343,098 | B2 | 1/2013 | Nystrom et al. |
| 8,377,077 | B2 | 2/2013 | Reis |
| 8,390,438 | B2 | 3/2013 | Olson et al. |
| 8,399,871 | B2 | 3/2013 | Beyar et al. |
| 8,403,909 | B2 | 3/2013 | Spohn et al. |
| D680,645 | S | 4/2013 | Murphy et al. |
| 8,409,172 | B2 | 4/2013 | Moll et al. |
| 8,467,853 | B2 | 6/2013 | Hunter et al. |
| D685,468 | S | 7/2013 | Murphy et al. |
| 8,480,618 | B2 | 7/2013 | Wenderow et al. |
| 8,498,691 | B2 | 7/2013 | Moll et al. |
| 8,506,555 | B2 | 8/2013 | Morales |
| 8,521,331 | B2 | 8/2013 | Itkowitz |
| 8,529,582 | B2 | 9/2013 | Devengenzo et al. |
| 8,540,698 | B2 | 9/2013 | Spohn et al. |
| 8,551,084 | B2 | 10/2013 | Hauck et al. |
| 8,613,730 | B2 | 12/2013 | Hieb et al. |
| 8,617,102 | B2 | 12/2013 | Moll et al. |
| 8,620,473 | B2 | 12/2013 | Diolaiti et al. |
| 8,671,817 | B1 | 3/2014 | Bogusky |
| 8,672,880 | B2 | 3/2014 | Cohen et al. |
| 8,684,953 | B2 | 4/2014 | Cabiri |
| 8,684,962 | B2 | 4/2014 | Kirschenman et al. |
| 8,694,157 | B2 | 4/2014 | Wenderow et al. |
| 8,740,840 | B2 | 6/2014 | Foley et al. |
| 8,747,358 | B2 | 6/2014 | Trombley et al. |
| 8,790,297 | B2 | 7/2014 | Bromander et al. |
| 8,799,792 | B2 | 8/2014 | Garibaldi et al. |
| 8,800,881 | B2 | 8/2014 | Biset et al. |
| 8,801,661 | B2 | 8/2014 | Moll et al. |
| 8,806,359 | B2 | 8/2014 | Garibaldi et al. |
| 8,828,021 | B2 | 9/2014 | Wenderow et al. |
| 8,833,293 | B2 | 9/2014 | Horn |
| 8,840,628 | B2 | 9/2014 | Green et al. |
| 8,852,162 | B2 | 10/2014 | Williams et al. |
| 8,852,167 | B2 | 10/2014 | Trombley et al. |
| 8,876,726 | B2 * | 11/2014 | Amit ................. A61B 18/1492 600/508 |
| 8,894,610 | B2 | 11/2014 | Macnamara et al. |
| 8,905,969 | B2 | 12/2014 | Nystrom et al. |
| 8,939,963 | B2 | 1/2015 | Rogers et al. |

(56) References Cited

U.S. PATENT DOCUMENTS

| | | | |
|---|---|---|---|
| 8,961,491 B2 | 2/2015 | Uber et al. |
| 8,968,333 B2 | 3/2015 | Yu et al. |
| 8,974,408 B2 | 3/2015 | Wallace et al. |
| 8,974,420 B2 | 3/2015 | Searfoss et al. |
| 8,979,871 B2 | 3/2015 | Tye |
| 8,986,246 B2 | 3/2015 | Foley et al. |
| 9,005,271 B2 | 4/2015 | Ivancev |
| 9,056,200 B2 | 6/2015 | Uber et al. |
| 9,066,740 B2 | 6/2015 | Carlson et al. |
| 9,070,486 B2 | 6/2015 | Guerrera et al. |
| 9,095,681 B2 | 8/2015 | Wenderow et al. |
| 9,101,379 B2 | 8/2015 | Au et al. |
| 9,111,016 B2 | 8/2015 | Besson et al. |
| 9,132,949 B2 | 9/2015 | Bidet et al. |
| 9,138,566 B2 | 9/2015 | Cabiri |
| 9,168,356 B2 | 10/2015 | Wenderow et al. |
| 9,186,046 B2 | 11/2015 | Ramamurthy et al. |
| 9,199,033 B1 | 12/2015 | Cowan et al. |
| 9,205,227 B2 | 12/2015 | Cohen et al. |
| 9,220,568 B2 | 12/2015 | Bromander et al. |
| 9,233,225 B2 | 1/2016 | Hebert |
| 9,241,768 B2 | 1/2016 | Sandhu et al. |
| 9,242,252 B2 | 1/2016 | Eberle et al. |
| 9,259,526 B2 | 2/2016 | Barron et al. |
| 9,295,527 B2 | 3/2016 | Kirschenman et al. |
| 9,314,306 B2 | 4/2016 | Yu |
| 9,314,307 B2 | 4/2016 | Richmond et al. |
| 9,314,310 B2 | 4/2016 | Kirschenman et al. |
| 9,314,311 B2 | 4/2016 | Wenderow et al. |
| 9,314,594 B2 | 4/2016 | Kirschenman |
| 9,320,479 B2 | 4/2016 | Wenderow et al. |
| 9,320,573 B2 | 4/2016 | Sandhu et al. |
| 9,333,324 B2 | 5/2016 | Cohen et al. |
| 9,345,859 B2 | 5/2016 | Blacker |
| 9,375,729 B2 | 6/2016 | Eberle et al. |
| 9,402,977 B2 | 8/2016 | Wenderow et al. |
| 9,408,669 B2 | 8/2016 | Kokish et al. |
| 9,427,515 B1 | 8/2016 | Nystrom |
| 9,427,562 B2 | 8/2016 | Blacker |
| 9,439,736 B2 | 9/2016 | Olson |
| 9,447,890 B2 | 9/2016 | Jennings et al. |
| 9,452,276 B2 | 9/2016 | Duindam et al. |
| 9,452,277 B2 | 9/2016 | Blacker |
| 9,474,857 B2 | 10/2016 | Riley et al. |
| 9,480,797 B1 | 11/2016 | Swantner et al. |
| 9,488,971 B2 | 11/2016 | Yip et al. |
| 9,498,291 B2 | 11/2016 | Bakaji et al. |
| 9,510,912 B2 | 12/2016 | Bencteux et al. |
| 9,517,305 B2 | 12/2016 | Uram et al. |
| 9,532,840 B2 | 1/2017 | Wong et al. |
| 9,533,121 B2 | 1/2017 | Pacheco et al. |
| 9,545,497 B2 | 1/2017 | Wenderow et al. |
| 9,549,783 B2 | 1/2017 | Zirps |
| 9,566,201 B2 | 2/2017 | Yu |
| 9,566,414 B2 | 2/2017 | Wong et al. |
| 9,572,481 B2 | 2/2017 | Duindam et al. |
| 9,585,806 B2 | 3/2017 | Herrig |
| 9,586,029 B2 | 3/2017 | Shekalim et al. |
| 9,603,573 B2 | 3/2017 | Leininger et al. |
| 9,623,209 B2 | 4/2017 | Wenderow et al. |
| 9,629,595 B2 | 4/2017 | Walker et al. |
| 9,636,479 B2 | 5/2017 | Bencteux et al. |
| 9,687,304 B2 | 6/2017 | Bencteux et al. |
| 9,700,698 B2 | 7/2017 | Pacheco et al. |
| 9,707,377 B2 | 7/2017 | Cohen et al. |
| 9,744,305 B2 | 8/2017 | Cowan et al. |
| 9,750,576 B2 | 9/2017 | Murphy et al. |
| 9,750,953 B2 | 9/2017 | Kalafut |
| 9,764,114 B2 | 9/2017 | Murphy et al. |
| 9,770,301 B2 | 9/2017 | Bencteux et al. |
| 9,782,130 B2 | 10/2017 | Hauck et al. |
| 9,782,564 B2 | 10/2017 | Zirps et al. |
| 9,789,285 B1 | 10/2017 | Blacker |
| 9,814,534 B2 | 11/2017 | Wenderow et al. |
| 9,825,455 B2 | 11/2017 | Sandhu et al. |
| 9,827,410 B2 | 11/2017 | Cowan et al. |
| 9,828,157 B2 | 11/2017 | Roesler |
| 9,833,293 B2 | 12/2017 | Wenderow et al. |
| 9,839,481 B2 | 12/2017 | Blumenkranz et al. |
| 9,855,101 B2 | 1/2018 | Wenderow et al. |
| 9,943,321 B2 | 4/2018 | Nita |
| 9,943,958 B2 | 4/2018 | Blacker et al. |
| 9,949,799 B2 | 4/2018 | Hingwe et al. |
| 9,962,229 B2 | 5/2018 | Blacker et al. |
| 9,981,109 B2 | 5/2018 | Blacker et al. |
| 9,993,614 B2 | 6/2018 | Pacheco et al. |
| 9,993,615 B2 | 6/2018 | Blacker |
| 9,999,751 B2 | 6/2018 | Pacheco et al. |
| 10,010,699 B2 | 7/2018 | Cohen et al. |
| 10,029,072 B2 | 7/2018 | Hebert |
| 10,046,140 B2 | 8/2018 | Kokish et al. |
| 10,052,761 B2 | 8/2018 | Langenfeld et al. |
| 10,071,224 B2 | 9/2018 | Hebert |
| 10,071,225 B2 | 9/2018 | Hebert |
| 10,085,805 B1 | 10/2018 | Blacker |
| 10,086,167 B2 | 10/2018 | Hebert |
| 10,105,486 B2 | 10/2018 | Trombley et al. |
| 10,123,843 B2 | 11/2018 | Wong et al. |
| 10,123,844 B2 | 11/2018 | Nowlin et al. |
| 10,124,149 B2 | 11/2018 | Hebert |
| 10,130,427 B2 | 11/2018 | Tanner et al. |
| 10,138,025 B2 | 11/2018 | Nakamura |
| 10,145,747 B1 | 12/2018 | Lin et al. |
| 10,178,995 B2 | 1/2019 | Cragg |
| 10,201,314 B2 | 2/2019 | Frederick et al. |
| 10,231,788 B2 | 3/2019 | Olson et al. |
| 10,238,456 B2 | 3/2019 | Murphy et al. |
| 10,245,112 B2 | 4/2019 | Kottenstette et al. |
| 10,258,285 B2 | 4/2019 | Hauck et al. |
| 10,271,910 B2 | 4/2019 | Wenderow et al. |
| 10,299,867 B2 | 5/2019 | Wenderow et al. |
| 10,307,061 B2 | 6/2019 | Cohen |
| 10,307,570 B2 | 6/2019 | Blacker |
| 10,322,277 B2 | 6/2019 | Nystrom |
| 10,342,953 B2 | 7/2019 | Wenderow et al. |
| 10,363,062 B2 | 7/2019 | Spencer et al. |
| 10,363,109 B2 | 7/2019 | Dachs, II et al. |
| 10,368,951 B2 | 8/2019 | Moll et al. |
| 10,391,234 B2 | 8/2019 | Sams et al. |
| 10,420,537 B2 | 9/2019 | Salahieh et al. |
| 10,426,557 B2 | 10/2019 | Amiri et al. |
| 10,426,559 B2 | 10/2019 | Graetzel et al. |
| 10,426,926 B2 | 10/2019 | Blacker et al. |
| 10,449,007 B2 | 10/2019 | Deboeuf et al. |
| 10,456,556 B2 | 10/2019 | Cabiri |
| 10,512,514 B2 | 12/2019 | Nowlin et al. |
| 10,522,250 B2 | 12/2019 | Spohn et al. |
| 10,531,883 B1 | 1/2020 | Deville et al. |
| 10,531,929 B2 | 1/2020 | Widenhouse et al. |
| 10,537,400 B2 | 1/2020 | Dachs, II et al. |
| 10,539,478 B2 | 1/2020 | Lin et al. |
| 10,549,071 B2 | 2/2020 | Falb et al. |
| 10,549,084 B2 | 2/2020 | Sokolov et al. |
| 10,555,780 B2 | 2/2020 | Tanner et al. |
| 10,556,092 B2 | 2/2020 | Yu et al. |
| 10,561,821 B2 | 2/2020 | Wenderow et al. |
| 10,568,539 B2 | 2/2020 | Kowshik et al. |
| 10,568,700 B2 | 2/2020 | Donhowe et al. |
| 10,583,276 B2 | 3/2020 | Zirps |
| 10,588,656 B2 | 3/2020 | Trosper et al. |
| 10,589,018 B2 | 3/2020 | Uber et al. |
| D881,234 S | 4/2020 | Capela |
| 10,611,391 B1 | 4/2020 | Klem et al. |
| 10,647,007 B2 | 5/2020 | Cordoba et al. |
| 10,653,863 B1 | 5/2020 | Blacker et al. |
| 10,660,814 B2 | 5/2020 | Soundararajan et al. |
| 10,661,453 B2 | 5/2020 | Koenig et al. |
| 10,687,903 B2 | 6/2020 | Lewis et al. |
| 10,695,140 B2 | 6/2020 | Overmyer et al. |
| 10,695,533 B2 | 6/2020 | Deboeuf et al. |
| 10,695,536 B2 | 6/2020 | Weitzner et al. |
| 10,709,510 B2 | 7/2020 | Kottenstette |
| 10,709,512 B2 | 7/2020 | Bajo et al. |
| 10,716,726 B2 | 7/2020 | Bergman et al. |

(56)  References Cited

U.S. PATENT DOCUMENTS

| | | | |
|---|---|---|---|
| 10,722,253 B2 | 7/2020 | Deville et al. | |
| 10,729,825 B2 | 8/2020 | Boyle, Jr. et al. | |
| 10,736,706 B2 | 8/2020 | Scheib | |
| 10,737,061 B2 | 8/2020 | Parmar | |
| 10,744,302 B2 | 8/2020 | Pacheco et al. | |
| 10,765,303 B2 | 9/2020 | Graetzel et al. | |
| 10,765,486 B2 | 9/2020 | Bajo et al. | |
| 10,779,775 B2 | 9/2020 | Bergman et al. | |
| 10,779,895 B2 | 9/2020 | Wenderow et al. | |
| 10,783,993 B2 | 9/2020 | Spohn et al. | |
| 10,799,305 B2 | 10/2020 | Murphy et al. | |
| 10,806,905 B2 | 10/2020 | Asmus | |
| 10,813,713 B2 | 10/2020 | Koch et al. | |
| 10,814,102 B2 | 10/2020 | Laby et al. | |
| 10,820,951 B2 | 11/2020 | Soundararajan et al. | |
| 10,820,954 B2 | 11/2020 | Marsot et al. | |
| 10,827,913 B2 | 11/2020 | Ummalaneni et al. | |
| 10,828,463 B2 | 11/2020 | Blacker | |
| 10,835,153 B2 | 11/2020 | Rafii-Tari et al. | |
| 10,835,329 B2 | 11/2020 | Wenderow et al. | |
| 10,835,668 B2 | 11/2020 | Novickoff et al. | |
| 10,849,702 B2 | 12/2020 | Hsu et al. | |
| 10,864,629 B2 | 12/2020 | Guerrera et al. | |
| 10,874,468 B2 | 12/2020 | Wallace et al. | |
| 10,881,472 B2 | 1/2021 | Sen et al. | |
| 10,881,474 B2 | 1/2021 | Blacker et al. | |
| 10,881,765 B2 | 1/2021 | Igarashi | |
| 10,898,082 B2 | 1/2021 | Sandgaard | |
| 10,898,288 B2 | 1/2021 | Dachs, II et al. | |
| 10,900,771 B2 | 1/2021 | Kottenstette et al. | |
| 10,912,624 B2 | 2/2021 | Prentakis et al. | |
| 10,912,924 B2 | 2/2021 | Park et al. | |
| 10,945,904 B2 | 3/2021 | de Jesus Ruiz et al. | |
| 10,953,206 B2 | 3/2021 | Blacker | |
| 10,959,789 B2 | 3/2021 | Yi et al. | |
| 10,959,792 B1 | 3/2021 | Huang et al. | |
| 10,987,179 B2 | 4/2021 | Ummalaneni et al. | |
| 10,987,491 B2 | 4/2021 | Wenderow et al. | |
| 10,994,102 B2 | 5/2021 | Blacker | |
| 11,007,118 B2 | 5/2021 | Cowan et al. | |
| 11,007,348 B2 | 5/2021 | Blacker | |
| 11,040,147 B2 | 6/2021 | Wagner | |
| 11,045,274 B2 | 6/2021 | Dachs, II et al. | |
| 11,052,226 B2 | 7/2021 | Salahieh et al. | |
| 11,058,508 B2 | 7/2021 | Scheib et al. | |
| 11,076,924 B2 | 8/2021 | Kim et al. | |
| 11,078,945 B2 | 8/2021 | Grout et al. | |
| 11,083,842 B2 | 8/2021 | Chassot | |
| 11,083,873 B2 | 8/2021 | Hebert | |
| 11,083,882 B2 | 8/2021 | Schrauder et al. | |
| 11,096,712 B2 | 8/2021 | Teigen et al. | |
| 11,104,012 B2 | 8/2021 | Cordoba et al. | |
| 11,109,919 B2 | 9/2021 | Murphy et al. | |
| 11,109,920 B2 | 9/2021 | Al-Jadda et al. | |
| 11,109,921 B2 | 9/2021 | Kottenstette et al. | |
| 11,110,217 B2 | 9/2021 | O'Brien et al. | |
| 11,114,918 B2 | 9/2021 | Zirps | |
| 11,129,602 B2 | 9/2021 | Wong et al. | |
| 11,141,566 B2 | 10/2021 | Cabiri | |
| 11,147,950 B2 | 10/2021 | Destrebecq et al. | |
| 11,179,213 B2 | 11/2021 | Huang et al. | |
| 11,179,546 B2 | 11/2021 | Martin | |
| 11,185,455 B2 | 11/2021 | Cagle et al. | |
| 11,191,893 B2 | 12/2021 | Capone et al. | |
| 11,197,683 B1 | 12/2021 | Teigen et al. | |
| 11,207,147 B2 | 12/2021 | Diamond et al. | |
| 11,209,300 B2 | 12/2021 | Johnson | |
| 11,213,356 B2 | 1/2022 | Tanner et al. | |
| 11,213,362 B2 | 1/2022 | Sharon et al. | |
| 11,213,654 B2 | 1/2022 | Murphy et al. | |
| 11,234,779 B2 | 2/2022 | Fuerst et al. | |
| 11,234,781 B2 | 2/2022 | Penny et al. | |
| 11,234,784 B2 | 2/2022 | Alden | |
| 11,241,291 B2 | 2/2022 | Sharon et al. | |
| 11,259,881 B2 | 3/2022 | Garcia Kilroy et al. | |
| 11,266,424 B2 | 3/2022 | Hofmann et al. | |
| 11,291,515 B2 | 4/2022 | Sharon et al. | |
| 11,298,198 B2 | 4/2022 | Fournier et al. | |
| 11,304,668 B2 | 4/2022 | Wenderow et al. | |
| 11,318,618 B2 | 5/2022 | Desai | |
| 11,331,157 B2 | 5/2022 | Russell et al. | |
| 11,337,712 B2 | 5/2022 | Teigen et al. | |
| 11,337,764 B2 | 5/2022 | Deboeuf et al. | |
| 11,357,586 B2 | 6/2022 | Huang et al. | |
| 11,357,597 B2 | 6/2022 | Jhaveri et al. | |
| 11,359,156 B2 | 6/2022 | Long et al. | |
| 11,376,086 B2 | 7/2022 | McGrogan et al. | |
| 11,389,360 B2 | 7/2022 | Koenig et al. | |
| 11,400,214 B2 | 8/2022 | Porter | |
| 11,406,402 B2 | 8/2022 | Deville et al. | |
| 11,413,101 B2 | 8/2022 | Sen et al. | |
| 11,413,431 B2 | 8/2022 | Blacker | |
| 11,419,977 B2 | 8/2022 | Cowan et al. | |
| 11,426,246 B2 | 8/2022 | Asadian et al. | |
| 11,432,835 B2 | 9/2022 | Shaffer et al. | |
| 11,432,840 B2 | 9/2022 | Grothe et al. | |
| 11,448,327 B2 | 9/2022 | Heffner et al. | |
| 11,464,587 B2 | 10/2022 | Yu et al. | |
| 11,464,589 B1 | 10/2022 | Roh et al. | |
| 11,472,030 B2 | 10/2022 | Ho et al. | |
| 11,478,329 B2 | 10/2022 | Gee et al. | |
| 11,490,911 B2 | 11/2022 | Panian | |
| 11,497,481 B2 | 11/2022 | Penny et al. | |
| 11,497,523 B2 | 11/2022 | Trosper et al. | |
| 11,497,568 B2 | 11/2022 | Ho et al. | |
| 11,510,736 B2 | 11/2022 | Rafii-Tari et al. | |
| D976,399 S | 1/2023 | Carmi | |
| 11,547,426 B2 | 1/2023 | Deville et al. | |
| 11,547,511 B2 | 1/2023 | Asadian et al. | |
| 11,564,649 B2 | 1/2023 | Kedmi-Shahar et al. | |
| 11,571,267 B2 | 2/2023 | Gonenc et al. | |
| 11,576,743 B2 | 2/2023 | Venkataraman et al. | |
| 11,577,382 B2 | 2/2023 | Cagle et al. | |
| 11,589,931 B2 | 2/2023 | Desai et al. | |
| 11,607,108 B2 | 3/2023 | Yu et al. | |
| 11,628,024 B2 | 4/2023 | Kapadia | |
| 11,633,247 B2 | 4/2023 | Johnson et al. | |
| 11,642,181 B2 | 5/2023 | Nobles et al. | |
| 11,653,905 B2 | 5/2023 | Wong et al. | |
| 11,660,151 B2 | 5/2023 | Schena | |
| 11,660,437 B2 | 5/2023 | Verma | |
| 11,672,602 B2 | 6/2023 | Monteverde et al. | |
| 11,678,943 B2 | 6/2023 | Zhou et al. | |
| 11,678,948 B2 | 6/2023 | Vargas et al. | |
| 11,684,759 B2 | 6/2023 | Hayzelden | |
| 11,690,985 B2 | 7/2023 | Calhoun et al. | |
| 11,696,808 B2 | 7/2023 | Blacker et al. | |
| 11,696,810 B2 | 7/2023 | Asadian et al. | |
| 11,701,196 B2 | 7/2023 | Scheib et al. | |
| 11,703,604 B2 | 7/2023 | Dissertori et al. | |
| 11,712,805 B2 | 8/2023 | Zhou et al. | |
| 11,713,376 B2 | 8/2023 | Leroux et al. | |
| 11,717,356 B2 | 8/2023 | Amiri et al. | |
| 11,717,640 B2 | 8/2023 | Fantuzzi et al. | |
| 11,723,739 B2 | 8/2023 | Asadian et al. | |
| 11,723,744 B2 | 8/2023 | Ergueta Tejerina et al. | |
| 11,730,499 B1 | 8/2023 | Thio et al. | |
| 11,737,821 B2 | 8/2023 | Algawi et al. | |
| 11,744,989 B2 | 9/2023 | Blacker | |
| 11,759,269 B2 | 9/2023 | Zhou et al. | |
| 11,764,873 B2 | 9/2023 | Burla et al. | |
| 11,765,360 B2 | 9/2023 | Schroers et al. | |
| 11,766,786 B2 | 9/2023 | Cordoba et al. | |
| 11,780,092 B2 | 10/2023 | Desai et al. | |
| 11,785,938 B2 | 10/2023 | Clavien et al. | |
| 11,786,329 B2 | 10/2023 | Fuerst et al. | |
| 11,789,315 B1 | 10/2023 | Yu et al. | |
| 11,793,500 B2 | 10/2023 | Vargas | |
| 11,793,597 B2 | 10/2023 | Vargas et al. | |
| 11,801,365 B2 | 10/2023 | Blacker et al. | |
| 11,813,203 B2 | 11/2023 | Timm et al. | |
| 11,819,295 B2 | 11/2023 | Wenderow et al. | |
| 11,832,904 B2 | 12/2023 | Wenderow et al. | |
| 11,844,580 B2 | 12/2023 | Sen et al. | |

(56) References Cited

U.S. PATENT DOCUMENTS

| | | |
|---|---|---|
| 11,844,732 B2 | 12/2023 | Klem et al. |
| 11,883,119 B2 | 1/2024 | Sen et al. |
| 11,883,245 B2 | 1/2024 | Fathollahi Ghezelghieh et al. |
| 11,890,024 B2 | 2/2024 | Panian |
| 11,890,432 B2 | 2/2024 | Awad et al. |
| 11,896,325 B2 | 2/2024 | Clark et al. |
| 11,903,669 B2 | 2/2024 | Cope et al. |
| 11,906,009 B2 | 2/2024 | Klem |
| 11,910,997 B2 | 2/2024 | Fuerst et al. |
| 11,911,120 B2 | 2/2024 | Freiin von Kapri et al. |
| 11,911,910 B2 | 2/2024 | Gonenc et al. |
| 11,918,240 B2 | 3/2024 | Deville et al. |
| 11,918,312 B2 | 3/2024 | Yu |
| 11,918,423 B2 | 3/2024 | Kottenstette et al. |
| 11,931,901 B2 | 3/2024 | Murphy et al. |
| 11,998,290 B2 | 6/2024 | Murphy et al. |
| 12,004,829 B2 | 6/2024 | Searfoss et al. |
| 12,005,589 B2 | 6/2024 | Rea et al. |
| 12,035,989 B2 | 7/2024 | Clark et al. |
| 12,046,363 B2 | 7/2024 | Shrivastava et al. |
| D1,038,990 S | 8/2024 | Inwood |
| 12,059,161 B2 | 8/2024 | Deville et al. |
| 12,059,225 B2 | 8/2024 | Zhou et al. |
| D1,043,739 S | 9/2024 | Hernandez |
| 12,076,036 B2 | 9/2024 | Baron et al. |
| 12,076,099 B2 | 9/2024 | Shrivastava et al. |
| 12,076,497 B2 | 9/2024 | Fantuzzi et al. |
| 12,076,505 B2 | 9/2024 | Haubert |
| 12,082,982 B2 | 9/2024 | Jhaveri et al. |
| 12,087,024 B2 | 9/2024 | Djelouah et al. |
| 12,102,290 B2 | 10/2024 | Sharon et al. |
| 12,114,940 B2 | 10/2024 | Garcia Kilroy et al. |
| 12,117,624 B2 | 10/2024 | Fuerst et al. |
| 12,133,700 B2 | 11/2024 | Miller et al. |
| 12,133,702 B2 | 11/2024 | Nowlin et al. |
| 12,133,965 B2 | 11/2024 | Chassot et al. |
| 12,137,990 B2 | 11/2024 | Walker et al. |
| 12,138,004 B2 | 11/2024 | Cone et al. |
| 12,138,130 B2 | 11/2024 | Garbus et al. |
| 12,144,564 B2 | 11/2024 | Barbagli et al. |
| 12,144,569 B2 | 11/2024 | Cone et al. |
| 12,144,575 B2 | 11/2024 | Torabi |
| 12,150,660 B1 | 11/2024 | Teigen et al. |
| 12,150,796 B2 | 11/2024 | Wenderow et al. |
| 12,156,666 B2 | 12/2024 | Trosper et al. |
| 12,156,667 B2 | 12/2024 | Trosper et al. |
| 12,156,711 B2 | 12/2024 | Liao et al. |
| 12,157,238 B2 | 12/2024 | Fredrickson et al. |
| 12,161,419 B2 | 12/2024 | Fuerst et al. |
| 12,171,505 B2 | 12/2024 | Barbagli et al. |
| 12,171,543 B2 | 12/2024 | Duindam et al. |
| 12,177,411 B2 | 12/2024 | Culman |
| 12,178,387 B2 | 12/2024 | McDowall et al. |
| 12,178,399 B2 | 12/2024 | Itkowitz et al. |
| 12,178,526 B2 | 12/2024 | McKenney et al. |
| 12,178,534 B2 | 12/2024 | Asadian et al. |
| 12,185,947 B2 | 1/2025 | Hart |
| 12,191,031 B2 | 1/2025 | Azizian et al. |
| 12,201,484 B2 | 1/2025 | Itkowitz et al. |
| 12,201,485 B2 | 1/2025 | McDowall et al. |
| 12,212,240 B2 | 1/2025 | Schulz |
| 12,377,206 B2 | 8/2025 | Bartholomew et al. |
| 2002/0091372 A1 | 7/2002 | Cragg et al. |
| 2002/0113501 A1 | 8/2002 | Doi |
| 2002/0192113 A1 | 12/2002 | Uffenheimer et al. |
| 2003/0071285 A1 | 4/2003 | Tsukernik |
| 2003/0100849 A1 | 5/2003 | Jang |
| 2003/0105451 A1 | 6/2003 | Westlund et al. |
| 2003/0114739 A1 | 6/2003 | Fuimaono et al. |
| 2003/0125673 A1 | 7/2003 | Houde et al. |
| 2004/0068248 A1 | 4/2004 | Mooney et al. |
| 2004/0097805 A1 | 5/2004 | Verard et al. |
| 2004/0143225 A1 | 7/2004 | Callan |
| 2005/0077225 A1 | 4/2005 | Usher et al. |
| 2005/0107667 A1 | 5/2005 | Danitz |
| 2005/0165276 A1 | 7/2005 | Belson et al. |
| 2005/0277912 A1 | 12/2005 | John |
| 2006/0011501 A1 | 1/2006 | Itou et al. |
| 2006/0095022 A1 | 5/2006 | Moll et al. |
| 2006/0200026 A1 | 9/2006 | Wallace et al. |
| 2006/0200191 A1 | 9/2006 | Zadno-Azizi |
| 2007/0060915 A1 | 3/2007 | Kucklick |
| 2007/0106208 A1 | 5/2007 | Uber et al. |
| 2007/0142824 A1 | 6/2007 | Devengenzo |
| 2007/0179473 A1 | 8/2007 | Masters et al. |
| 2007/0270639 A1 | 11/2007 | Long |
| 2008/0027464 A1 | 1/2008 | Moll et al. |
| 2008/0086051 A1 | 4/2008 | Voegele |
| 2008/0234631 A1 | 9/2008 | Reis |
| 2008/0262513 A1 | 10/2008 | Stahler et al. |
| 2008/0319387 A1 | 12/2008 | Amisar et al. |
| 2009/0076445 A1 | 3/2009 | Furnish |
| 2009/0131955 A1 | 5/2009 | Wenderow et al. |
| 2009/0153374 A1 | 6/2009 | Maw et al. |
| 2009/0171332 A1 | 7/2009 | Bonneau |
| 2009/0204078 A1 | 8/2009 | Mitchell et al. |
| 2009/0254083 A1 | 10/2009 | Wallace et al. |
| 2009/0259200 A1 | 10/2009 | Lampropoulos |
| 2009/0264785 A1 | 10/2009 | Causevic et al. |
| 2010/0069833 A1 | 3/2010 | Wenderow et al. |
| 2010/0175701 A1 | 7/2010 | Reis et al. |
| 2010/0204712 A1 | 8/2010 | Mallaby |
| 2010/0204713 A1 | 8/2010 | Ruiz Morales |
| 2010/0280363 A1 | 11/2010 | Skarda et al. |
| 2010/0286756 A1 | 11/2010 | Dorn |
| 2011/0004223 A1 | 1/2011 | Leeflang |
| 2011/0015484 A1 | 1/2011 | Alvarez et al. |
| 2011/0144658 A1 | 6/2011 | Wenderow et al. |
| 2011/0166447 A1 | 7/2011 | Windolf |
| 2011/0238010 A1 | 9/2011 | Kirschenman et al. |
| 2011/0288544 A1 | 11/2011 | Verin et al. |
| 2011/0313318 A1 | 12/2011 | Rule et al. |
| 2012/0071895 A1 | 3/2012 | Stahler et al. |
| 2012/0172798 A1 | 7/2012 | Miller et al. |
| 2012/0179032 A1 | 7/2012 | Bromander et al. |
| 2012/0316458 A1 | 12/2012 | Rahman |
| 2013/0030408 A1 | 1/2013 | Piferi |
| 2013/0035537 A1 | 2/2013 | Wallace |
| 2013/0053704 A1 | 2/2013 | Bernak et al. |
| 2013/0096551 A1 | 4/2013 | Govari et al. |
| 2013/0131499 A1 | 5/2013 | Chan et al. |
| 2013/0214912 A1 | 8/2013 | Beyar et al. |
| 2013/0231678 A1 | 9/2013 | Wenderow |
| 2014/0058321 A1 | 2/2014 | Wenderow et al. |
| 2014/0066900 A1 | 3/2014 | Blacker |
| 2014/0150782 A1 | 6/2014 | Vazales |
| 2014/0163364 A1 | 6/2014 | Perers |
| 2014/0216250 A1 | 8/2014 | Meyer |
| 2014/0228762 A1 | 8/2014 | Capone |
| 2014/0243742 A1* | 8/2014 | Pacheco ............. A61M 25/0113 |
| | | 604/95.04 |
| 2014/0276016 A1 | 9/2014 | Stigall |
| 2014/0276233 A1 | 9/2014 | Murphy |
| 2014/0276389 A1 | 9/2014 | Walker |
| 2014/0276948 A1 | 9/2014 | Zirps |
| 2014/0318702 A1 | 10/2014 | Tegg |
| 2015/0005738 A1 | 1/2015 | Blacker |
| 2015/0005745 A1 | 1/2015 | Bergman et al. |
| 2015/0073391 A1 | 3/2015 | Hutchins et al. |
| 2015/0088002 A1 | 3/2015 | Podhajsky |
| 2015/0157252 A1 | 6/2015 | Sabesan |
| 2015/0272683 A1 | 10/2015 | Yang et al. |
| 2015/0314105 A1 | 11/2015 | Gasparyan |
| 2015/0327875 A1 | 11/2015 | Look |
| 2015/0374483 A1 | 12/2015 | Janardhan |
| 2016/0058513 A1 | 3/2016 | Giorgi |
| 2016/0067448 A1 | 3/2016 | Blacker et al. |
| 2016/0074057 A1 | 3/2016 | Jezierski et al. |
| 2016/0184032 A1 | 6/2016 | Romo |
| 2016/0310702 A1 | 10/2016 | Cabiri |
| 2016/0374590 A1 | 12/2016 | Wong et al. |
| 2017/0000576 A1 | 1/2017 | Zirps |
| 2017/0014998 A1 | 1/2017 | Langenfeld et al. |
| 2017/0020627 A1 | 1/2017 | Tesar et al. |

(56)     References Cited

U.S. PATENT DOCUMENTS

| | | |
|---|---|---|
| 2017/0027653 A1 | 2/2017 | Kirschenman |
| 2017/0135773 A1 | 5/2017 | Lohmeier et al. |
| 2017/0143416 A1 | 5/2017 | Guler et al. |
| 2017/0224224 A1 | 8/2017 | Yu |
| 2017/0252025 A1 | 9/2017 | Cabiri et al. |
| 2017/0281054 A1 | 10/2017 | Stever et al. |
| 2017/0281288 A1 | 10/2017 | Au |
| 2017/0317937 A1 | 11/2017 | Dillon |
| 2017/0333000 A1 | 11/2017 | Nystrom et al. |
| 2017/0348060 A1 | 12/2017 | Blacker |
| 2018/0126122 A1 | 5/2018 | Cabiri |
| 2018/0153477 A1 | 6/2018 | Nagale et al. |
| 2018/0161001 A1 | 6/2018 | Seip |
| 2018/0168751 A1 | 6/2018 | Yi et al. |
| 2018/0185104 A1 | 7/2018 | Olson et al. |
| 2018/0199916 A1 | 7/2018 | Sugihara et al. |
| 2018/0250086 A1 | 9/2018 | Grubbs |
| 2018/0360398 A1 | 12/2018 | Wenderow et al. |
| 2019/0008360 A1 | 1/2019 | Peh et al. |
| 2019/0008591 A1 | 1/2019 | Desai |
| 2019/0030324 A1 | 1/2019 | Grace et al. |
| 2019/0076640 A1 | 3/2019 | Bhatnagar et al. |
| 2019/0111237 A1 | 4/2019 | Cabiri et al. |
| 2019/0133666 A1 | 5/2019 | Johnson |
| 2019/0209026 A1 | 7/2019 | Han et al. |
| 2019/0231373 A1 | 8/2019 | Quick |
| 2019/0254690 A1 | 8/2019 | Cabiri et al. |
| 2019/0254754 A1 | 8/2019 | Johnson |
| 2019/0255297 A1 | 8/2019 | Fischell et al. |
| 2019/0269368 A1 | 9/2019 | Hauck et al. |
| 2019/0274809 A1 | 9/2019 | Kapec |
| 2019/0301913 A1 | 10/2019 | Johnson |
| 2019/0304108 A1 | 10/2019 | Carrell et al. |
| 2019/0336227 A1 | 11/2019 | Murphy et al. |
| 2019/0336674 A1 | 11/2019 | Schermeier |
| 2019/0365485 A1 | 12/2019 | Kottenstette et al. |
| 2019/0380825 A1 | 12/2019 | Perkins et al. |
| 2020/0008891 A1 | 1/2020 | Wenderow et al. |
| 2020/0008896 A1 | 1/2020 | Cone et al. |
| 2020/0009354 A1 | 1/2020 | Wenderow et al. |
| 2020/0016371 A1 | 1/2020 | Blacker |
| 2020/0028181 A1 | 1/2020 | Arugula et al. |
| 2020/0054399 A1 | 2/2020 | Duindam |
| 2020/0054403 A1 | 2/2020 | Zhou et al. |
| 2020/0085528 A1 | 3/2020 | Olson et al. |
| 2020/0129740 A1 | 4/2020 | Kottenstette et al. |
| 2020/0163726 A1 | 5/2020 | Tanner et al. |
| 2020/0170630 A1 | 6/2020 | Wong et al. |
| 2020/0242767 A1 | 7/2020 | Zhao et al. |
| 2020/0282186 A1 | 9/2020 | Blacker et al. |
| 2020/0289219 A1 | 9/2020 | Denlinger et al. |
| 2020/0297444 A1 | 9/2020 | Camarillo et al. |
| 2020/0297973 A1 | 9/2020 | Blacker et al. |
| 2020/0306064 A1 | 10/2020 | Perkins et al. |
| 2020/0316340 A1 | 10/2020 | Wenderow et al. |
| 2020/0324084 A1 | 10/2020 | Falb et al. |
| 2020/0338308 A1 | 10/2020 | Saber et al. |
| 2020/0345979 A1 | 11/2020 | Loh et al. |
| 2020/0352494 A1 | 11/2020 | Gable et al. |
| 2020/0368494 A1 | 11/2020 | Parmar |
| 2020/0375671 A1 | 12/2020 | Wenderow et al. |
| 2020/0376249 A1 | 12/2020 | Lockhart |
| 2020/0390503 A1 | 12/2020 | Casas et al. |
| 2020/0397451 A1 | 12/2020 | Feltyberger et al. |
| 2020/0405408 A1 | 12/2020 | Shelton, IV et al. |
| 2020/0405410 A1 | 12/2020 | Shelton, IV et al. |
| 2020/0405950 A1 | 12/2020 | Burren |
| 2021/0007816 A1 | 1/2021 | Huang et al. |
| 2021/0022816 A1 | 1/2021 | DeBuys et al. |
| 2021/0030492 A1 | 2/2021 | Wenderow et al. |
| 2021/0045622 A1 | 2/2021 | Petroff et al. |
| 2021/0046284 A1 | 2/2021 | Mauch |
| 2021/0060767 A1 | 3/2021 | Guerrera et al. |
| 2021/0068852 A1 | 3/2021 | Spence |
| 2021/0077211 A1 | 3/2021 | Blacker et al. |
| 2021/0093406 A1 | 4/2021 | Blacker et al. |
| 2021/0100980 A1 | 4/2021 | Blacker |
| 2021/0145532 A1 | 5/2021 | Tucker et al. |
| 2021/0178032 A1 | 6/2021 | Hsu et al. |
| 2021/0178036 A1 | 6/2021 | Nazarifar et al. |
| 2021/0186534 A1 | 6/2021 | Hunt et al. |
| 2021/0192759 A1 | 6/2021 | Lang |
| 2021/0196242 A1 | 7/2021 | Perez |
| 2021/0196413 A1 | 7/2021 | Inoue |
| 2021/0212792 A1 | 7/2021 | Shelton et al. |
| 2021/0220064 A1 | 7/2021 | Kottenstette et al. |
| 2021/0228841 A1 | 7/2021 | Falb et al. |
| 2021/0244434 A1* | 8/2021 | Popa ............... A61B 17/00234 |
| 2021/0247396 A9 | 8/2021 | Penny |
| 2021/0251472 A1 | 8/2021 | Baez |
| 2021/0259884 A1 | 8/2021 | Heeren et al. |
| 2021/0282863 A1 | 9/2021 | Rafii-Tari et al. |
| 2021/0282867 A1 | 9/2021 | Tegg et al. |
| 2021/0282875 A1 | 9/2021 | Sharon et al. |
| 2021/0282893 A1 | 9/2021 | Leo et al. |
| 2021/0290310 A1 | 9/2021 | Laby et al. |
| 2021/0290320 A1 | 9/2021 | Mao et al. |
| 2021/0290324 A1 | 9/2021 | Mintz et al. |
| 2021/0298847 A1 | 9/2021 | Mao et al. |
| 2021/0298850 A1 | 9/2021 | Huang et al. |
| 2021/0298857 A1 | 9/2021 | Zheng et al. |
| 2021/0298954 A1 | 9/2021 | Alvarez et al. |
| 2021/0305639 A1 | 9/2021 | Ho et al. |
| 2021/0315596 A1 | 10/2021 | Buck et al. |
| 2021/0353129 A1 | 11/2021 | Roelle et al. |
| 2021/0361366 A1 | 11/2021 | Murphy et al. |
| 2021/0369370 A1 | 12/2021 | Malanoski |
| 2021/0378696 A1 | 12/2021 | Yang et al. |
| 2021/0393338 A1 | 12/2021 | Graetzel et al. |
| 2021/0401527 A1 | 12/2021 | Hassan |
| 2022/0031415 A1 | 2/2022 | Vargas et al. |
| 2022/0040450 A1 | 2/2022 | Haubert |
| 2022/0047344 A1 | 2/2022 | Stepanauskas |
| 2022/0167984 A1 | 6/2022 | Shelton, IV |
| 2022/0168000 A1 | 6/2022 | Naglretter et al. |
| 2022/0168001 A1 | 6/2022 | Naglretter et al. |
| 2022/0168002 A1 | 6/2022 | Naglretter et al. |
| 2022/0168049 A1 | 6/2022 | Tanner et al. |
| 2022/0211452 A1 | 7/2022 | Clark et al. |
| 2022/0233263 A1 | 7/2022 | Canale et al. |
| 2022/0233264 A1 | 7/2022 | Klem |
| 2022/0233820 A1 | 7/2022 | Clark et al. |
| 2022/0241490 A1 | 8/2022 | Marass |
| 2022/0313375 A1 | 10/2022 | Zhang et al. |
| 2022/0323096 A1 | 10/2022 | Naglretter et al. |
| 2022/0331509 A1 | 10/2022 | Buck et al. |
| 2022/0370161 A1 | 11/2022 | Yu |
| 2022/0370706 A1 | 11/2022 | Meganck |
| 2022/0378522 A1 | 12/2022 | Zemlok et al. |
| 2023/0000563 A1 | 1/2023 | Bell et al. |
| 2023/0035508 A1 | 2/2023 | Clark et al. |
| 2023/0035946 A1 | 2/2023 | Kapadia |
| 2023/0043432 A1 | 2/2023 | Kapadia |
| 2023/0046468 A1 | 2/2023 | Lau et al. |
| 2023/0047098 A1 | 2/2023 | Lau et al. |
| 2023/0048055 A1 | 2/2023 | Lau et al. |
| 2023/0048388 A1 | 2/2023 | Lau et al. |
| 2023/0052862 A1 | 2/2023 | Lau et al. |
| 2023/0107693 A1 | 4/2023 | Walker et al. |
| 2023/0116327 A1 | 4/2023 | Walker et al. |
| 2023/0116700 A1 | 4/2023 | Yu et al. |
| 2023/0117715 A1 | 4/2023 | Ho et al. |
| 2023/0126545 A1 | 4/2023 | Liu et al. |
| 2023/0202040 A1 | 6/2023 | Lin et al. |
| 2023/0209018 A1 | 6/2023 | Alexanderson et al. |
| 2023/0218816 A1 | 7/2023 | Germain et al. |
| 2023/0310100 A1 | 10/2023 | Wenderow et al. |
| 2023/0347110 A1 | 11/2023 | Wenderow et al. |
| 2023/0380914 A1 | 11/2023 | Meglan et al. |
| 2023/0380915 A1 | 11/2023 | Hundertmark |
| 2024/0001101 A1 | 1/2024 | Wallin et al. |
| 2024/0016560 A1 | 1/2024 | Canale et al. |
| 2024/0019042 A1 | 1/2024 | Lim |
| 2024/0032949 A1 | 2/2024 | Yang et al. |

(56)  References Cited

U.S. PATENT DOCUMENTS

| | | |
|---|---|---|
| 2024/0033016 A1 | 2/2024 | Yang et al. |
| 2024/0033017 A1 | 2/2024 | Yang et al. |
| 2024/0033018 A1 | 2/2024 | Yang et al. |
| 2024/0033019 A1 | 2/2024 | Lau et al. |
| 2024/0033486 A1 | 2/2024 | Lau et al. |
| 2024/0041480 A1 | 2/2024 | Bartholomew |
| 2024/0042124 A1 | 2/2024 | Bartholomew |
| 2024/0042142 A1 | 2/2024 | Bartholomew |
| 2024/0122612 A1 | 4/2024 | Bartholomew |
| 2024/0138862 A1 | 5/2024 | Beach |
| 2024/0165415 A1 | 5/2024 | Grosskopf et al. |
| 2024/0180635 A1 | 6/2024 | Lau et al. |
| 2024/0180640 A1 | 6/2024 | Lau et al. |
| 2024/0180641 A1 | 6/2024 | Lau et al. |
| 2024/0180642 A1 | 6/2024 | Lau et al. |
| 2024/0180643 A1 | 6/2024 | Lau et al. |
| 2024/0180650 A1 | 6/2024 | Lau et al. |
| 2024/0180652 A1 | 6/2024 | Lau et al. |
| 2024/0180653 A1 | 6/2024 | Lau et al. |
| 2024/0180654 A1 | 6/2024 | Lau et al. |
| 2024/0180658 A1 | 6/2024 | Lau et al. |
| 2024/0180659 A1 | 6/2024 | Lau et al. |
| 2024/0181207 A1 | 6/2024 | Lau et al. |
| 2024/0181208 A1 | 6/2024 | Lau et al. |
| 2024/0181213 A1 | 6/2024 | Lau et al. |
| 2024/0181214 A1 | 6/2024 | Lau et al. |
| 2024/0181224 A1 | 6/2024 | Lau et al. |
| 2024/0181298 A1 | 6/2024 | Lau et al. |
| 2024/0183382 A1 | 6/2024 | Lau et al. |
| 2024/0197416 A1 | 6/2024 | Gonzalez |
| 2024/0197418 A1 | 6/2024 | Jourdan |
| 2024/0198051 A1 | 6/2024 | Jourdan |
| 2024/0207570 A1 | 6/2024 | Mar |
| 2024/0398495 A1 | 12/2024 | Lee et al. |
| 2025/0032201 A1 | 1/2025 | Bartholomew et al. |
| 2025/0195835 A1 | 6/2025 | Totten |

FOREIGN PATENT DOCUMENTS

| | | |
|---|---|---|
| CN | 103976766 | 8/2014 |
| CN | 104042259 | 9/2014 |
| CN | 203935213 | 11/2014 |
| CN | 204428157 | 7/2015 |
| CN | 105534599 | 5/2016 |
| CN | 105616008 | 6/2016 |
| CN | 105640648 | 6/2016 |
| CN | 105662586 | 6/2016 |
| CN | 105662588 | 6/2016 |
| CN | 105662589 | 6/2016 |
| CN | 105796179 | 7/2016 |
| CN | 205598007 | 9/2016 |
| CN | 106691414 | 5/2017 |
| CN | 107307909 | 11/2017 |
| CN | 107349514 | 11/2017 |
| CN | 107374737 | 11/2017 |
| CN | 107374738 | 11/2017 |
| CN | 107374739 | 11/2017 |
| CN | 107374740 | 11/2017 |
| CN | 107374741 | 11/2017 |
| CN | 107550570 | 1/2018 |
| CN | 107684459 | 2/2018 |
| CN | 107744405 | 3/2018 |
| CN | 107744406 | 3/2018 |
| CN | 107744616 | 3/2018 |
| CN | 107811624 | 3/2018 |
| CN | 108158656 | 6/2018 |
| CN | 108175504 | 6/2018 |
| CN | 207970143 | 10/2018 |
| CN | 207979770 | 10/2018 |
| CN | 207979771 | 10/2018 |
| CN | 207980153 | 10/2018 |
| CN | 109567947 | 4/2019 |
| CN | 208693445 | 4/2019 |
| CN | 109730779 A | 5/2019 |
| CN | 109821137 A | 5/2019 |
| CN | 208989133 | 6/2019 |
| CN | 209136865 | 7/2019 |
| CN | 209137698 | 7/2019 |
| CN | 110151310 A | 8/2019 |
| CN | 110236679 | 9/2019 |
| CN | 209713130 | 12/2019 |
| CN | 211271130 | 12/2019 |
| CN | 210056225 | 2/2020 |
| CN | 111035453 | 4/2020 |
| CN | 111110353 | 5/2020 |
| CN | 111110354 | 5/2020 |
| CN | 111407416 | 7/2020 |
| CN | 111437033 | 7/2020 |
| CN | 111449752 | 7/2020 |
| CN | 210962301 | 7/2020 |
| CN | 111658154 | 9/2020 |
| CN | 111772801 | 10/2020 |
| CN | 211610046 | 10/2020 |
| CN | 211723416 U | 10/2020 |
| CN | 111916214 | 11/2020 |
| CN | 111931626 | 11/2020 |
| CN | 111933268 | 11/2020 |
| CN | 112017516 | 12/2020 |
| CN | 212089719 | 12/2020 |
| CN | 212089720 | 12/2020 |
| CN | 112546396 | 3/2021 |
| CN | 112546397 | 3/2021 |
| CN | 112587241 | 4/2021 |
| CN | 213465314 | 6/2021 |
| CN | 113303913 | 8/2021 |
| CN | 113304393 | 8/2021 |
| CN | 113693733 | 11/2021 |
| EP | 1 776 057 | 11/2009 |
| EP | 2 124 705 | 5/2019 |
| FR | 3118406 | 7/2022 |
| WO | WO 2000/18290 | 4/2000 |
| WO | WO 2007/102134 | 9/2007 |
| WO | WO 2008/057887 | 10/2008 |
| WO | WO 2013/103885 | 7/2013 |
| WO | WO 2016/191307 | 12/2016 |
| WO | WO 2017/220010 | 12/2017 |
| WO | WO 2019/222641 | 11/2019 |
| WO | WO 2020/031147 | 2/2020 |
| WO | WO 2020/061240 | 3/2020 |
| WO | WO 2020/123671 | 6/2020 |
| WO | WO 2020/130924 | 6/2020 |
| WO | WO 2021/004255 | 6/2020 |
| WO | WO 2020/142340 | 7/2020 |
| WO | WO 2021/011551 | 7/2020 |
| WO | WO 2020/167749 | 8/2020 |
| WO | WO 2020/263630 | 12/2020 |
| WO | WO 2021/011533 | 1/2021 |
| WO | WO 2021/011554 | 1/2021 |
| WO | WO 2021/015990 | 1/2021 |
| WO | WO 2021/126698 | 6/2021 |
| WO | WO 2021/127426 | 6/2021 |
| WO | WO 2021/183444 | 9/2021 |
| WO | WO 2021/184444 | 9/2021 |
| WO | WO 2022/048984 | 3/2022 |
| WO | WO 2022/115717 | 6/2022 |
| WO | WO 2022/154979 | 7/2022 |

OTHER PUBLICATIONS

US 12,108,960 B1, 10/2024, Teigen et al. (withdrawn)

Bao et al., Feb. 2018, A cooperation of catheters and guidewires-based novel remote-controlled vascular interventional robot, Biomedical Microdevices, 20(1):20.

Bell, Apr. 4, 2019, Coding for Empathy, https://www.youtube.com/watch?v=13tzbxofDVc, screenshot of video.

Bency et al., Apr. 25, 2019, Neural Path Planning: Fixed Time, Near-Optimal Path Generation via Oracle Imitation, arXiv:1904.11102v1 [cs.RO], 8 pp.

Bergman et al., 2020, Robotic-assisted percutaneous coronary intervention, Handbook of Robotic and Image-Guided Surgery, doi: https.//doi.org/10.1016/B978-0-12-814245-5.00020-7.

(56)                References Cited

OTHER PUBLICATIONS

Chen et al., Feb. 14, 2020, Deep learning robotic guidance for autonomous vascular access, Nature Machine Intelligence, https://doi.org/10.1038/s42256-020-0148-7, 12 pp.

Das et al., Feb. 21, 2019, Learning-Based Proxy Collision Detection for Robot Motion Planning Applications, arXiv:1902.08164v1 [cs.RO], 19 pp.

Das et al., May 29, 2020, Stochastic Modeling of Distance to Collision for Robot Manipulators, arXiv:2005. 14391v1 [cs.RO], 8 pp.

Evard, Jun. 2018, Catheter localization utilizing a sensor-enabled guidewire design of a proof-of-concept system, Masters Thesis, California Polytechnic State University, San Luis Obispo, 186 pp.

Fagogenis et al., Apr. 2019, Autonomous Robotic Intracardiac Catheter Navigation Using Haptic Vision, Science Robotics, 4(29):1-12.

Guo et al., Apr. 13, 2018, Study on real-time force feedback for a master-slave interventional surgical robotic system, Biomedical Microdevices, 20(2):37, 12 pp.

Guo et al., May 20, 2020, Machine learning-based operation skills assessment with vascular difficultyindex for vascular intervention surgery, Medical & Biological Engineering & Computing, https://doi.org/10.1007/s11517-020-02195-9, 15 pp.

Guo et al., Oct. 16, 2020, An Improved Visual Auxiliary Algorithm for the Vascular Interventional Surgical Robot based on Neural Network, Proceedings of 2020 IEEE International Conference on Mechatronics and Automation, http://www.guolab.org/Papers/2020/ICMA2020-329.pdf, pp. 1923-1928.

Jiang et al., 2018, Initial clinical trial of robot of endovascular treatment with force feedback and cooperating of catheter and guidewire, Applied Bionics and Biomechanics, vol. 2018, Article ID 9735979, 10 pp.

Johnson et al., Aug. 12, 2020, Dynamically Constrained Motion Planning Networks for Non-Holonomic Robots, arXiv:2008. 05112v1 [cs.RO}, 7 pp.

Kagiyama et al., Jul. 31, 2019, First experience of robotic-assisted percutaneous coronary intervention in Japan, Intern Med Advance Publication, doi: 10/2016/internalmedicine.3272-19.

Kuang et al., Apr. 2020, Vibration-Based Multi-Axis Force Sensing: Design, Characterization, and Modeling, IEEE Robotics and Automation Letters, 5(2):3082-3089.

Li et al., 2022, An endovascular catheterization robotic system using collaborative operation with magnetically controlled haptic force feedback, Micromachines, 13:505.

Li et al., Jan. 17, 2021, MPC-MPNet: Model-Predictive Motion Planning Networks for Fast, Near-Optimal Planning Under Kinodynamic Constraints, arXiv:2101.06798v1 [cs.RO], 8 pp.

Liu et al., 2021, Animal experiment of a novel neurointerventional surgical robotic system with master-slave mode, Applied Bionics and Biomechanics, vol. 2021, Article ID 8836268, 8 pp.

Qureshi et al., Feb. 2021, Motion Planning Networks: Bridging the Gap Between Learning-Based and Classical Motion Planners, IEEE Transactions on Robotics, 37(1), 19 pp.

Qureshi et al., Jul. 3, 2021, Constrained Motion Planning Networks X, arXiv:2010.08702v2 [cs.RO), 20 pp.

Qureshi et al., Oct. 25-29, 2020, Neural Manipulation Planning on Constraint Manifolds, IEEE Robotics and Automation Letters, 5(4), 8 pp.

Richter et al., Apr. 2021, Autonomous Robotic Suction to Clear the Surgical Field for Hemostasis Using Image-Based Blood Flow Detection, IEEE Robotics and Automation Letters, 6(2), 8 pp.

Sapsalev et al., 2016, Structural model of a magnetic coupling, 17th International Conference of Young Specialists on Micro/Nanotechnologies and Electron Devices EDM 2016, pp. 555-558.

Schreiber et al., Sep. 15, 2020, ARCSnake: An Archimedes Screw-Propelled, Reconfigurable Serpentine Robot for Complex Environments, 2020 IEEE International Conference on Robotics and Automation (ICRA), 6 pp.

Sganga et al., Sep. 15, 2018, OffsetNet: Deep Learning for Localization in the Lung using Rendered Images, arXiv:1809.05645v1 [cs.CV], 7 pp.

Sganga, May 22, 2020, Webinar: Autonomous Surgical Robots, https://www.youtube.com/watch?v=QRO2KnfGlgo, screenshot of video.

Wang et al., Feb. 3, 2018, Online measuring and evaluation of guidewire inserting resistance for robotic interventional surgery systems, Microsystem Technologies, https://doi/org/10.1007/s00542-018-03750-4.

Wilcox et al., Jan. 2020, SOLAR-GP: Sparse Online Locally Adaptive Regression Using Gaussian Processes for Bayesian Robot Model Learning and Control, EEE Robotics and Automation Letters, 5(2), 8 pp.

Yip et al., 2017, Autonomous Control of Continuum Robot Manipulators for Complex Cardiac Ablation Tasks, Journal of Medical Robotics Research, 2(1),:1750002-1-1750002-13.

Yip et al., Jul. 10, 2017, Robot Autonomy for Surgery, https://arxiv.org/pdf/1707.03080.pdf, 33 pp.

Zhao et al., Apr. 2, 2018, Operating force information on-line acquisition of a novel slave manipulator for vascular interventional surgery, Biomedical Microdevices, 20(2):33, 13 pp.

Zhou et al., 2021, ADRC-based control method for the vascular intervention master-slave surgical robotic system, Micromachines, 12:1439.

International Search Report and Written Opinion dated May 8, 2024 in application No. PCT/US2023/081889.

International Search Report and Written Opinion dated Apr. 26, 2024 in application No. PCT/US2023/081880.

Bergam et al., 2020, Robotic assisted percutaneous coronary interventions, in Handbook of Robotic and Image Guided Surgery, Elsevier Inc., pp. 341-362.

* cited by examiner $$C = e_0 \times \frac{A}{d} \, (F)$$

Side View of Puck and Carriage

Equivalent System

2215d

2210d

2202d

2202g'

2258g'

2202h'

2272bh'

2272ah'

2270h'

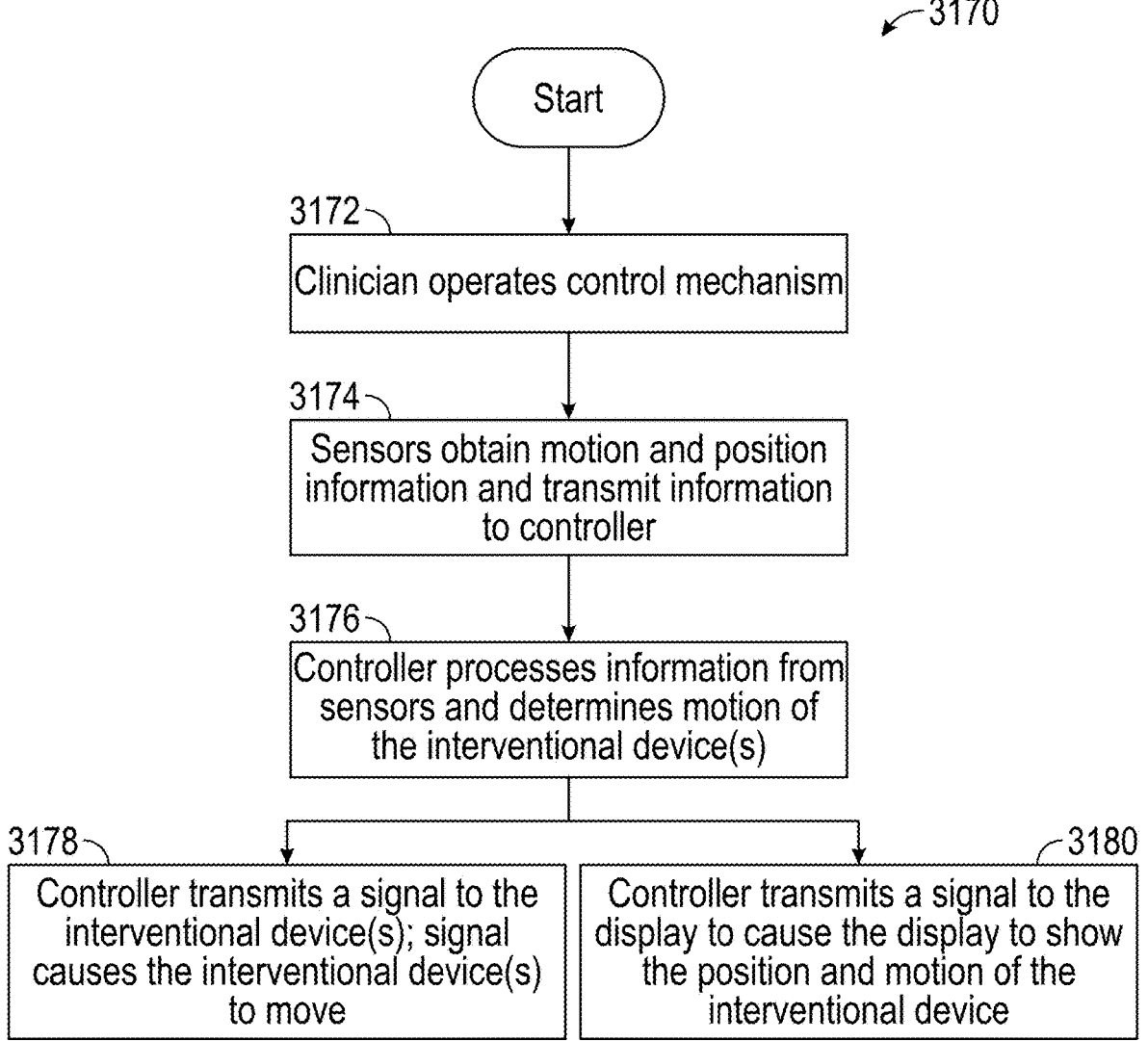

3170

Start

3172 —
Clinician operates control mechanism

3174 —
Sensors obtain motion and position information and transmit information to controller 3176 —
Controller processes information from sensors and determines motion of the interventional device(s)

3178 —
Controller transmits a signal to the interventional device(s); signal causes the interventional device(s) to move 3180
Controller transmits a signal to the display to cause the display to show the position and motion of the interventional device

Figure 30F:
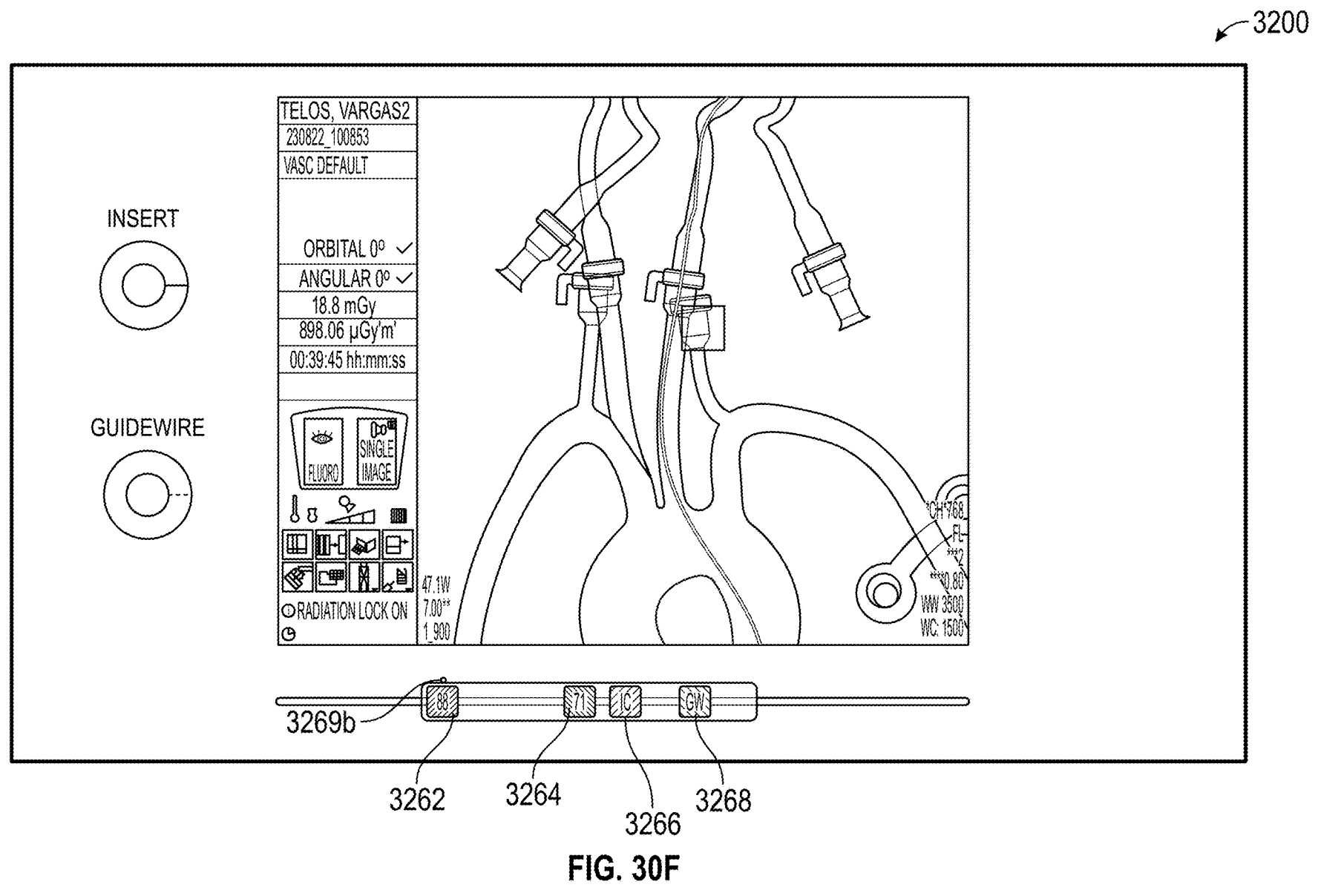

TELOS, VARGAS2

230822_100853

VASC DEFAULT

ORBITAL 0°

ANGULAR 0°

18.8 mGy 898.06 μGy·m²

00:39:45 hh:mm:ss

FLUORO     SINGLE IMAGE

RADIATION LOCK ON 47.1W
7.00***
1.900

INSERT

GUIDEWIRE

TELOS, VARGAS2

230822_100853

VASC DEFAULT

ORBITAL 0°

ANGULAR 0°

18.8 mGy 898.06 µGy·m²

00:39:45 hh:mm:ss 47.1W 7.00 ***

1,900

FLUORO

SINGLE IMAGE

RADIATION LOCK ON

RCH:768

FL 0.80

WW:3600

WC:1500

SPEED

LOW MED HIGH

ROTATION

IC    GW

3271

3262

3264

3271

3266  3268

3271

3271

3200

TELOS, VARGAS2
230822_100853
VASC DEFAULT

ORBITAL 0°
ANGULAR 0°
18.8 mGy
898.06 μGy·m²
00:39:45 hh:mm:ss

FLUORO

SINGLE IMAGE

RADIATION LOCK ON 47.1W
7.00**
1.900

3271

3262
3264
3271
3266 3268

SPEED

LOW MED HIGH

ROTATION

USER INTERFACE FOR ROTATIONAL DEVICE MOVEMENT

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 C.F.R. § 1.57. The present application claims priority to U.S. Provisional Patent Application No. 63/429,502, filed Dec. 1, 2022, titled CONTROLLER FOR ROBOTIC CATHETER DRIVE SYSTEM, the entire content of which is incorporated by reference herein for all purposes and forms a part of this specification.

BACKGROUND

Field

The present application relates to neurovascular procedures, and more particularly, to catheter assemblies and robotic control systems for neurovascular site access.

Description of the Related Art

A variety of neurovascular procedures can be accomplished via a transvascular access, including thrombectomy, diagnostic angiography, embolic coil deployment and stent placement. However, the delivery of neurovascular care is limited or delayed by a variety of challenges. For example, there are not enough trained interventionalists and centers to meet the current demand for neurointerventions. Neuro interventions are difficult, with complex set up requirements and demands on the surgeon's dexterity. With two hands, the surgeon must exert precise control over 3-4 coaxial catheters plus manage the fluoroscopy system and patient position. Long, tortuous anatomy, requires delicate, precise maneuvers. Inadvertent catheter motion can occur due to energy storage and release caused by frictional interplay between coaxial shafts and the patient's vasculature. Supra-aortic access necessary to reach the neurovasculature is challenging to achieve, especially Type III arches. Once supra-aortic access is achieved, adapting the system for neurovascular treatments is time consuming and requires guidewire and access catheter removal and addition of a procedure catheter (and possibly one or more additional catheters) to the stack.

Thus, there remains a need for a supra-aortic access and neurovascular site access system that addresses some or all these challenges and increases the availability of neurovascular procedures. Preferably, the system is additionally capable of driving devices further distally through the supra-aortic access to accomplish procedures in the intracranial vessels.

SUMMARY

There is provided in accordance with one aspect of the present disclosure a supra-aortic access robotic control system. The system comprises a guidewire hub configured to adjust each of an axial position and a rotational position of a guidewire; a guide catheter hub configured to adjust a guide catheter in an axial direction; and an access catheter hub configured to adjust each of an axial position and a rotational position of an access catheter. The access catheter hub may also laterally deflect a distal deflection zone of the access catheter. The guidewire hub may additionally be configured to laterally deflect a distal portion of the guidewire.

There may also be provided a procedure catheter hub configured to manipulate a procedure catheter. Following robotic placement of the guidewire, access catheter and guide catheter such that the guide catheter achieves supra aortic access, the guidewire and access catheter may be proximally withdrawn and the procedure catheter advanced through and beyond the guide catheter, with or without guidewire support (said guidewire may be smaller in diameter and/or more flexible than the guidewire used to gain supra aortic access), to reach a more distal neurovascular treatment site. The procedure catheter may be an aspiration catheter; an embolic deployment catheter; a stent deployment catheter; a flow diverter deployment catheter, an access catheter; a diagnostic angiographic catheter; a guiding catheter, an imaging catheter, a physiological sensing/measuring catheter, an infusion or injection catheter, an ablation catheter, an RF ablation catheter or guidewire, a balloon catheter, or a microcatheter used to deliver a stent retriever, a balloon catheter or a stent retriever.

The control system may further comprise a driven magnet on each of a guidewire hub, an access catheter hub and a guide catheter hub, configured to cooperate with corresponding drive magnets such that the driven magnet moves in response to movement of the corresponding drive magnet. The drive magnets may each be independently axially movably carried by a support table. The drive magnets may be located outside of the sterile field, separated from the driven magnets by a barrier, and the driven magnets may within the sterile field. The barrier may comprise a tray made from a thin polymer membrane, or any membrane of non-ferromagnetic material.

The control system may further comprise a control console which may be connected to the support table or may be located remotely from the support table. The position of each driven magnet and corresponding hub is movable in response to manual manipulation of a guidewire drive control, access catheter drive control, or procedure catheter drive control on the console or on a particular controller not associated with the console.

The control system may further comprise a processor for controlling the position of the drive magnets. The processor may be in wired communication with the control console, or in wireless communication with the control console. The driven magnets may be configured to remain engaged with the corresponding drive magnets until application of an axial disruption force of at least about 300 grams.

There is also provided a robotically driven interventional device. The device comprises an elongate, flexible body, having a proximal end and a distal end. A hub is provided on the proximal end. At least one rotatable roller is provided on a first surface of the hub; and at least one magnet is provided on the first surface of the hub. The roller may extend further away from the first surface than the magnet. The hub may be further provided with at least a second roller.

Any of the guidewire hub, access catheter hub and procedure catheter hub may be further provided with a rotational drive, for rotating the corresponding interventional device with respect to the hub. The hub may be further provided with an axial drive mechanism to distally advance or proximally retract a control element extending axially through the interventional device, to adjust a characteristic such as shape or flexibility of the interventional device. In some embodiments, at least one control element may be an axially movable tubular body or fiber, ribbon, or wire such as a pull wire extending through the interventional device to, for example, a distal deflection zone. In some embodiments, any number of control elements may be advanced, retracted, or otherwise moved in a similar manner.

There is also provided a control system for controlling movement of interventional devices. In one configuration, the control system comprises a guidewire control, configured to control axial travel and rotation of a guidewire; an access catheter control, configured to control axial and rotational movement of an access catheter; and a guide catheter control, configured to control axial movement and/or rotation of a guide catheter.

The control system may further comprise a deflection control, configured to control deflection of the access catheter or procedure catheter, and may be configured for wired or wireless communication with a robotic catheter drive system.

The control system may be configured to independently control the three or more hubs in a variety of modes. For example, two or more hubs may be selectively ganged together so that they drive the respective devices simultaneously and with the same motion. Alternatively, the control system may be configured to drive respective devices simultaneously but with different motions.

The control system may further comprise a physician interface for operating the control system. The physician interface may be carried by a support table having a robotic interventional device drive system. Alternatively, the physician interface for operating the control system may be carried on a portable, handheld device or desktop computer, and may be located in the same room as the patient, the same facility as the patient, or in a remote facility.

The control system may further comprise a graphical user interface with at least one display for indicating the status of at least one device parameter, and/or indicating the status of at least one patient parameter.

There is also provided a sterile packaging assembly for transporting interventional devices to a robotic surgery site. The packaging assembly may comprise a base and a sterile barrier configured to enclose a sterile volume. At least one interventional device may be provided within the sterile volume, the device including a hub and an elongate flexible body. The hub may include at least one magnet and at least one roller configured to roll on the base.

In one implementation, the sterile barrier is removably attached to the base to define the enclosed volume between the sterile barrier and the base. In another implementation, the sterile barrier is in the form of a tubular enclosure for enclosing the sterile volume. The tubular enclosure may surround the base and the at least one interventional device, which are within the sterile volume.

The hub may be oriented within the packaging such that the roller and the magnet face the base. Alternatively, the base may be in the form of a tray having an elongate central axis. An upper, sterile field side of the tray may have an elongate support surface for supporting and permitting sliding movement of one or more hubs. At least one and optionally two elongate trays may be provided, extending parallel to the central axis. At least one hub and interventional device may be provided in the tray, and the sterile tray with sterile hub and interventional device may be positioned in a sterile volume defined by a sterile barrier.

The base may be configured to reside on a support table adjacent a patient, with an upper surface of the base within a sterile field and a lower surface of the base outside of the sterile field.

Any of the hubs disclosed herein may further comprise a fluid injection port and/or a wireless RF transceiver for communications and/or power transfer. The hub may comprise a visual indicator, for indicating the presence of a clot. In some embodiments, the hub may also comprise wired electrical communications and power port. The visual indicator may comprise a clot chamber having a transparent window. A filter may be provided in the clot chamber.

Any of the hubs disclosed herein may further comprise a sensor for detecting a parameter of interest such as the presence of a clot. The sensor, in some instances, may be positioned on a flexible body. The sensor may comprise a pressure sensor or an optical sensor. In some embodiments, the sensor may comprise one or more of a force sensor, a positioning sensor, a temperature sensor, and/or an oxygen sensor. In some embodiments, the sensor may comprise a Fiber Bragg grating sensor. For example, a Fiber Bragg grating sensor (e.g., an optical fiber) may detect strain locally that can facilitate the detection and/or determination of force being applied. The device may further include a plurality of sensors. The plurality of sensors may each comprise one or more of any type of sensor disclosed herein. In some embodiments, a plurality (e.g., 3 or more) of sensors (e.g., Fiber Bragg grating sensors) may be distributed around a perimeter to facilitate the detection and/or determination of shape. The position of the device, in some instance, may be determined through the use of one or more sensors to detect and/or determine the position. For example, one or more optical encoders may be located in or proximate to one or more the motors that drive linear motion such that the optical encoders may determine a position.

There is also provided a method of performing a neurovascular procedure, in which a first phase includes robotically achieving supra-aortic access, and a second phase includes manually or robotically performing a neurovascular procedure via the supra-aortic access. The method comprises the steps of providing an access catheter having an access catheter hub; coupling the access catheter hub to a hub adapter movably carried by a support table; driving the access catheter in response to movement of the hub adapter along the table until the access catheter is positioned to achieve supra-aortic access. The access catheter and access catheter hub may then be decoupled from the hub adapter; and a procedure catheter hub having a procedure catheter may then be coupled to the hub adapter.

The method may additionally comprise advancing the procedure catheter hub to position a distal end of the procedure catheter at a neurovascular treatment site. The driving the access catheter step may comprise driving the access catheter distally through a guide catheter. The driving the access catheter step may include the step of laterally deflecting a distal region of the access catheter to achieve supra-aortic access. In some embodiments, the driving the access catheter step may also include rotating the access catheter.

There is also provided a method of performing a neurovascular procedure, comprising the steps of providing an access assembly comprising a guidewire, access catheter and guide catheter. The access assembly may be releasably coupled to a robotic drive system. The access assembly may be driven by the robotic drive system to achieve access to a desired point, such as to achieve supra-aortic access. The guidewire and the access catheter may then be decoupled from the access assembly, leaving the guide catheter in place. A procedure assembly may be provided, comprising at least a guidewire and a first procedure catheter. The procedure assembly may be releasably coupled to the robotic drive system; and a neurovascular procedure may be accomplished using the procedure assembly. A second procedure catheter may also be provided, for extending through the first procedure catheter to a treatment site.

The coupling the access assembly step may comprise magnetically coupling a hub on each of the guidewire, access catheter and guide catheter, to separate corresponding couplers carrying corresponding drive magnets independently movably carried by the drive table. The procedure assembly may comprise a guidewire, a first catheter and a second catheter. The guidewire and first catheter may be positioned concentrically within the second catheter. The procedure assembly may be advanced as a unit through at least a portion of the length of the guide catheter, and the procedure may comprise a neurovascular thrombectomy.

There is also provided a method of performing a neurovascular procedure. The method includes the steps of providing a multi-catheter assembly including an access catheter, a guide catheter, and a procedure catheter, coupling the assembly to a robotic drive system, driving the assembly to achieve supra-aortic access, driving a subset of the assembly to a neurovascular site, wherein the subset includes the guide catheter and the procedure catheter, proximally removing the access catheter, and performing a neurovascular procedure using the procedure catheter.

The neurovascular procedure can include a neurovascular thrombectomy. The assembly may further include a guidewire, wherein each of the guidewire, the access catheter, the guide catheter, and the procedure catheter are configured to be adjusted by a respective hub. Coupling the assembly to the robotic drive system can include magnetically coupling a first hub of the guidewire to a first drive magnet, magnetically coupling a second hub of the access catheter to a second drive magnet, magnetically coupling a third hub of the guide catheter to a third drive magnet, and magnetically coupling a fourth hub of the procedure catheter to a fourth drive magnet. The first drive magnet, the second drive magnet, the third drive magnet, and the fourth drive magnet can each be independently movably carried by a drive table. The procedure catheter can be an aspiration catheter. The procedure catheter can be an embolic deployment catheter. The procedure catheter can be a stent deployment catheter. The procedure catheter can be a flow diverter deployment catheter. The procedure catheter can be a diagnostic angiographic catheter. The procedure catheter can be a stent retriever catheter. The procedure catheter can be a clot retriever. The procedure catheter can be a balloon catheter. The procedure catheter can be a catheter to facilitate percutaneous valve repair or replacement. The procedure catheter can be an ablation catheter.

There is also provided a method of performing an intracranial procedure. The method includes the steps of providing an assembly including a guidewire, an access catheter, a guide catheter, and a procedure catheter coaxially moveably assembled into a single multi-catheter assembly, coupling the assembly to a drive system, driving the assembly to achieve supra-aortic access, driving a subset of the assembly to an intracranial site, wherein the subset includes the guidewire, the guide catheter, and the procedure catheter, and performing an intracranial procedure using the subset of the assembly.

The intracranial procedure can include an intracranial thrombectomy. Each of the guidewire, the access catheter, the guide catheter, and the procedure catheter can be configured to be adjusted by a respective hub. Coupling the assembly to the drive system can include magnetically coupling a first hub of the guidewire to a first drive magnet, magnetically coupling a second hub of the access catheter to a second drive magnet, magnetically coupling a third hub of the guide catheter to a third drive magnet, and magnetically coupling a fourth hub of the procedure catheter to a fourth drive magnet. The drive system can be a robotic drive system, and the first drive magnet, the second drive magnet, the third drive magnet, and the fourth drive magnet can each be independently movably carried by a drive table associated with the robotic drive system. The first drive magnet, the second drive magnet, the third drive magnet, and the fourth drive magnet can each be independently movably carried by a drive table.

There is also provided a method of performing a neurovascular procedure. The method can include the steps of providing an assembly including a guidewire, an access catheter, a guide catheter, and a procedure catheter, advancing the assembly to achieve supra-aortic access, advancing a subset of the assembly to a neurovascular site, wherein the subset includes the guidewire, the guide catheter, and the procedure catheter, and performing a neurovascular procedure using the subset of the assembly.

The neurovascular procedure can include a neurovascular thrombectomy. The procedure catheter can be an aspiration catheter. The procedure catheter can be an embolic deployment catheter. The procedure catheter can be a stent deployment catheter. The procedure catheter can be a flow diverter deployment catheter. The procedure catheter can be a diagnostic angiographic catheter. The procedure catheter can be a stent retriever catheter. The procedure catheter can be a clot retriever. The procedure catheter can be a balloon catheter. The procedure catheter can be a catheter to facilitate percutaneous valve repair or replacement. The procedure catheter can be an ablation catheter.

A method of robotically controlling interventional devices is also provided. The method includes providing an interventional device assembly including a plurality of interventional devices, the plurality of interventional devices including a first interventional device and a second interventional device. The method includes advancing the first interventional device and the second interventional device from a first set of positions to a second set of positions in response to movement of a control of the controller, wherein a relative distance between a distal end of the first interventional device and a distal end of the second interventional device at the second set of positions is different from a relative distance between the distal end of the first interventional device and the distal end of the second interventional device at the first set of positions.

A method of robotically controlling interventional devices is provided. The method incudes providing an interventional device assembly including a plurality of interventional devices, the plurality of interventional devices including a first interventional device and a second interventional device, wherein the first interventional device is coupled to a first control so that movement of the first control causes a responsive movement of the first interventional device and the second interventional device is coupled to a second control so that movement of the second control causes a responsive movement of the second interventional device. The method includes linking movement of the second interventional device to movement of the first interventional device so that the second interventional device moves at a same speed in a same direction as the first interventional device when a movement of the first control would cause a responsive movement of the first interventional device that would result in a separation distance between the first interventional device and the second interventional device greater than permitted by a drivable surface of a drive table.

In some embodiments, the method can include determining, by one or more hardware processors, that the movement of the first control would cause the responsive movement of the first interventional device that would result in the separation distance between the first interventional device and the second interventional device greater than permitted by the drivable surface of the drive table. In some embodiments, the first interventional device is a guide catheter and the second interventional device is a guidewire. In some embodiments, the method can include unlinking the second interventional device from the first interventional device in response to movement of the second control to cause a response movement of the second interventional device in the direction.

A method of robotically controlling interventional devices is provided. The method incudes providing an interventional device assembly including a plurality of interventional devices, the plurality of interventional devices including a first interventional device coupled to a first hub and a second interventional device coupled to a second hub, wherein the first hub is coupled to a first control so that movement of the first control causes a responsive movement of the first hub and the second hub is coupled to a second control so that movement of the second control causes a responsive movement of the second hub. The method includes linking movement of the second hub to movement of the first hub so that the second hub moves at a same speed in a same direction as the first hub when a movement of the first control would cause a responsive movement of the first hub that would result in a separation distance between the first hub and the second hub greater than permitted by a drivable surface of a drive table.

In some embodiments, the method can include determining, by one or more hardware processors, that the movement of the first control would cause the responsive movement of the first hub that would result in the separation distance between the first hub and the second hub greater than permitted by the drivable surface of the drive table. In some embodiments, the first hub is a guide catheter hub and the second hub is a guidewire hub. In some embodiments, the method can include unlinking the second hub from the first hub in response to movement of the second control to cause a response movement of the second hub in the direction.

A method of robotically controlling interventional devices is provided. The method incudes providing an interventional device assembly including a plurality of interventional devices, the plurality of interventional devices including a first interventional device coupled to a first hub adapter and a second interventional device coupled to a second hub adapter, wherein the first hub adapter is coupled to a first control so that movement of the first control causes a responsive movement of the first hub adapter and the second hub adapter is coupled to a second control so that movement of the second control causes a responsive movement of the second hub adapter. The method includes linking movement of the second hub adapter to movement of the first hub adapter so that the second hub adapter moves at a same speed in a same direction as the first hub adapter when a movement of the first control would cause a responsive movement of the first hub adapter that would result in a separation distance between the first hub adapter and the second hub adapter greater than permitted by a drivable surface of a drive table.

In some embodiments, the method can include determining, by one or more hardware processors, that the movement of the first control would cause the responsive movement of the first hub adapter that would result in the separation distance between the first hub adapter and the second hub adapter greater than permitted by the drivable surface of the drive table. In some embodiments, the first interventional device is a guide catheter and the second interventional device is a guidewire. In some embodiments, the method can include unlinking the second hub adapter from the first hub adapter in response to movement of the second control to cause a response movement of the second hub adapter in the direction. In some embodiments, the drivable surface is a shuttle configured to move axially within the drive table.

A robotic catheter control system is also provided. The robotic catheter control system includes a first control associated with a first interventional device; and a second control associated with a second interventional device; wherein movement of the first control in an axial direction from a starting axial position causes a responsive movement of the first interventional device in a corresponding axial direction, wherein an axial velocity of the first interventional device in the corresponding axial direction or an amount of axial movement of the first interventional device in the corresponding axial direction corresponds to an amount of axial movement of the first control in the axial direction; wherein movement of the first control in a rotational direction from a starting rotational position causes a responsive movement of the first interventional device in a corresponding rotational direction, wherein a rotational velocity of the first interventional device in the corresponding rotational direction or an amount of rotational movement of the first interventional device in the corresponding rotational direction corresponds to an amount of rotational movement of the first control in the rotational direction.

In some aspects, an axial arrangement of the first interventional device and the second interventional device can correspond to a corresponding axial arrangement of the first control and the second control. The second interventional device can be positioned distal to the first interventional device and the second control can be positioned distal to the second control.

In some aspects, the robotic catheter control system can include one or more hardware processors configured to generate a user interface including information regarding the first interventional device and the second interventional device. In some aspects, the robotic catheter control system can further include at least one sensor configured to detect movement of at least one of the first interventional device and the second interventional device; and one or more hardware processors configured to receive motion data from the at least one sensor. The motion data can be indicative of whether the first interventional device and the second interventional device are moving. In some aspects, the one or more hardware processors can be further configured to, based on the motion data, generate a user interface comprising an instrument window, the instrument window comprising a first representation of the first interventional device and a second representation of the second interventional device; and a first interventional device marker associated with the first representation and a second interventional device marker associated with the second representation. The first representation and the second representation can be configured to provide a visual indication about the position of the first and second interventional devices with respect to each other.

A robotic catheter control system is also provided. The robotic catheter control system includes a first control operable to control movement of a first interventional device, the first control including a unique first indicator identifying the first interventional device. The robotic catheter control system includes a second control operable to control movement of a second interventional device, the second control including a second indicator identifying the second interventional device. An axial arrangement of the first interventional device and the second interventional device corresponds to a corresponding axial arrangement of the first control and the second control.

In some aspects, the robotic catheter control system can include one or more hardware processors configured to generate a user interface including information regarding the first interventional device and the second interventional device. In some aspects, the robotic catheter control system can further include at least one sensor configured to detect movement of at least one of the first interventional device and the second interventional device; and one or more hardware processors configured to receive motion data from the at least one sensor. The motion data can be indicative of whether the first interventional device and the second interventional device are moving. In some aspects, the one or more hardware processors can be further configured to, based on the motion data, generate a user interface comprising an instrument window, the instrument window comprising a first representation of the first interventional device and a second representation of the second interventional device; and a first interventional device marker associated with the first representation and a second interventional device marker associated with the second representation. The first representation and the second representation can be configured to provide a visual indication about the position of the first and second interventional devices with respect to each other.

A robotic catheter user interface method is also provided. The method includes detecting, by a sensor, movement of a first control associated with a first interventional device; determining, using at least one processor, a first position of the first control; and presenting, in a first display view, a first position and first orientation of the first interventional device based at least in part on the first position of the first control.

In some aspects, presenting the position of the first interventional device can include presenting an axial position bar including a first end, a second end, and a length extending between the first and second ends. The method can further include presenting a first axial position indicator in the axial position bar corresponding to the position of the first interventional device inside a patient. The method can further include presenting, in a second display view, at least one of a second position and a second orientation of the first interventional device corresponding to a second position of the first control, wherein the first control transitions from the first position to the second position when the first control is moved. The method can further include generating a signal, using the at least one processor, to cause the first interventional device to move according to the movement of the first interventional device. The method can further include obtaining fluoroscopic imaging representative of a patient's vasculature and the first interventional device; and presenting, in the first display view, the fluoroscopic imaging.

A robotic catheter control system is also provided. The robotic catheter control system includes a display; a first control associated with a first interventional device; at least one processor, the processor causing at least one view to be displayed on the display, the at least one view adapted to present data representative of a position of the first interventional device in a vasculature of a patient; and a first sensor configured to detect movement of the first control and determine a position of the first control. A first view presents a first position of the first interventional device, and a second view presents a second position of the first interventional device. The processor determines, based on the position of the first control, a change in position of the first control and causes the display to transition from the first view to the second view.

In some aspects, the position of the interventional device can be presented along an axial position bar including a first end, a second end, and a first position indicator. The first position indicator can be configured to move along the axial position bar when the display transitions from the first view to the second view. In some aspects, a rotational position of the first interventional device can be presented in a rotational position indicator. In some aspects, the processor can be further configured to receive fluoroscopic imaging representative of a patient's vasculature and the first interventional device and present, on the display, the fluoroscopic imaging.

A method for generating a user interface for a robotic catheter system is also provided. The method includes receiving a user input configured to a move a first interventional device; detecting a first position of the first interventional device; and generating a first user interface for display. The first user interface includes an image feed portion configured to display a visual representation of a region of interest; a position bar including a first end representing a direction proximal to a patient and a second end representing a direction proximal to a patient; and a first position indicator included in relation to the position bar, said first position indicator corresponding to the detected first position of the first interventional device.

A method of robotically controlling interventional devices is also provided. The method includes providing an interventional device assembly including a plurality of interventional devices; advancing a first subset of the plurality of interventional devices into an ostium of the descending aorta in a first operation mode in response to movement of a control of a controller, wherein the first subset of the plurality of interventional devices is linked to the control in the first operation mode; switching from the first operation mode to a second operation mode in response to a user input using the controller, wherein switching from the first operation mode to the second operation mode causes a second subset of the plurality of interventional devices to be linked to the control of the controller, the second subset of the plurality of interventional devices being different than the first subset of the plurality of interventional devices; and advancing the second subset of the plurality of interventional devices to a treatment site in the second operation mode in response to movement of the control of the controller.

In some aspects, the first subset of the plurality of interventional devices includes a guide catheter, a procedure catheter, and an access catheter. In some aspects, the guide catheter, the procedure catheter, and the access catheter can be configured to move simultaneously in response to movement of the control in the first operation mode. In some aspects, the second subset of the plurality of interventional devices can include the guide catheter and the procedure catheter. In some aspects, the guide catheter and the procedure catheter can be configured to move simultaneously in the second operation mode. In some aspects, the control includes a first control, the method further including advancing a guidewire into the ostium in the first operation mode in response to movement of a second control of the controller. In some aspects, the first control can include a first joystick and the second control can include a second joystick. In some aspects, the techniques described herein relate to a method, further including linking one of the guide catheter, the procedure catheter, and the access catheter to the second control in response to a user input such that movement of the second control causes movement of the one of the guide catheter, the procedure catheter, and the access catheter. In some aspects, advancing the guidewire into the ostium in the first operation mode in response to movement of the second control can include advancing the guidewire in response to movement of the second control along a first axis, the method further including rotating the guidewire in response to movement of the second control along a second axis perpendicular to the first axis. In some aspects, the method further includes performing a neurovascular procedure at the treatment site by a procedure catheter in response to receiving a user input on the controller. In some aspects, performing the neurovascular procedure can include aspirating a clot. In some aspects, in the first operation mode, movement of the control can be configured to cause responsive movement of the first subset of the plurality of interventional devices within a first range of velocities. In the second operation mode, movement of the control can be configured to cause responsive movement of the second subset of the plurality of interventional devices within a second range of velocities different from the first range of velocities. In some aspects, the controller can be in communication with a control system having one or more hardware processors. The control system may further be in communication with a drive table configured to drive movement of the plurality of interventional devices. The one or more hardware processors may control movement of the plurality of interventional devices in response to user inputs using the controller. The one or more hardware processors may additionally generate a user interface including information regarding the plurality of interventional devices. The control system may receive information regarding the plurality of interventional devices or the drive table from one or more sensors of a sensors system. The one or more sensors can include a sensor configured to detect movement of a first interventional device and a second interventional device and provide motion data to the control system. The one or more hardware processors can, based on the motion data, generate a user interface comprising a representation of the first interventional device and the second interventional device configured to provide an indication of the relative positions of the first interventional device and the second interventional device.

A method of robotically controlling interventional devices is also provided. The method includes providing a multi-catheter assembly including: an access catheter, a guide catheter, and a procedure catheter; driving the multi-catheter assembly to achieve supra-aortic access in response to movement of a control of a controller; driving a subset of the multi-catheter assembly to a neurovascular site in response to movement of the control of the controller, wherein the subset includes the guide catheter and the procedure catheter; and performing a neurovascular procedure using the procedure catheter in response to a user input on the controller.

In some aspects, driving the multi-catheter assembly to achieve supra-aortic access can include advancing the access catheter, the guide catheter, and the procedure catheter simultaneously in response to movement of the control of the controller. In some aspects, driving the subset of the multi-catheter assembly to the neurovascular site can include advancing the guide catheter and the procedure catheter simultaneously in response to movement of the control of the controller. In some aspects, the control can include a first control, the method including driving a guidewire to achieve supra-aortic access in response to movement of a second control of the controller. In some aspects, the first control can include a first joystick and the second control can include a second joystick. In some aspects, the method can further include linking one of the access catheter, the guide catheter, and the procedure catheter to the second control in response to a user input such that movement of the second control causes movement of the one of the guide catheter, the procedure catheter, and the access catheter. In some aspects, the neurovascular procedure can include aspirating a clot. In some aspects, the controller can be in communication with a control system having one or more hardware processors. The control system may further be in communication with a drive table configured to drive movement of the multi-catheter assembly. The one or more hardware processors may control movement of the multi-catheter assembly in response to user inputs using the controller. The one or more hardware processors may additionally generate a user interface including information regarding the multi-catheter assembly. The control system may receive information regarding the multi-catheter assembly or the drive table from one or more sensors of a sensors system. The one or more sensors can include a sensor configured to detect movement of a first interventional device and a second interventional device and provide motion data to the control system. The one or more hardware processors can, based on the motion data, generate a user interface comprising a representation of the first interventional device and the second interventional device configured to provide an indication of the relative positions of the first interventional device and the second interventional device.

A method of robotically controlling interventional devices is also provided. The method includes driving a first interventional device of an interventional device assembly in response to movement of a joystick of a controller, wherein the first interventional device is linked to the joystick such that movement of the joystick causes responsive movement of the first interventional device; receiving a user input; and in response to receiving the user input, linking a second interventional device of the interventional device assembly to the joystick so that movement of the joystick causes responsive movement of the second interventional device.

In some aspects, the method can further include driving the second interventional device using the joystick after linking the second interventional device to the joystick. In some aspects, linking the second interventional device to the joystick can include linking the second interventional device to the joystick so that movement of the joystick causes simultaneous responsive movement of both the first interventional device and the second interventional device. In some aspects, the first interventional device can include a guidewire and the second interventional device can include a guide catheter. In some aspects, the first interventional device can include a guide catheter or a procedure catheter and the second interventional device can include an access catheter. In some aspects, the user input can include actuation of a button of the controller. The controller can be configured to link the second interventional device to the joystick while the button is actuated. In some aspects, driving the first interventional device of the interventional device assembly in response to movement of the joystick can include driving the first interventional device of the interventional device assembly in response to movement of the joystick along a first axis. The method can further include rotating the first interventional device of the interventional device assembly in response to movement of the joystick along a second axis different from the first axis. In some aspects, the second axis can be perpendicular to the first axis. In some aspects, the first interventional device can be a guidewire. In some aspects, the first interventional device can be an access catheter. In some aspects, driving the first interventional device of the interventional device assembly in response to movement of the joystick of the controller can include advancing the first interventional device to achieve supra-aortic access. In some aspects, the method can further include driving the second interventional device to a treatment site for performing a neurovascular procedure in response to movement of the joystick. In some aspects, the method can further include performing the neurovascular procedure in response to a user input on the controller. In some aspects, performing the neurovascular procedure can include aspirating a clot. In some aspects, the controller can be in communication with a control system having one or more hardware processors. The control system may further be in communication with a drive table configured to drive movement of the plurality of interventional devices. The one or more hardware processors may control movement of the interventional devices in response to user inputs using the controller. The one or more hardware processors may additionally generate a user interface including information regarding the interventional devices. The control system may receive information regarding the interventional devices or the drive table from one or more sensors of a sensors system. The one or more sensors can include a sensor configured to detect movement of the first interventional device and the second interventional device and provide motion data to the control system. The one or more hardware processors can, based on the motion data, generate a user interface comprising a representation of the first interventional device and the second interventional device configured to provide an indication of the relative positions of the first interventional device and the second interventional device.

A robotic device control system is also provided. The robotic device control system includes a controller in communication with a plurality of hubs, each of the plurality of hubs coupled to one of a plurality of interventional devices, the controller including a control and an operation mode actuator; wherein the controller is configured to transition between a first operation mode and a second operation mode in response to actuation of the operation mode actuator; wherein in the first operation mode, the control is linked to a first subset of the plurality of hubs such that movement of the control causes a responsive movement of the first subset of the plurality of hubs; and wherein in the second operation mode, the control is linked to a second subset of the plurality of hubs such that movement of the control causes a responsive movement of the second subset of the plurality of hubs, the second subset of the plurality of hubs being different from the first subset of the plurality of hubs.

In some aspects, the first subset of the plurality of hubs can include a guide catheter hub, a procedure catheter hub, and an access catheter hub. In some aspects, when the control is linked to the first subset of the plurality of hubs, movement of the control can be configured to move each of the guide catheter hub, the procedure catheter hub, and the access catheter hub simultaneously. In some aspects, when the control is linked to the first subset of the plurality of hubs, movement of the control can be configured to move each of the guide catheter hub, the procedure catheter hub, and the access catheter hub successively over a same distance. In some aspects, the second subset of the plurality of hubs can include the guide catheter hub and the procedure catheter hub. In some aspects, when the control is linked to the second subset of the plurality of hubs, movement of the control can be configured to move each of the guide catheter hub and the procedure catheter hub simultaneously. In some aspects, when the control is linked to the second subset of the plurality of hubs, movement of the control can be configured to move each of the guide catheter hub and the procedure catheter hub successively over a same distance. In some aspects, the control can include a first control, and the system can include a second control linked to a third subset of the plurality of hubs in the first operation mode. In some aspects, the first subset of the plurality of hubs includes one or more of a guide catheter hub, a procedure catheter hub, and an access catheter hub. The third subset of the plurality of hubs can include a guidewire hub. In some aspects, the first control can include a first joystick and the second control can include a second joystick. In some aspects, the control can be configured to move along a first axis and a second axis different from the first axis, movement of the control along the first axis can be configured to cause a responsive axial movement of hubs of the plurality of hubs linked to the control, and movement of the control along the second axis can be configured to cause rotational movement of at least some of the interventional devices coupled to the hubs linked to the control. In some aspects, the controller can be in communication with a control system having one or more hardware processors. The control system may further be in communication with a drive table configured to drive movement of the plurality of hubs. The one or more hardware processors may control movement of the plurality of hubs in response to user inputs using the controller. The one or more hardware processors may additionally generate a user interface including information regarding the plurality of interventional devices or hubs. The control system may receive information regarding the plurality of interventional devices, plurality of hubs, or the drive table from one or more sensors of a sensors system. The one or more sensors can include a sensor configured to detect movement of a first hub coupled to a first interventional device and a second hub coupled to a second interventional device and provide motion data to the control system. The one or more hardware processors can, based on the motion data, generate a user interface comprising a representation of the first interventional device and the second interventional device configured to provide an indication of the relative positions of the first interventional device and the second interventional device.

A robotic device control system is also provided. The robotic device control system can include a controller in communication with a plurality of interventional devices, the controller including a control and an operation mode actuator; wherein the controller is configured to transition between a first operation mode and a second operation mode in response to actuation of the operation mode actuator; wherein in the first operation mode, the control is linked to a first subset of the plurality of interventional devices such that movement of the control causes a responsive movement of the first subset of the plurality of interventional devices; and wherein in the second operation mode, the control is linked to a second subset of the plurality of interventional devices such that movement of the control causes a responsive movement of the second subset of the plurality of interventional devices, the second subset of the plurality of interventional devices being different from the first subset of the plurality of interventional devices.

In some aspects, the first subset of the plurality of interventional devices can include a guide catheter, a procedure catheter, and an access catheter. In some aspects, when the control is linked to the first subset of the plurality of interventional devices, movement of the control can be configured to move each of the guide catheter, the procedure catheter, and the access catheter simultaneously. In some aspects, when the control is linked to the first subset of the plurality of interventional devices, movement of the control can be configured to move each of the guide catheter, the procedure catheter, and the access catheter successively over a same distance. In some aspects, the second subset of the plurality of interventional devices can include the guide catheter and the procedure catheter. In some aspects, when the control is linked to the second subset of the plurality of interventional devices, movement of the control can be configured to move each of the guide catheter and the procedure catheter simultaneously. In some aspects, when the control is linked to the second subset of the plurality of interventional devices, movement of the control can be configured to move each of the guide catheter and the procedure catheter successively over a same distance. In some aspects, the control can include a first control. The system can include a second control linked to a third subset of the plurality of interventional devices in the first operation mode. In some aspects, the first subset of the plurality of interventional devices can include one or more of a guide catheter hub, a procedure catheter, and an access catheter. The third subset of the plurality of interventional devices can include a guidewire. In some aspects, the first control can include a first joystick and the second control can include a second joystick. In some aspects, the control can be configured to move along a first axis and a second axis different from the first axis, wherein movement of the control along the first axis is configured to cause a responsive axial movement of the interventional devices linked to the control, wherein movement of the control along the second axis is configured to cause rotational movement of at least some of at least some of the interventional devices linked to the control.

In some aspects, the controller can be in communication with a control system having one or more hardware processors. The control system may further be in communication with a drive table configured to drive movement of the plurality of interventional devices. The one or more hardware processors may control movement of the plurality of interventional devices in response to user inputs using the controller. The one or more hardware processors may additionally generate a user interface including information regarding the plurality of interventional devices. The control system may receive information regarding the plurality of interventional devices or the drive table from one or more sensors of a sensors system. The one or more sensors can include a sensor configured to detect movement of a first interventional device and a second interventional device and provide motion data to the control system. The one or more hardware processors can, based on the motion data, generate a user interface comprising a representation of the first interventional device and the second interventional device configured to provide an indication of the relative positions of the first interventional device and the second interventional device.

A robotic device control system is also provided. The robotic device control system can include a controller in communication with a plurality of hubs, each of the plurality of hubs coupled to one of a plurality of interventional devices, the controller including: a joystick; and a plurality of hub actuators, wherein actuation of each of the plurality of hub actuators causes the joystick to be linked with one of the plurality of hubs such that movement of the joystick causes a corresponding responsive movement of the one of the plurality of hubs.

In some aspects, actuation of a first hub actuator of the plurality of hub actuators and a second hub actuator of the plurality of hub actuators at the same time can cause the joystick to be linked with a first hub associated with the first hub actuator and a second hub associated with the second hub actuator such that movement of the joystick causes a corresponding responsive movement of the first hub and the second hub. In some aspects, the system further includes a velocity actuator. Actuation of the velocity actuator can change a range of axial velocities over which responsive movement of the one of the plurality of hubs linked to the joystick occurs in response to movement of the joystick. In some aspects, the system can further include a second joystick. The second joystick can be linked to at least one of the plurality of hubs such that movement of the second joystick causes a responsive movement in the at least one of the plurality of hubs linked to the second joystick. In some aspects, the system can further include at least one additional hub actuator. Actuation of the at least one additional hub actuator can be configured to link the second joystick with a different one of the plurality of hubs such that movement of the second joystick causes a responsive movement in the different one of the plurality of hubs. In some aspects, the joystick can be configured to move along a first axis and a second axis different from the first axis. Movement of the joystick along the first axis can be configured to cause a responsive axial movement of the hubs linked to the joystick. Movement of the joystick along the second axis can be configured to cause rotational movement of at least some of the interventional devices coupled to the hubs linked to the joystick. The plurality of hubs can include a guide catheter hub configured to couple to a guide catheter, an access catheter hub configured to couple to an access catheter, and a procedure catheter hub configured to couple to a procedure catheter. The plurality of hubs comprises a guidewire hub configured to couple to a guidewire. In some aspects, the controller can be in communication with a control system having one or more hardware processors. The control system may further be in communication with a drive table configured to drive movement of the plurality of hubs. The one or more hardware processors may control movement of the plurality of hubs in response to user inputs using the controller. The one or more hardware processors may additionally generate a user interface including information regarding the plurality of interventional devices or hubs. The control system may receive information regarding the plurality of interventional devices, plurality of hubs, or the drive table from one or more sensors of a sensors system. The one or more sensors can include a sensor configured to detect movement of a first hub coupled to a first interventional device and a second hub coupled to a second interventional device and provide motion data to the control system. The one or more hardware processors can, based on the motion data, generate a user interface comprising a representation of the first interventional device and the second interventional device configured to provide an indication of the relative positions of the first interventional device and the second interventional device.

A robotic device control system is also provided. The robotic device control system includes a controller in communication with a plurality of interventional devices, the controller including: a joystick; and a plurality of interventional device actuators, wherein actuation of each of the plurality of interventional device actuators causes the joystick to be linked with one of the plurality of interventional devices such that movement of the joystick causes a corresponding responsive movement of the one of the plurality of interventional devices.

In some aspects, actuation of a first interventional device actuator of the plurality of interventional device actuators and a second interventional device actuator of the plurality of interventional device actuators at the same time can cause the joystick to be linked with a first interventional device associated with the first interventional device actuator and a second interventional device associated with the second interventional device actuator such that movement of the joystick causes a corresponding responsive movement of the first interventional device and the second interventional device. In some aspects, the system can further include a velocity actuator. Actuation of the velocity actuator can change a range of axial velocities over which responsive movement of the one of the plurality of interventional devices linked to the joystick occurs in response to movement of the joystick. In some aspects, the system can further include a second joystick. The second joystick can be linked to at least one of the plurality of interventional devices such that movement of the second joystick causes a responsive movement in the at least one of the plurality of interventional devices linked to the second joystick. In some aspects, the system can further include at least one additional interventional device actuator. Actuation of the at least one additional interventional device actuator can be configured to link the second joystick with a different one of the plurality of interventional devices such that movement of the second joystick causes a responsive movement in the different one of the plurality of interventional devices. In some aspects, the joystick can be configured to move along a first axis and a second axis different from the first axis. Movement of the joystick along the first axis can be configured to cause a responsive axial movement of the interventional devices linked to the joystick. Movement of the joystick along the second axis can be configured to cause rotational movement of at least some of the interventional devices linked to the joystick. The plurality of interventional devices can include a guide catheter, an access catheter, and a procedure catheter. The plurality of interventional devices can include a guidewire. In some aspects, the controller can be in communication with a control system having one or more hardware processors. The control system may further be in communication with a drive table configured to drive movement of the plurality of interventional devices. The one or more hardware processors may control movement of the plurality of interventional devices in response to user inputs using the controller. The one or more hardware processors may additionally generate a user interface including information regarding the plurality of interventional devices. The control system may receive information regarding the plurality of interventional devices or the drive table from one or more sensors of a sensors system. The one or more sensors can include a sensor configured to detect movement of a first interventional device and a second interventional device and provide motion data to the control system. The one or more hardware processors can, based on the motion data, generate a user interface comprising a representation of the first interventional device and the second interventional device configured to provide an indication of the relative positions of the first interventional device and the second interventional device.

A robotic interventional device control system is also provided. The robotic interventional device control system can include a first interventional device having a first distal end; a second interventional device having a second distal end, wherein the first interventional device is configured to be concentrically nested within the second interventional device; a sensor system configured to detect a first position of the first interventional device and a second position of the second interventional device; one or more hardware processors configured to generate a user interface, the user interface including an instrument window, the instrument window including, a first representation of the first interventional device, said first representation of the first interventional device including a first visual indication of the first distal end of the first interventional device; and a second representation of the second interventional device, said second representation of the second interventional device including a second visual indication of the second distal end of the second interventional device, wherein the second visual indication of the second distal end is positioned relative to the first visual indication of the first distal end of the first interventional device based on the detected first and second positions received from the sensor system, thereby the first and second visual indications provide an indication on the user interface how far apart the first distal end of the first interventional device is from the second distal end of the second interventional device; and a display configured to display the user interface.

In some aspects, the user interface further can include a first window configured to display fluoroscopy imagery from a vasculature of a patient; a second window configured to display one or more messages indicative of an operational status of the robotic interventional device control system; and a third window including a live feed. The instrument window can be positioned on a central portion of the user interface. In some cases, the user interface can include some but not all of the first, second, and third windows. In some aspects, the first window, the second window, and the third window can be positioned around the instrument window. In some aspects, the first visual indication can correspond to a shape of the first distal end of the first interventional device. In some aspects, the shape of the first distal end of the first interventional device can include a beveled surface. In some aspects, the first visual indication can correspond to a first shape of the first distal end of the first interventional device. The second visual indication can correspond to a second shape of the second distal end of the second interventional device. The first shape and the second shape can be different from each other. In some aspects, the second visual indication can correspond to a shape of the second distal end of the second interventional device. In some aspects, the first representation of the first interventional device and the second representation of the second interventional device can extend along a central longitudinal axis. In some aspects, the first representation of the first interventional device can include a first shape. In some aspects, the first shape can correspond to a shape of a portion of the first interventional device. In some aspects, the first shape can include a cylindrical shape. In some aspects, the second representation of the second interventional device can include a second shape different than the first shape of the first representation. In some aspects, the second representation of the second interventional device can include a second shape. In some aspects, the second shape corresponds to a shape of a portion of the second interventional device. In some aspects, the first visual indication of the first distal end can include a beveled edge. In some aspects, the first visual indication of the first distal end can include a first point on a distal edge of the shape. In some aspects, the second visual indication can correspond to a second shape of the second distal end of the second interventional device, wherein the second visual indication of the second distal end includes a second point on a second distal edge of the second shape, and wherein a first distance between the first point and the second point provides a visual indication about a second distance between the first distal end of the first interventional device and the second distal end of the second interventional device. In some aspects, the first distance can include a scaled distance of the second distance. In some aspects, the first distance and the second distance can be the same. In some aspects, the system can further include a controller having one or more controls configured to cause movement of at least one of the first interventional device and the second interventional device responsive to a user input. In some aspects, the controller can be configured to transition between a first operation mode and a second operation mode in response to a user input. In the first operation mode, one of the controls can be linked to a first subset of a plurality of interventional devices or interventional device hubs such that movement of the control causes a responsive movement of the first subset of the plurality of interventional devices or interventional device hubs. In the second operation mode, the control can be linked to a second subset of the plurality of interventional devices or interventional device hubs such that movement of the control causes a responsive movement of the second subset of the plurality of interventional devices or interventional device hubs, the second subset of the plurality being different from the first subset.

A robotic interventional device control system is also provided. The robotic interventional device control system can includes an interventional device; a controller in communication with the interventional device, the controller including: a first control; and a second control; one or more hardware processors in communication with the interventional device and the controller, the one or more hardware processors being configured to: selectively link the interventional device to the first control or the second control such that movement of the selected control causes a corresponding responsive movement of the interventional device; generate a user interface, the user interface including an instrument window including, a representation of the interventional device; and an interventional device marker positioned relative to the representation of the interventional device, wherein the position of the interventional device marker relative to the representation of the interventional device indicates whether the interventional device is linked to the first control or the second control; and a display configured to display the user interface.

In some aspects, the controller can include a first side and a second side, the first control positioned on the first side of the controller and the second control positioned on the second side of the controller. In some aspects, the representation of the interventional device can extend along a central longitudinal axis. In some aspects, the interventional device marker can be configured to be positioned on a first side of the central longitudinal axis when the interventional device is linked to the first control, and wherein the interventional device marker is configured to be positioned on a second side of the central longitudinal axis when the interventional device is linked to the second control. In some aspects, the first side of central longitudinal axis can mirror the first side of the controller, and wherein the second side of the central longitudinal axis mirrors the second side of the controller. In some aspects, the instrument window can be configured to display an indicator on a top portion of the interventional device marker, the indicator configured to extend outside the top portion of the interventional device marker when an axial movement of the interventional device in a distal direction is restricted. In some aspects, the instrument window can be configured to display an indicator on a bottom portion of the interventional device marker, the indicator configured to extend outside the bottom portion of the interventional device marker when an axial movement of the interventional device in a proximal direction is restricted. In some aspects, the interventional device marker can include a first animation state and a second animation state. In some aspects, the interventional device marker can be configured to transition from the first animation state to the second animation state upon an occurrence of an interventional device event. In some aspects, the interventional device event can include aspiration being available at the interventional device. In some aspects, the interventional device event can include aspiration being unavailable at the interventional device. In some aspects, the interventional device event can include aspiration being active at the interventional device. In some aspects, the interventional device event can include contrast injection being available at the interventional device. In some aspects, the interventional device event can include contrast injection being unavailable at the interventional device. In some aspects, the interventional device event can include contrast injection being active at the interventional device. In some aspects, at least one of the first control and the second control of the controller can be configured to cause movement of the interventional device responsive to a user input. In some aspects, the controller can be configured to transition between a first operation mode and a second operation mode in response to a user input. In the first operation mode, one of the controls can be linked to a first subset of a plurality of interventional devices or interventional device hubs such that movement of the control causes a responsive movement of the first subset of the plurality of interventional devices or interventional device hubs. In the second operation mode, the control can be linked to a second subset of the plurality of interventional devices or interventional device hubs such that movement of the control causes a responsive movement of the second subset of the plurality of interventional devices or interventional device hubs, the second subset of the plurality being different from the first subset.

A robotic interventional device control system is also provided. The robotic interventional device control system can includes an interventional device; a controller configured to control axial movement of the interventional device along a drive table; a sensor system configured to detect axial movement of the interventional device along the drive table; one or more hardware processors configured to receive motion data from the sensor system, the motion data indicative of whether the interventional device is axially moving along the drive table; wherein the one or more hardware processors are further configured to, based on the motion data, generate a user interface including an instrument window, the instrument window including, a representation of the interventional device; and an interventional device marker associated with the representation of the interventional device, the interventional device marker configured to transition from a first configuration to a second configuration when the interventional device is moving axially along the drive table; and a display configured to display the user interface.

In some aspects, the instrument window further includes a speed indicator configured to indicate a speed at which the interventional device is configured to move in a distal direction or a proximal direction. In some aspects, the representation of the interventional device can extend along a central longitudinal axis. In some aspects, in the first configuration, the interventional device marker can be in a first position. In the second configuration, the interventional device marker can be in a second position. In some aspects, the first position can be closer to the central longitudinal axis than the second position. In some aspects, the interventional device marker can be configured to be in the first configuration when the interventional device is not moving axially along the drive table. In some aspects, the representation of the interventional device can include a visual indication of a distal end of the interventional device. In some aspects, the visual indication can correspond to a shape of the distal end of the interventional device. In some aspects, the representation of the interventional device can extend along a central longitudinal axis. In some aspects, the representation of the interventional device can include a shape corresponding to a shape of a portion of the interventional device. In some aspects, the instrument window can further include an interventional device marker positioned relative to the representation of the interventional device. The position of the interventional device marker relative to the representation of the interventional device can indicate whether the interventional device is linked to a first control or a second control of the controller. In some aspects, the controller can include a first side and a second side, the first control positioned on the first side of the controller and the second control positioned on the second side of the controller. In some aspects, the representation of the interventional device can extend along a central longitudinal axis. The interventional device marker can be configured to be positioned on a first side of the central longitudinal axis when the interventional device is linked to the first control. The interventional device marker can be configured to be positioned on a second side of the central longitudinal axis when the interventional device is linked to the second control. In some aspects, the instrument window can further include a pointer extending between the representation of the interventional device and the interventional device marker. In some aspects, the pointer can include a line. When the interventional device marker is in the first configuration, the line can include a first length. When the interventional device marker is in the second configuration, the line can include a second length different than the first length. In some aspects, the controller can be further configured to control rotational movement of the interventional device about a longitudinal axis of the interventional device. In some aspects, the interventional device marker can further include a radial progress indicator configured to provide a visual indication of a degree of rotation relative to a threshold of the interventional device about the longitudinal axis. In some aspects, the controller can be configured to control axial movement of the interventional device along the drive table responsive to a user input. In some aspects, the controller can be configured to transition between a first operation mode and a second operation mode in response to a user input. In the first operation mode, one of the controls can be linked to a first subset of a plurality of interventional devices or interventional device hubs such that movement of the control causes a responsive movement of the first subset of the plurality of interventional devices or interventional device hubs. In the second operation mode, the control can be linked to a second subset of the plurality of interventional devices or interventional device hubs such that movement of the control causes a responsive movement of the second subset of the plurality of interventional devices or interventional device hubs, the second subset of the plurality being different from the first subset.

A robotic interventional device control system is also provided. The robotic interventional device control system includes an interventional device including a longitudinal axis and configured to rotate about the longitudinal axis; a controller configured to control rotational movement of the interventional device about the longitudinal axis; at least one sensor configured to detect rotational movement of the interventional device about the longitudinal axis; one or more hardware processors configured to receive motion data from the at least one sensor, the motion data indicative of whether the interventional device is rotating about the longitudinal axis; wherein the one or more hardware processors are further configured to, based on the motion data, generate a user interface including an instrument window, the instrument window including, a representation of the interventional device; an interventional device marker associated with the representation of the interventional device, the interventional device marker including a radial progress indicator configured to provide a visual indication of a degree of rotation relative to a threshold of the interventional device about the longitudinal axis.

In some aspects, the threshold can represent a maximum rotation of the interventional device. In some aspects, the radial progress indicator can include a ring shaped progress bar configured to fill up. The ring shaped progress bar can be further configured to be empty when the interventional device is not rotating. The ring shaped progress bar can be further configured to be full when the interventional device completes a full revolution about the longitudinal axis. In some aspects, the radial progress indicator can include a ring shaped progress bar configured to fill in at least one of a clockwise direction and a counterclockwise direction. The radial progress indicator filling in the clockwise direction can provide a visual indication that the interventional device is rotating in the clockwise direction. The radial progress indicator filling in the counterclockwise direction can provide a visual indication that the interventional device is rotating in the counterclockwise direction. In some aspects, the representation of the interventional device can extend along a central longitudinal axis. In some aspects, the controller can be further configured to control axial movement of the interventional device along a drive table. The representation of the interventional device can be configured to transition from a first configuration to a second configuration along a central longitudinal axis when the interventional device is moving axially along the drive table. In some aspects, in the first configuration, the representation of the interventional device can be in a first position. In the second configuration, the representation of the interventional device can be in a second position. In some aspects, the first position can be closer to a bottom end of the central longitudinal axis than the second position. In some aspects, the first position can be closer to a top end of the central longitudinal axis than the second position. In some aspects, the interventional device marker can include a first animation state and a second animation state. In some aspects, the interventional device marker can be configured to transition from the first animation state to the second animation state upon an occurrence of an interventional device event. In some aspects, the interventional device event can include aspiration being available at the interventional device. In some aspects, the interventional device event can include aspiration being unavailable at the interventional device. In some aspects, the interventional device event can include aspiration being active at the interventional device. In some aspects, the interventional device event can include contrast injection being available at the interventional device. In some aspects, the interventional device event can include contrast injection being unavailable at the interventional device. In some aspects, the controller can be configured to control rotational movement of the interventional device about the longitudinal axis responsive to a user input. In some aspects, the controller can be configured to transition between a first operation mode and a second operation mode in response to a user input. In the first operation mode, one of the controls can be linked to a first subset of a plurality of interventional devices or interventional device hubs such that movement of the control causes a responsive movement of the first subset of the plurality of interventional devices or interventional device hubs. In the second operation mode, the control can be linked to a second subset of the plurality of interventional devices or interventional device hubs such that movement of the control causes a responsive movement of the second subset of the plurality of interventional devices or interventional device hubs, the second subset of the plurality being different from the first subset.

A robotic interventional device control system is also provided. The robotic interventional device control system includes a robotic drive system; and an interventional device assembly including a plurality of interventional devices configured to couple to the robotic drive system, each of the plurality of interventional devices including an identifier; a plurality of sensors, each of the plurality of sensors being configured to identify one of the plurality of interventional devices based on the identifier when the one of the plurality of interventional devices is coupled to the robotic drive system; one or more hardware processors configured to receive interventional device identity data from the plurality of sensors and, based on the interventional device identity data, generate a user interface including an instrument window, the instrument window including, a plurality of interventional device representations, each of the plurality of interventional device representations representing one of the plurality of interventional devices; a plurality of interventional device markers, each of the plurality of interventional device markers being associated with one of the plurality of interventional device representations and configured to indicate a type of the interventional device represented by the one of the plurality of interventional device representations; and a display configured to display the user interface. The one or more controls can include a first control linked to a first interventional device such that movement of the first control causes a responsive movement of the first interventional device; and a second control linked to a second interventional device such that movement of the second control causes a responsive movement of the second interventional device. The first interventional device can be a guide catheter and the second interventional device can be a guidewire. The controller further can further include an interventional device actuator, wherein actuation of the interventional device actuator causes the first interventional device to be linked to the second control such that movement of the second control causes a responsive movement of the first interventional device. The one or more controls can include a first control operatable in a first drive mode and a second drive mode, wherein movement of the first control is configured to cause a responsive movement of a first subset of the plurality of interventional devices in the first drive mode and operation of the first control is configured to cause a responsive movement of a second subset of the plurality of interventional devices in the second drive mode. The first subset of the plurality of interventional devices can be a guide catheter, a procedure catheter, and an access catheter. The second subset of the plurality of interventional devices can include the guide catheter and the procedure catheter.

In some aspects, the user interface can further include a window configured to display fluoroscopy imagery from a vasculature of a patient. In some aspects, the user interface can further include a window configured to display one or more messages indicative of an operational status of the robotic interventional device control system. In some aspects, the user interface can further include a window configured to display a live feed. In some aspects, the instrument window can be positioned on a central portion of the user interface. In some aspects, each of the plurality of interventional device markers can be configured to transition from a first configuration to a second configuration when the plurality of interventional devices are moving axially along a drive table. In some aspects, in the first configuration, each of the plurality of interventional device markers can be in a first position. In the second configuration, each of the plurality of interventional device markers can be in a second position. In some aspects, the first position can be closer to a central longitudinal axis of the plurality of interventional device representations than the second position. In some aspects, the plurality of interventional device markers can be configured to be in the first configuration when the plurality of interventional devices are not moving axially along the drive table. In some aspects, the system can further include a plurality of interventional device hubs, each of the plurality of interventional devices being coupled to one of the plurality of interventional device hubs; a plurality of hub adapters, wherein each of the plurality of interventional device hubs is configured to be coupled to one of the plurality of hub adapters; and a support table, wherein the plurality of hub adapters are configured to move along the support table to drive the interventional device assembly. In some aspects, the plurality of interventional device representations can be arranged based on an arrangement of the plurality of hub adapters on the support table. In some aspects, the system can further include a controller having one or more controls configured to cause movement of at least one of the plurality of interventional devices responsive to a user input. In some aspects, the controller can be configured to transition between a first operation mode and a second operation mode in response to a user input. In the first operation mode, one of the controls can be linked to a first subset of a plurality of interventional devices or interventional device hubs such that movement of the control causes a responsive movement of the first subset of the plurality of interventional devices or interventional device hubs. In the second operation mode, the control can be linked to a second subset of the plurality of interventional devices or interventional device hubs such that movement of the control causes a responsive movement of the second subset of the plurality of interventional devices or interventional device hubs, the second subset of the plurality being different from the first subset.

A method of robotically controlling interventional devices is also provided. The method includes driving a first hub adapter coupled to a first interventional device of an interventional device assembly in response to movement of a control of a controller, wherein the first hub adapter is linked to the control such that movement of the control causes responsive movement of the first hub adapter, wherein a second hub adapter coupled to a second interventional device is not linked to the first control, wherein the first hub adapter and the second hub adapter are axially movably coupled to a shuttle, the shuttle configured to move axially within a drive table, wherein driving the first hub adapter in response to movement of the control comprises driving movement of the shuttle a first distance in a first direction to move the first hub adapter, wherein in response to movement of the hub adapter by the first distance in the first direction in response to movement of the control, the second hub adapter is configured to move a second distance equal to the first distance in a second direction opposite of the first direction.

A robotic interventional device control system can include one or more of the features of the foregoing description.

A method of using the robotic interventional device control system can include one or more features of the foregoing description.

An interventional device controller can include one or more of the features of the foregoing description.

A method of using an interventional device controller can include one or more features of the foregoing description.

A robotic interventional device control system can include one or more of the features of the foregoing description for use in cardiovascular procedures.

A method of using the robotic interventional device control system can include one or more features of the foregoing description for use in cardiovascular procedures.

An interventional device controller can include one or more of the features of the foregoing description for use in cardiovascular procedures.

Any of the features, components, or details of any of the arrangements or embodiments disclosed in this application, including without limitation any of the controllers, control mechanisms, and user interfaces disclosed below, are interchangeably combinable with any other features, components, or details of any of the arrangements or embodiments disclosed herein to form new arrangements and embodiments.

BRIEF DESCRIPTION OF THE DRAWINGS

FIGS. 25B-25D illustrate cross-sectional views of the control mechanism shown in FIG. 25A.

FIG. 25E illustrates an alternative embodiment of the controllers shown in FIGS. 25A-25D.

FIG. 29B illustrates an embodiment of a process for displaying position and movement of interventional devices.

FIGS. 30A-30K illustrate embodiments of a user interface for controlling interventional devices.

FIGS. 47-59 illustrate additional embodiments of a user interface for controlling interventional devices.

DETAILED DESCRIPTION

In certain embodiments, a system is provided for advancing a guide catheter from a femoral artery or radial artery access into the ostium of one of the great vessels at the top of the aortic arch, thereby achieving supra-aortic access. A surgeon can then take over and advance interventional devices into the cerebral vasculature via the robotically placed guide catheter.

In some implementations, the system may additionally be configured to robotically gain intra-cranial vascular access and to perform an aspiration thrombectomy or other neuro vascular procedure.

A drive table can be positioned over or alongside the patient, and configured to axially advance, retract, and in some cases rotate and/or laterally deflect two or three or more different (e.g., concentrically or side by side oriented) intravascular devices. The hub is moveable along a path along the surface of the drive table to advance or retract the interventional device as desired. Each hub may also contain mechanisms to rotate or deflect the device as desired, and is connected to fluid delivery tubes (not shown) of the type conventionally attached to a catheter hub. Each hub can be in electrical communication with an electronic control system, either via hard wired connection, RF wireless connection or a combination of both.

Each hub is independently movable across the surface of a sterile field barrier membrane carried by the drive table. Each hub is releasably magnetically coupled to a unique drive carriage on the table side of the sterile field barrier. The drive system independently moves each hub in a proximal or distal direction across the surface of the barrier, to move the corresponding interventional device proximally or distally within the patient's vasculature.

The carriages on the drive table, which magnetically couple with the hubs to provide linear motion actuation, are universal. Functionality of the catheters/guidewire are provided based on what is contained in the hub and the shaft designs. This allows flexibility to configure the system to do a wide range of procedures using a wide variety of interventional devices on the same drive table. Additionally, the interventional devices and methods disclosed herein can be readily adapted for use with any of a wide variety of other drive systems (e.g., any of a wide variety of robotic surgery drive systems).

Figure 1:
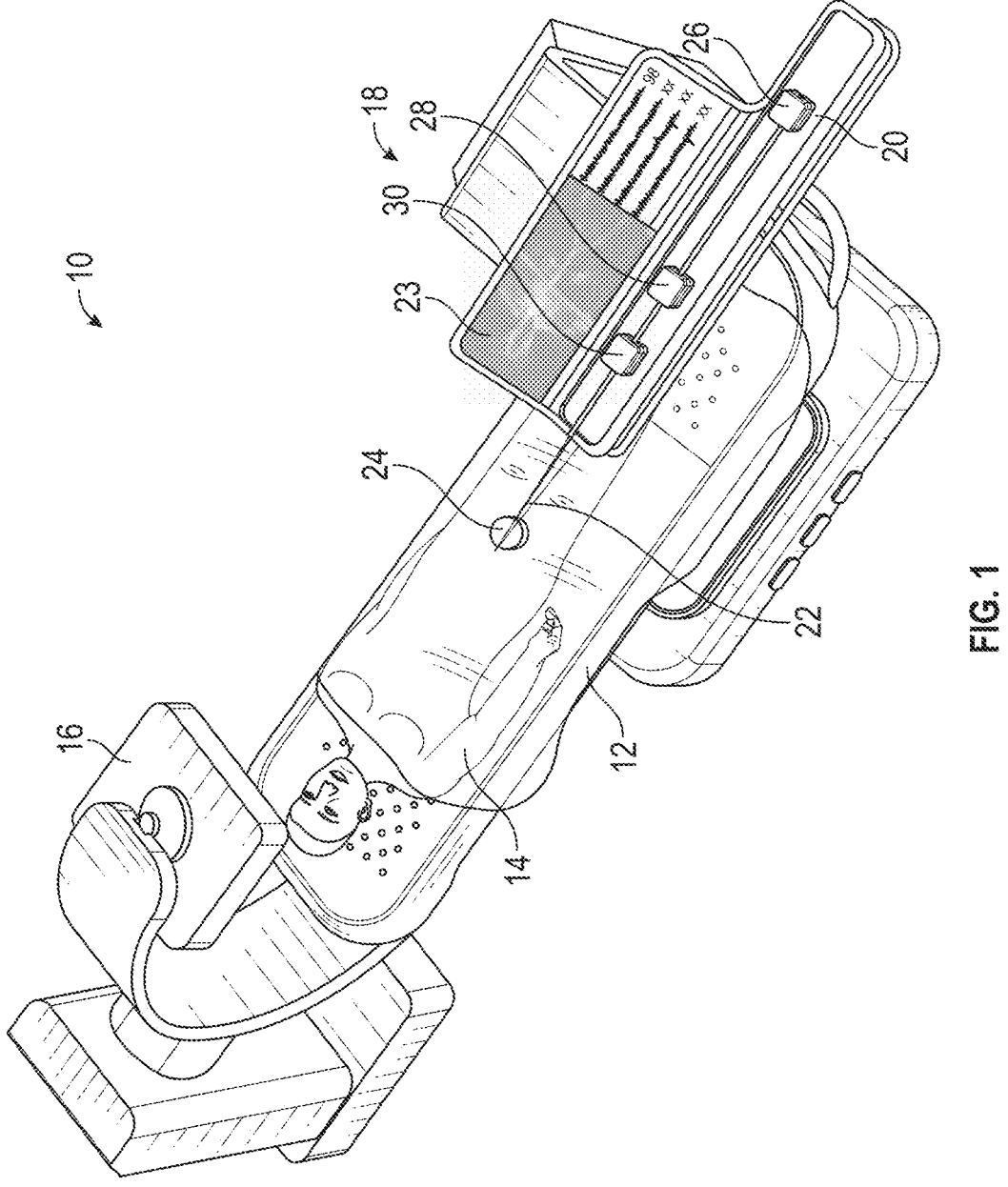
FIG. 1 is a schematic perspective view of an interventional setup having an imaging system, a patient support table, and a robotic drive system in accordance with the present disclosure.

FIG. 1 is a schematic perspective view of an interventional setup 10 having a patient support table 12 for supporting a patient 14. An imaging system 16 may be provided, along with a robotic interventional device drive system 18 in accordance with the present disclosure.

The drive system 18 may include a support table 20 for supporting, for example, a guidewire hub 26, an access catheter hub 28 and a guide catheter hub 30. In the present context, the term 'access' catheter can be any catheter having a lumen with at least one distally facing or laterally facing distal opening, that may be utilized to aspirate thrombus, provide access for an additional device to be advanced therethrough or therealong, or to inject saline or contrast media or therapeutic agents.

More or fewer interventional device hubs may be provided depending upon the desired clinical procedure. For example, in certain embodiments, a diagnostic angiogram procedure may be performed using only a guidewire hub 26 and an access catheter hub 28 for driving a guidewire and an access catheter (in the form of a diagnostic angiographic catheter), respectively. Multiple interventional devices 22 extend between the support table 20 and (in the illustrated example) a femoral access point 24 on the patient 14. Depending upon the desired procedure, access may be achieved by percutaneous or cut down access to any of a variety of arteries or veins, such as the femoral artery or radial artery. Although disclosed herein primarily in the context of neuro vascular access and procedures, the robotic drive system and associated interventional devices can readily be configured for use in a wide variety of additional medical interventions, in the peripheral and coronary arterial and venous vasculature, gastrointestinal system, lymphatic system, cerebral spinal fluid lumens or spaces (such as the spinal canal, ventricles, and subarachnoid space), pulmonary airways, treatment sites reached via trans ureteral or urethral or fallopian tube navigation, or other hollow organs or structures in the body (for example, intra-cardiac or structural heart applications, such as valve repair or replacement, or in in any endoluminal procedures).

A display 23 such as for viewing fluoroscopic images, catheter data (e.g., fiber Bragg grating fiber optics sensor data or other force or shape sensing data) or other patient data may be carried by the support table 20 and or patient support 12. Alternatively, the physician input/output interface including display 23 may be remote from the patient, such as behind radiation shielding, in a different room from the patient, or in a different facility than the patient.

In the illustrated example, a guidewire hub 26 is carried by the support table 20 and is moveable along the table to advance a guidewire into and out of the patient 14. An access catheter hub 28 is also carried by the support table 20 and is movable along the table to advance the access catheter into and out of the patient 14. The access catheter hub may also be configured to rotate the access catheter in response to manipulation of a rotation control, and may also be configured to laterally deflect a deflectable portion of the access catheter, in response to manipulation of a deflection control.

Figure 2:
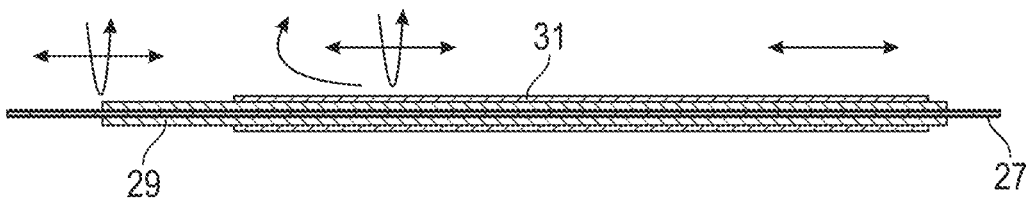
FIG. 2 is a longitudinal cross section showing the concentric relationship between a guidewire having two degrees of freedom, an access catheter having 3 degrees of freedom and a guide catheter having one degree of freedom.

FIG. 2 is a longitudinal cross section schematically showing the motion relationship between a guidewire 27 having two degrees of freedom (axial and rotation), an access catheter 29 having three degrees of freedom (axial, rotational and lateral deflection) and a guide catheter 31, having one degree of freedom (axial).

Figure 3A:
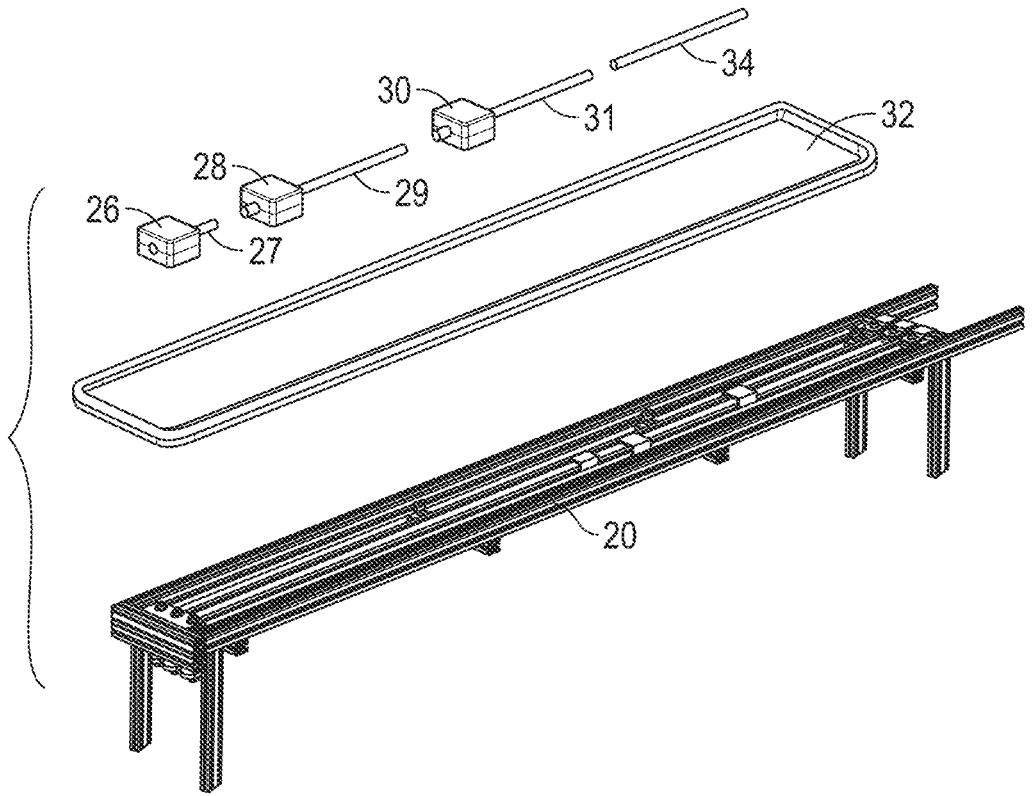
FIG. 3A is an exploded schematic view of interventional device hubs separated from a support table by a sterile barrier.

Referring to FIG. 3A, the support table 20 includes a drive mechanism described in greater detail below, to independently drive the guidewire hub 26, access catheter hub 28, and guide catheter hub 30. An anti-buckling feature 34 may be provided in a proximal anti-buckling zone for resisting buckling of the portion of the interventional devices spanning the distance between the support table 20 and the femoral artery access point 24. The anti-buckling feature 34 may comprise a plurality of concentric telescopically axially extendable and collapsible tubes through which the interventional devices extend.

Alternatively, a proximal segment of one or more of the device shafts may be configured with enhanced stiffness to reduce buckling under compression. For example, a proximal reinforced segment may extend distally from the hub through a distance of at least about 5 centimeters or 10 centimeters but typically no more than about 120 centimeters or 100 centimeters to support the device between the hub and the access point 24 on the patient. Reinforcement may be accomplished by using metal or polymer tubing or embedding at least one or two or more axially extending elements into the wall of the device shafts, such as elongate wires or ribbons. In some implementations, the extending element may be hollow and protect from abrasion, buckling, or damage at the inputs and outputs of the hubs. In some embodiments, the hollow extending element may be a hollow and flexible coating attached to a hub. The hollow, extending element (e.g., a hollow and flexible coating) may cover a portion of the device shaft when threaded through the hubs. In some embodiments in which the hollow extending element is a coating, the coating may be attached to a portion of a hub such that threading the catheter device through the hub 26, 28, or 30 threads the catheter device through the coating as well. In some implementations, an anti-buckling device may be installed on or about or surrounding a device shaft to avoid misalignment or insertion angle errors between hubs or between a hub and an insertion point. The anti-buckling device may be a laser cut hypotube, a spring, telescoping tubes, tensioned split tubing, or the like.

In some implementations, a number of deflection sensors may be placed along a catheter length to identify buckling. Identifying buckling may be performed by sensing that a hub is advancing distally, while the distal tip of the catheter or interventional device has not moved. In some implementations, the buckling may be detected by sensing that an energy load (e.g., due to friction) has occurred between catheter shafts.

Alternatively, thin tubular stiffening structures can be embedded within or carried over the outside of the device wall, such as a tubular polymeric extrusion or length of hypo-tube. Alternatively, a removable stiffening mandrel may be placed within a lumen in the proximal segment of the device, and proximally removed following distal advance of the hub towards the patient access site, to prevent buckling of the proximal shafts during distal advance of the hub. Alternatively, a proximal segment of one or more of the device shafts may be constructed as a tubular hypo tube, which may be machined (e.g., with a laser) so that its mechanical properties vary along its length. This proximal segment may be formed of stainless steel, nitinol, and/or cobalt chrome alloys, optionally in combination with polymer components which may provide for lubricity and hydraulic sealing. In some embodiments, this proximal segment may be formed of a polymer, such as polyether ether ketone (PEEK). Alternatively, the wall thickness or diameter of the interventional device can be increased in the anti-buckling zone.

In certain embodiments, a device shaft having advanced stiffness (e.g., axially and torsionally) may provide improved transmission of motion from the proximal end of the device shaft to the distal end of the device shaft. For example, the device shafts may be more responsive to motion applied at the proximal end. Such embodiments may be advantageous for robotic driving in the absence of haptic feedback to a user.

In some embodiments, a flexible coating can be applied to a device shaft and/or hub to reduce frictional forces between the device shaft and/or hub and a second device shaft when the second device shaft passes therethrough.

The interventional device hubs may be separated from the support table 20 by sterile barrier 32. Sterile barrier 32 may comprise a thin plastic membrane such as polyethylene terephthalate (PET), polyethylene terephthalate glycol (PETG), polyethylene terephthalate (PETE), high-density polyethylene (HDPE), polyvinyl chloride (PVC), low-density polyethylene (LDPE), polypropylene (PP), polystyrene (PS), or styrene. This allows the support table 20 and associated drive system to reside on a non-sterile (lower) side of sterile barrier 32. The guidewire hub 26, access catheter hub 28, guide catheter hub 30 and the associated interventional devices are all on a sterile (top) side of the sterile barrier 32. The sterile barrier is preferably waterproof and can also serve as a tray used in the packaging of the interventional devices, discussed further below. The interventional devices can be provided individually or as a coaxially preassembled kit that is shipped and stored in the tray and enclosed within a sterile packaging.

FIGS. 3B-3F schematically illustrate an alternate sterile barrier in the form of a dual function sterile barrier for placement on the support table during the interventional procedure, and shipping tray, having one or more storage channels for carrying sterile interventional devices. The sterile barrier may also act as a sterile work surface for preparation of catheters or other devices during a procedure.

Figure 3B:
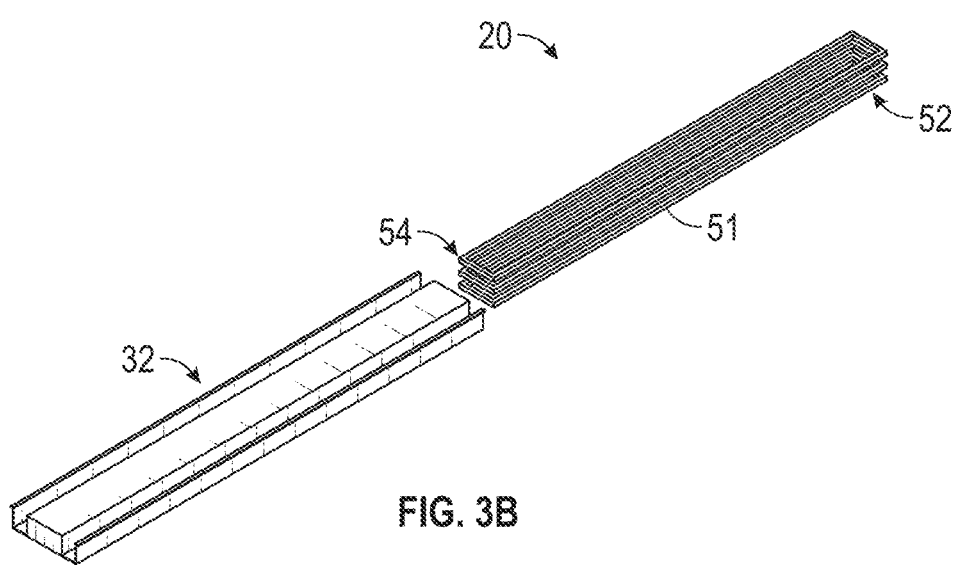
FIGS. 3B-3F show an alternate sterile barrier in the form of a shipping tray having one or more storage channels for carrying interventional devices.
Figure 3C:
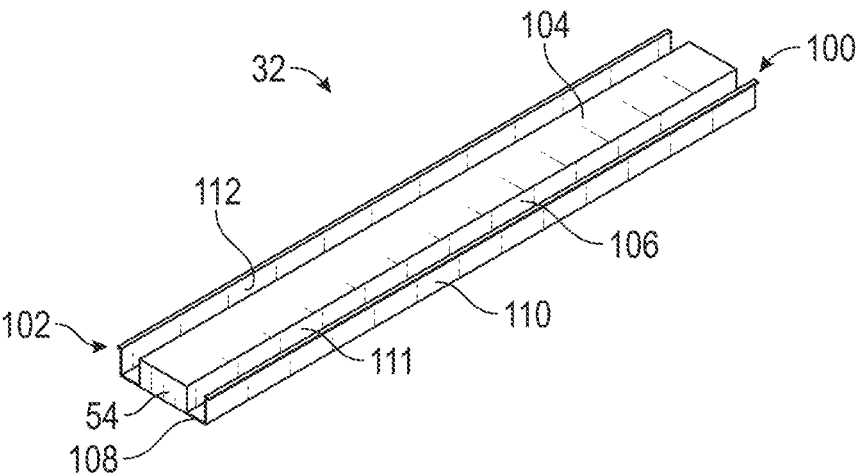

Referring to FIGS. 3B and 3C, there is illustrated a sterile barrier 32 in the form of a pre-shaped tray, for fitting over an elongate support table 20. In use, the elongate support table 20 would be positioned below the sterile barrier 32. The sterile barrier 32 extends between a proximal end 100 and a distal end 102 and includes an upper support surface 104 for supporting the interventional device hubs. In one implementation, the support surface 104 has an axial length greater than the length of the intended interventional devices, in a linear drive configuration.

The length of support surface 104 will typically be at least about 100 centimeters and within the range of from about 100 centimeters to about 2.7 meters. Shorter lengths may be utilized in a system configured to advance the drive couplers along an arcuate path. In some embodiments, two or more support surfaces may be used instead of a single support surface 104. The two or more support surfaces may have a combined length between 100 centimeters to about 2.7 meters. The width of the linear drive table is preferably no more than about 30 to about 80 centimeters.

At least a first channel 106 may be provided, extending axially at least a portion of the length of the support table 20. In the illustrated implementation, first channel 106 extends the entire length of the support table 20. Preferably, the first channel 106 has a sufficient length to hold the interventional devices, and sufficient width and depth to hold the corresponding hubs (for example, by providing lateral support to prevent dislodgment of the hubs when forces are applied to the hubs). First channel 106 is defined within a floor 108, outer side wall 110 and inner side wall 111, forming an upwardly facing concavity. Optionally, a second channel 112 may be provided. Second channel 112 may be located on the same side or the opposite side of the upper support surface 104 from the first channel 106. Two or three or more additional recesses such as additional channels or wells may be provided, to hold additional medical devices or supplies that may be useful during the interventional procedure as well as to collect fluids and function as wash basins for catheters and related devices.

Figures 3D, 3E, 3F:
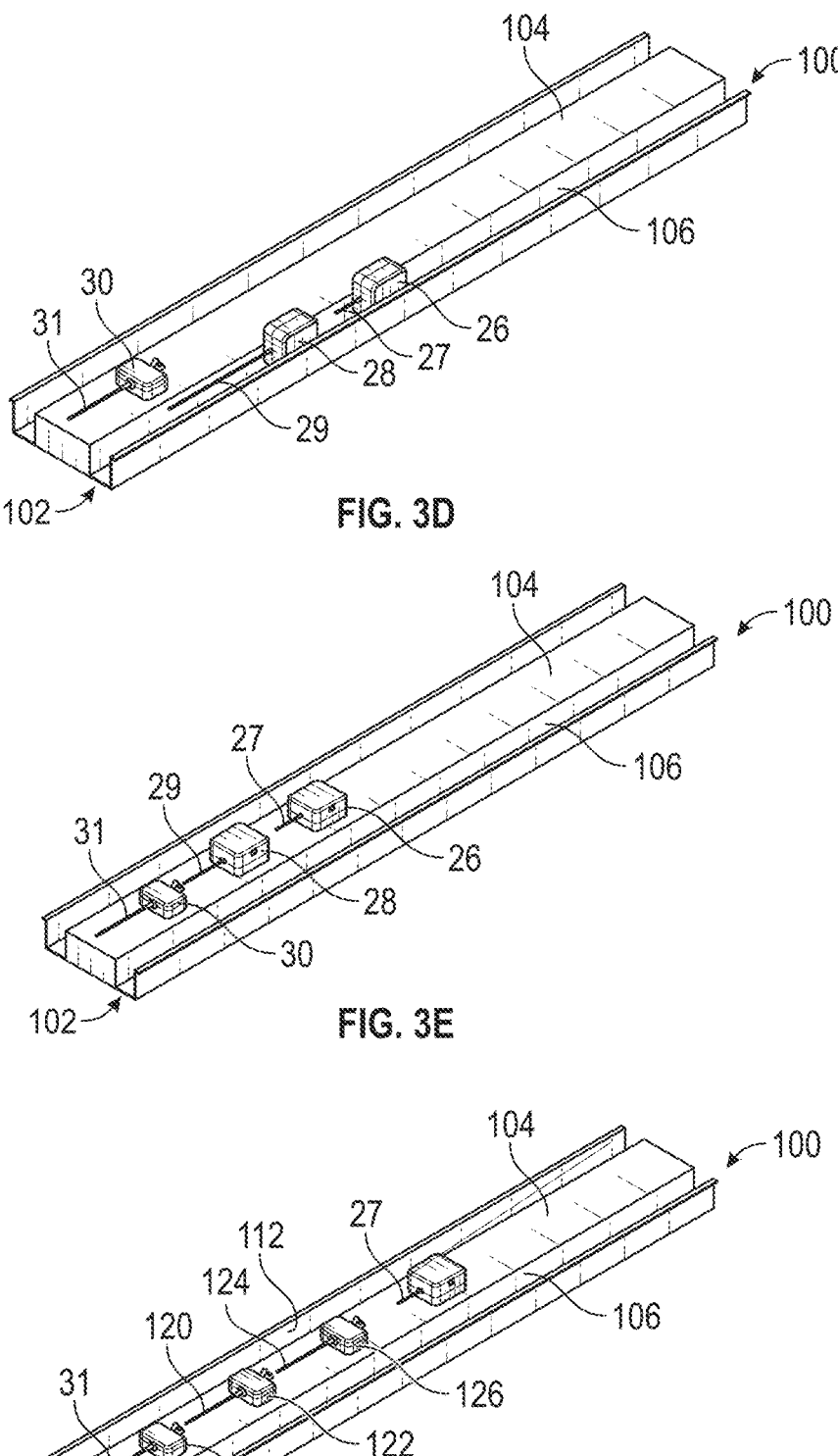

Referring to FIG. 3D, the guide catheter hub 30 is shown positioned on the upper support surface 104, and magnetically coupled to the corresponding coupler holding the drive magnets, positioned beneath the sterile barrier 32. The access catheter hub 28 and access catheter 29, and guidewire hub 26 and guidewire 27 are illustrated residing within the first channel 106 such as before introduction through the guide catheter 31 or following removal from the guide catheter 31.

The interventional devices may be positioned within the channel 106 and enclosed in a sterile barrier for shipping. At the clinical site, an upper panel of the sterile barrier may be removed, or a tubular sterile barrier packaging may be opened and axially removed from the support table 20 and sterile barrier 32 assembly, exposing the sterile top side of the sterile barrier tray and any included interventional devices. The interventional devices may be separately carried in the channel, or preassembled into an access assembly or procedure assembly, discussed in additional detail below.

FIGS. 3D-3F illustrate the support table with sterile barrier in place, and in FIG. 3E, the interventional devices configured in an access assembly for aortic access, following coupling of the access assembly to the corresponding carriages beneath the sterile barrier. The access assembly may be preassembled with the guidewire fully advanced through the access catheter which is in turn fully advanced through the guide catheter. In embodiments in which the access catheter or other catheters are pre-shaped (i.e., pre-curved or not straight), the guidewire and/or outer catheters may be positioned so that relatively stiff sections are not superimposed with curved stiffer sections of the pre-shaped catheter, for example, to avoid creep or straightening of the pre-shaped catheter and/or introduction of a curve into an otherwise straight catheter. This access assembly may be lifted out of the channel 106 and positioned on the support surface 104 for coupling to the respective drive magnets and introduction into the patient. The guide catheter hub 30 is the distal most hub. Access catheter hub 28 is positioned proximally of the guide catheter hub, so that the access catheter 29 can extend distally through the guide catheter. The guidewire hub 26 is positioned most proximally, in order to allow the guidewire 27 to advance through the access catheter 29 and guide catheter 31.

A procedure assembly is illustrated in FIG. 3F following introduction of the procedure assembly through the guide catheter 31 that was used to achieve supra-aortic access. In this implementation, guide catheter 31 remains the distal most of the interventional devices. A first procedure catheter 120 and corresponding hub 122 is illustrated extending through the guide catheter 31. An optional second procedure catheter 124 and corresponding hub 126 is illustrated extending through the first procedure catheter 120. The guidewire 27 extends through at least a portion of the second procedure catheter 124 in a rapid exchange version of second procedure catheter 124, or the entire length of second procedure catheter 124 in an over the wire implementation.

As is discussed in greater detail in connection with FIG. 17, the multi catheter stack may be utilized to achieve both access and the intravascular procedure without the need for catheter exchange. This may be accomplished in either a manual or a robotically driven procedure. In one example, the guide catheter 31 may comprise a catheter having an inner diameter of at least about 0.08 inches and in one implementation about 0.088 inches. The first procedure catheter 120 may comprise a catheter having an inner diameter within the range of from about 0.065 inches to about 0.075 inches and in one implementation catheter 120 has an inner diameter of about 0.071 inches. The second procedure catheter 124 may be an access catheter having an OD sized to permit advance through the first procedure catheter 120. The second procedure catheter maybe steerable, having a deflection control 2908 configured to laterally deflect a distal end of the catheter. The second procedure (access) catheter may also have an inner lumen sized to allow an appropriately sized guidewire to remain inside the second procedure catheter while performing contrast injections through the second procedure catheter.

In certain embodiments, the catheter 31 may be a 'large bore' access catheter or guide catheter having a diameter of at least about 0.075 or at least about 0.080 inches in diameter. The catheter 120 may be an aspiration catheter having a diameter within the range of from about 0.060 to about 0.075 inches. The catheter 124 may be a steerable catheter with a deflectable distal tip, having a diameter within the range of from about 0.025 to about 0.050 inches. The guidewire 27 may have a diameter within the range of from about 0.014 to about 0.020 inches. In one example, the catheter 31 may have a diameter of about 0.088 inches, the catheter 120 about 0.071 inches, the catheter 124 about 0.035 inches, and the guidewire 27 may have a diameter of about 0.018 inches.

In one commercial execution, a preassembled access assembly (guide catheter, access catheter and guidewire) may be carried within a first channel on the sterile barrier tray and a preassembled procedure assembly (one or two procedure catheters and a guidewire) may be carried within the same or a different, second channel on the sterile barrier tray. One or two or more additional catheters or interventional tools may also be provided, depending upon potential needs during the interventional procedure.

Figures 3G, 3H, 3I, 3J, 3K, 3L, 3M:
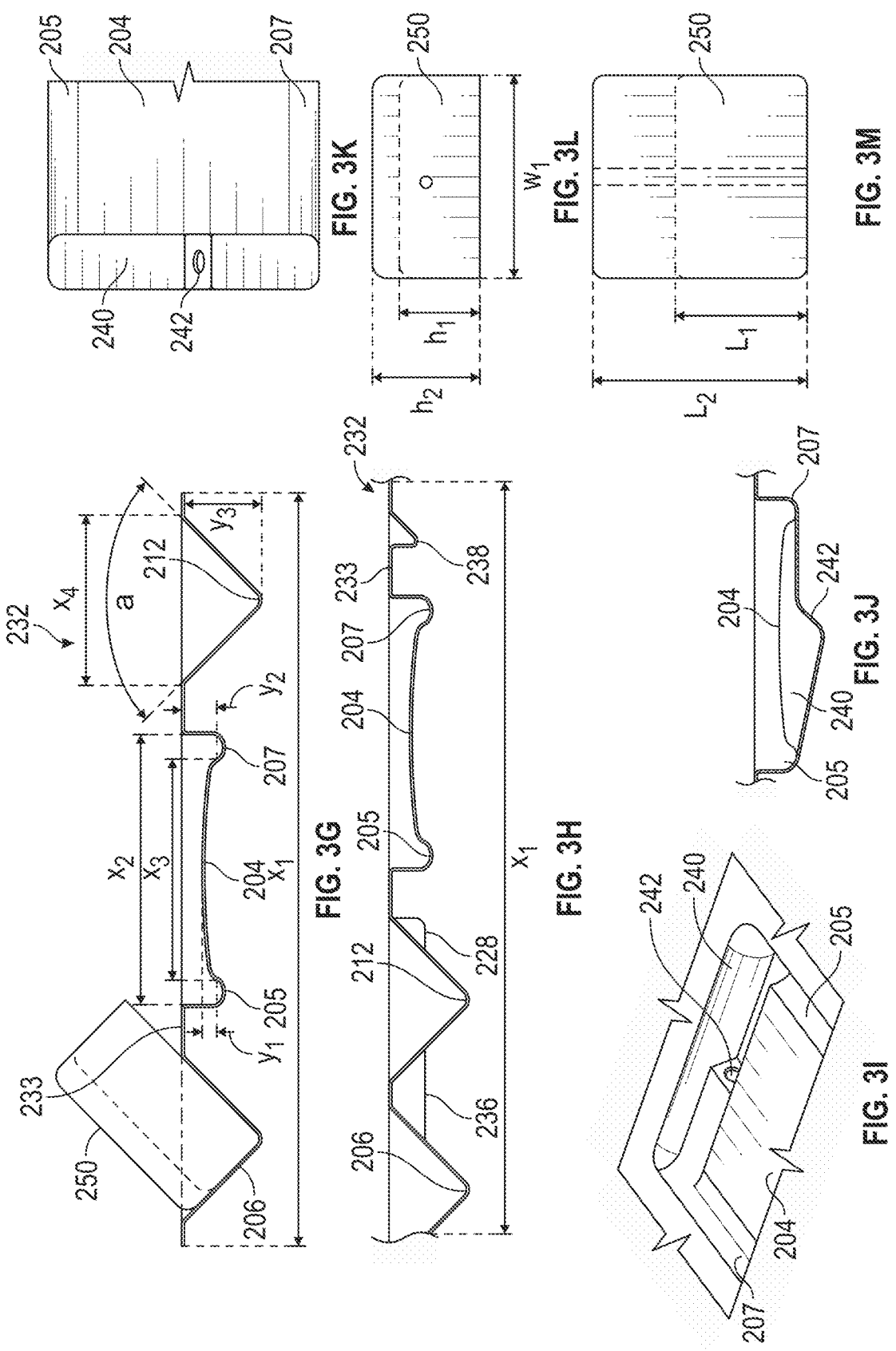
FIGS. 3G-3K show embodiments of an alternate sterile barrier having a convex drive surface.
FIGS. 3L and 3M depict an example of a hub that may be used with the sterile barriers of FIGS. 3G-3K.

FIGS. 3G-3K illustrate embodiments of an alternate sterile barrier having a convex drive surface (e.g., a convex, crowned road like drive surface). FIG. 3G is a cross-sectional view of a sterile barrier 232. The sterile barrier 232 includes a convex upper support surface 204. Fluid channels 205 and 207 are positioned laterally of and below the support surface 204 for self-clearing or draining of fluids from the support surface 204 (for example, during an interventional procedure). The fluid channels 205 and 207 may extend axially at least a portion of the length of the sterile barrier.

FIGS. 3I, 3J, and 3K illustrate a sectional perspective view, a cross-sectional view, and a top sectional view, respectively, of a proximal end of the sterile barrier 232. As shown, in FIGS. 3I-3K, the sterile barrier 232 can include a trough 240 in communication with the fluid channels 205 and 207. The trough 240 can receive fluids from the channels 205 and 207 (for example, during an interventional procedure). The trough 240 may be positioned at least partially below the fluid channels 205 and 207 so that fluid within the channels 205 and 207 flows into the trough 240. In certain embodiments, the fluid channels 205 and 207 may be angled relative to a horizontal plane (for example, may decline from an end of the channel furthest from the trough 240 to the trough 240) so that fluid within the channels 205 and 207 is directed to the trough 240. For example, the channels 205 and 207 may increase in depth from an end of the channels furthest from the trough 240 to the trough 240. Alternatively, the sterile barrier 232 and/or support table may be positioned at an angle relative to a horizontal plane, during part of or an entirety of an interventional procedure, such that the end of the channels 205 and 207 furthest from the trough 240 is positioned higher than the trough 240. For example, the sterile barrier 232 and/or support table may be constructed or arranged in an angled arrangement so that an end of the sterile barrier 232 and/or support table opposite the trough 240 is positioned higher than the trough 240. Alternatively or additionally, a drive mechanism may temporarily tilt the sterile barrier 232 and/or support table so that an end of the sterile barrier 232 and/or support table opposite the trough 240 is positioned higher than the trough 240 (for example, by lifting an end of the sterile barrier and/or support table opposite the trough 240 or lowering an end of the sterile barrier 232 and/or support table at which the trough 240 is positioned) so that fluids within the channels 205 and 207 flow into the trough 240.

Figure 31:
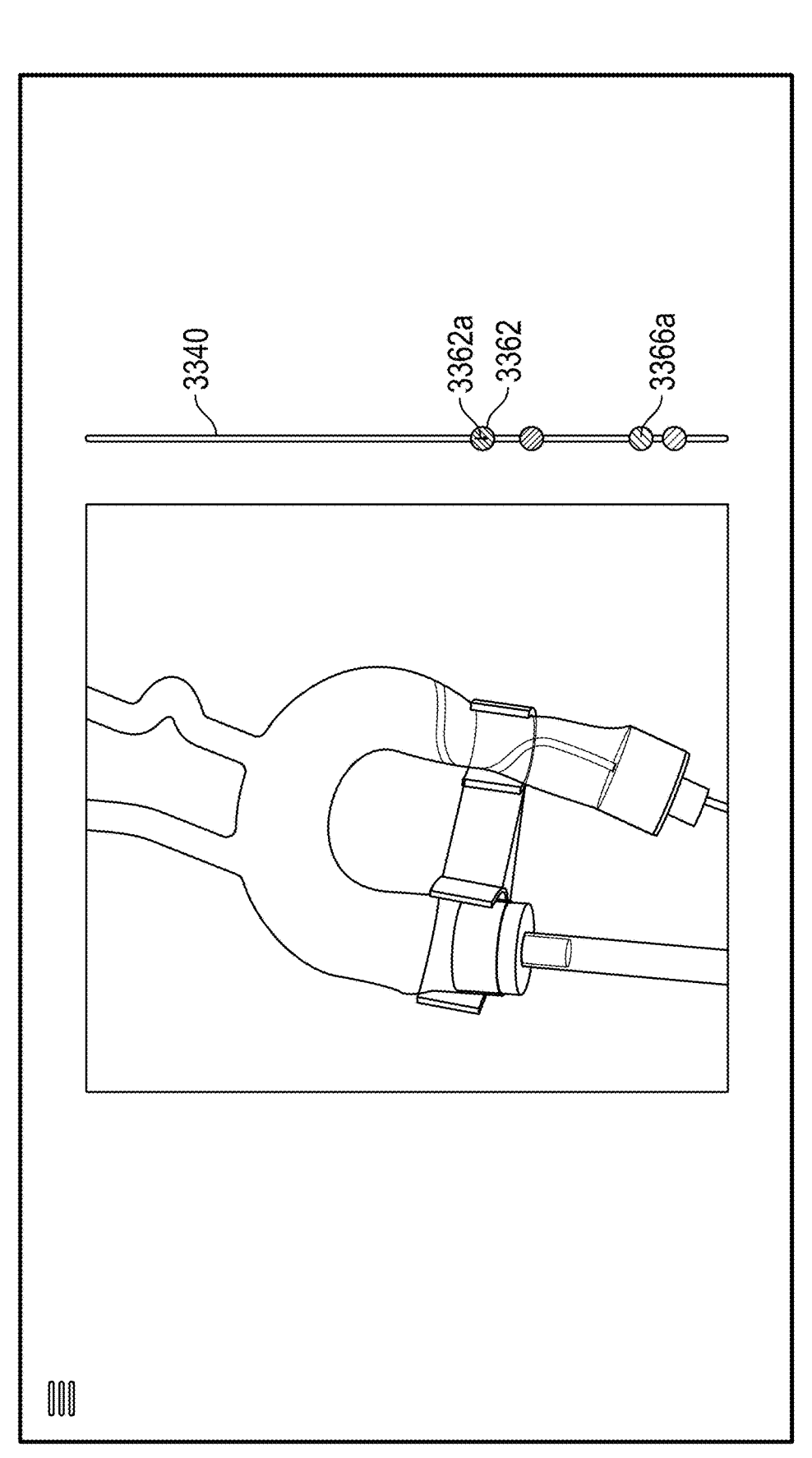
FIGS. 31-42 illustrate alternative embodiments of a user interface for controlling interventional devices.

The trough 240 can include a drain hole 242. The trough 240 can be shaped, dimensioned, and/or otherwise config- ured so that fluid within the trough 240 empties to the drain hole 242. The drain hole 242 can include tubing, a barb fitting, and/or an on-off valve for removal of fluids from the trough 240. As shown in FIGS. 31-3K, the trough 240 can be positioned at the proximal end of the sterile barrier 232. In alternate embodiments, the trough 240 may be positioned at a distal end of the sterile barrier 232. In some embodi- ments, the sterile barrier 232 can include a first trough 240 at the proximal end and a second trough 240 at the distal end. In some embodiments, the trough 240 can also be used as a wash basin.

A first channel 206 may extend axially at least a portion of the length of the sterile barrier 232. The channel 206 can have a sufficient length to hold the interventional devices, and sufficient width and depth to hold the corresponding hubs (for example, by providing support to prevent dis- lodgement of the hubs when forces are applied to the hubs). Optionally, a second channel 212 may be provided. The second channel 212 may be located on the same side or the opposite side of the upper support surface 204 from the first channel 206. FIG. 3G illustrates the channel 212 located on the opposite side of the support surface 204 from the channel 206. FIG. 3H is a cross-sectional view illustrating an alter- nate embodiment of the sterile barrier 232 in which the channel 212 is on the same side of the support surface 204 as the channel 206.

As shown in FIGS. 3G and 3H, the channels 206 and 212 can have generally triangular, wedge-shaped, or otherwise angled cross-sections, so as to hold the hubs at an angle relative to a horizontal plane. Holding the hubs at an angle relative to the horizontal plane can allow for smaller width of the sterile barrier 232.

Two or three or more additional recesses such as addi- tional channels or wells may be provided, to hold additional medical devices or supplies that may be useful during the interventional procedure as well as to collect fluids and function as wash basins for catheters and related devices.

In some embodiments, the sterile barrier 232 can include one or more structural ribs 236. The sterile barrier 232 can further include one or more frame support bosses 228 and 238.

In the embodiment of the sterile barrier 232 shown in FIG. 3G, a width $x_1$ can be 14 in, about 14 in, between 12 in and 16 in, between 10 in and 18 in, or any other suitable width. In the embodiment of the sterile barrier 232 shown in FIG. 3H, the width $x_1$ can be 15 in, about 15 in, between 13 in and 17 in, between 11 in and 19 in, or any other suitable width.

A height $y_1$ of the support surface 204 can be 0.125 in, about 0.125 in, between 0.1 and 0.15 in, or any other suitable height. In some embodiments, the support surface 204 can be recessed from a top surface 233 of the sterile barrier 232. A height $y_2$ between a bottom of the support surface 204 and the top surface 233 can be 0.5 in, about 0.5 in, between 0.25 in and 0.75 in, or any other suitable height. A width $x_2$ from a lateral edge of the channel 205 to a lateral edge of the channel 207 can be 5 in, about 5 in, between 4 in and 6 in, or any other suitable width. A width $x_3$ of the support surface 204 can be 4 in, about 4 in, between 3 in and 5 in, or any other suitable width. A height $y_3$ of the channel 206 and/or channel 212 can be 1.5 in, about 1.5 in, between 1 in and 2 in, or any other suitable height. A width $x_4$ of the channel 206 and/or channel 212 can be 3 in, about 3 in, between 2 in and 4 in, or any other suitable width. The channel 206 and/or channel 212 can be defined by an arc angle $\alpha$ of 90°, about 90°, between 80° and 100°, or any other suitable angle, and a radius of curvature of 0.125 in, about 0.125 in, between 0.1 and 0.15 in, or any other suitable radius of curvature. In certain embodiments, an arc angle $\alpha$ of 90° or about 90° may be used to hold a hub having a rectangular or generally rectangular cross-section. The support surface 204 can be defined by a radius of curvature of 13 in, about 13 in, between 11 in and 15 in, or any other suitable radius of curvature. The channel 205 and/or channel 207 can be defined by a radius of curvature of 0.25 in, about 0.25 in, between 0.15 in and 0.35 in, or any other suitable radius of curvature.

FIGS. 3L and 3M depict example dimensions of a hub 250 that may be used with the sterile barrier 232 as shown in FIGS. 3G-3K. The hub 250 may be any of the hubs described herein. In certain embodiments, the hub 250 can have a width $w_1$ of 3.75 in, about 3.75 in, between 3.25 in and 4.25 in, or any other suitable width. The hub 250 can have a height h1 of 1.5 in, about 1.5 in, between 1.25 in and 1.75 in, or any other suitable height. Alternatively, the hub 250 can have a height $h_2$ of 2 in, about 2 in, between 1.75 in and 2.25 in, or any other suitable height. In some embodiments, the hub 250 can have a length $L_1$ of 2.5 in, about 2.5 in, between 2 in and 3 in or any other suitable length. Alternatively, the hub 250 can have a length $L_2$ of 4 in, about 4 in, between 3.25 in and 4.75 in, or any other suitable length.

In some embodiments, a top surface of the support table can include surface features that generally correspond to those of the sterile barrier 232. For example, the support table can include a convex surface configured to correspond to the shape, size, and location of the support surface 204 and/or one or more recesses configured to correspond to the shape, size, and location of the channels 205 and 207.

In alternate embodiments, a planar support surface (for example, support surface 104 of sterile barrier 32) can be positioned at an angle to a horizontal plane to facilitate the draining of fluids. In some embodiments, the sterile barrier and/or support table may be positioned, during part of or the entirety of an interventional procedure, at an angle to a horizontal plane to facilitate the draining of fluids. For example, the sterile barrier and/or support table may be constructed or arranged in an angled arrangement (for example, so that one lateral side of the planar support surface is positioned higher than the other lateral side of the planar support surface, the proximal end is higher than the distal end, or the distal end is higher than the proximal end) to facilitate the drainage of fluids. Alternatively or addition- ally, a drive mechanism may temporarily tilt the sterile barrier and/or support table (for example, so that one lateral side of the planar support surface is positioned higher than the other lateral side of the planar support surface, the proximal end is higher than the distal end, or the distal end is higher than the proximal end) to facilitate the drainage of fluids. For example, the drive mechanism may raise or lower one lateral side of the sterile barrier and/or support table, the proximal end of the sterile barrier and/or support table, and/or the distal end of the sterile barrier and/or support table.

In certain embodiments, a support surface (for example, support surface 104 of sterile barrier 32) can be positioned in a vertical configuration instead in the horizontal configuration shown, for example, in FIGS. 3A-3F. For example, the support surface 104 can be positioned at about 90 degrees (or any other suitable angle) from a horizontal plane (e.g., rotated 90 degrees about a long axis of the support surface 104 relative to the embodiment shown in of FIGS. 3A-3F). A vertical configuration may provide for easier interaction with the drive system 18 by a physician. A vertical configuration may also provide for a lower axis of catheter travel closer to a patient without adding standoff height to the drive system 18.

In some embodiments, the drive system 18 may be positioned, during part of or the entirety of an interventional procedure, at an angle to a horizontal plane to facilitate the draining of fluids. For example, the drive system 18 may be constructed or arranged in an angled arrangement (for example, so that one lateral side of the planar support surface is positioned higher than the other lateral side of the planar support surface, the proximal end is higher than the distal end, or the distal end is higher than the proximal end) to facilitate the drainage of fluids. Alternatively or additionally, a drive mechanism may temporarily tilt the drive system 18 (for example, so that one lateral side of the drive system 18 is positioned higher than the other lateral side of the drive system 18, the proximal end is higher than the distal end, or the distal end is higher than the proximal end) to facilitate the drainage of fluids. For example, the drive mechanism may raise or lower one lateral side of the system 18, the proximal end of the drive system 18, and/or the distal end of the drive system 18. In some embodiments, the drive system 18 may be angled so that it extends at an angle away from axis point 24 (for example, so that the proximal end is higher than the distal end), for example, to allow for clearance of a patient's feet.

Figures 4, 5A, 5B:
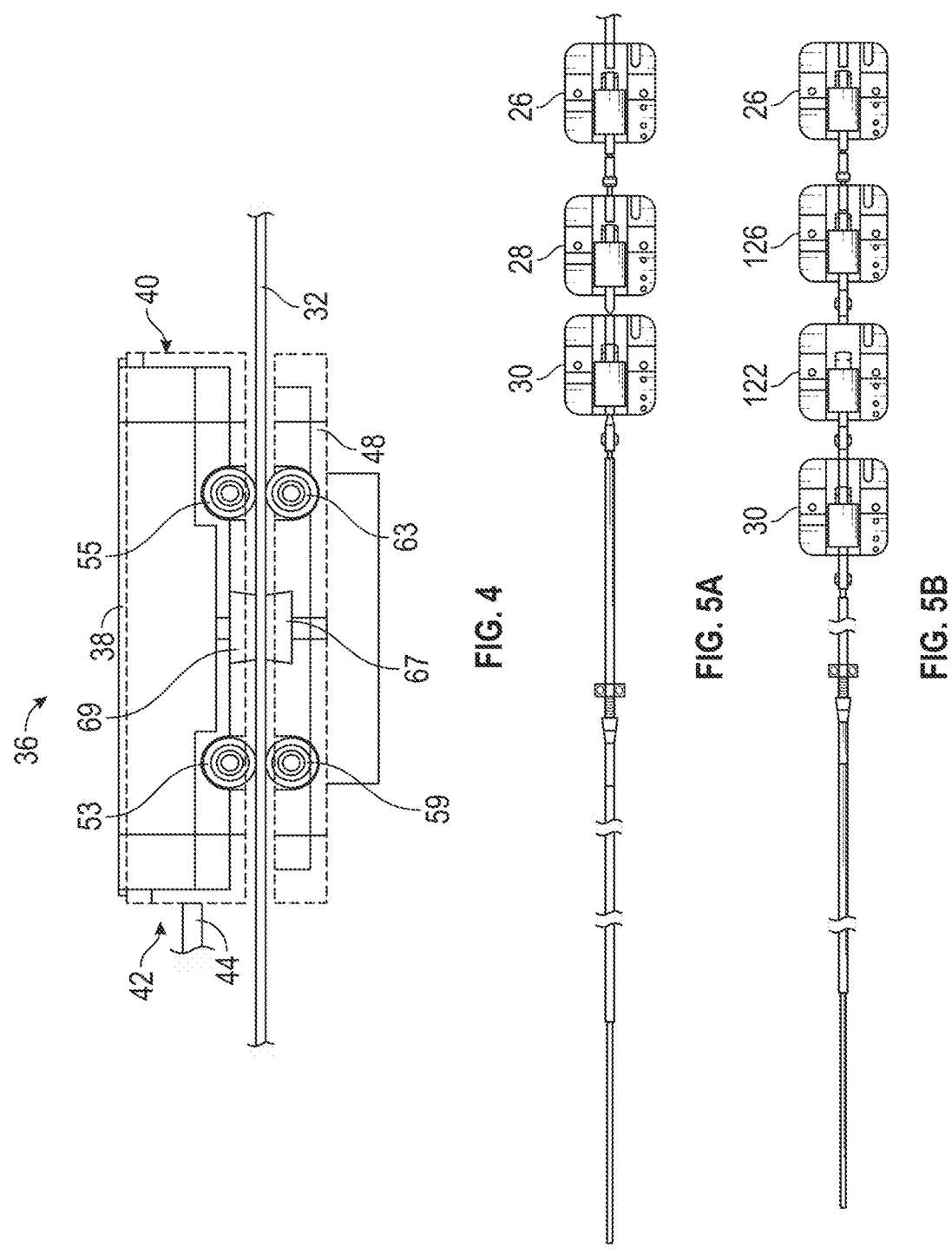
FIG. 4 is a schematic elevational cross section through a hub adapter having a drive magnet separated from an interventional device hub and driven magnet by a sterile barrier.
FIGS. 5A and 5B schematically illustrate a three interventional device and a four interventional device assembly.

Referring to FIG. 4, hub 36 may represent any of the hubs previously described. Hub 36 includes a housing 38 which extends between a proximal end 40 and a distal end 42. An interventional device 44, which could be any of the interventional devices disclosed herein, extends distally from the hub 36 and into the patient 14 (not illustrated). A hub adapter 48 or carriage acts as a shuttle by advancing proximally or distally along a track in response to operator instructions or controller manipulations. The hub adapter 48 includes at least one drive magnet 67 configured to couple with a driven magnet 69 carried by the hub 36. This provides a magnetic coupling between the drive magnet 67 and driven magnet 69 through the sterile barrier such that the hub 36 is moved across the top of the sterile barrier 32 in response to movement of the hub adapter 48 outside of the sterile field. Movement of the hub adapter is driven by a drive system carried by the support table and described in additional detail below. The hub adapter may act as a robotic drive for an interventional device coupled thereto.

To reduce friction in the system, the hub 36 may be provided with at least a first roller 53 and a second roller 55 which may be in the form of wheels or rotatable balls or drums. The rollers space the sterile barrier apart from the surface of the driven magnet 69 by at least about 0.02 centimeters (about 0.008 inches) and generally no more than about 0.08 centimeters (about 0.03 inches). In some implementations, the space is within the range of from about 0.03 centimeters (about 0.010 inches) and about 0.041 centimeters (about 0.016 inches). The space between the drive magnet 67 and driven magnet 69 is generally no more than about 0.38 centimeters (about 0.15 inches) and in some implementations is no more than about 0.254 centimeters (about 0.10 inches) such as within the range of from about 0.216 centimeters (about 0.085 inches) to about 0.229 centimeters (about 0.090 inches). The hub adapter 48 may similarly be provided with at least a first hub adapter roller 59 and the second hub adapter roller 63, which may be positioned opposite the respective first roller 53 and second roller 55 as illustrated in FIG. 4.

Figure 6:
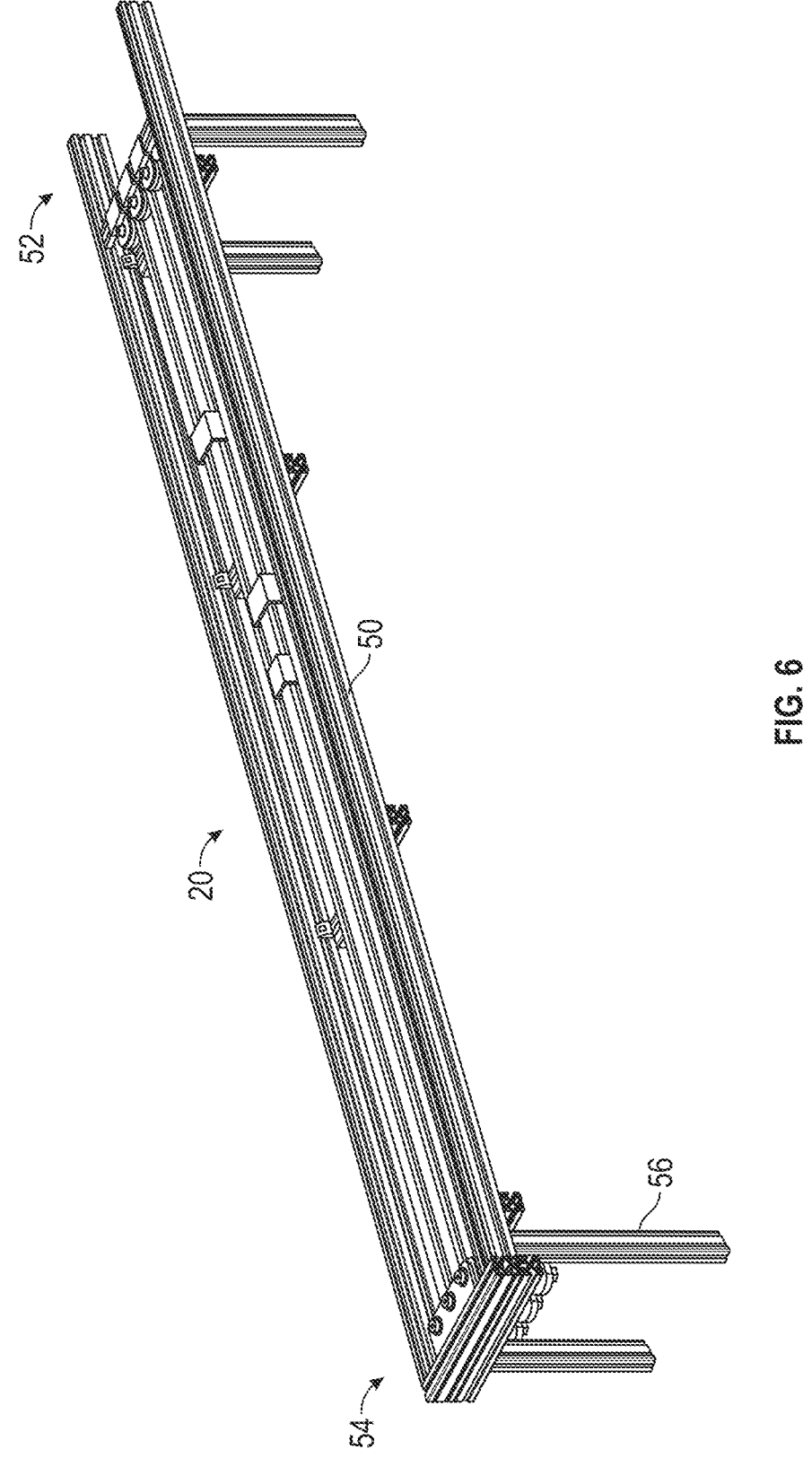
FIG. 6 is a perspective view of a support table.

Referring to FIG. 6, there is schematically illustrated one example of a low-profile linear drive support table 20. Support table 20 comprises an elongated frame 51 extending between a proximal end 52 and a distal end 54. At least one support table support 56 is provided to stabilize the support table 20 with respect to the patient (not illustrated). Support 56 may comprise one or more legs or preferably an articulating arm configured to allow movement and positioning of the frame 51 over or adjacent to the patient.

Figure 7:
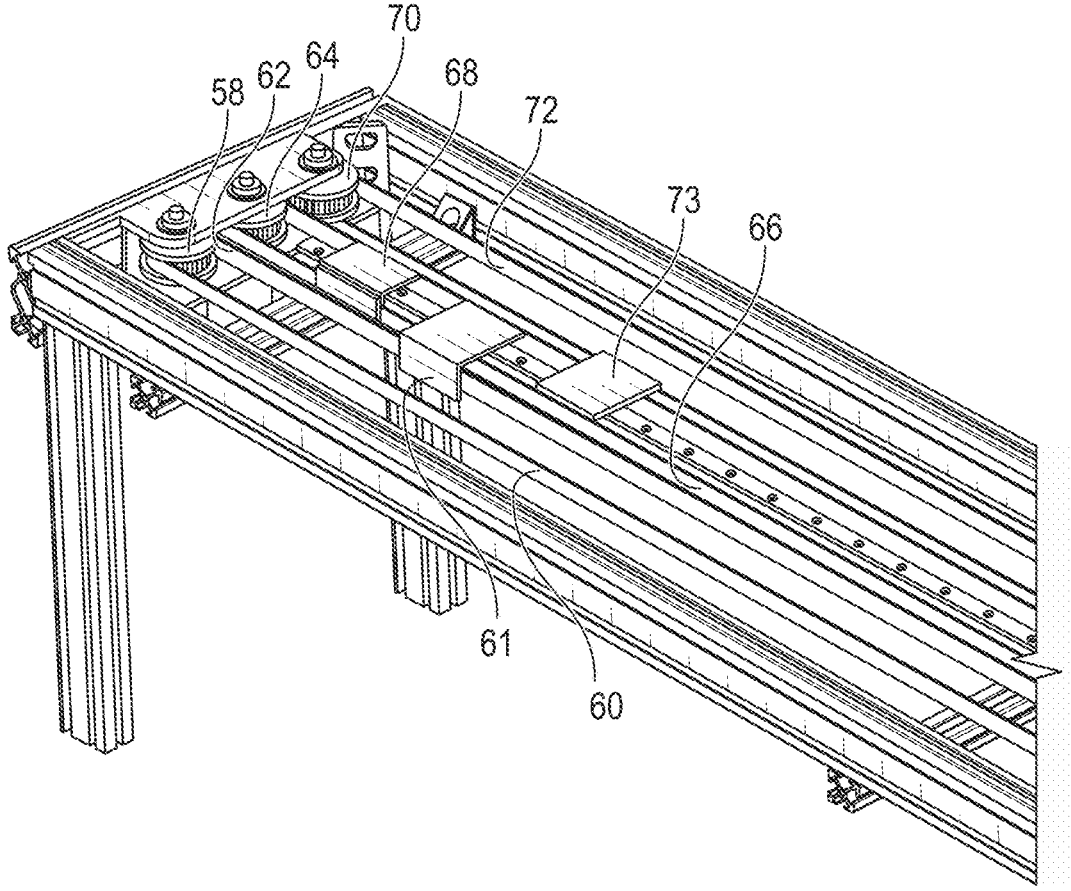
FIG. 7 is a close-up view of the motor drive end of a support table.

One example of a linear drive table 20 illustrated in FIG. 7 includes three distinct drives. However, two drives or four or more drives (e.g., up to eight drives) may be included depending upon the desired clinical performance. A first drive pulley 58 engages a first drive belt 60. A first carriage bracket 61 is secured to the first drive belt 60 such that rotation of the first drive pulley 58 causes rotation of the first drive belt 60 through an elongate closed loop path. The first carriage bracket 61 may be advanced in a proximal or distal direction along the longitudinal axis of the support table 20 depending upon the direction of rotation of the drive pully 58. In the illustrated implementation, the drive pulley 58 is provided with surface structures such as a plurality of drive pulley teeth 62 for engaging complementary teeth on the first drive belt 60.

A second drive pulley 64 may engage a second drive belt 66 configured to axially move a second carriage bracket 68 along an axial path on the support table 20. A third drive pulley 70 may be configured to drive a third drive belt 72, to advance a third carriage bracket 73 axially along the support table 20. Each of the carriage brackets may be provided with a drive magnet assembly discussed previously but not illustrated in FIG. 7, to form couplers for magnetically coupling to a corresponding driven magnet within the hub of an interventional device as has been discussed.

Figure 8:
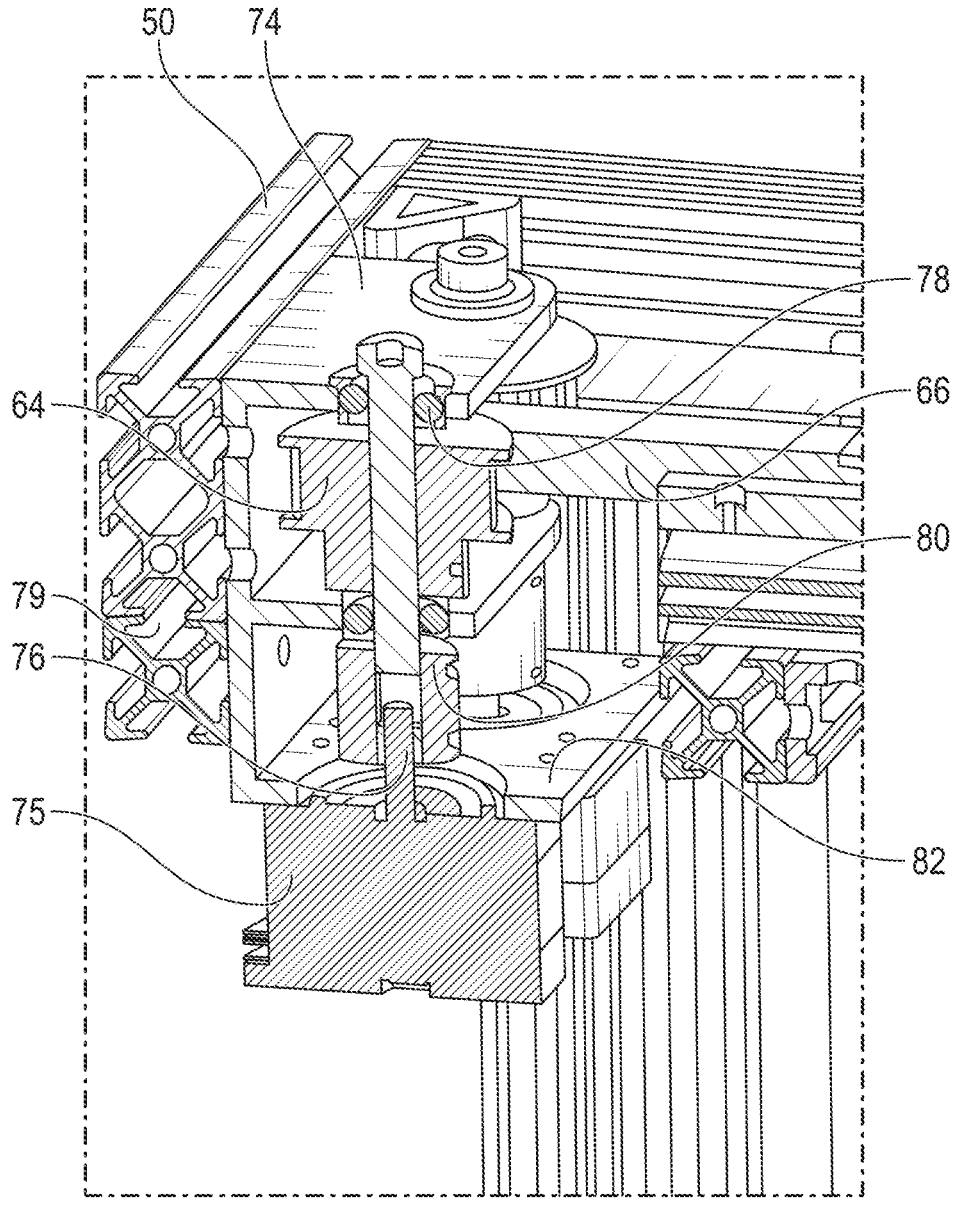
FIG. 8 is an elevational cross section through a motor and belt drive assembly.

A detailed view of a drive system is shown schematically in FIG. 8. A drive support 74 may be carried by the frame 51 for supporting the drive assembly. The second drive pulley 64 is shown in elevational cross section as rotationally driven by a motor 75 via a rotatable shaft 76. The rotatable shaft 76 may be rotatably carried by the support 74 via a first bearing 78, a shaft coupling 80 and second bearing 79. Motor 75 may be stabilized by a motor bracket 82 connected to the drive support 74 and or the frame 51. The belt drive assemblies for the first drive belt 60 and third drive belt 72 maybe similarly constructed and are not further detailed herein. In some embodiments, the drive systems described herein may be a rack and pinion drive table system that is foldable. In such embodiments, motors 75 may be attached to and move with the carriages.

Figure 9:
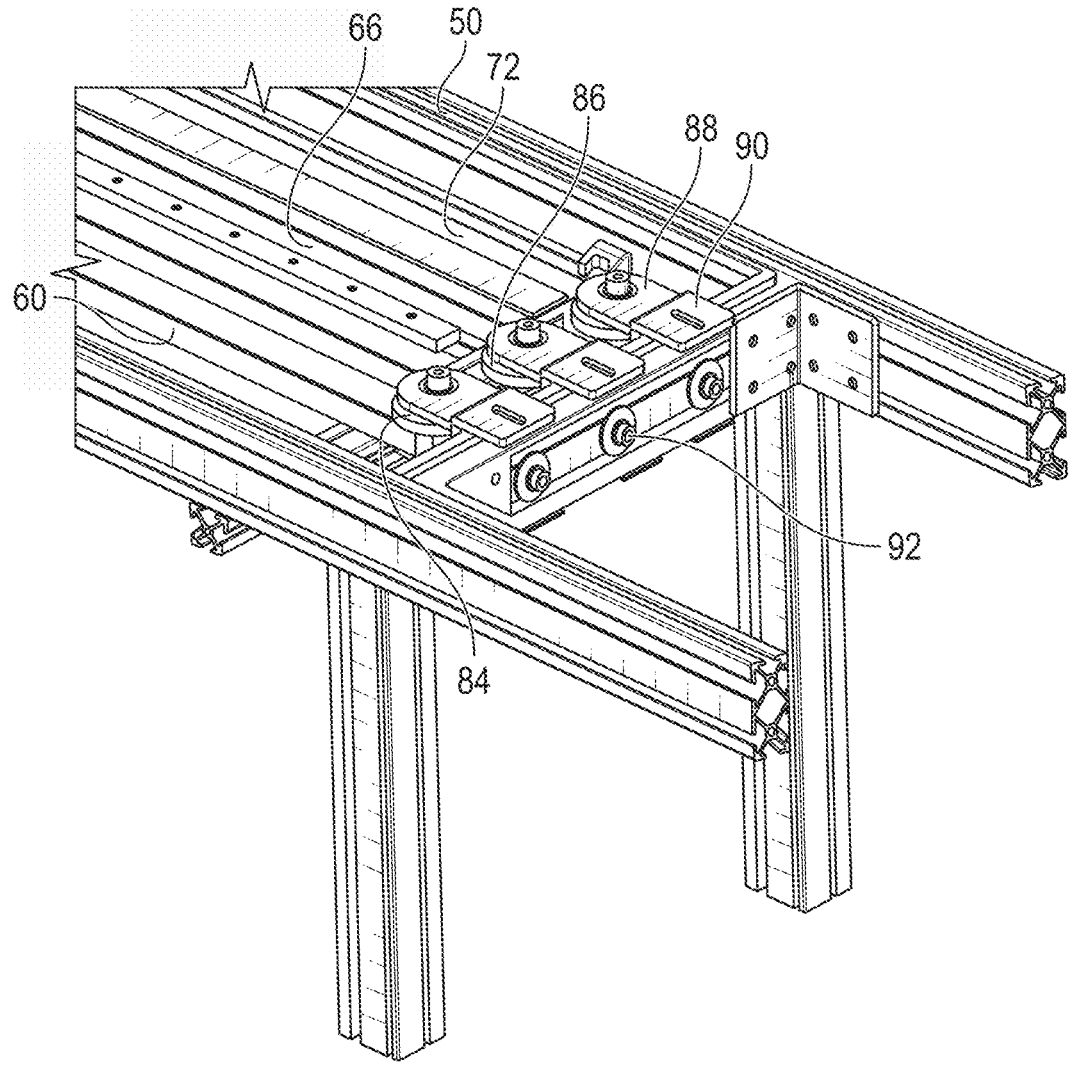
FIG. 9 is a close-up view of a pulley end of the support table.
Figure 10:
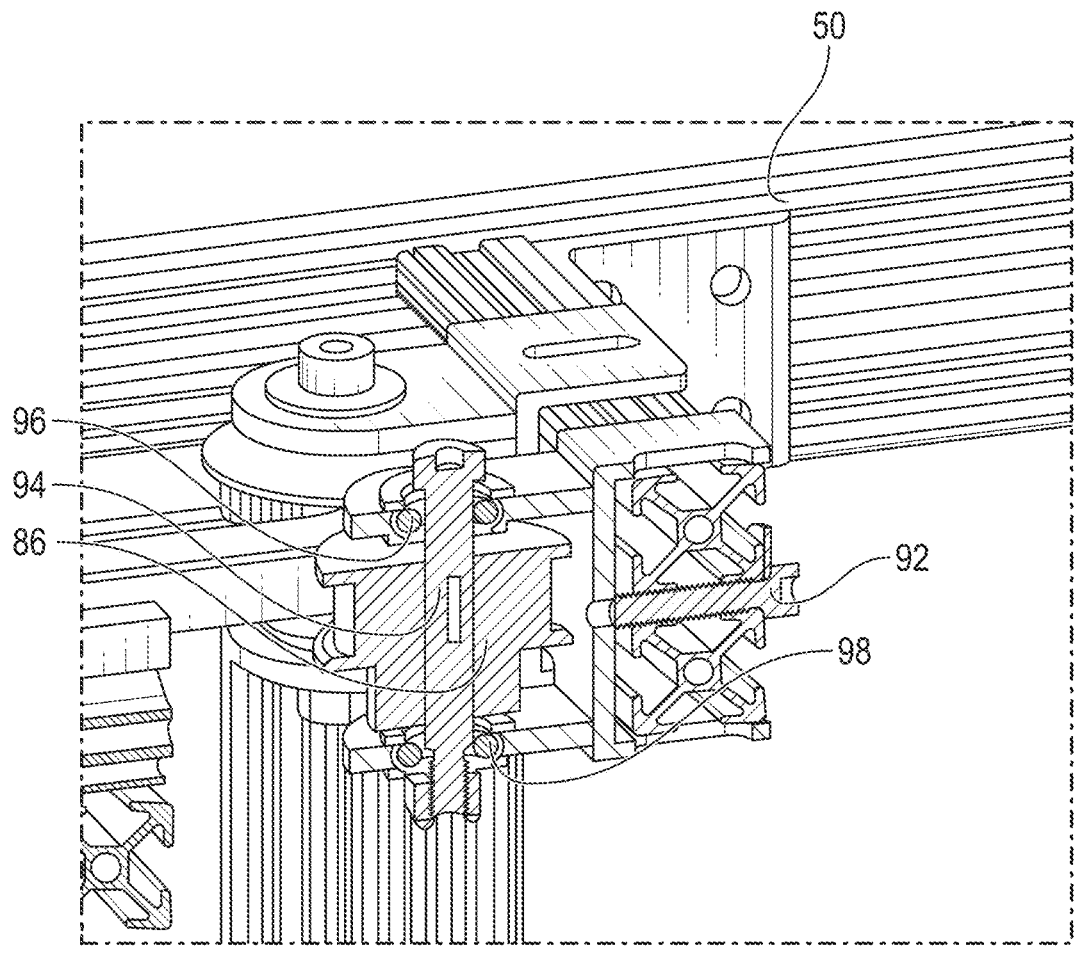
FIG. 10 is an elevational cross section through a belt pully.

Referring to FIGS. 9 and 10, each of the first second and third drive belts extends around a corresponding first idler pulley 84 second idler pulley 86 and third idler pulley 88. Each idler pulley may be provided with a corresponding tensioning bracket 90, configured to adjust the idler pulleys in a proximal or distal direction in order to adjust the tension of the respective belt. Each tensioning bracket 90 is therefore provided with a tensioning adjustment 92 such as a rotatable screw.

As seen in FIG. 10, the second idler pulley 86, for example, may be carried by a rotatable shaft 94, rotatably secured with respect to the mounting bracket by a first bearing 96 and second bearing 98.

Figure 11:
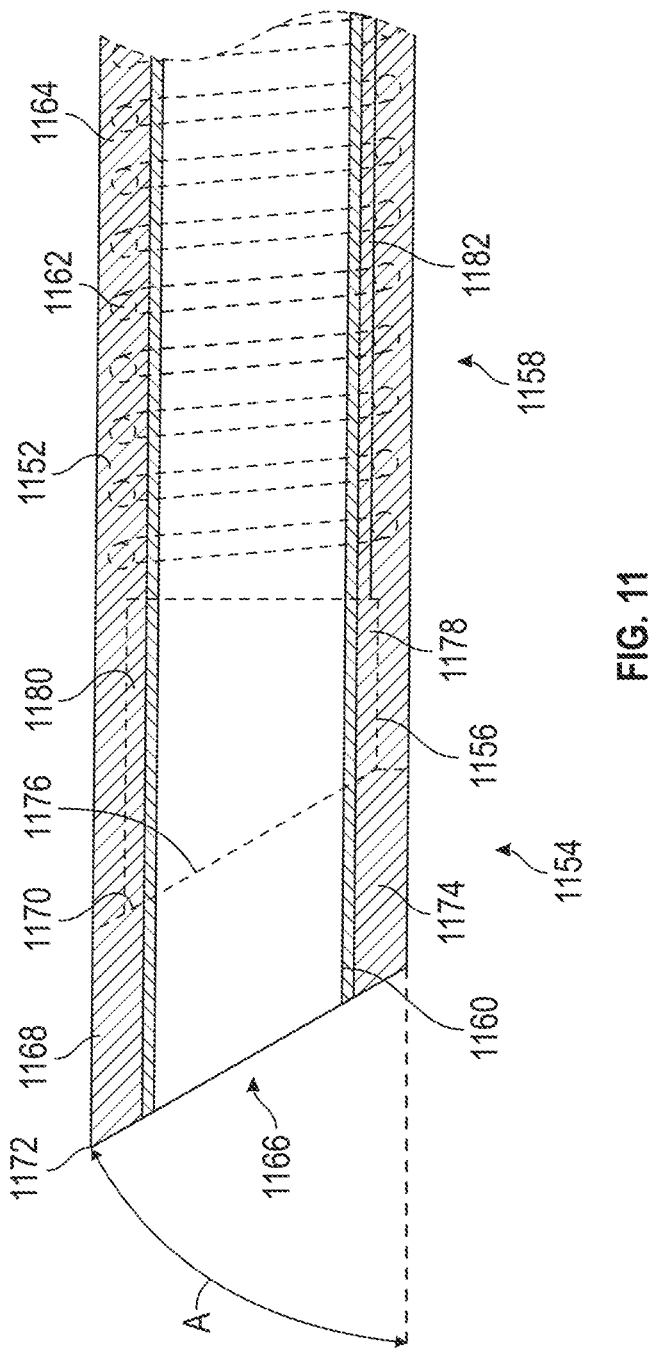
FIG. 11 is a side elevational cross-section through a distal portion of a catheter such as any of those shown in FIGS. 5A and 5B.

Any of the catheters illustrated, for example, in FIG. 5A, 5B or 11 generally comprise an elongate tubular body extending between a proximal end and a distal functional end. The length and diameter of the tubular body depends upon the desired application. For example, lengths in the area of from about 90 centimeters to about 195 centimeters or more are typical for use in femoral access percutaneous transluminal coronary applications. Intracranial or other applications may call for a different catheter shaft length depending upon the vascular access site.

Any of the catheters disclosed herein may be provided with an inclined distal tip. Referring to FIG. 11, distal catheter tip 1150 comprises a tubular body 1152 which includes an advance segment 1154, a marker band 1156 and a proximal segment 1158. An inner tubular liner 1160 may extend throughout the length of the distal catheter tip 1150, and may comprise dip coated or extruded PTFE or other lubricious material.

A reinforcing element 1162 such as a braid and/or spring coil is embedded in an outer jacket 1164 which may extend the entire length of the catheter.

The advance segment 1154 terminates distally in an angled face 1166, to provide a leading side wall portion 1168 having a length measured between the distal end 130 of the marker band 1156 and a distal tip 1172. In some embodiments, the entire distal tip may be shaped to avoid snagging the tip in areas of arterial bifurcation. A trailing side wall portion 1174 of the advance segment 1154, has an axial length in the illustrated embodiment of approximately equal to the axial length of the leading side wall portion 1168 as measured at approximately 180 degrees around the catheter from the leading side wall portion 1168. The leading side wall portion 1168 may have an axial length within the range of from about 0.1 millimeters to about 5 millimeters and generally within the range of from about 1 to 3 millimeters. The trailing side wall portion 1174 may be equal to or at least about 0.1 or 0.5 or 1 millimeter or 2 millimeters or more shorter than the axial length of the leading side wall portion 1168, depending upon the desired performance.

The angled face 1166 inclines at an angle A within the range of from about 45 degrees to about 80 degrees from the longitudinal axis of the catheter. For certain implementations, the angle is within the range of from about 55 degrees to about 65 degrees from the longitudinal axis of the catheter. In one implementation, the angle A is about 60 degrees. One consequence of an angle A of less than 90 degrees is an elongation of a major axis of the area of the distal port which increases the surface area of the port and may enhance clot aspiration or retention. Compared to the surface area of the circular port (angle A is 90 degrees), the area of the angled port is generally at least about 105 percent, and no more than about 130 percent, in some implementations within the range of from about 110 percent and about 125 percent, and in one example is about 115 percent of the area of the corresponding circular port (angle A is 90 degrees).

In the illustrated embodiment, the axial length of the advance segment is substantially constant around the circumference of the catheter, so that the angled face 1166 is approximately parallel to the distal surface 1176 of the marker band 1156. The marker band 1156 has a proximal surface approximately transverse to the longitudinal axis of the catheter, producing a marker band 1156 having a right trapezoid configuration inside elevational view. A short sidewall 1178 is rotationally aligned with the trailing side wall portion 1174, and has an axial length within the range of from about 0.2 millimeters to about 4 millimeters, and typically from about 0.5 millimeters to about 2 millimeters. An opposing long sidewall 1180 is rotationally aligned with the leading side wall portion 1168. Long sidewall 1180 of the marker band 1156 is generally at least about 10 percent or 20 percent longer than short sidewall 1178 and may be at least about 50 percent or 70 percent or 90 percent or more longer than short sidewall 1178, depending upon desired performance. Generally, the long sidewall 1180 will have a length of at least about 0.5 millimeters or 1 millimeter and less than about 5 millimeters or 4 millimeters.

The marker band may be a continuous annular structure, or may have at least one and optionally two or three or more axially extending slits throughout its length. The slit may be located on the short sidewall 1178 or the long sidewall 1180 or in between, depending upon desired bending characteristics. The marker band may comprise any of a variety of radiopaque materials, such as a platinum/iridium alloy, with a wall thickness preferably no more than about 0.003 inches and in one implementation is about 0.001 inches.

The fluoroscopic appearance of the marker bands may be unique or distinct for each catheter size or type when a plurality of catheters is utilized so that the marker bands can be distinguishable from one another by a software algorithm. Distinguishing the marker bands of a plurality of catheters may be advantageous when the multiple catheters are used together, for example, in a multi catheter assembly or stack as described herein. In some embodiments, the marker band of a catheter may be configured so that a software algorithm can detect motion of the catheter tip.

The marker band zone of the assembled catheter may have a relatively high bending stiffness and high crush strength, such as at least about 50 percent or at least about 100 percent less than proximal segment 18 but generally no more than about 200 percent less than proximal segment 1158. The high crush strength may provide radial support to the adjacent advance segment 1154 and particularly to the leading side wall portion 1168, to facilitate the functioning of distal tip 1172 as an atraumatic bumper during transluminal advance and to resist collapse under vacuum. The proximal segment 1158 preferably has a lower bending stiffness than the marker band zone, and the advance segment 1154 preferably has even a lower bending stiffness and crush strength than the proximal segment 1158.

The advance segment 1154 may comprise a distal extension of the outer tubular jacket 1164 and optionally the inner liner 1160, without other internal supporting structures distally of the marker band 1156. Outer jacket 1164 may comprise extruded polyurethane, such as Tecothane®. The advance segment 1154 may have a bending stiffness and radial crush stiffness that is no more than about 50 percent, and in some implementations no more than about 25 percent or 15 percent or 5 percent or less than the corresponding value for the proximal segment 1158.

The catheter may further comprise an axial tension element or support such as a ribbon or one or more filaments or fibers for increasing the tension resistance and/or influencing the bending characteristics in the distal zone. The tension support may comprise one or more axially extending mono strand or multi strand filaments. The one or more tension element 1182 may be axially placed inside the catheter wall near the distal end of the catheter. The one or more tension element 1182 may serve as a tension support and resist tip detachment or elongation of the catheter wall under tension (e.g., when the catheter is being proximally retracted through a kinked outer catheter or tortuous or narrowed vasculature).

At least one of the one or more tension element 1182 may proximally extend along the length of the catheter wall from within about 1.0 centimeters from the distal end of the catheter to less than about 10 centimeters from the distal end of the catheter, less than about 20 centimeters from the distal end of the catheter, less than about 30 centimeters from the distal end of the catheter, less than about 40 centimeters from the distal end of the catheter, or less than about 50 centimeters from the distal end of the catheter.

The one or more tension element 1182 may have a length greater than or equal to about 40 centimeters, greater than or equal to about 30 centimeters, greater than or equal to about 20 centimeters, greater than or equal to about 10 centimeters, or greater than or equal to about 5 centimeters.

At least one of the one or more tension element 1182 may extend at least about the most distal 50 centimeters of the length of the catheter, at least about the most distal 40 centimeters of the length of the catheter, at least about the most distal 30 centimeters or 20 centimeters or 10 centimeters of the length of the catheter.

In some implementations, the tension element extends proximally from the distal end of the catheter along the length of the coil 24 and ends proximally within about 5 centimeters or 2 centimeters or less either side of a transition between a distal coil and a proximal braid. The tension element may end at the transition without overlapping with the braid.

The one or more tension element 1182 may be placed near or radially outside the inner liner 1160. The one or more tension element 1182 may be placed near or radially inside the braid and/or the coil. The one or more tension element 1182 may be carried between the inner liner 1160 and the helical coil, and may be secured to the inner liner or other underlying surface by an adhesive prior to addition of the next outer adjacent layer such as the coil. Preferably, the tension element 1182 is secured to the marker band 1156 such as by adhesives or by mechanical interference. In one implementation, the tension element 1182 extends distally beyond the marker band on a first (e.g., inside) surface of the marker band, then wraps around the distal end of the marker band and extends along a second (e.g., outside) surface in either or both a proximal inclined or circumferential direction to wrap completely around the marker band.

When more than one tension element 1182 or filament bundles are spaced circumferentially apart in the catheter wall, the tension elements 1182 may be placed in a radially symmetrical manner. For example, the angle between two tension elements 1182 with respect to the radial center of the catheter may be about 180 degrees. Alternatively, depending on desired clinical performances (e.g., flexibility, trackability), the tension elements 1182 may be placed in a radially asymmetrical manner. The angle between any two tension elements 1182 with respect to the radial center of the catheter may be less than about 180 degrees, less than or equal to about 165 degrees, less than or equal to about 135 degrees, less than or equal to about 120 degrees, less than or equal to about 90 degrees, less than or equal to about 45 degrees or, less than or equal to about 15 degrees.

The one or more tension element 1182 may comprise materials such as Vectran®, Kevlar®, Polyester®, Spectra®, Dyneema®, Meta-Para-Aramide®, or any combinations thereof. At least one of the one or more tension element 1182 may comprise a single fiber or a multi-fiber bundle, and the fiber or bundle may have a round or rectangular (e.g., ribbon) cross section. The terms fiber or filament do not convey composition, and they may comprise any of a variety of high tensile strength polymers, metals or alloys depending upon design considerations such as the desired tensile failure limit and wall thickness. The cross-sectional dimension of the one or more tension element 1182, as measured in the radial direction, may be no more than about 2 percent, 5 percent, 8 percent, 15 percent, or 20 percent of that of the catheter 10.

The cross-sectional dimension of the one or more tension element 1182, as measured in the radial direction, may be no more than about 0.03 millimeters (about 0.001 inches), no more than about 0.0508 millimeters (about 0.002 inches), no more than about 0.1 millimeters (about 0.004 inches), no more than about 0.15 millimeters (about 0.006 inches), no more than about 0.2 millimeters (about 0.008 inches), or about 0.38 millimeters (about 0.015 inches).

The one or more tension element 1182 may increase the tensile strength of the distal zone of the catheter before failure under tension (e.g., marker band detachment) to at least about 1 pound, at least about 2 pounds, at least about 3 pounds, at least about 4 pounds, at least about 5 pounds, at least about 6 pounds, at least about 7 pounds, at least about 8 pounds, or at least about 10 pounds or more.

Figure 12A:
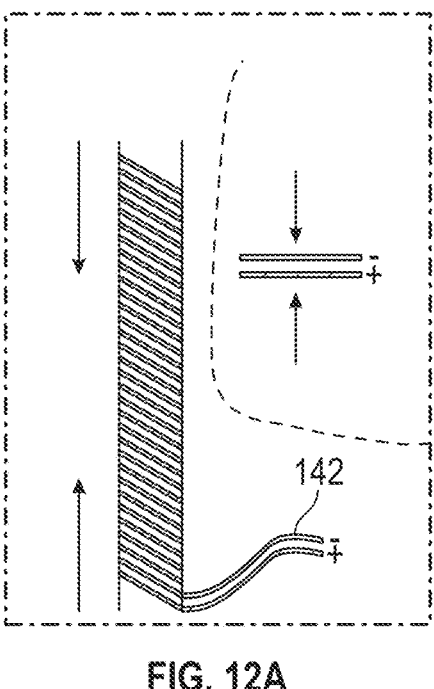
FIGS. 12A and 12B schematically illustrate a force sensor integrated into the sidewall of the catheter.

Any of a variety of sensors may be provided on any of the catheters, hubs, carriages, or table, depending upon the desired data. For example, in some implementations, it may be desirable to measure axial tension or compression force applied to the catheter such as along a force sensing zone. The distal end of the catheter would be built with a similar construction as illustrated in FIG. 11, with a helical coil distal section. But instead of using a single helical coil of nitinol wire, a first conductor 140 and second conductor 142 are wrapped into intertwined helical coils and electrically isolated from each other such as by the plastic/resin of the tubular body. See FIG. 12A. Each coil is in electrical communication with the proximal hub by a unique electrical conductor such as a conductive trace or proximal extension of the wire.

Figure 12B:
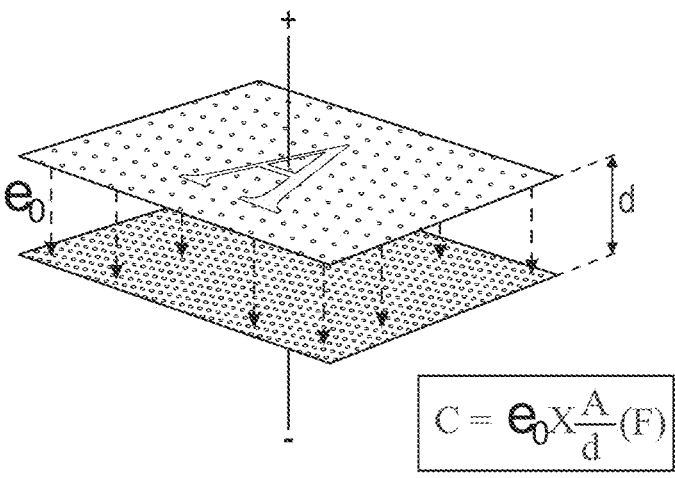

This construction of double, electrically isolated helical coils creates a capacitor. This is roughly equivalent to two plates of nitinol with a plastic layer between them, illustrated in FIG. 12B. The capacitance is inversely proportional to the distance between wires. The only variable that would be changing would be d, the distance between the plates. If an axial compressive force is applied to the catheter, the wires (e.g., conductor 140 and conductor 142) will move closer together, thus increasing the capacitance. If an axial tensile force is applied, the wires will get further apart, decreasing the capacitance. This capacitance can be measured at the proximal end of the catheter, giving a measurement of the force at the helical capacitor. Although referred to as a capacitor, this sensor is measuring the electrical interaction between the two coils of wire. There may be a measurable change in inductance or other resulting change due to applied axial forces.

At least a first helical capacitor may have at least one or five or ten or more complete revolutions of each wire. A capacitor may be located within the distal most 5 or 10 or 20 centimeters of the catheter body to sense forces experienced at the distal end. At least a second capacitor may be provided within the proximal most 5 or 10 or 20 centimeters of the catheter body, to sense forces experienced at the proximal end of the catheter.

Figure 13A:
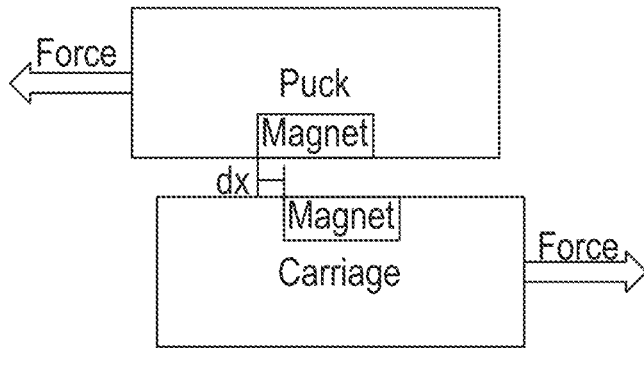
FIGS. 13A and 13B schematically illustrate a sensor for measuring elastic forces at the magnetic coupling between the hub and corresponding carriage.
Figure 13B:

It may also be desirable to measure elastic forces across the magnetic coupling between the hub and corresponding carriage, using the natural springiness (compliance) of the magnetic coupling to measure the force applied to the hub. The magnetic coupling between the hubs and carriages creates a spring. When a force is applied to the hub, the hub will move a small amount relative to the carriage. See FIG. 13A. In robotics, this is called a series elastic actuator. This property can be used to measure the force applied from the carriage to the hub. To measure the force, the relative distance between the hub and the carriage (dx shown in FIG. 13A) is determined and characterize some effective spring constant k between the two components. See FIG. 13B.

The relative distance could be measured in multiple different ways. One method for measuring the relative distance between the hub and carriage is a magnetic sensor (e.g., a Hall effect Sensor between hub and carriage). A magnet is mounted to either the hub or carriage, and a corresponding magnetic sensor is mounted on the other device (carriage or hub). The magnetic sensor might be a hall effect sensor, a magnetoresistive sensor, or another type of magnetic field sensor. Generally, multiple sensors may be used to increase the reliability of the measurement. This reduces noise and reduces interference from external magnetic fields.

Other non-contact distance sensors can also be used. These include optical sensors, inductance sensors, and capacitance sensors. Optical sensors would preferably be configured in a manner that avoids accumulation of blood or other fluid in the interface between the hubs and carriages. In some implementations, wireless (i.e., inductive) power may be used to translate movement and/or transfer information across the sterile barrier between a drive carriage and a hub, for example.

The magnetic coupling between the hub and the carriage has a shear or axial break away threshold which may be about 300 grams or 1000 grams or more. The processor can be configured to compare the axial force applied to the catheter to a preset axial trigger force which if applied to the catheter is perceived to create a risk to the patient. If the trigger force is reached, the processor may be configured to generate a response such as a visual, auditory or tactile feedback to the physician, and/or intervene and shut down further advance of the catheter until a reset is accomplished. An override feature may be provided so the physician can elect to continue to advance the catheter at forces higher than the trigger force, in a situation where the physician believes the incremental force is warranted.

Force and or torque sensing fiber optics (e.g., Fiber Bragg Grating (FBG) sensors) may be built into the catheter side wall to measure the force and/or torque at various locations along the shaft of a catheter or alternatively may be integrated into a guidewire. The fiber measures axial strain, which can be converted into axial force or torque (when wound helically). At least a first FBG sensor can be integrated into a distal sensing zone, proximal sensing zone and/or intermediate sensing zone on the catheter or guidewire, to measure force and or torque in the vicinity of the sensor.

It may also be desirable to understand the three-dimensional configuration of the catheter or guidewire during and/or following transvascular placement. Shape sensing fiber optics such as an array of FBG fibers to sense the shape of catheters and guidewires. By using multiple force sensing fibers that are a known distance from each other, the shape along the length of the catheter/guidewire can be determined.

A resistive strain gauge may be integrated into the body of the catheter or guidewire to measure force or torque. Such as at the distal tip and/or proximal end of the device.

Measurements of force and/or torque applied to the catheter or guidewire shafts can be used to determine applied force and/or torque above a safety threshold. When an applied force and/or torque exceeds a safety threshold, a warning may be provided to a user. Applied force and/or torque measurements may also be used to provide feedback related to better catheter manipulation and control. Applied force and/or torque measurements may also be used with processed fluoroscopic imaging information to determine or characterize distal tip motion.

Absolute position of the hubs (and corresponding catheters) along the length of the table may be determined in a variety of ways. For example, a non-contact magnetic sensor may be configured to directly measure the position of the hubs through the sterile barrier. The same type of sensor can also be configured to measure the position of the carriages. Each hub may have at least one magnet attached to it. The robotic table would have a linear array of corresponding magnetic sensors going the entire length of the table. A processor can be configured to determine the location of the magnet along the length of the linear sensor array, and display axial position information to the physician.

The foregoing may alternatively be accomplished using a non-contact inductive sensor to directly measure the position of the hubs through the sterile barrier. Each hub or carriage may be provided with an inductive "target" in it. The robotic table may be provided with an inductive sensing array over the entire working length of the table. As a further alternative, an absolute linear encoder may be used to directly measure the linear position of the hubs or carriages. The encoder could use any of a variety of different technologies, including optical, magnetic, inductive, and capacitive methods.

In one implementation, a passive (no electrical connections) target coil may be carried by each hub. A linear printed circuit board (PCB) may run the entire working length of the table (e.g., at least about 1.5 meters to about 1.9 meters) configured to ping an interrogator signal which stimulates a return signal from the passive coil. The PCB is configured to identify the return signal and its location.

Axial position of the carriages may be determined using a multi-turn rotary encoder to measure the rotational position of the pulley, which directly correlates to the linear position of the carriage. Direct measurement of the location of the carriage may alternatively be accomplished by recording the number of steps commanded to the stepper motor to measure the rotational position of the pulley, which directly correlates to the linear position of the carriage.

The location of the catheters and guidewires within the anatomy may also be determined by processing the fluoroscopic image with machine vision, such as to determine the distal tip position, distal tip orientation, and/or guidewire shape. Comparing distal tip position or movement or lack thereof to commanded or actual proximal catheter or guidewire movement at the hub, may be used to detect a loss of relative motion, which may be indicative of a device shaft buckling, prolapse, kinking, or a similar outcome (for example, along the device shaft length inside the body (e.g., in the aorta) or outside the body between hubs. The processing may be done in real time to provide position/orientation data at up to 30 Hertz, although this technique would only provide data while the fluoroscopic imaging is turned on. In some embodiments, machine vision algorithms can be used to generate and suggest optimal catheter manipulations to access or reach anatomical landmarks, similar to driver assist. The machine vision algorithms may utilize data to automatically drive the catheters depending on the anatomy presented by fluoroscopy.

Figure 14:
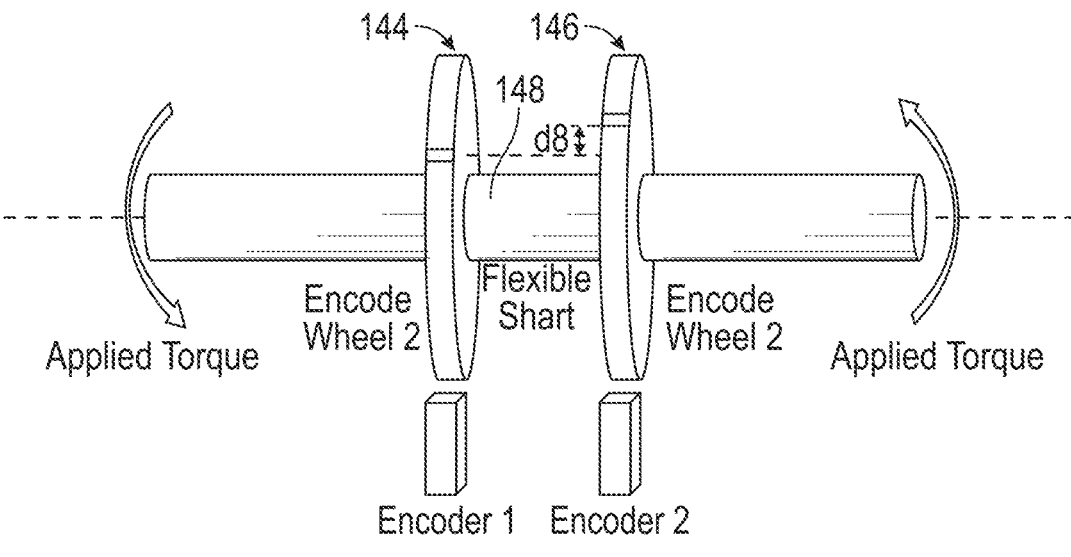
FIG. 14 schematically illustrates a dual encoder torque sensor for use with a catheter of the present disclosure.

Proximal torque applied to the catheter or guidewire shaft may be determined using a dual encoder torque sensor. Referring to FIG. 14, a first encoder 144 and a second encoder 146 may be spaced axially apart along the shaft 148, for measuring the difference in angle over a length of flexible catheter/tube. The difference in angle is interpolated as a torque, since the catheter/tube has a known torsional stiffness. As torque is applied to the shaft, the slightly flexible portion of the shaft will twist. The difference between the angles measured by the encoders ($d\theta$) tells us the torque. $T=k*d\theta$, where k is the torsional stiffness.

Confirming the absence of bubbles in fluid lines may also be accomplished using bubble sensors, particularly where the physician is remote from the patient. This may be accomplished using a non-contact ultrasonic sensor that measures the intensity and doppler shift of the reflected ultrasound through the sidewall of fluid tubing to detect bubbles and measure fluid flow rate or fluid level. An ultrasonic or optical sensor may be positioned adjacent an incoming fluid flow path within the hub, or in a supply line leading to the hub. To detect the presence of air bubbles in the infusion line (that is formed of ultrasonically or optically transmissive material) the sensor may include a signal source on a first side of the flow path and a receiver on a second side of the flow path to measure transmission through the liquid passing through the tube to detect bubbles. Alternatively, a reflected ultrasound signal may be detected from the same side of the flow path as the source due to the relatively high echogenicity of bubbles.

Preferably, a bubble removal system is automatically activated upon detection of in line bubbles. A processor may be configured to activate a valve positioned in the flow path downstream of the bubble detector, upon the detection of bubbles. The valve diverts a column of fluid out of the flow path to the patient and into a reservoir. Once bubbles are no longer detected in the flow path and after the volume of fluid in the flow path between the detector and the valve has passed through the valve, the valve may be activated to reconnect the source of fluid with the patient through the flow path. In other embodiments, the bubble removal system can include a pump and control system upstream of the bubble detector for removal of in line bubbles. A processor may be configured to activate the pump upon detection of bubbles to reverse the fluid flow and clear the bubbles into a waste reservoir before reestablishing bubble free forward flow.

Figure 15:
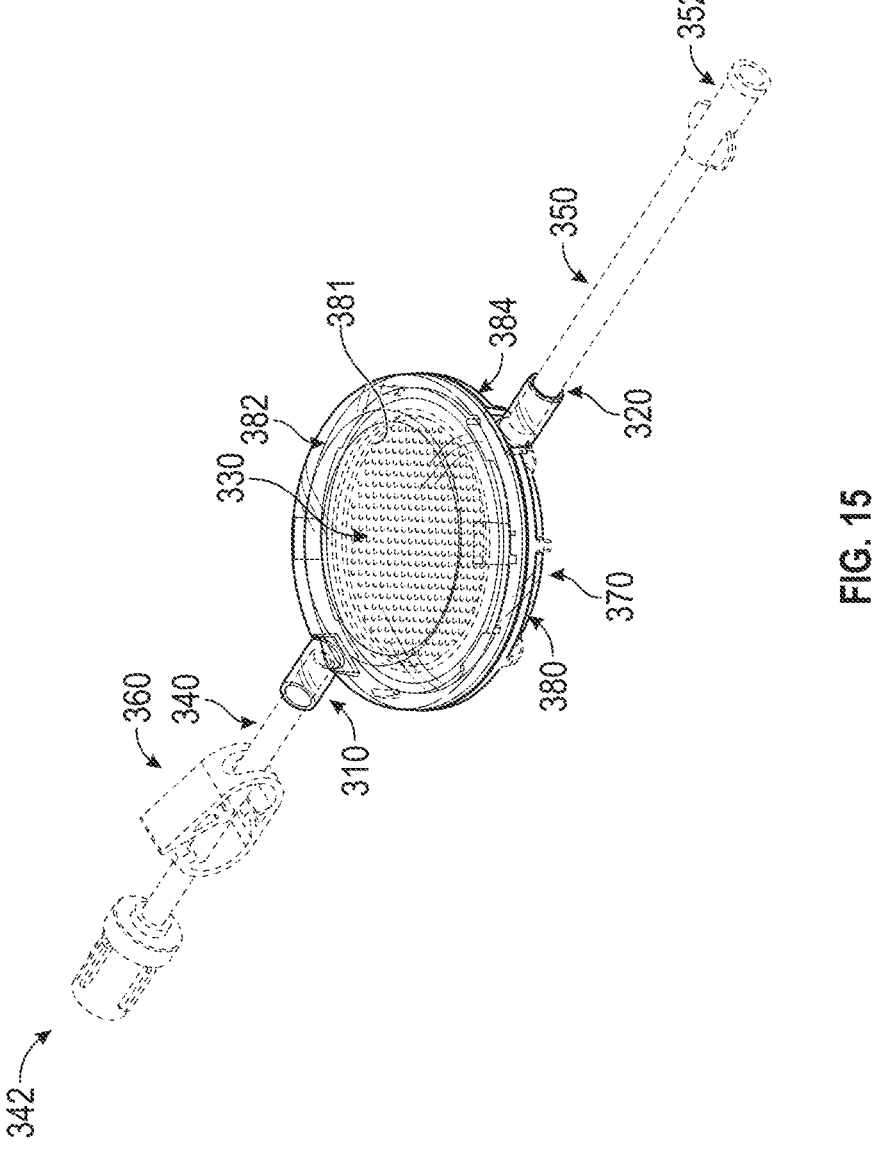
FIG. 15 illustrates a clot capture and visualization device that can be integrated into a hub and/or connected to an aspiration line.

It may additionally be desirable for the physician to be able to view aspirated clot at a location within the sterile field and preferably as close to the patient as practical for fluid management purposes. This may be accomplished by providing a clot retrieval device mounted on the hub, or in an aspiration line leading away from the hub in the direction of the pump. Referring to FIG. 15, one example of a clot retrieval device 370 can include a body 380 enclosing a chamber 381 which communicates with a first port 310 and a second port 320.

In some embodiments, the body 380 includes a housing having a top portion 382 and a bottom portion 384. The body 380 may include a filter 330 positioned in the chamber 381 between the top portion 382, and the bottom portion 384. In some examples, the first port 310 is configured to connect to a first end of a first tube 340 that is fluidly connected to a proximal end of an aspiration catheter.

In an embodiment that is configured to be connected downstream from the hub, the first tube 340 includes a connector 342 positioned at a second end of the first tube 340 that is configured to engage or mate with a corresponding connector on or in communication with the hub. The first port 310 directly communicates with the chamber on the upstream (e.g., top side) of the filter, and the second port 320 directly communicates with the chamber on the downstream (e.g., bottom side) of the filter to facilitate direct visualization of material caught on the upstream side of the filter.

In an implementation configured for remote operation, any of a variety of sensors may be provided to detect clot passing through the aspiration line and/or trapped in the filter, such as an optical sensor, pressure sensor, flow rate sensor, ultrasound sensor or others known in the art.

In some embodiments, the second port 320 is configured to connect to a first end of a second tube 350 that is fluidly connected to an aspiration source (e.g., a pump). In some embodiments, the second tube 350 includes a connector 352 positioned at a second end of the second tube 350 that is configured to engage or mate with a corresponding connector on the pump.

In some examples, the system 300 can include an on-off valve 360 such as a clamp. The clamp can be positioned in between the filter 330 and the patient, such as over the first tube 340 to allow the user to engage the clamp and provide flow control by isolating the patient from the clot retrieval device 370. Closing the valve 360 and operating the remote vacuum pump (not illustrated) causes the canister associated with the vacuum pump and the chamber 381 to reach the same low pressure. Due to the short distance and small line volume of the lumen between the chamber 381 end the distal end of the catheter, a sharp negative pressure spike is experienced at the distal end of the catheter rapidly following opening of the valve 360. Additional details are disclosed in U.S. Pat. No. 11,259,821 issued Mar. 1, 2022 to Buck et al., entitled Aspiration System with Accelerated Response, the entirety of which is hereby expressly incorporated by reference herein. In some embodiments, a vacuum may be cycled against a clot to retrieve the clot. The vacuum may be automatically and robotically controlled to remove the clot.

The body 380 can have a top surface spaced apart from a bottom surface by a tubular side wall. In the illustrated implementation, the top and bottom surfaces are substantially circular, and spaced apart by a cylindrical side wall. The top surface may have a diameter that is at least about three times, or five times or more than the axial length (transverse to the top and bottom surfaces) of the side wall, to produce a generally disc shaped housing. Preferably at least a portion of the top wall is optically transparent to improve clot visualization once it is trapped in the clot retrieval device 370. Additional details may be found in U.S. Patent Application No. 63/256,743, the entirety of which is hereby incorporated by reference herein.

In some examples, the body 380 can include a flush port (not illustrated) that is configured to allow the injection of an optically transparent media such as air, saline or other fluid into the chamber 381 to clear an optical path between the window and the filter to improve clot visualization once it is trapped in the filter 330.

The foregoing represents certain specific implementations of a drive table and associated components and catheters. A wide variety of different drive table constructions can be made, for supporting and axially advancing and retracting two or three or four or more drive magnet assemblies to robotically drive interventional devices, fluid elements, and electrical umbilical elements for communicating electrical signals and fluids to the catheter hubs, as will be appreciated by those of skill in the art in view of the disclosure herein. Additional details may be found in U.S. patent application Ser. No. 17/527,393, the entirety of which is hereby incorporated by reference herein.

While the foregoing describes robotically driven interventional devices and manually driven interventional devices, the devices may be manually driven, robotically driven, or a combination of both manually and robotically driven interventional devices, as will be appreciated by those of skill in the art in view of the disclosure herein.

In a manual catheter procedure, a physician often stands to a patient's right side and inserts interventional devices from the physician's right to the physician's left when facing the patient. Certain embodiments of robotic control mechanisms described herein may be configured to mimic the movements a physician makes in a manual catheter procedure. For example, certain embodiments of robotic control mechanisms described herein include controls that are operated by left/right motion from the perspective of a user (e.g., a physician) operating the control to command insertion/withdrawal of an interventional device. Certain embodiments of robotic control mechanisms described herein include controls that are operated by rolling or rotational motion from the perspective of a user (e.g., a physician) operating the control to command roll or rotation of an interventional device.

Figure 16A:
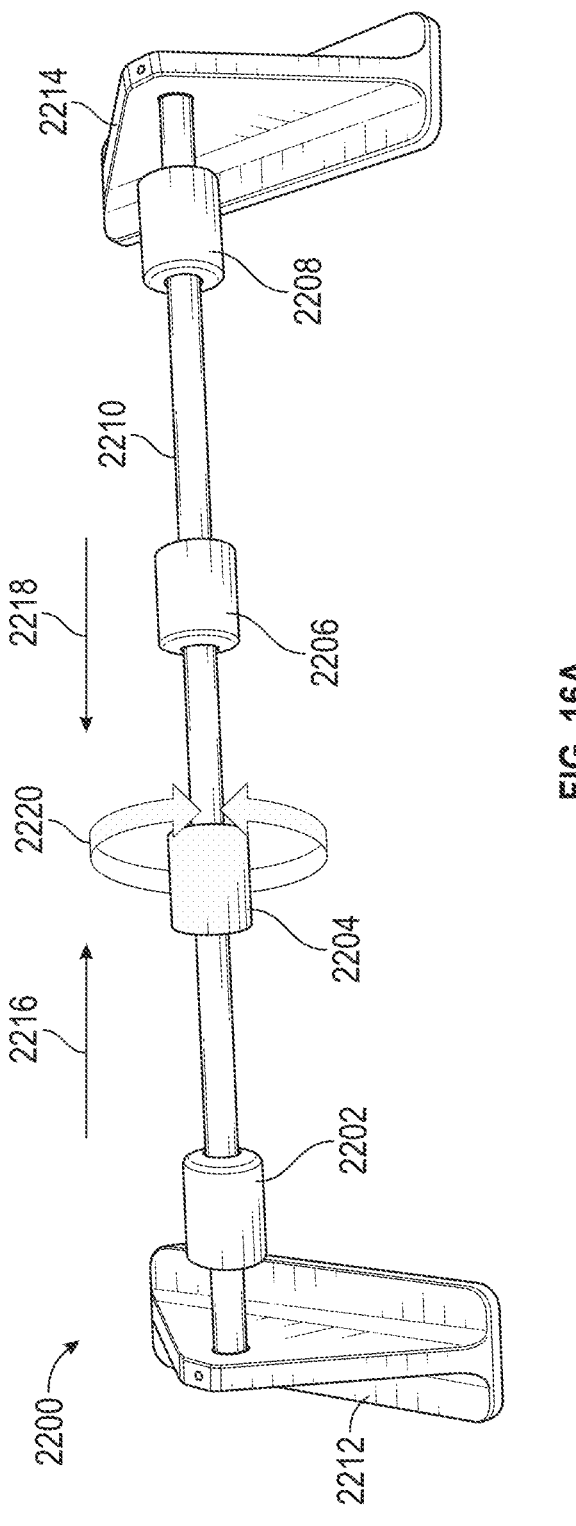
FIGS. 16A-16C illustrate an example control mechanism for manipulating interventional devices driven by respective hubs.
Figure 16B:
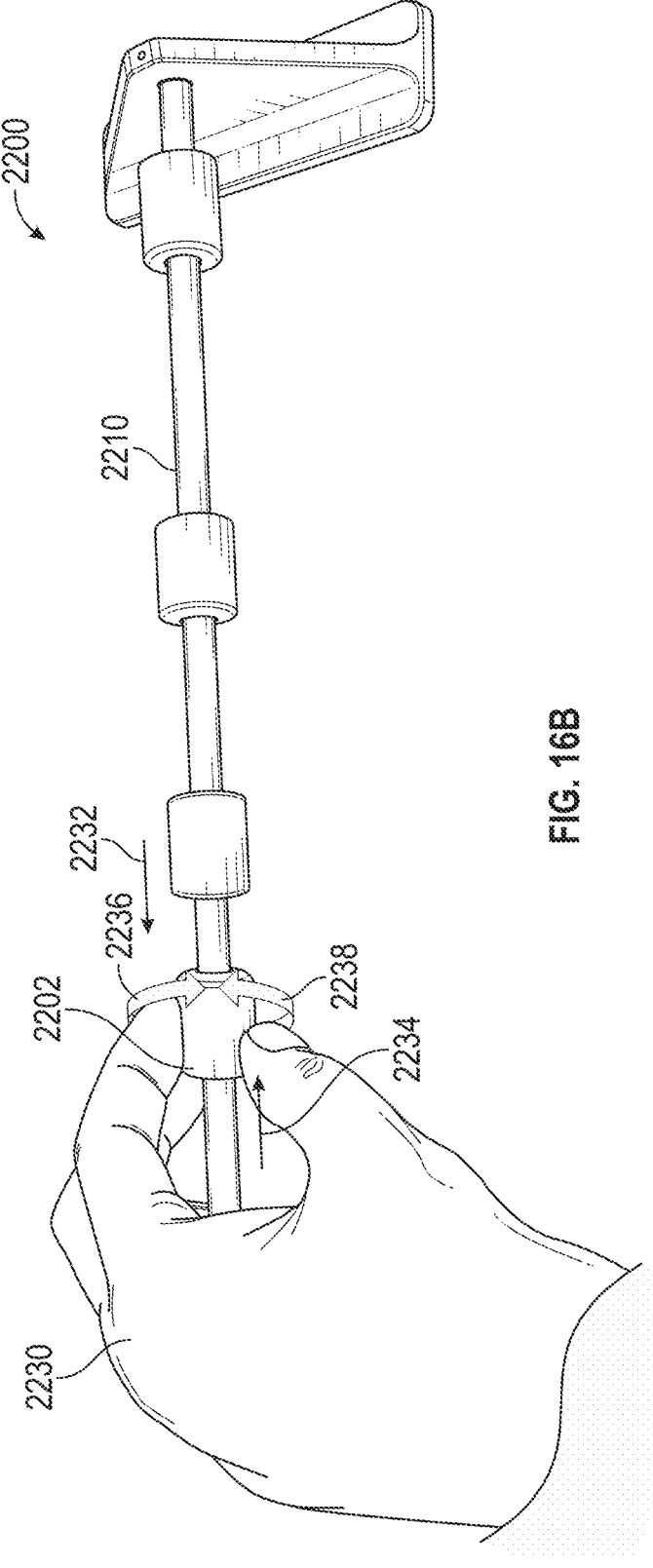
Figure 16C:
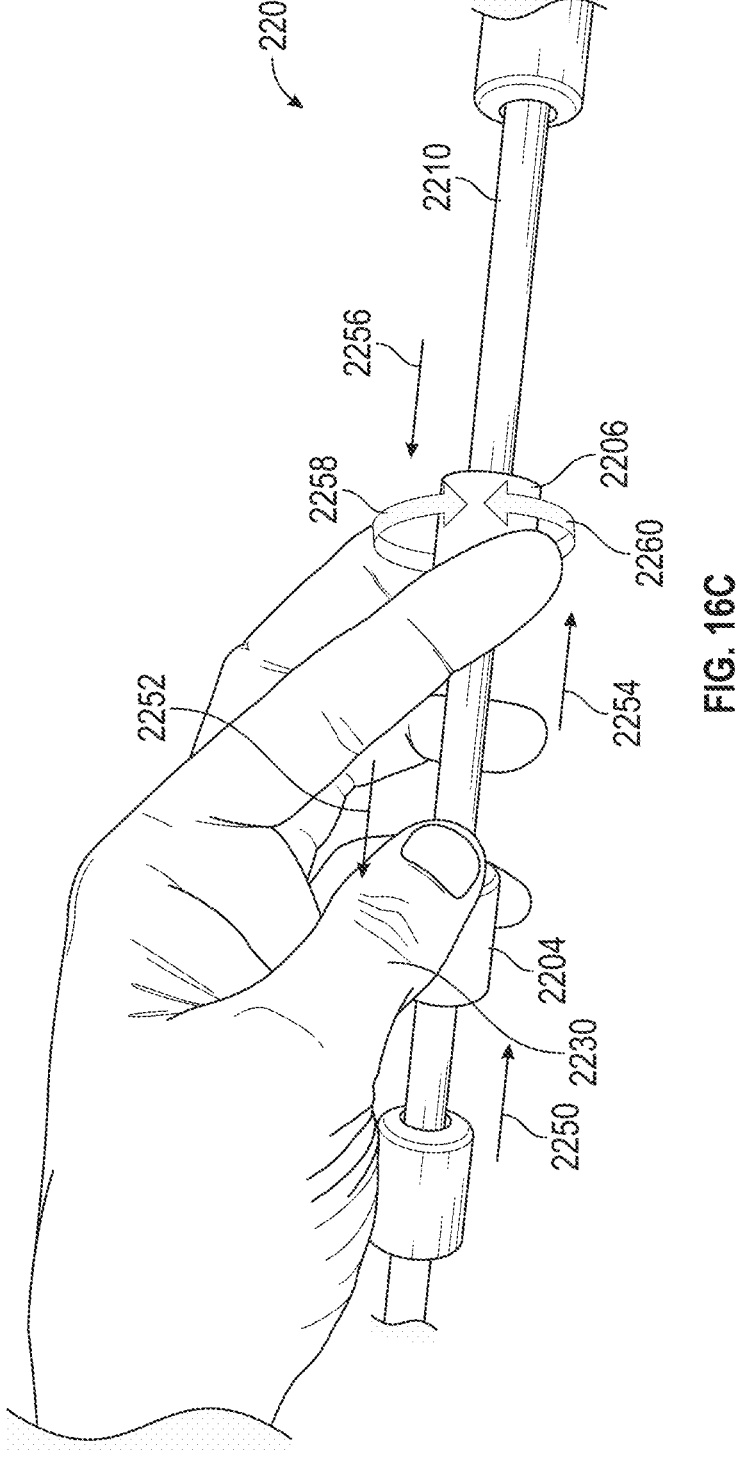

FIGS. 16A-16C illustrate an example control mechanism 2200 for manipulating interventional devices driven by (or otherwise associated with) respective hubs. For example, each hub may be manipulated and/or otherwise moved using at least one control installed in control mechanism 2200. Each control may be adapted to move a unique hub and associated interventional device during an interventional procedure.

As shown in FIG. 16A, the control mechanism 2200 include a first control 2202, a second control 2204, a third control 2206, and a fourth control 2208. More or fewer controls may be provided, depending upon the intended interventional devices configuration. Each control 2202-2208 is movably carried on a shaft 2210 that is coupled to a distal bracket 2212 and to a proximal bracket 2214. The controls 2202-2208 may advance distally or retract proximally on the shaft 2210, as indicated by arrow 2218 and arrow 2216. In addition, each control 2202-2208 may also be rotated about the shaft 2210, as indicated by arrow 2220. Each control movement may trigger a responsive movement in a corresponding carriage on the support table, which may in turn drive movement of a corresponding hub as has been discussed.

The control mechanism 2200 may be positioned on or near to a patient support table having a set of hubs and catheters/interventional devices. In some implementations, the control mechanism 2200 may be positioned remote from the support table such as behind a radiation shield or in a different room or different geographical location in a telemedicine implementation.

Each control 2202-2208 may correspond to and drive movement of a hub and/or a hub and interventional device combination. For example, the control 2202 may be configured to drive hub 30 (FIG. 3F) to move an interventional device such as an 0.088 inch guide catheter corresponding to the hub 30. Similarly, the control 2204 may be configured to drive hub 28 (122) to move an interventional device such as an 0.071 inch procedure catheter. The control 2206 may be configured to drive hub 126 to move an interventional device such as a steerable access catheter. The control 2208 may be configured to drive hub 26 to axially and rotationally move an interventional device such as a guidewire.

FIG. 16B illustrates an example of manually manipulating the control 2202 on control mechanism 2200. In operation, if the user 2230 moves the control 2202 axially along shaft 2210 and distally, as shown by arrow 2232, a corresponding coupled hub and/or interventional device may move responsively in the same direction by a same or scaled amount. If the user 2230 rotates the control 2202 about the shaft 2210 and advances the control proximally, as shown by arrow 2234, a corresponding coupled interventional device will responsively move rotationally and proximally by a same or scaled amount. If the user 2230 moves the control 2202 rotationally about the shaft 2210, as shown by arrow 2236 or arrow 2238, a corresponding coupled hub will drive the corresponding interventional device rotationally in the same direction and/or by a same or scaled amount.

Other axes and degrees of freedom may be defined to enable control 2202 to perform movements that may be translated to movement of hubs and/or interventional devices. For example, the control mechanism may be provided with one or more deflection controls configured to initiate a lateral deflection in a deflection zone on the corresponding interventional device. The control mechanism may further be provided with one or more fluidics controls for controlling components of a fluidics system, for example, to initiate and/or terminate the introduction of fluids to a catheter (e.g., saline, contrast, etc.) and/or to initiate and/or terminate aspiration of fluids from a catheter.

Axial movement of a control may be configured to move the coupled hub on a 1:1 basis, or on a non 1:1 scaled basis. For example, if the user 2230 advances the control 2202 about 5 millimeters distally along the shaft 2210, then the corresponding hub may responsively move 5 millimeters in the distal direction.

If the user 2230 rotates the control 2202 about its rotational axis by 5 degrees, the coupled hub will cause the corresponding interventional device to rotate on a 1:1 basis or on a non 1:1 scaled basis. The scaled amount may be selected to reduce or increase the amount of distance and rotation that a hub and/or interventional device moves in accordance with the control movement.

In some implementations, the scaled amount described herein may be determined using a scale factor. The scale factor may apply to one or both translational and rotational movement. In some implementations, a first scale factor is selected for translational movement and a second scale factor, different than the first scale factor, is selected for rotational movement. The axial scaling factor may drive proximal catheter movement at a faster speed than distal catheter movement for a given proximal or distal manipulation of the control.

The rotational scale factor may be 1:1 while the axial scale factor may move the hub by a greater distance than movement of the control such that hub travel to control travel is at least about 2:1 or 5:1 or 10:1 or more depending upon the desired axial length of the control assembly.

The control mechanism 2200 may be configured to enable the clinician to adjust the scale factor for different parts of the procedure. For example, distal advance of the procedure catheter and access catheter through the guide catheter and up to the selected ostium may desirably be accomplished in a 'fast' mode. But more distal travel into the neuro vasculature may desirably be accomplished in a relatively slow mode by actuation of a speed control.

In another implementation, one or more controls may be configured to progressively drive advance or retraction speeds of the corresponding hub and associated catheter. For example, distal control 2202 may drive the guide catheter. A slight distal movement of the control 2202 may advance the guide catheter distally at a slow speed, while advancing the control 2202 by a greater distance distally increases the rate of distal travel of the guide catheter.

Controlling the speed of the corresponding hubs either axially or both axially and rotationally may enhance the overall speed of the procedure. For example, advance of the various devices from the femoral access point up to the aortic arch may desirably be accomplished at a faster rate than more distal navigation closer to the treatment site. Also proximal retraction of the various devices, particularly the guidewire, access catheter and procedure catheter may be desirably accomplished at a relatively higher speeds than distal advance.

FIG. 16C illustrates another example of manually manipulating a control on the control mechanism 2200 to move hubs and/or other interventional devices. In some implementations, two or more controls 2202-2208 may be moved in combination to trigger movement of one or more hubs and/or related interventional devices. In the depicted example, the user 2230 moves control 2204 and control 2206 in combination (e.g., sequentially, simultaneously) such as to simultaneously move the 0.088 guide catheter and the 0.071 aspiration catheter as a unit. Example movement of control 2204 may include axial proximal movement in the directions shown by arrows 2250. Sequentially or simultaneously, the user 2230 may move control 2206 axially in either of the directions shown by arrows 2254 and 2256 while also moving control 2206 rotationally in either of the directions shown by arrows 2258 and 2260. In some embodiments, may simultaneously control components of a fluidics system (e.g., for introduction of fluids and/or aspiration) while controlling axial and/or rotational movement of a catheter.

Figure 19A:
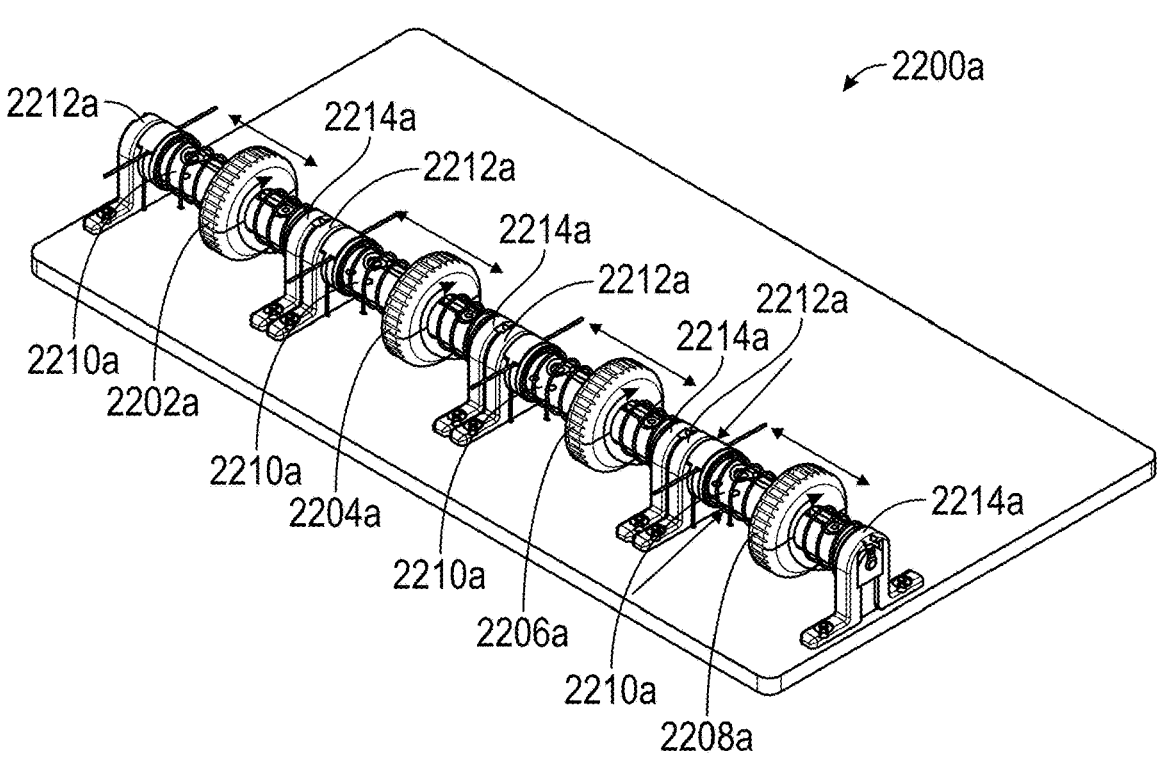
FIGS. 19A-19C illustrate an example control mechanism for manipulating interventional devices driven by respective hubs.
Figure 19B:
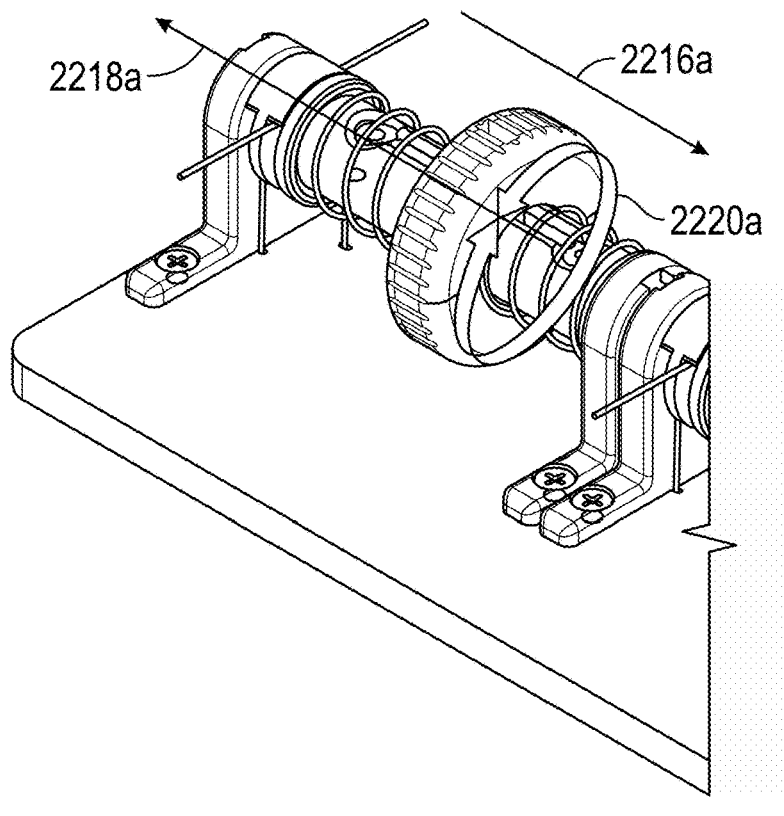
Figure 19C:

FIGS. 19A-19C illustrate another example of a control mechanism for manipulating interventional devices driven by (or otherwise associated with) respective hubs. In certain embodiments, each hub and/or interventional device may be manipulated and/or otherwise moved using at least one control installed in the control mechanism. Each control may be adapted to move a unique hub and/or interventional device during an interventional procedure. For example, each control movement may trigger a responsive movement in a corresponding hub and/or interventional device. In certain embodiments, at least some movements of each control may trigger a responsive movement in a corresponding carriage on the support table, which may in turn drive movement of a corresponding hub.

As shown in FIG. 19A, the control mechanism 2200a can include a first control 2202a, a second control 2204a, a third control 2206a, and a fourth control 2208a. More or fewer controls may be provided, depending upon the intended interventional device configuration. Each control 2202a-2208a can be movably carried on a shaft 2210a that is coupled to a distal bracket 2212a and to a proximal bracket 2214a. The controls 2202a-2208a may advance distally or retract proximally along the shaft 2210a, as indicated by arrow 2218a and arrow 2216a, respectively. Additionally or alternatively, each control 2202a-2208a may be rotated about the shaft 2210a, as indicated by arrow 2220a.

Each control 2202a-2208a can have a starting axial and/or rotational position. The control mechanism can be configured so that each control 2202a-2208a returns to its starting axial and/or rotational position when the controls 2202a-2208a are not being manipulated by a user.

The control mechanism 2200a may be positioned on or near to a patient support table having a set of hubs and catheters/interventional devices. In some implementations, the control mechanism 2200a may be positioned remote from the support table such as behind a radiation shield or in a different room or different geographical location in a telemedicine implementation.

Each control 2202a-2208a may correspond to and drive movement of a hub and/or interventional device. In certain embodiments, the control 2202a may be configured to move (e.g., axially and/or rotationally) an interventional device such as an 0.088 inch guide catheter (e.g., guide catheter 31 or guide catheter 2906), for example, by driving a hub (e.g., hub 30 or hub 2914) associated with the interventional device. Similarly, the control 2204a may be configured to move (e.g., axially and/or rotationally) an interventional device such as an 0.071 inch procedure catheter (e.g., catheter 29, catheter 120, or catheter 2904), for example, by driving a hub (e.g., hub 28, hub 122, or hub 2912) associated with the interventional device. The control 2206a may be configured to move (e.g., axially and/or rotationally) an interventional device such as a steerable access catheter (e.g., catheter 124 or catheter 2902), for example, by driving a hub (e.g., hub 126 or hub 2910) associated with the interventional device. The control 2208a may be configured to move (e.g., axially and/or rotationally) an interventional device such as a guidewire (e.g., guidewire 27 or guidewire 2907), for example, by driving a hub (e.g., hub 26 or hub 2909) associated with the interventional device.

In operation, if the user moves the control 2202a axially along shaft 2210a and distally, as shown by arrow 2218a, or proximally, as shown by arrow 2116a, a corresponding coupled hub and/or interventional device may move responsively in the same direction at a predefined axial or linear velocity. The corresponding coupled hub and/or interventional device can continue to move in the same direction at the predefined linear velocity until the user releases (e.g., stops manipulating) the control 2202a or further moves the control. When the user stops manipulating the control 2202a, the control 2202a can return to its starting axial position. If the user moves the control 2202a rotationally about the shaft 2210a (e.g., clockwise or counterclockwise), as shown by arrow 2220a, the corresponding interventional device can be driven rotationally (e.g., by a corresponding hub) in the same direction at a predefined angular velocity. When the user stops manipulating the control 2202a, the control 2202a can return to its starting rotational position. If the user rotates the control 2202a about the shaft 2210a and advances the control axially (either distally or proximally), a corresponding coupled interventional device can responsively move rotationally at a predefined angular velocity and proximally at a predefined linear velocity. The corresponding coupled interventional device can continue to move rotationally at the predefined angular velocity and can continue to move axially at the predefined linear velocity until the user releases (e.g., stops manipulating) the control 2202a or further moves the control. When the user stops manipulating the control 2202a, the control 2202a can return to its starting axial and rotational position.

One or more linear position sensors can be used to measure the axial movement of each control 2202a-2208a relative to the starting position of each control. For example, the one or more linear sensors can be configured to measure the distance (e.g., 5 mm) traveled by a control from its starting position. In some embodiments, the predefined linear velocity at which the corresponding hub and/or interventional device will move can depend on the measurement by the one or more linear position sensors. The one or more linear position sensors can include, for example, a linear potentiometer. In some cases, the control mechanism 2200a can include a linear position sensor for each control.

Similarly, one or more rotation sensors can be used to measure the rotational movement of each control 2202a-2208a relative to the starting position of each control. For example, the one or more rotation sensors can be configured to measure the rotational movement (e.g., 5 degrees) of a control from its starting position. The predefined angular velocity at which the corresponding interventional device will move can depend on the measurement by the one or more rotation sensors. The one or more rotation sensors can include, for example, an encoder, a potentiometer, a hall effect sensor, or a combination thereof. In some cases, the control mechanism 2200a can include a rotation sensor for each control.

Axial movement of a control may be configured to move a corresponding hub and/or interventional device at a predefined linear velocity. For example, if the user advances the control 2202a about 5 millimeters distally along the shaft 2210a, then the corresponding hub and/or interventional device may responsively move distally at a linear velocity of 5 mm/second. The predefined linear velocity can vary according to the user's movement of the control. For example, if the user advances the control 2202a about 10 millimeters proximally along the shaft 2210a, then the corresponding hub and/or interventional device may responsively move proximally at a linear velocity of 10 mm/second. The corresponding hub and/or interventional device can continue to move in the direction of axial movement of the control 2202a at the predefined linear velocity as long the user is maintaining the control at the same axial position. The corresponding hub and/or interventional device may stop moving when the user stops manipulating the control and the control returns to its starting axial position.

Axial movement of a control may be configured to move the corresponding hub and/or interventional device on a 1:1 basis, or on a non 1:1 scaled basis. For example, if the user advances the control 2202a about 5 millimeters distally along the shaft 2210a, then the corresponding hub may responsively move at a predefined linear velocity of 5 mm/second in the distal direction.

Rotational movement of a control may be configured to move the coupled hub at a predefined rotational velocity. For example, if the user rotates the control 2202a about 5 degrees clockwise about the shaft 2210a, then the corresponding interventional device may responsively rotate clockwise at an angular velocity of 5 degrees/second. The predefined angular velocity can vary according to the user's movement of the control. For example, if the user rotates the control 2202a about 10 degrees counterclockwise about the shaft 2210a, then the corresponding interventional device may responsively rotate counterclockwise at an angular velocity of 10 degrees/second. The corresponding interventional device can continue to move in the direction of rotational movement of the control 2202a at the predefined angular velocity as long as the user is maintaining the control at the same rotational position. The interventional device may stop moving when the user stops manipulating the control and the control returns to its starting rotational position.

Rotational movement of a control may be configured to move the coupled interventional device on a 1:1 basis, or on a non 1:1 scaled basis. For example, if the user rotates the control 2202a about its rotational axis by 5 degrees, then the corresponding interventional device may responsively move at a predefined angular velocity of 5 degrees/second.

The control mechanism 2200a can be configured to enable the clinician to adjust the predefined linear velocity and/or the predefined angular velocity. For example, distal advance of a procedure catheter and an access catheter through a guide catheter and up to the selected ostium, as described herein, may desirably be accomplished in a 'fast' mode. More distal travel into the neuro vasculature may desirably be accomplished in a relatively slow mode by actuation of a speed control. For example, for stages of a procedure where the clinician wishes to proceed in a "fast" mode, the clinician may adjust the predefined linear velocity to 10 mm/second when the control moves 5 mm distally or proximally along the shaft. For stages of the procedure where the clinician wishes to proceed in a relatively slow mode, the clinician may adjust the predefined linear velocity to 2 mm/second when the control moves 5 mm distally or proximally along the shaft.

While the foregoing describes example operations of the control 2202a, it will be understood by one of skill in the art that any of the controls 2204a, 2206a, and 2208a may be operated in the same manner. In certain embodiments, each of the controls 2202a, 2204a, 2206a, and 2208a can control axial and rotational movement of corresponding interventional devices. In other embodiments, one or more of the controls 2202a, 2204a, 2206a, and 2208a may control only axial movement or only rotational movement of a corresponding interventional device.

Figure 20:
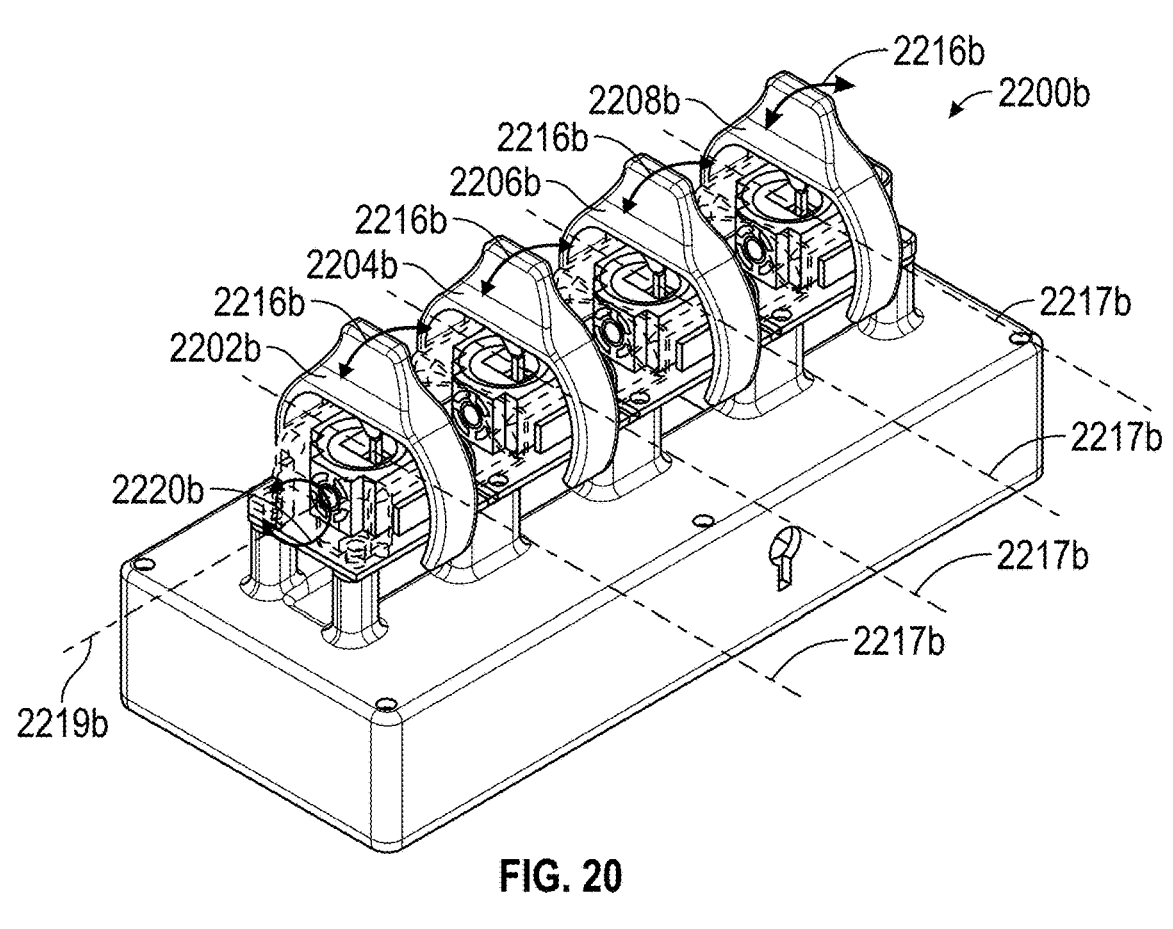
FIGS. 20-21 illustrate an example control mechanism for manipulating interventional devices driven by respective hubs.

FIG. 20 illustrates an additional embodiment of a control mechanism 2200b for manipulating interventional devices driven by (or otherwise associated with) respective hubs. The control mechanism of FIG. 20 may include any of the same or similar features and/or functions as any of the other control mechanisms described herein. For example, each hub and/or interventional device may be manipulated and/or otherwise moved using at least one control installed in the control mechanism. Each control can include a joystick (e.g., a two-axis joystick). In certain embodiments, a joystick may provide for improved grasp and more precise movements in comparison to other controls. The size and feel of the joysticks can be customized to suit a physician's particular needs. For example, some physicians may prefer larger or smaller joysticks. Each control may be adapted to move a unique hub and/or interventional device during an interventional procedure.

As shown in FIG. 20, the control mechanism 2200b can include a first control 2202b, a second control 2204b, a third control 2206b, and a fourth control 2208b. More or fewer controls may be provided, depending upon the intended interventional device configuration. Each control 2202b-2208b may rotate around a first axis 2217b, as indicated by arrows 2216b, to cause axial movement of a corresponding hub and/or interventional device. In addition, each control 2202b-2208b may rotate about a second axis 2219b, as indicated by arrow 2220*b* to cause rotational movement of a corresponding hub and/or interventional device. The second axis 2219*b* may be the same axis for each control 2202*b*-2208*b*. The first axis 2217*b* for each control 2202*b*-2208*b* can be transverse to the second axis 2219*b*. Each control movement may trigger a responsive movement in a corresponding hub and/or interventional device. In certain embodiments, at least some movements of each control may trigger a responsive movement in a corresponding carriage on the support table, which may in turn drive movement of a corresponding hub.

Each control 2202*b*-2208*b* can have a starting position. The control mechanism can be configured so that each control 2202*b*-2208*b* returns to its starting position when the controls 2202*b*-2208*b* are not being manipulated by a user.

The control mechanism 2200*b* may be positioned on or near to a patient support table having a set of hubs and catheters/interventional devices. In some implementations, the control mechanism 2200*b* may be positioned remote from the support table such as behind a radiation shield or in a different room or different geographical location in a telemedicine implementation.

Each control 2202*b*-2208*b* may correspond to and drive movement of a hub and/or interventional device. In certain embodiments, the control 2202*b* may be configured to move (e.g., axially and/or rotationally) an interventional device such as an 0.088 inch guide catheter (e.g., guide catheter 31 or guide catheter 2906), for example, by driving a hub (e.g., hub 30 or hub 2914) associated with the interventional device. Similarly, the control 2204*b* may be configured to move (e.g., axially and/or rotationally) an interventional device such as an 0.071 inch procedure catheter (e.g., catheter 29, catheter 120, or catheter 2904), for example, by driving a hub (e.g., hub 28, hub 122, or hub 2912) associated with the interventional device. The control 2206*b* may be configured to move (e.g., axially and/or rotationally) an interventional device such as a steerable access catheter (e.g., catheter 124 or catheter 2902), for example, by driving a hub (e.g., hub 126 or hub 2910) associated with the interventional device. The control 2208*b* may be configured to move (e.g., axially and/or rotationally) an interventional device such as a guidewire (e.g., guidewire 27 or guidewire 2907), for example, by driving a hub (e.g., hub 26 or hub 2909) associated with the interventional device.

In operation, if the user rotates the control 2202*b* (e.g., counterclockwise or clockwise) about the axis 2217*b*, as shown by the arrow 2216*b*, a corresponding coupled hub and/or interventional device may axially move responsively at a predefined linear velocity (e.g., proximally for counterclockwise movement of the control 2202*b* and distally for clockwise movement of the control 2217*b*). The corresponding coupled hub and/or interventional device can continue to move in the same direction at the predefined linear velocity until the user releases (e.g., stops manipulating) the control 2202*b* or further moves the control 2202*b*. When the user stops manipulating the control 2202*b*, the control 2202*b* can return to its starting position. If the user moves the control 2202*b* rotationally about the axis 2219*b* (e.g., clockwise or counterclockwise), as shown by the arrow 2220*b*, the corresponding interventional device can be driven rotationally (e.g., by a corresponding hub) in the same direction at a predefined angular velocity. When the user stops manipulating the control 2202*b*, the control 2202*b* can return to its starting position. If the user moves the control 2202*b* rotationally about the axis 2217*b*, as shown by of the arrow 2216*b*, and rotationally about the axis 2219*b*, as shown by arrow 2220*b*, a corresponding coupled interventional device can responsively move rotationally at a predefined angular velocity (in response to movement of the control 2202*b* about the axis 2219*b*) and axially at a predefined linear velocity (in response to movement of the control 2202*b* about the axis 2217*b*). The corresponding coupled interventional device can continue to move rotationally at the predefined angular velocity and can continue to move axially at the predefined linear velocity until the user releases (e.g., stops manipulating) the control 2202*b* or further moves the control 2202*b*. When the user stops manipulating the control 2202*b*, the control 2202*b* can return to its starting position.

One or more rotation sensors can be used to measure the rotational movement of each control 2202*b*-2208*b* about the axis 2217*b* and/or the axis 2219*b* relative to the starting position of each control. For example, the one or more rotation sensors can be configured to measure the rotational movement (e.g., 5 degrees) of a control from its starting position. The linear velocity and/or predefined angular velocity at which the corresponding interventional device will move can depend on the measurement by the one or more rotation sensors. The one or more rotation sensors can include, for example, an encoder, a potentiometer, a hall effect sensor, or a combination thereof. In some cases, the control mechanism 2200*b* can include one or more rotation sensors for each control. In some embodiments, the control mechanism 2200*b* can include separate rotation sensors for measuring rotation about the axis 2217*b* and rotation about the axis 2219*b*.

Rotational movement of a control about the axis 2217*b*, as shown by the arrows 2216*b*, may be configured to move the corresponding hub and/or interventional device at a predefined linear velocity. For example, if the user moves the control 2202*b* (e.g., counterclockwise) about 5 degrees about the axis 2217*b*, then the corresponding hub and/or interventional device may responsively move (e.g., proximally) at a linear velocity of 5 mm/second. The predefined linear velocity can vary according to the user's movement of the control. For example, if the user moves the control 2202*b* about 10 degrees about the axis 2217*b*, then the corresponding hub may responsively move axially at a linear velocity of 10 mm/second. The corresponding hub and/or interventional device can continue to move axially at the predefined linear velocity as long the user maintains the control at the same rotational position. The corresponding hub can stop moving as soon as the user stops manipulating the control and the control can return to its starting position.

Rotational movement of a control about the axis 2217*b* may be configured to move the corresponding hub and/or interventional device on a 1:1 basis, or on a non 1:1 scaled basis. For example, if the user moves the control 2202*b* rotationally about 5 degrees in the direction of arrow 2216*b*, then the corresponding hub may responsively move at a predefined linear velocity of 5 mm/second in a corresponding direction.

Rotational movement of a control about the axis 2219*b* may be configured to move the coupled hub at a predefined rotational velocity. For example, if the user rotates the control 2202*b* about the axis 2219*b* about 5 degrees clockwise, then the corresponding interventional device may responsively rotate clockwise at an angular velocity of 5 degrees/second. The predefined angular velocity can vary according to the user's movement of the control. For example, if the user rotates the control 2202*b* about the axis 2219*b* about 10 degrees counterclockwise, then the corresponding interventional device may responsively rotate counterclockwise at an angular velocity of 10 degrees/ second. The corresponding interventional device can continue to move in the direction of rotational movement of the control 2202*b* at the predefined angular velocity as long the user is maintaining the control at the same rotational position. The interventional device may stop moving when the user stops manipulating the control and the control returns to its starting rotational position.

Rotational movement of a control about the axis 2219*b* may be configured to rotate the corresponding interventional device on a 1:1 basis, or on a non 1:1 scaled basis. For example, if the user moves the control 2202*b* about 5 millimeters about the axis 2219*b*, then the corresponding interventional device may responsively move at a predefined angular velocity of 5 degrees/second.

The control mechanism 2200*b* can be configured to enable the clinician to adjust the predefined linear velocity and/or the predefined angular velocity. For example, advance of a procedure catheter and an access catheter through a guide catheter and up to the selected ostium, as described herein, may desirably be accomplished in a 'fast' mode. Distal travel into the neuro vasculature may desirably be accomplished in a relatively slow mode by actuation of a speed control. For example, for stages of a procedure where the clinician wishes to proceed in a "fast" mode, the clinician may adjust the predefined linear velocity to 10 mm/second when the control moves 5 degrees about the axis 2217*b*. For stages of the procedure where the clinician wishes to proceed in a relatively slow mode, the clinician may adjust the predefined linear velocity to 2 mm/second when the control moves 5 degrees about the axis 2217*b*.

While the foregoing describes example operations of the control 2202*b*, it will be understood by one of skill in the art that any of the controls 2204*b*, 2206*b*, and 2208*b* may be operated in the same manner. In certain embodiments, each of the controls 2202*b*, 2204*b*, 2206*b*, and 2208*b* can control axial and rotational movement of corresponding interventional devices. In other embodiments, one or more of the controls 2202*b*, 2204*b*, 2206*b*, and 2208*b* may control only axial movement or only rotational movement of a corresponding interventional device.

Figure 21:
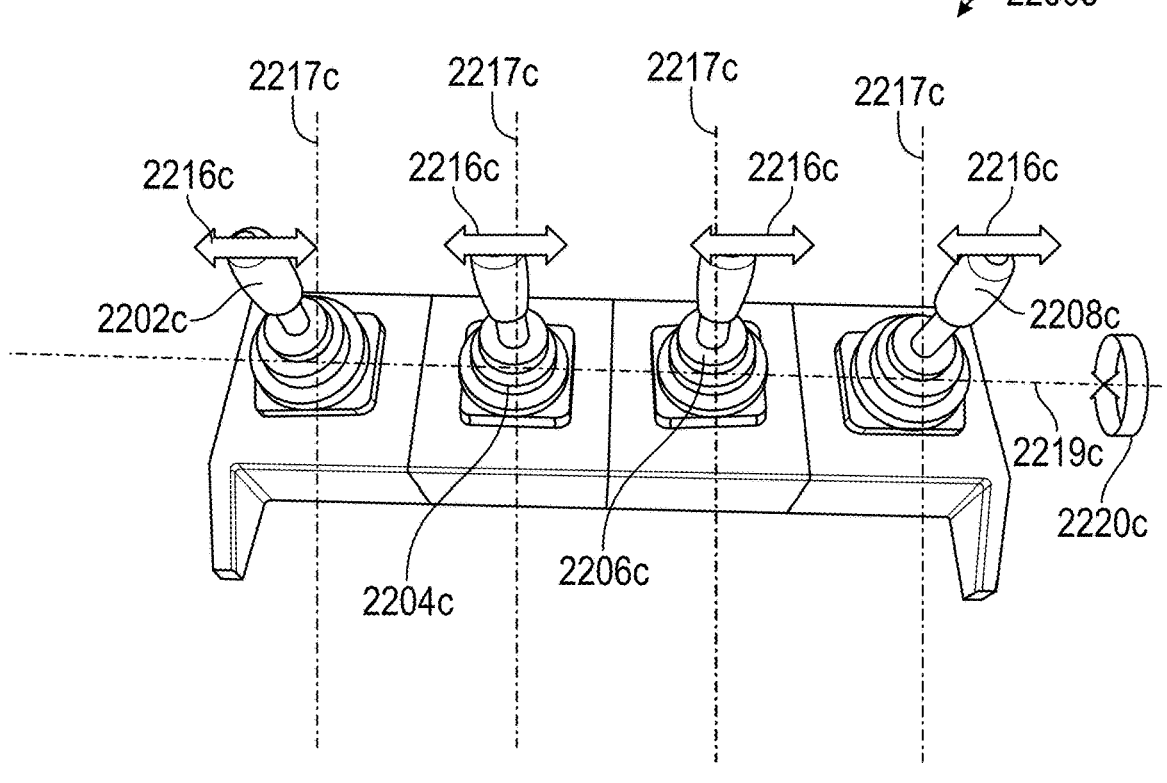

FIG. 21 illustrates an alternative embodiment of the control mechanism 2200*b* for manipulating interventional devices driven by (or otherwise associated with) respective hubs shown in FIG. 20. The control mechanism of FIG. 21 may include any of the same or similar features and/or functions as the control mechanism 2200*b* described herein and shown in FIG. 20. For example, each hub and/or interventional device may be manipulated and/or otherwise moved using at least one control installed in the control mechanism. Each control can include a joystick (e.g., a two-axis joystick). In certain embodiments, a joystick may provide for improved grasp and more precise movements in comparison to other controls. The size and feel of the joysticks can be customized to suit a physician's particular needs. For example, some physicians may prefer larger or smaller joysticks. Each control may be adapted to move a unique hub and/or interventional device during an interventional procedure.

As shown in FIG. 21, the control mechanism 2200*c* can include a first control 2202*c*, a second control 2204*c*, a third control 2206*c*, and a fourth control 2208*c*. More or fewer controls may be provided, depending upon the intended interventional device configuration. Each control 2202*c*-2208*c* may rotate around a first axis 2217*c*, as indicated by arrows 2216*c*, to cause axial movement of a corresponding hub and/or interventional device. In addition, each control 2202*c*-2208*c* may rotate about a second axis 2219*c*, as indicated by arrow 2220*c* to cause rotational movement of a corresponding hub and/or interventional device. The second axis 2219*c* may be the same axis for each control 2202*b*-2208*b*. The first axis 2217*c* for each control 2202*c*-2208*c* can be transverse to the second axis 2219*c*. Each control movement may trigger a responsive movement in a corresponding hub and/or interventional device. In certain embodiments, at least some movements of each control may trigger a responsive movement in a corresponding carriage on the support table, which may in turn drive movement of a corresponding hub.

Figure 22A:
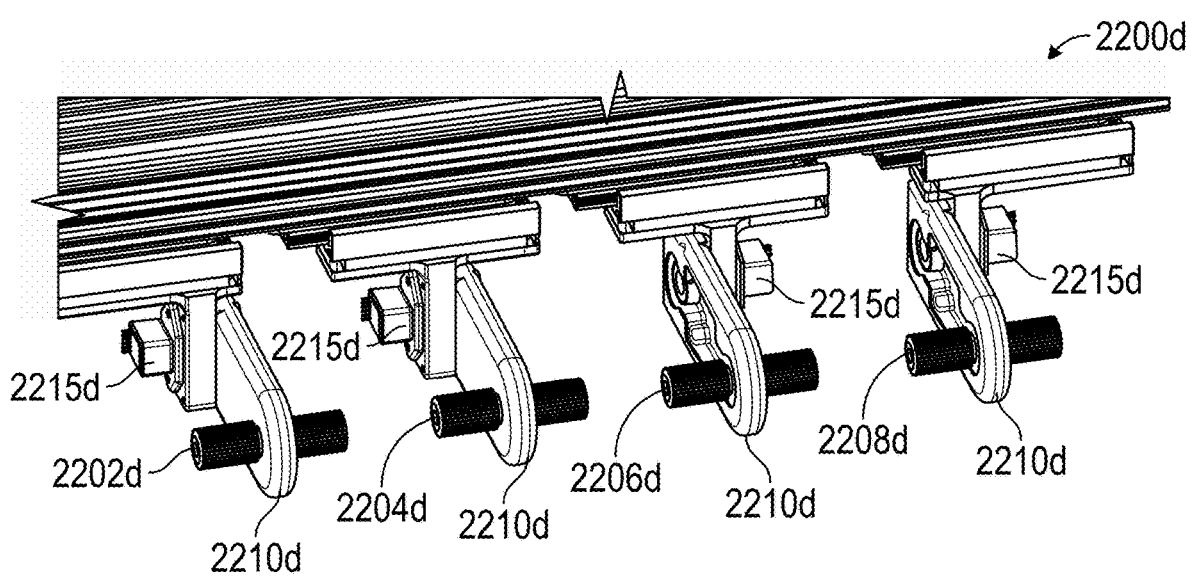
FIGS. 22A-22C illustrate an example control mechanism for manipulating interventional devices driven by respective hubs.
Figure 22B:
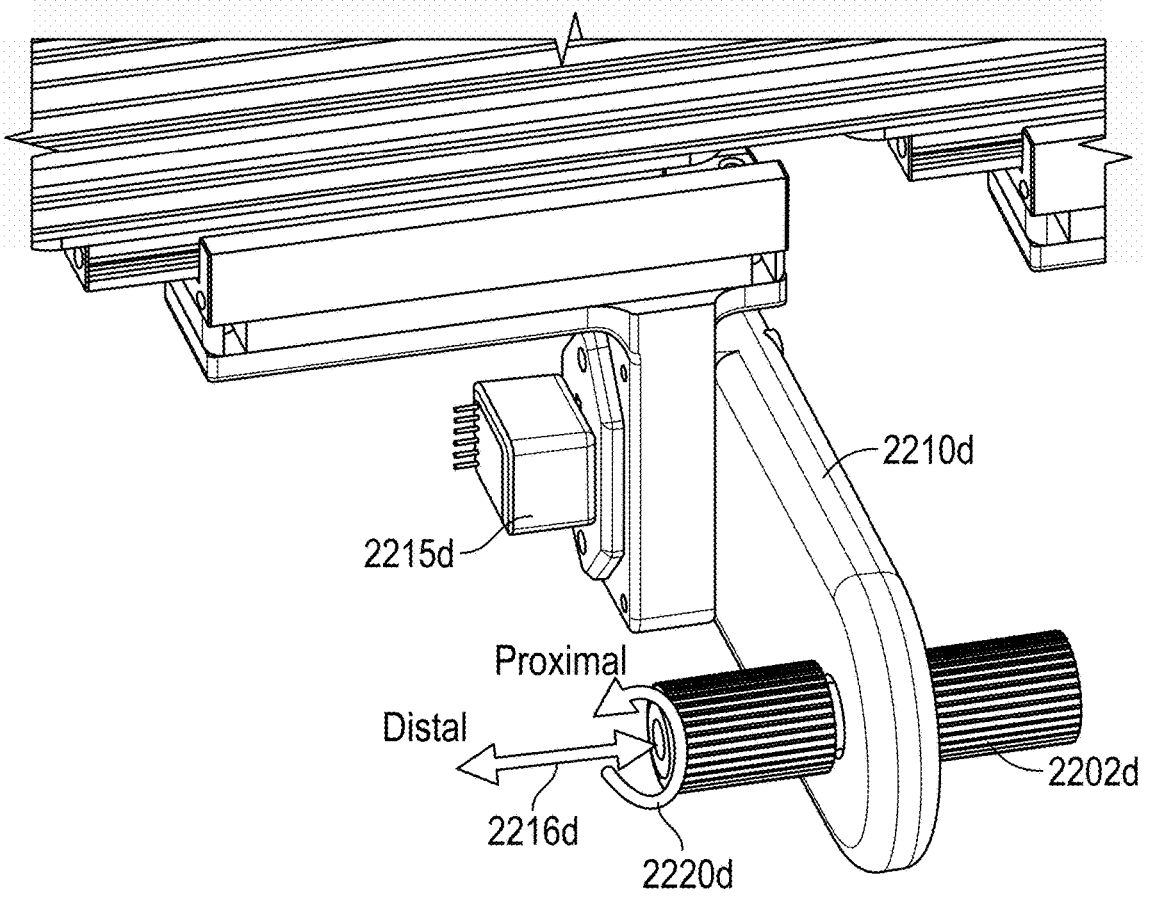
Figure 22C:
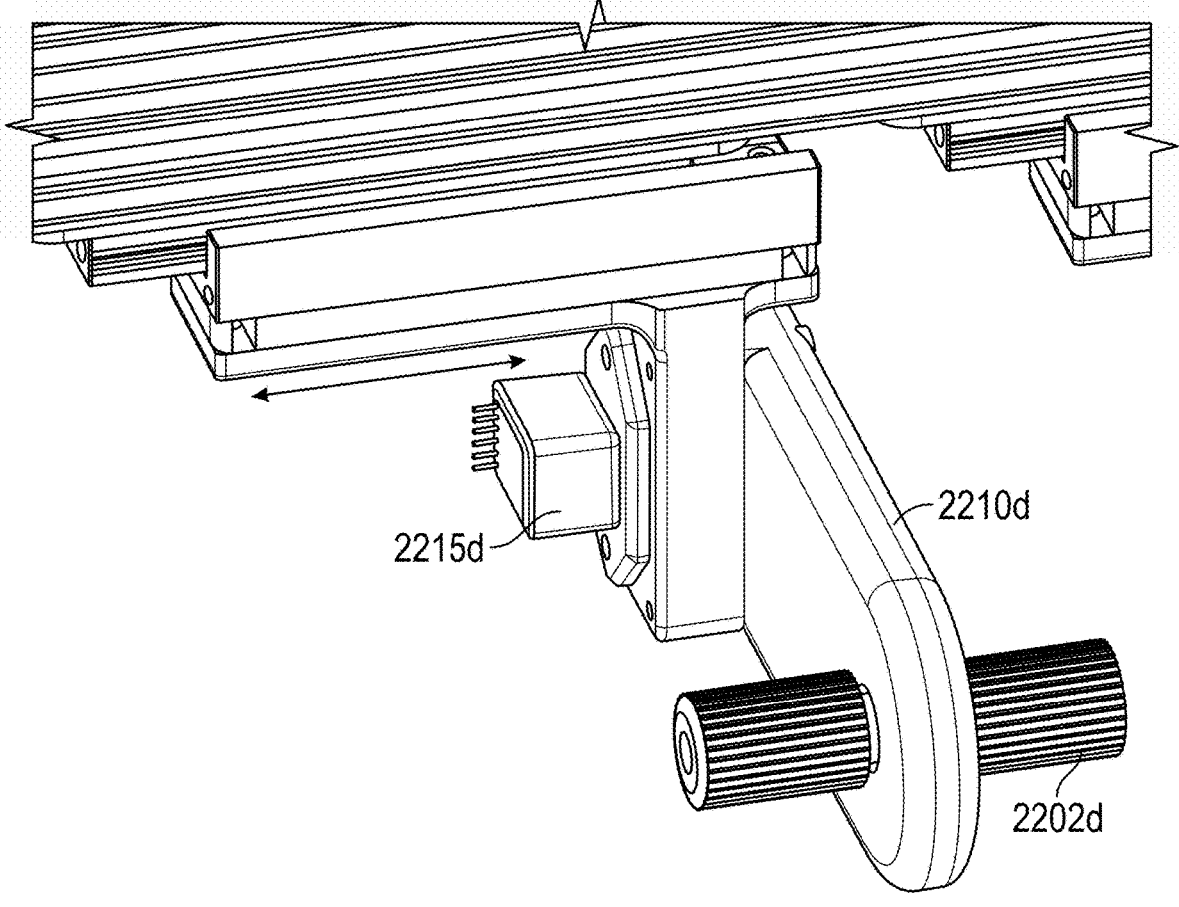

FIGS. 22A-22C illustrate another example of a control mechanism for manipulating interventional devices driven by (or otherwise associated with) respective hubs. The control mechanism of FIGS. 22A-22C may include any of the same or similar features and/or functions as any of the other control mechanisms described herein. In certain embodiments, each hub may be manipulated and/or otherwise moved using at least one control installed in the control mechanism. Each control may be adapted to move a unique hub and/or interventional device during an interventional procedure. For example, each control movement may trigger a responsive movement in a corresponding hub and/or interventional device. In certain embodiments, at least some movements of each control may trigger a responsive movement in a corresponding carriage on the support table, which may in turn drive movement of a corresponding hub.

As shown in FIG. 22A, the control mechanism 2200*d* can include a first control 2202*d*, a second control 2204*d*, a third control 2206*d*, and a fourth control 2208*d*. More or fewer controls may be provided, depending upon the intended interventional device configuration. Each control 2202*d*-2208*d* can be movably carried on a support structure 2210*d*. The controls 2202*d*-2208*d* may advance distally or retract proximally, as indicated by arrow 2216*d*. Additionally or alternatively, each control 2202*d*-2208*d* may be rotated within the support structure 2210*d*, as indicated by arrow 2220*d*.

Each control 2202*d*-2208*d* can have a starting axial position. The control mechanism can be configured so that each control 2202*d*-2208*d* returns to its starting axial position when the controls 2202*d*-2208*d* are not being advanced along the support structure 2210*d*.

The control mechanism 2200*d* may be positioned on or near to a patient support table having a set of hubs and catheters/interventional devices. In some implementations, the control mechanism 2200*d* may be positioned remote from the support table such as behind a radiation shield or in a different room or different geographical location in a telemedicine implementation.

Each control 2202*d*-2208*d* may correspond to and drive movement of a hub and/or a hub and/or interventional device. In certain embodiments, the control 2202*d* may be configured to move (e.g., axially and/or rotationally) an interventional device such as an 0.088 inch guide catheter (e.g., guide catheter 31 or guide catheter 2906), for example, by driving a hub (e.g., hub 30 or hub 2914) associated with the interventional device. Similarly, the control 2204*d* may be configured to move (e.g., axially and/or rotationally) an interventional device such as an 0.071 inch procedure catheter (e.g., catheter 29, catheter 120, or catheter 2904), for example, by driving a hub (e.g., hub 28, hub 122, or hub 2912) associated with the interventional device. The control 2206*d* may be configured to move (e.g., axially and/or rotationally) an interventional device such as a steerable access catheter (e.g., catheter 124 or catheter 2902), for example, by driving a hub (e.g., hub 126 or hub 2910)

associated with the interventional device. The control 2208*d* may be configured to move (e.g., axially and/or rotationally) an interventional device such as a guidewire (e.g., guidewire 27 or guidewire 2907), for example, by driving a hub (e.g., hub 26 or hub 2909) associated with the interventional device.

In operation, if the user moves the control 2202*d* axially along the support structure 2210*d* (e.g., proximally or distally), as shown by arrow 2216*d*, a corresponding coupled hub and/or interventional device may move responsively in the same direction by a predefined linear velocity. The corresponding coupled hub and/or interventional device can continue to move in the same direction at the predefined linear velocity until the user releases (e.g., stops manipulating) the control 2202*d* or further moves the control. When the user stops manipulating the control 2202*d*, the control 2202*d* can return to its starting axial position. If the user moves the control 2202*d* rotationally within the support structure 2210*d* (e.g., clockwise or counterclockwise), as shown by arrow 2220*d*, the corresponding interventional device can be driven rotationally (e.g., by a corresponding hub) in the same direction and/or by a same or scaled amount. If the user rotates the control 2202*d* within the support structure 2210*d* and advances the control axially (either distally or proximally), a corresponding coupled interventional device can responsively move rotationally by a same or scaled amount and axially at a predefined linear velocity. The corresponding coupled interventional device can continue to move axially at the predefined linear velocity until the user releases (e.g., stops manipulating) the control 2202*d* or further axially moves the control 2202*d*. When the user stops manipulating the control 2202*d*, the control 2202*d* can return to its starting axial position.

As shown in FIG. 22C, the control mechanism 2200*d* can include at least one linear position sensor (also referred hereto as linear sensor) and at least one rotation sensor. One or more linear position sensors can be used to measure the axial movement of each control 2202*d*-2208*d* relative to the starting position of each control. For example, the one or more linear sensors can be configured to measure the distance (e.g., 5 mm) traveled by a control from its starting position. The linear position sensor can command velocity of the corresponding hub and/or interventional device. For example, in some embodiments, the predefined linear velocity at which the corresponding hub and/or interventional device will move can depend on the measurement by the one or more linear position sensors. The one or more linear position sensors can include, for example, a linear potentiometer. In some cases, the control mechanism 2200*d* can include a linear position sensor for each control.

Similarly, one or more rotation sensors 2215*d* can be used to measure the rotational movement of each control 2202*d*-2208*d* relative to a starting position of each control. In some cases, the one or more rotation sensors can be supported by a support structure, such as support structure 2210*d*, as shown in FIG. 22C. The one or more rotation sensors can be configured to measure the rotational movement (e.g., 5 degrees) of a control from its starting position. The rotation sensor can command orientation of the corresponding hub and/or interventional device. For example, in some embodiments, the angular distance which the corresponding hub will move depends on the measurement by the one or more rotation sensor. The one or more rotation sensors can include, for example, an encoder, a potentiometer, a hall effect sensor, or a combination thereof. In some cases, the control mechanism 2200*d* can include a rotation sensor for each control.

Axial movement of a control may be configured to move a corresponding hub and/or interventional device at a predefined linear velocity. For example, if the user advances the control 2202*d* about 5 millimeters distally along the support structure 2210*d*, then the corresponding hub and/or interventional device may responsively move distally at a linear velocity of 5 mm/second. The predefined linear velocity can vary according to the user's movement of the control. For example, if the user advances the control 2202*d* about 10 millimeters proximally along the support structure 2210*d*, then the corresponding hub and/or interventional device may responsively move proximally at a linear velocity of 10 mm/second. The corresponding hub and/or interventional device can continue to move axially at the predefined linear velocity as long the user is manipulating the control to maintain the same axial position. The corresponding hub can stop moving when the user stops manipulating the control and the control will return to its starting axial position.

Axial movement of a control may be configured to move the corresponding hub and/or interventional device on a 1:1 basis, or on a non 1:1 scaled basis. For example, if the user advances the control 2202*d* about 5 millimeters distally along the support structure 2210*d*, then the corresponding hub and/or interventional device may responsively move at a predefined linear velocity of 5 mm/second in the distal direction.

Rotational movement of a control may be configured to move the corresponding interventional device on a 1:1 basis, or on a non 1:1 scaled basis. For example, if the user rotates the control 2202*d* about its rotational axis by 5 degrees, then the corresponding interventional device may responsively move an angular distance of 5 degrees. In certain embodiments, when a user stops rotationally manipulating the control, the control maintains its position and does not return to a previous initial rotational position. In certain embodiments, each rotational position of the control may correspond to a unique rotational position of the corresponding interventional device.

The control mechanism 2200*d* can be configured to enable the clinician to adjust the predefined linear velocity and/or rotational distance or position. For example, distal advance of a procedure catheter and an access catheter through a guide catheter and up to the selected ostium, as described herein, may desirably be accomplished in a 'fast' mode. More distal travel into the neuro vasculature may desirably be accomplished in a relatively slow mode by actuation of a speed control. For example, for stages of a procedure where the clinician wishes to proceed in a "fast" mode, the clinician may adjust the predefined linear velocity to 10 mm/second when the control moves 5 mm distally or proximally along the shaft. For stages of the procedure where the clinician wishes to proceed in a relatively slow mode, the clinician may adjust the predefined linear velocity to 2 mm/second when the control moves 5 mm distally or proximally along the shaft.

While the foregoing describes example operations of the control 2202*d*, it will be understood by one of skill in the art that any of the controls 2204*d*, 2206*d*, and 2208*d* may be operated in the same manner. In certain embodiments, each of the controls 2202*d*, 2204*d*, 2206*d*, and 2208*d* can control axial and rotational movement of corresponding interventional devices. In other embodiments, one or more of the controls 2202*d*, 2204*d*, 2206*d*, and 2208*d* may control only axial movement or only rotational movement of a corresponding interventional device.

Figure 23A:
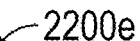
FIGS. 23A-23C illustrate an example control mechanism for manipulating interventional devices driven by respective hubs.
Figure 23A:
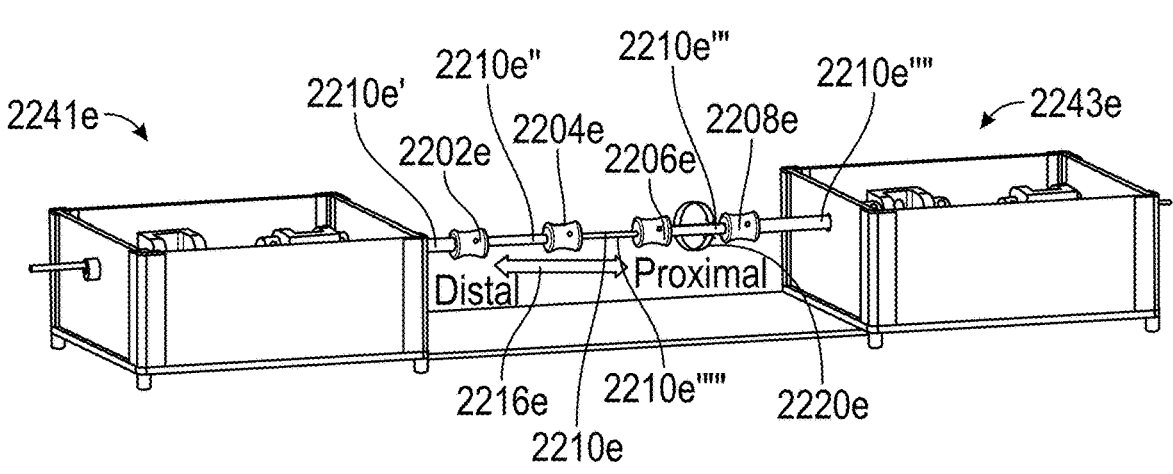
Figure 23B:
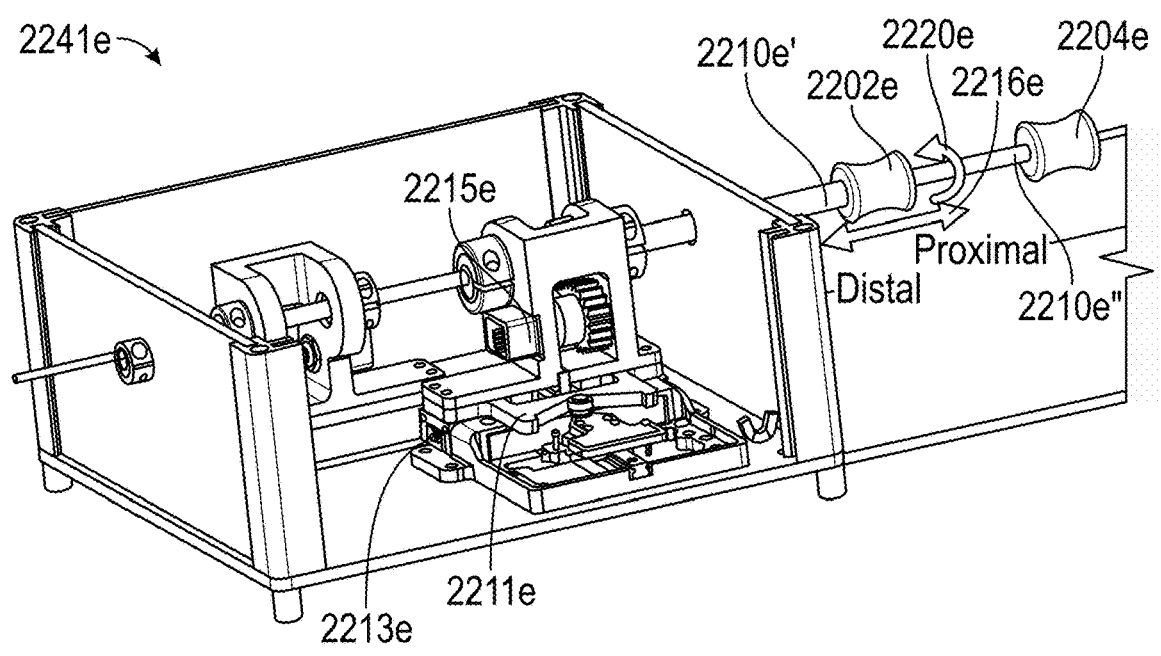
Figure 23C:
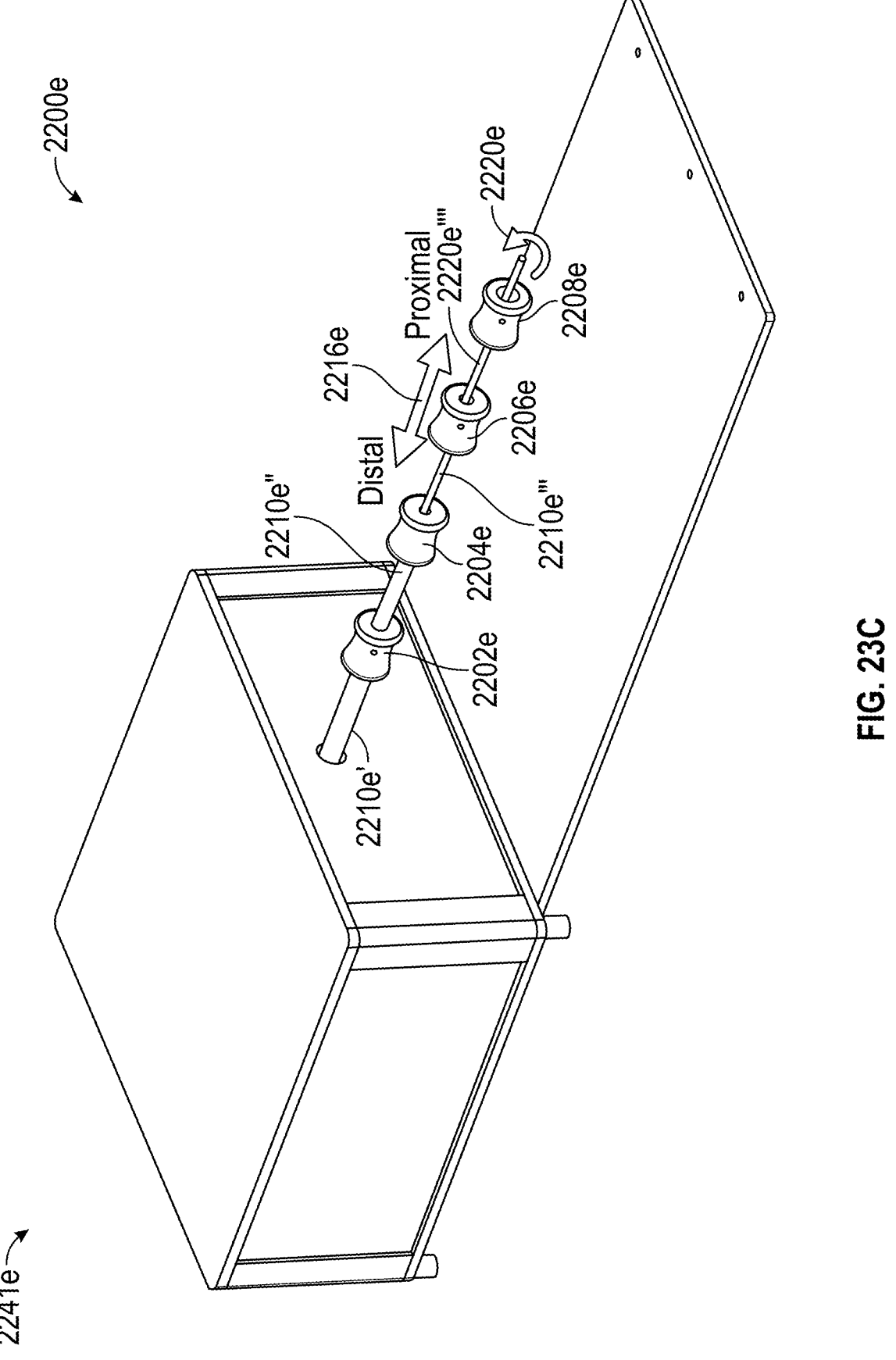

FIGS. 23A-23C illustrate another example of a control mechanism for manipulating interventional devices driven by (or otherwise associated with) respective hubs. The control mechanism of FIGS. 23A-23C may include any of the same or similar features and/or functions as any of the other control mechanisms described herein. For example, each hub may be manipulated and/or otherwise moved using at least one control installed in the control mechanism. Each control may be adapted to move a unique hub and/or interventional device during an interventional procedure. For example, each control movement may trigger a responsive movement in a corresponding hub and/or interventional device. In certain embodiments, at least some movements of each control may trigger a responsive movement in a corresponding carriage on the support table, which may in turn drive movement of a corresponding hub.

As shown in FIG. 23A, the control mechanism 2200e can include a first control 2202e, a second control 2204e, a third control 2206e, and a fourth control 2208e. More or fewer controls may be provided, depending upon the intended interventional devices configuration. Each control 2202e-2208e can be movably carried on a shaft assembly 2210e. The controls 2202e-2208e may advance distally or retract proximally within the shaft assembly 2210e, as indicated by arrow 2216e. Additionally or alternatively, each control 2202e-2208e may be rotated within the shaft assembly 2210e, as indicated by arrow 2220e.

Each control 2202e-2208e can have a starting axial position. The control mechanism can be configured so that each control 2202e-2208e returns to its starting axial position when the controls 2202e-2208e are not being advanced or retracted within the shaft assembly 2210c.

As shown in FIGS. 23A-23B, the controls 2202e-2208e can be arranged in a coaxial configuration. Each control 2202e-2208e can be carried on a unique shaft of the assembly 2210e. In some embodiments, the shaft assembly 2210e can have one or more shafts having different diameters thereby allowing, for example, at least one shaft associated with a unique control to fit and extend through another shaft associated with a unique control. For example, and as shown in FIG. 23A, a first shaft 2210e' can be associated with control 2202e, a second shaft 2210e" can be associated with control 2204e", a third shaft 2210e''' can be associated with control 2206e, and a third shaft 2210e'''' can be associated with control 2208e. The shafts 2210e'-2210e'''' can be configured to move axially and/or rotationally with their associated controls. For example, the second shaft 2210e" can have a smaller diameter than the first shaft 2210e' thereby allowing the second shaft 2210e" to at least partially extend inside and move within the first shaft 2210e'. In some embodiments, each control 2202e-2208e can be associated with unique shafts having different diameters from each other. Smaller shafts can at least partially extend inside and move/rotate within larger shafts, thereby allowing telescopic movement of two or more shaft sections. The shaft assembly 2210e may further include a shaft 2210e'''' that extends through each of the shafts 2210e'-2210e'''' to provide structural support.

The control mechanism 2200e may be positioned on or near to a patient support table having a set of hubs and catheters/interventional devices. In some implementations, the control mechanism 2200e may be positioned remote from the support table such as behind a radiation shield or in a different room or different geographical location in a telemedicine implementation.

Each control 2202e-2208e may correspond to and drive movement of a hub and/or interventional device. In certain embodiments, the control 2202e may be configured to move (e.g., axially and/or rotationally) an interventional device such as an 0.088 inch guide catheter (e.g., guide catheter 31 or guide catheter 2906), for example, by driving a hub (e.g., hub 30 or hub 2914) associated with the interventional device. Similarly, the control 2204e may be configured to move (e.g., axially and/or rotationally) an interventional device such as an 0.071 inch procedure catheter (e.g., catheter 29, catheter 120, or catheter 2904), for example, by driving a hub (e.g., hub 28, hub 122, or hub 2912) associated with the interventional device. The control 2206e may be configured to move (e.g., axially and/or rotationally) an interventional device such as a steerable access catheter (e.g., catheter 124 or catheter 2902), for example, by driving a hub (e.g., hub 126 or hub 2910) associated with the interventional device. The control 2208e may be configured to move (e.g., axially and/or rotationally) an interventional device such as a guidewire (e.g., guidewire 27 or guidewire 2907), for example, by driving a hub (e.g., hub 26 or hub 2909) associated with the interventional device.

In operation, if the user moves the control 2202e (and as a result the shaft 2210e') axially within the shaft assembly 2210e (e.g., proximally or distally), as shown by arrow 2216e, a corresponding coupled hub and/or interventional device may move responsively in the same direction by a predefined linear velocity. The corresponding coupled hub and/or interventional device can continue to move in the same direction at the predefined linear velocity until the user releases (e.g., stops manipulating) the control 2202e or further moves the control. When the user stops manipulating the control 2202e, the control 2202e can return to its starting axial position. If the user moves the control 2202e (and as a result the shaft 2210e') rotationally within the shaft assembly 2210e (e.g., clockwise or counterclockwise), as shown by arrow 2220e, the corresponding interventional device can be driven rotationally (e.g., by a corresponding hub) in the same direction and/or by a same or scaled amount. If the user rotates the control 2202e within the shaft assembly 2210e and advances the control axially (either distally or proximally), a corresponding coupled interventional device will responsively move rotationally by a same or scaled amount and axially at a predefined linear velocity. The corresponding coupled interventional device can continue to move axially at the predefined linear velocity until the user releases (e.g., stops manipulating) the control 2202e or further axially moves the control 2202e. When the user stops manipulating the control 2202e, the control 2202e can return to its starting axial position.

In some embodiments, and as shown in FIG. 23A, the control mechanism 2200e can include a first housing section 2241e and a second housing section 2243e. The first housing section 2241e and the second housing section 2243e can f each receive and support one or more shafts 2210e'-2210e''''. For example, in certain embodiments, the housing section 2241e can receive and support shaft 2210e' and 2210e" and the housing section 2243e can receive and support shafts 2210e''' and 2210e''''. The shaft 2210e'''' may extend through both housing sections 2241e and 2243e.

One or more linear position sensors 2213e can be used to measure the axial movement of each control 2202e-2208e relative to the starting position of each control (e.g., by measuring the axial movement of the corresponding shafts 2210e'-2210e'''' relative to their starting positions), as shown in FIG. 23B. The one or more linear position sensors can be included as part of the first and second housing sections 2241e, 2243e. In some embodiments, the one or more linear sensors 2213e can be configured to measure the distance (e.g., 5 mm) traveled by a control from its starting position. In some embodiments, the predefined linear velocity at which the corresponding hub will move can depend on the measurement by the one or more linear position sensor. The one or more linear position sensors can include, for example, a linear potentiometer. In some cases, the control mechanism 2200e can include a linear position sensor 2213e for each control.

Similarly, one or more rotation sensors 2215e can be used to measure the rotational movement of each control 2202e-2208e relative to a starting position of each control (e.g., by measuring the rotational movement of the corresponding shafts 2210e'-2210e"" relative to their starting positions), as shown in FIG. 23B. For example, the one or more rotation sensors can be configured to measure the rotational movement (e.g., 5 degrees) of a control from its starting position. The angular distance which the corresponding hub will move depends on the measurement by the one or more rotation sensors. The one or more rotation sensors can include, for example, an encoder, a potentiometer, a hall effect sensor, or a combination thereof. In some cases, the control mechanism 2200e can include a rotation sensor for each control.

Axial movement of a control may be configured to move a corresponding hub and/or interventional device at a predefined linear velocity. For example, if the user advances the control 2202e about 5 millimeters distally within the shaft assembly 2210e, then the corresponding hub and/or interventional device may responsively move distally at a linear velocity of 5 mm/second. The predefined linear velocity can vary according to the user's movement of the control. For example, if the user advances the control 2202e about 10 millimeters proximally within the shaft assembly 2210e, then the corresponding hub and/or interventional device may responsively move proximally at a linear velocity of 10 mm/second. The corresponding hub and/or interventional device can continue to move axially at the predefined linear velocity as long the user is manipulating the control to maintain the same axial position. The corresponding hub and/or interventional device can stop moving when the user stops manipulating the control and the control can return to its starting axial position. In some embodiments, a centering mechanism 2211e, as shown in FIG. 23B, can facilitate return of a control to its starting axial position. For example, the centering mechanism 2211e can be configured to move the control in the distal or proximal direction (by moving the corresponding shaft), depending on whether the user moved a control in a distal or proximal direction, back to its starting axial position when the user stops manipulating the control.

Axial movement of a control may be configured to move the corresponding hub and/or interventional device on a 1:1 basis, or on a non 1:1 scaled basis. For example, if the user advances the control 2202e about 5 millimeters distally, then the corresponding hub and/or interventional device may responsively move at a predefined linear velocity of 5 mm/second in the distal direction.

Rotational movement of a control may be configured to move the corresponding interventional device on a 1:1 basis, or on a non 1:1 scaled basis. For example, if the user rotates the control 2202 about its rotational axis by 5 degrees, then the corresponding interventional device may responsively move an angular distance of 5 degrees. In certain embodiments, when a user stops rotationally manipulating the control, the control maintains its position and does not return to a previous initial rotational position. In certain embodiments, each rotational position of the control may correspond to a unique rotational position of the corresponding interventional device.

The control mechanism 2200e can be configured to enable the clinician to adjust the predefined linear velocity and/or rotational distance or position. For example, distal advance of a procedure catheter and an access catheter through a guide catheter and up to the selected ostium, as described herein, may desirably be accomplished in a 'fast' mode. More distal travel into the neuro vasculature may desirably be accomplished in a relatively slow mode by actuation of a speed control. For example, for stages of a procedure where the clinician wishes to proceed in a "fast" mode, the clinician may adjust the predefined linear velocity to 10 mm/second when the control moves 5 mm distally or proximally. For stages of the procedure where the clinician wishes to proceed in a relatively slow mode, the clinician may adjust the predefined linear velocity to 2 mm/second when the control moves 5 mm distally or proximally.

While the foregoing describes example operations of the control 2202e, it will be understood by one of skill in the art that any of the controls 2204e, 2206e, and 2208e may be operated in the same manner. In certain embodiments, each of the controls 2202e, 2204e, 2206e, and 2208e can control axial and rotational movement of corresponding interventional devices. In other embodiments, one or more of the controls 2202e, 2204e, 2206e, and 2208e may control only axial movement or only rotational movement of a corresponding interventional device.

FIG. 23C illustrates an alternative embodiment of the control mechanism 2200e in which each of the shafts 2210e'-2210e"" are received and supported within a single housing section 2241e. The housing section 2241e may include linear sensors 2213e and rotation sensors 2215e for each control.

In certain embodiments, the shafts 2210e'-2210e"" and/or the controls 2202e, 2204e, 2206e, and 2208e can be removably received within the housing section 2241e. The shafts 2210e'-2210e"" and/or the controls 2202e, 2204e, 2206e, and 2208e may be single-use and/or disposable components. The housing section 2241e and internal components such as the sensors 2213e, 2215e, and centering mechanism 2211e may be configured for multiple uses and can couple to a plurality of shafts 2210e'-2210e"" and/or the controls 2202e, 2204e, 2206e, and 2208e.

FIGS. 24A-24E illustrate additional examples of control mechanisms for manipulating interventional devices driven by (or otherwise associated with) respective hubs. The control mechanism of FIGS. 24A-24E may include any of the same or similar features and/or functions as any of the other control mechanisms described herein. In certain embodiments, each hub may be manipulated and/or otherwise moved using at least one control installed in the control mechanism. Each control may be adapted to move a unique hub and/or interventional device during an interventional procedure. For example, each control movement may trigger a responsive movement in a corresponding hub and/or interventional device. In certain embodiments, at least some movements of each control may trigger a responsive movement in a corresponding carriage on the support table, which may in turn drive movement of a corresponding hub.

Figures 24A, 24B:
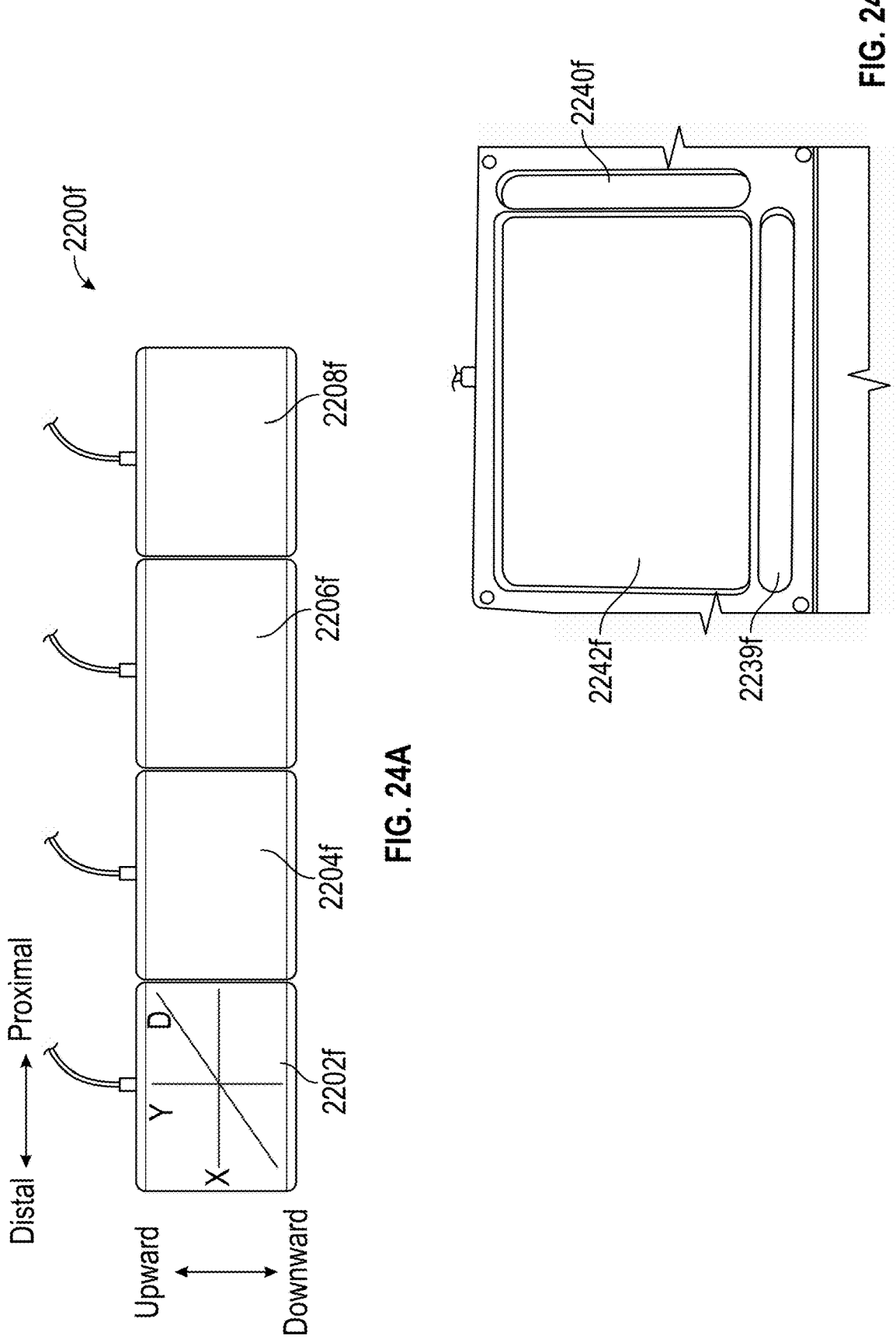
FIGS. 24A-24E illustrate an example control mechanism for manipulating interventional devices driven by respective hubs.

As shown in FIG. 24A, the control mechanism 2200f can include a first control 2202f, a second control 2204f, a third control 2206f, and a fourth control 2208f. More or fewer controls may be provided, depending upon the intended interventional devices configuration. Each control 2202f-2208f can include a capacitive screen, a resistive screen, a touch pad, or other touch-based sensing device.

The control mechanism 2200f may be positioned on or near to a patient support table having a set of hubs and catheters/interventional devices. In some implementations, the control mechanism 2200f may be positioned remote from the support table such as behind a radiation shield or in a different room or different geographical location in a telemedicine implementation.

In certain embodiments, the control 2202f may be configured to move (e.g., axially and/or rotationally) an interventional device such as an 0.088 inch guide catheter (e.g., guide catheter 31 or guide catheter 2906), for example, by driving a hub (e.g., hub 30 or hub 2914) associated with the interventional device. Similarly, the control 2204f may be configured to move (e.g., axially and/or rotationally) an interventional device such as an 0.071 inch procedure catheter (e.g., catheter 29, catheter 120, or catheter 2904), for example, by driving a hub (e.g., hub 28, hub 122, or hub 2912) associated with the interventional device. The control 2206f may be configured to move (e.g., axially and/or rotationally) an interventional device such as a steerable access catheter (e.g., catheter 124 or catheter 2902), for example, by driving a hub (e.g., hub 126 or hub 2910) associated with the interventional device. The control 2208f may be configured to move (e.g., axially and/or rotationally) an interventional device such as a guidewire (e.g., guidewire 27 or guidewire 2907), for example, by driving a hub (e.g., hub 26 or hub 2909) associated with the interventional device.

In operation, if the user swipes a finger across the touchpad of the control 2202f along a horizontal axis (either proximally or distally), as shown by axis X, a corresponding coupled hub and/or interventional device may move axially in the same direction by a same or scaled amount. If the user swipes a finger across the touchpad of the control 2202f along a vertical axis, as shown by axis Y, a corresponding coupled hub and/or interventional device may move rotationally by a same or scaled amount. For example, if the user swipes a finger across the touchpad in a vertically upward direction, the interventional device may rotate in a clockwise direction and if the user swipes a finger across the touchpad vertically in a downward direction, the interventional device may rotate in a counterclockwise direction.

If the user 2230 swipes a finger across the touchpad of the control 2202f in a direction having both horizontal and vertical components (e.g., along a substantially diagonal axis, as shown by axis D), a corresponding coupled hub and/or interventional device may move axially in the same direction by a same or scaled amount as the horizontal component and rotationally by a same or scaled amount as the vertical component. The axial movement, and the rotational movement of the corresponding coupled hub and/or interventional device when a user swipes a finger across the touchpad along the diagonal axis D can depend on the horizontal distance traveled along axis X and the vertical distance traveled along axis Y by the user's finger along the touchpad. In certain embodiments, a user may swipe a finger across the touchpad along a non-linear path to adjust axial movement and rotational movement at different rates at different portions of the procedure.

In other embodiments, rotational control of the corresponding interventional device can be achieved by performing a substantially circular motion on the touchpad. For example, and without limitation, if the user performs a circular motion (e.g., clockwise or counterclockwise) on the touchpad, the interventional device can move rotationally in the same direction by a same or scaled amount. That is, if the user performs a circular motion three times in a clockwise direction, the corresponding hub and/or interventional device can rotate three times in a clockwise direction. As another example, if a user performs a half-circle motion in a counterclockwise direction (i.e., 180 degrees), the corresponding hub and/or interventional device can rotate 180 degrees in a counter clockwise direction.

In some embodiments, if the user clicks the surface of the touchpad of the control 2202 along an edge of the touchpad, a corresponding coupled hub and/or interventional device may move responsively at a predefined linear velocity. The corresponding coupled hub and/or interventional device can continue to move at the predefined linear velocity until the user clicks on a surface of the touchpad again.

The touchpad of each control 2202f-2208f can be configured to move the coupled hub at a predefined linear velocity. For example, if the user clicks the touchpad along an edge of the touchpad, then the corresponding hub may responsively move distally or proximally at a linear velocity of 5 mm/second. For example, clicking a left edge of controller 2202f can cause the coupled hub to advance distally at a predefined linear velocity. Similarly, clicking a right edge of controller 2202f can cause the coupled hub to advance proximally at a predefined linear velocity. The predefined linear velocity can be adjusted by the clinician. For example, and without limitation, clicking an edge of the touchpad can cause the corresponding hub to move at a linear velocity of about 5 mm/second, 6 mm/second, 8 mm/second, 10 mm/second, 12 mm/second, 14 mm/second, etc. The corresponding hub can continue to move distally or proximally at the predefined linear velocity until the user clicks the surface of the touchpad again.

The control may be configured to move the coupled hub axially on a 1:1 basis, or on a non 1:1 scaled basis. For example, if the user swipes a finger 10 mm across the touchpad along axis X, then the corresponding hub may responsively move proximally or distally a distance of 10 mm.

The control may be configured to move the coupled hub rotationally on a 1:1 basis, or on a non 1:1 scaled basis. For example, if the user swipes a finger 10 mm across the touchpad along axis Y, then the corresponding hub may responsively move rotationally by 10 degrees.

The control mechanism 2200f can be configured to enable the clinician to adjust the predefined linear velocity. For example, distal advance of a procedure catheter and an access catheter through a guide catheter and up to the selected ostium may desirably be accomplished in a 'fast' mode. But more distal travel into the neuro vasculature may desirably be accomplished in a relatively slow mode by actuation of a speed control. For example, for stages of a procedure where the clinician wishes to proceed in a "fast" mode, the clinician may adjust the predefined linear velocity to 10 mm/second when the user clicks the touchpad along an edge. For stages of the procedure where the clinician wishes to proceed in a relatively slow mode, the clinician may adjust the predefined linear velocity to 2 mm/second when the user clicks the touchpad along the edge.

In some cases, the touchpad of each control 2202f-2208f can include one or more guided areas to assist the clinician's operation of each control 2202f-2208f. For example, and as shown in FIG. 24B, the touchpad of each control 2202f-2208f can include two guided areas 2239f, 2240f and an unguided area 2242f. The first and second guided areas 2239f, 2240f can provide visual and tactile assistance to the clinician when the clinician is operating each control 2202f-2208f. The first guided area 2239f can comprise a substantially horizontal region. The horizontal region of the first guided area 2239f can beneficially prevent a clinician from accidentally swiping a finger in a vertical direction. The second guided area 2240*f* can comprise a substantially vertical region. The vertical region of the second guided area 2240*f* can beneficially prevent a clinician from accidentally swiping a finger in a horizontal direction. In operation, a clinician can swipe a finger across the first guided area 2239*f* or the second guided area 2240*f* to control a corresponding hub and/or interventional device in a particular direction. For example, the clinician may swipe a finger across the first guided area 2239*f* to axially move the corresponding hub and/or interventional device. Because the first guided area restricts a clinician's ability to swipe a finger in a vertical direction, the probability of a clinician accidentally or mistakenly controlling a hub and/or interventional device in an undesired manner (e.g., rotating instead of axially advancing or retracting) can be reduced. Similarly, because the second guided 2240*f* area restricts a clinician's ability to swipe a finger in a horizontal direction, the probability of a clinician accidentally or mistakenly controlling a hub and/or interventional device in an undesired manner (e.g., axially advancing or retracting instead of rotating) can be reduced.

Figure 24C:
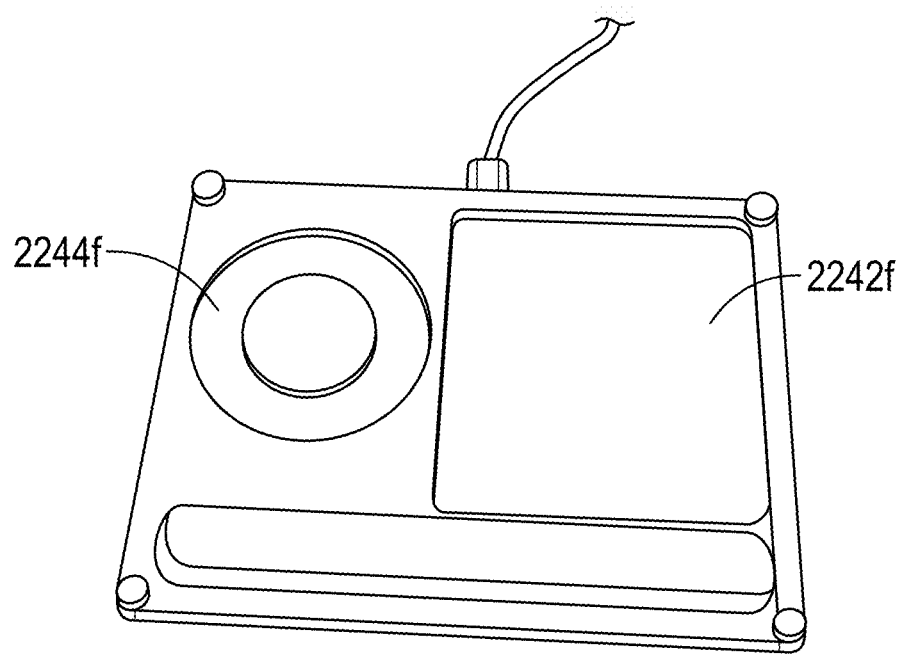

In some cases, the touchpad can also include an unguided area 2242*f*, as shown in FIGS. 24B and 24C. The unguided area can be used by a clinician to control axial and rotational movement of the corresponding hub and/or interventional device at the same time. For example, if a clinician wants a corresponding hub and/or interventional device to move both axially and rotationally, the clinician can perform swipe gestures on the unguided area of the touchpad. A diagonal swipe gesture would cause the corresponding hub and/or interventional device to both move in an axial direction and rotate. In some cases, however, a clinician can use two fingers to perform swipe gestures on the first guided area 2239*f* and the second guided area 2240*f* at the same time, which can cause the corresponding hub and/or interventional device to move axially and rotationally.

In some cases, the touchpad can include a circular guided area 2244*f*, as shown in FIG. 24C. The circular guided area can improve users' accuracy when operating a control 2202*f*-2208*f* configured to move the corresponding hub and/or interventional device rotationally when a substantially circular gesture is performed on the touchpad.

Figure 24D:
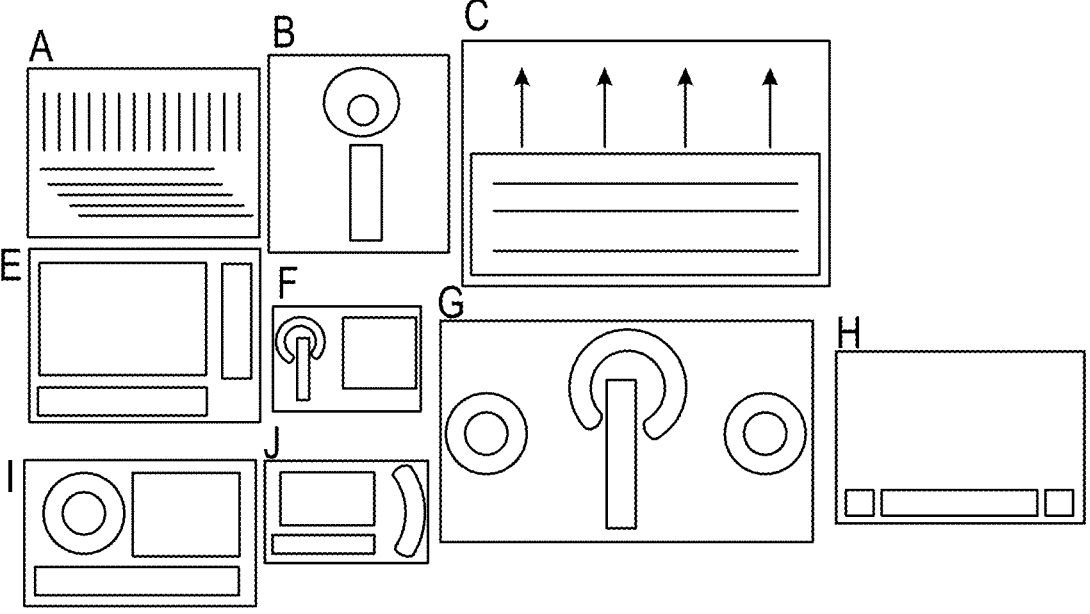

FIG. 24D shows additional examples of touchpad arrangements and swiping gestures that can cause a corresponding hub and/or interventional device to move axially and rotationally. In some embodiments a vertical, circular, or semi-circular gesture can cause a corresponding hub and/or interventional device to rotate. The controls can include guided areas including vertical, circular, and semi-circular areas. In some embodiments a vertical or horizontal gesture can cause a corresponding hub and/or interventional device to move in an axial direction. The controls can include guided areas including vertical and/or horizontal areas.

Figure 24E:
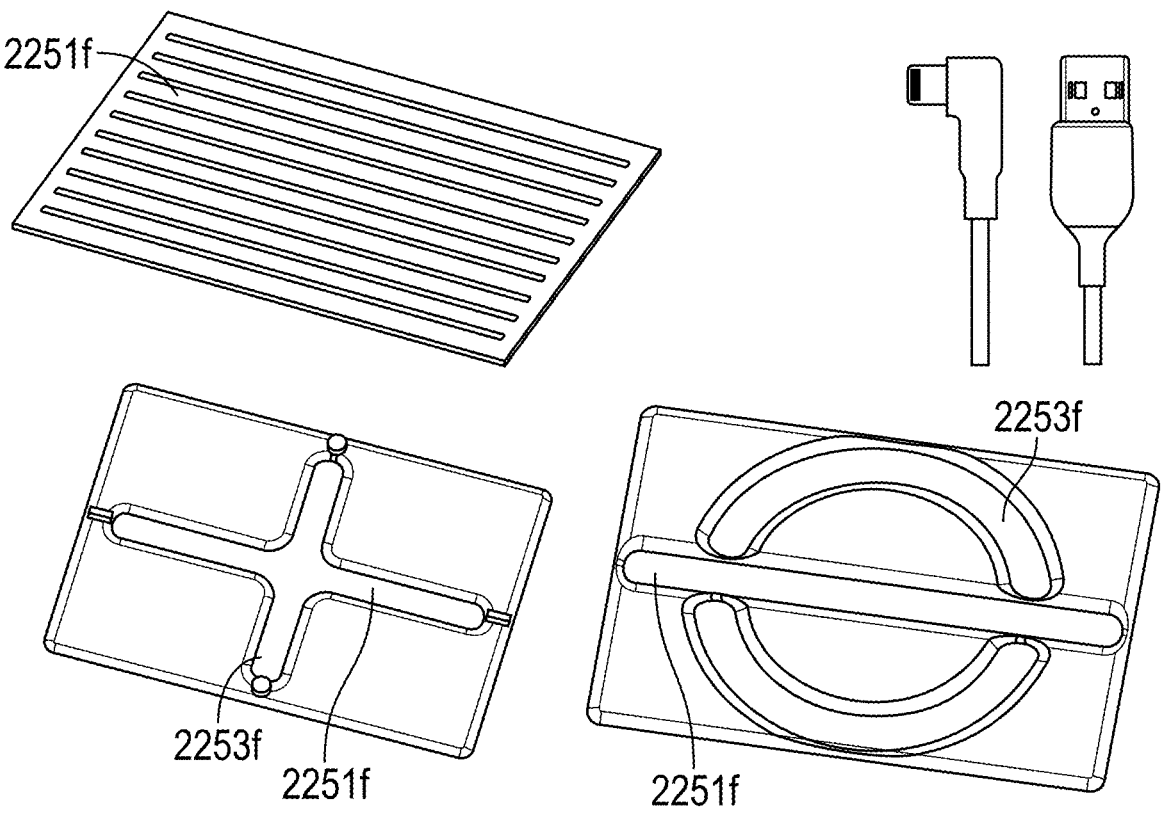

FIG. 24E shows additional examples of configurations of guided areas 2251*f*, 2253*f* for controls. The controls can include guided areas 2251*f* including horizontal areas. The controls can also include guided areas 2253*f* including vertical, circular, or semi-circular areas. In some embodiments, the controls can include one or more parallel ridges. Each parallel ridge can be used to control movement of a different interventional device.

While the foregoing describes example operations of the control 2202*f*, it will be understood by one of skill in the art that any of the controls 2204*f*, 2206*f*, and 2208*f* may be operated in the same manner. In certain embodiments, each of the controls 2202*f*, 2204*f*, 2206*f*, and 2208*f* can control axial and rotational movement of corresponding interventional devices. In other embodiments, one or more of the controls 2202*f*, 2204*f*, 2206*f*, and 2208*f* may control only axial movement or only rotational movement of a corresponding interventional device.

FIGS. 25A-25D illustrate another example of a control mechanism for manipulating interventional devices driven by (or otherwise associated with) respective hubs. The control mechanism of FIGS. 25A-25C may include any of the same or similar features and/or functions as any of the other control mechanisms described herein. In certain embodiments, each hub may be manipulated and/or otherwise moved using at least one control installed in the control mechanism. Each control may be adapted to move a unique hub and/or interventional device during an interventional procedure. For example, each control movement may trigger a responsive movement in a corresponding hub and/or interventional device. In certain embodiments, at least some movements of each control may trigger a responsive movement in a corresponding carriage on the support table, which may in turn drive movement of a corresponding hub.

Figure 25A:
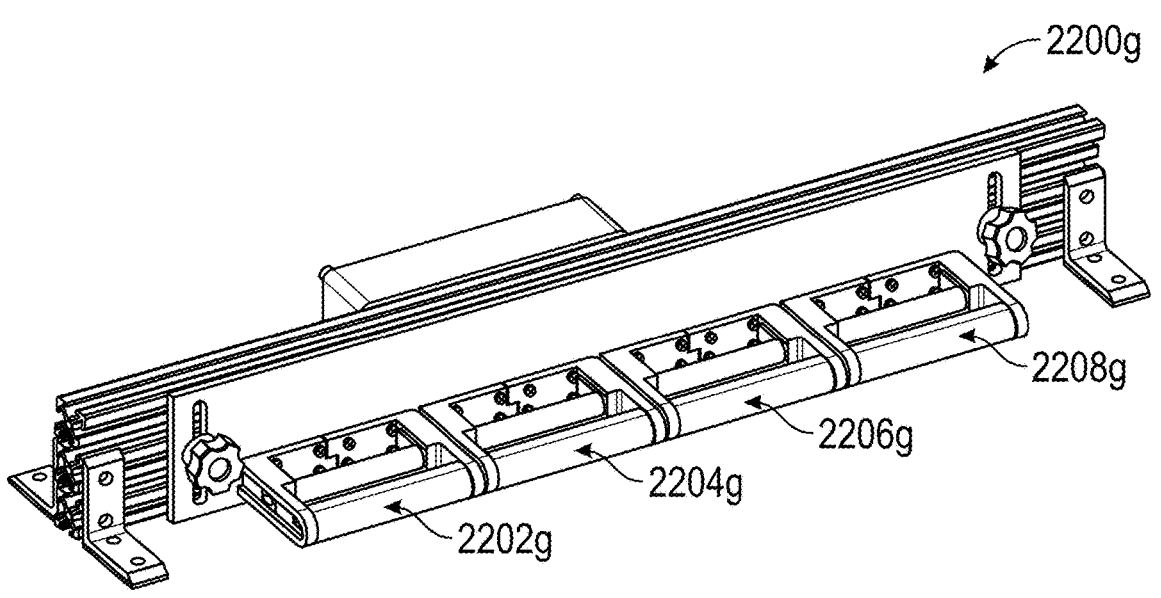
FIGS. 25A-25E illustrate an example control mechanism for manipulating interventional devices driven by respective hubs.
Figure 25B:
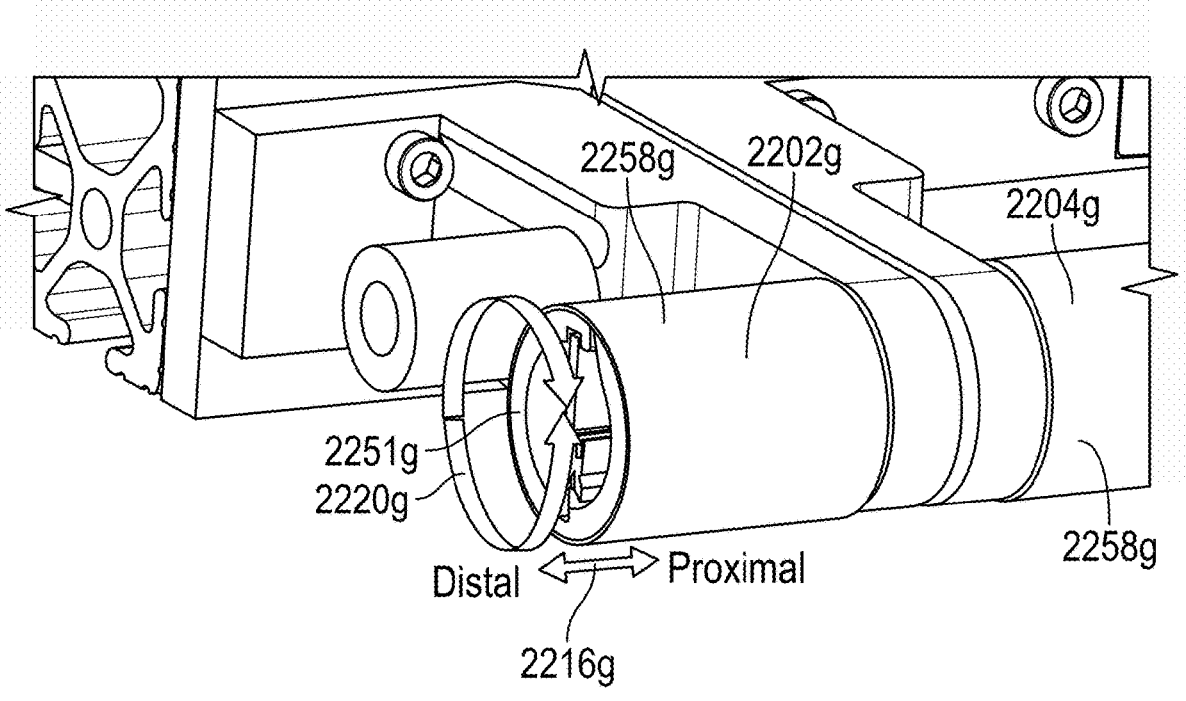

As shown in FIG. 25B, the control mechanism 2200*g* can include a first control 2202*g*, a second control 2204*g*, a third control 2206*g*, and a fourth control 2208*g*. More or fewer controls may be provided, depending upon the intended interventional device configuration. Each control 2202*g*-2208*g* can include a surface 2258*g* having a capacitive screen, a resistive screen, a touch pad, or other touch-based sensing device. The control mechanism 2200*g* may be positioned on or near to a patient support table having a set of hubs and catheters/interventional devices. In some implementations, the control mechanism 2200*g* may be positioned remote from the support table such as behind a radiation shield or in a different room or different geographical location in a telemedicine implementation.

Each control 2202*g*-2208*g* may correspond to and drive movement of a hub and/or interventional device. In certain embodiments, the control 2202*g* may be configured to move (e.g., axially and/or rotationally) an interventional device such as an 0.088 inch guide catheter (e.g., guide catheter 31 or guide catheter 2906), for example, by driving a hub (e.g., hub 30 or hub 2914) associated with the interventional device. Similarly, the control 2204*g* may be configured to move (e.g., axially and/or rotationally) an interventional device such as an 0.071 inch procedure catheter (e.g., catheter 29, catheter 120, or catheter 2904), for example, by driving a hub (e.g., hub 28, hub 122, or hub 2912) associated with the interventional device. The control 2206*g* may be configured to move (e.g., axially and/or rotationally) an interventional device such as a steerable access catheter (e.g., catheter 124 or catheter 2902), for example, by driving a hub (e.g., hub 126 or hub 2910) associated with the interventional device. The control 2208*g* may be configured to move (e.g., axially and/or rotationally) an interventional device such as a guidewire (e.g., guidewire 27 or guidewire 2907), for example, by driving a hub (e.g., hub 26 or hub 2909) associated with the interventional device.

In operation, if the user swipes a finger across the surface 2258*g* of the control 2202*g* (e.g., distally or proximally), as shown by the direction of arrow 2216*g*, a corresponding coupled hub and/or interventional device may move in the same direction by a same or scaled amount. If the user rotates the control 2202*g* (e.g., clockwise or counterclockwise) as shown by arrow 2220*g*, the corresponding interventional device can be driven rotationally (e.g., by a corresponding hub) in the same direction and/or by a same or scaled amount. If the user rotates the control 2202*g* about an axis of the controller, as shown by arrow 2220*g*, and swipes a finger across the capacitive touch region of the control 2202g, as shown by the arrow 2216g, a corresponding coupled interventional device can responsively move rotationally by a same or scaled amount and axially by a same or scaled amount.

Each control 2202g-2208g can include a slip ring 2257g and a stationary cylinder 2251g. Beneficially, the slip ring 2257g can allow infinite rotations of each control 2202g-2208g relative to the stationary cylinder 2251g. The stationary cylinder 2251g of each control 2202g-2208g can include a diameter smaller than the diameter of the controllers 2202g-2208g. In operation, when a user rotates the control 2202g, the control 2202g can rotate relative to the stationary cylinder 2251g.

The control may be configured to move the coupled hub axially on a 1:1 basis, or on a non 1:1 scaled basis. For example, if the user swipes a finger 10 mm across capacitive touch region of the control, then the corresponding hub may responsively move proximally or distally a distance of 10 mm.

The control may be configured to move the coupled hub rotationally on a 1:1 basis, or on a non 1:1 scaled basis. For example, if the user rotates the control 2202g about the stationary cylinder 2251g by 5 degrees, then the corresponding hub may responsively move an angular distance of 5 degrees.

The control mechanism can be configured to enable the clinician to adjust the linear displacement and/or rotational distance. For example, distal advance of a procedure catheter and an access catheter through a guide catheter and up to the selected ostium may desirably be accomplished in a 'fast' mode. But more distal travel into the neuro vasculature may desirably be accomplished in a relatively slow mode by actuation of a speed control. For example, for stages of a procedure where the clinician wishes to proceed in a "fast" mode, the clinician may adjust the control so that a 5 mm swipe across the capacitive touch region of the control causes the corresponding hub and/or interventional device to move in the same direction by 10 mm. For stages of the procedure where the clinician wishes to proceed in a relatively slow mode, the clinician may adjust the control so that a 5 mm swipe across the capacitive touch region of the control causes the corresponding hub and/or interventional device to move in the same direction by 1 mm. In some embodiments, one or more of the control 2202g, a second control 2204g, a third control 2206g, and a fourth control 2208g can be mounted together on a platform (e.g., a sled) that may be axially moveable to cause each of the corresponding interventional devices to translate together in the "fast" mode during either insertion or retraction. In such embodiments, the capacitive touch regions of the individual controls may be used to move their corresponding interventional devices in the "slow" mode.

Figure 25C:
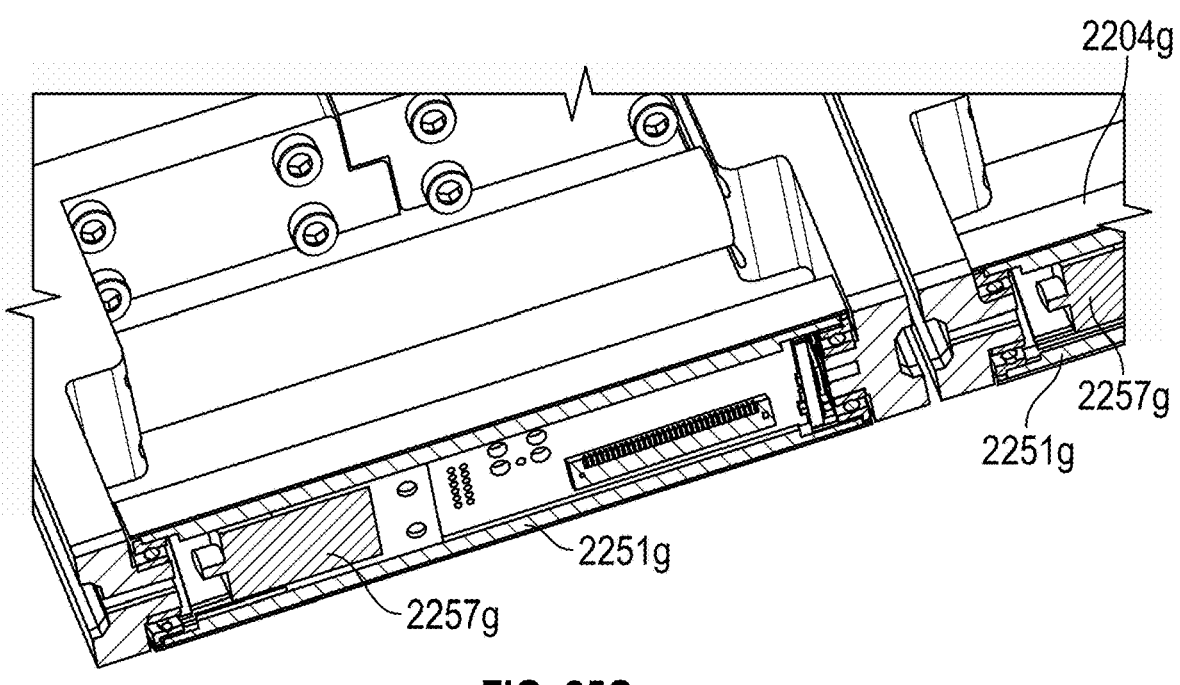
Figure 25D:
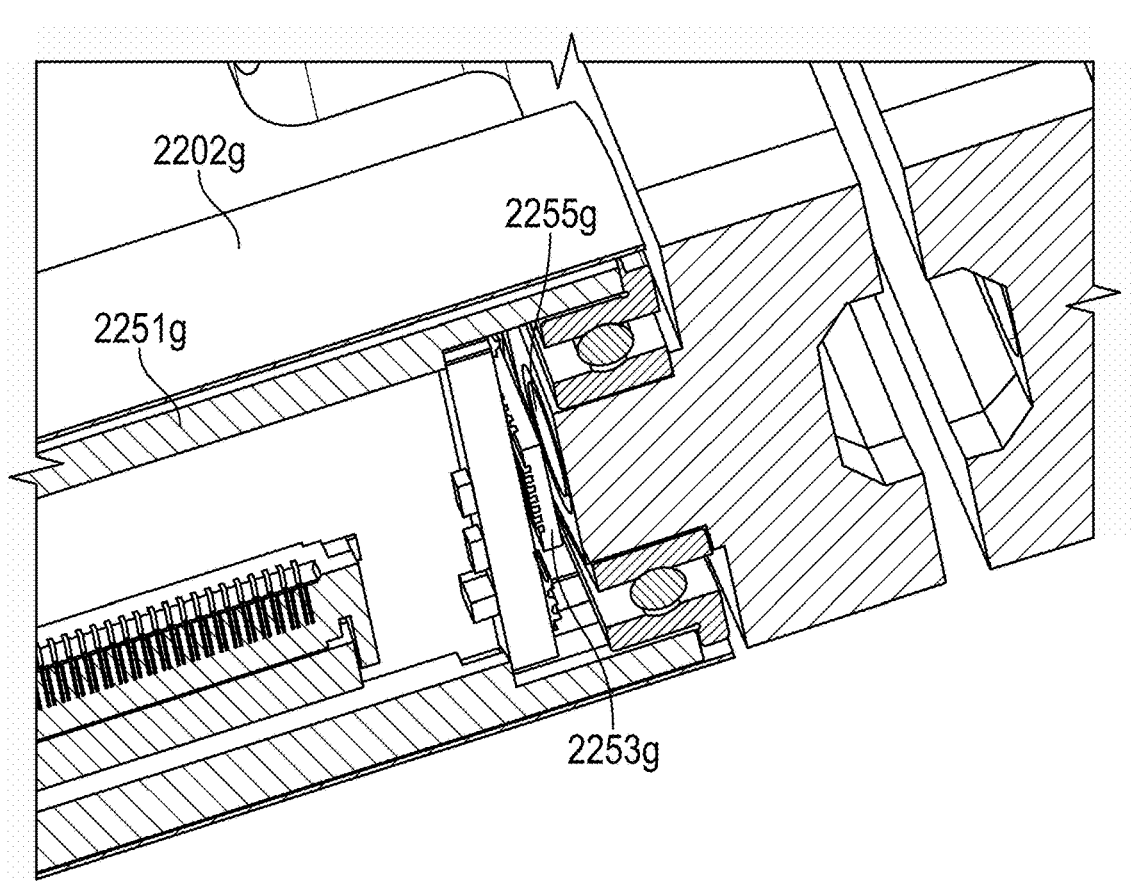

One or more rotation sensors 2253g can be used to measure the rotational movement of the control relative to the stationary cylinder 2251g, as shown in FIGS. 25B-D. Each control 2202g-2208g, can include a stationary cylinder 2251g. The one or more rotation sensors 2253g can be configured to measure the rotational movement (e.g., 5 degree) of a control relative to the stationary cylinder 2251g corresponding to an individual control. The rotational distance the corresponding interventional device will move can depend, among other things, on the rotational movement measurement by the one or more rotation sensors. The one or more rotation sensors can include, for example, a magnet 2255g, as shown in FIG. 25D, a magneto resistive element, an encoder, a potentiometer, a hall effect sensor, or a combination thereof. The control mechanism 2200g can include a rotation sensor for each control.

While the foregoing describes example operations of the control 2202g, it will be understood by one of skill in the art that any of the controls 2204g, 2206g, and 2208g may be operated in the same manner. In certain embodiments, each of the controls 2202g, 2204g, 2206g, and 2208g can control axial and rotational movement of corresponding interventional devices. In other embodiments, one or more of the controls 2202g, 2204g, 2206g, and 2208g may control only axial movement or only rotational movement of a corresponding interventional device.

Figure 25E:
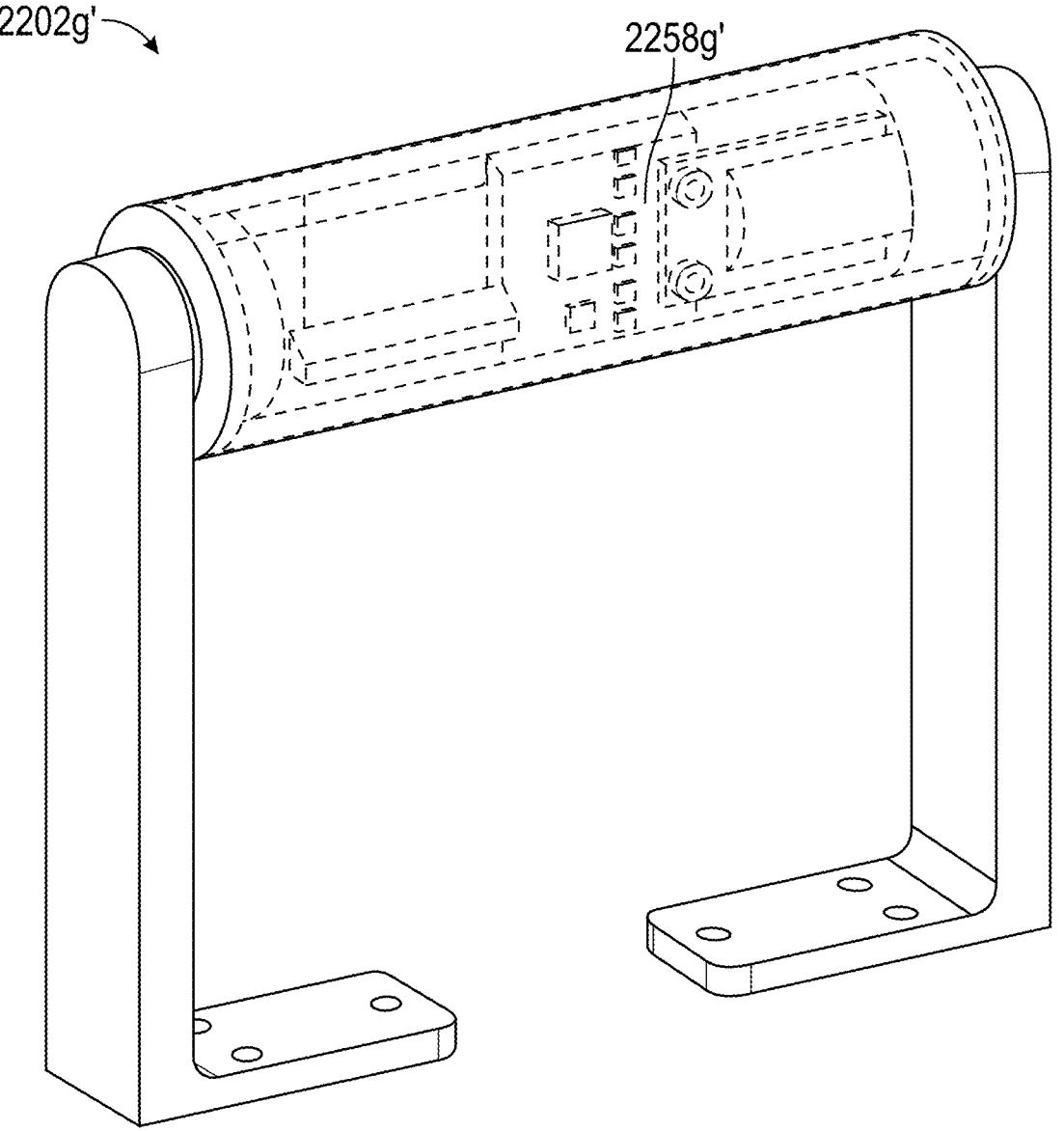

The control 2202g' shown in FIG. 25E, is an alternative embodiment of one of the control 2202g-2208g shown in FIGS. 25A-25D. Similarly, control 2202g' can include a surface 2258g' having a capacitive screen, a resistive screen, a touch pad, or other touch-based sensing device.

Figure 26A:
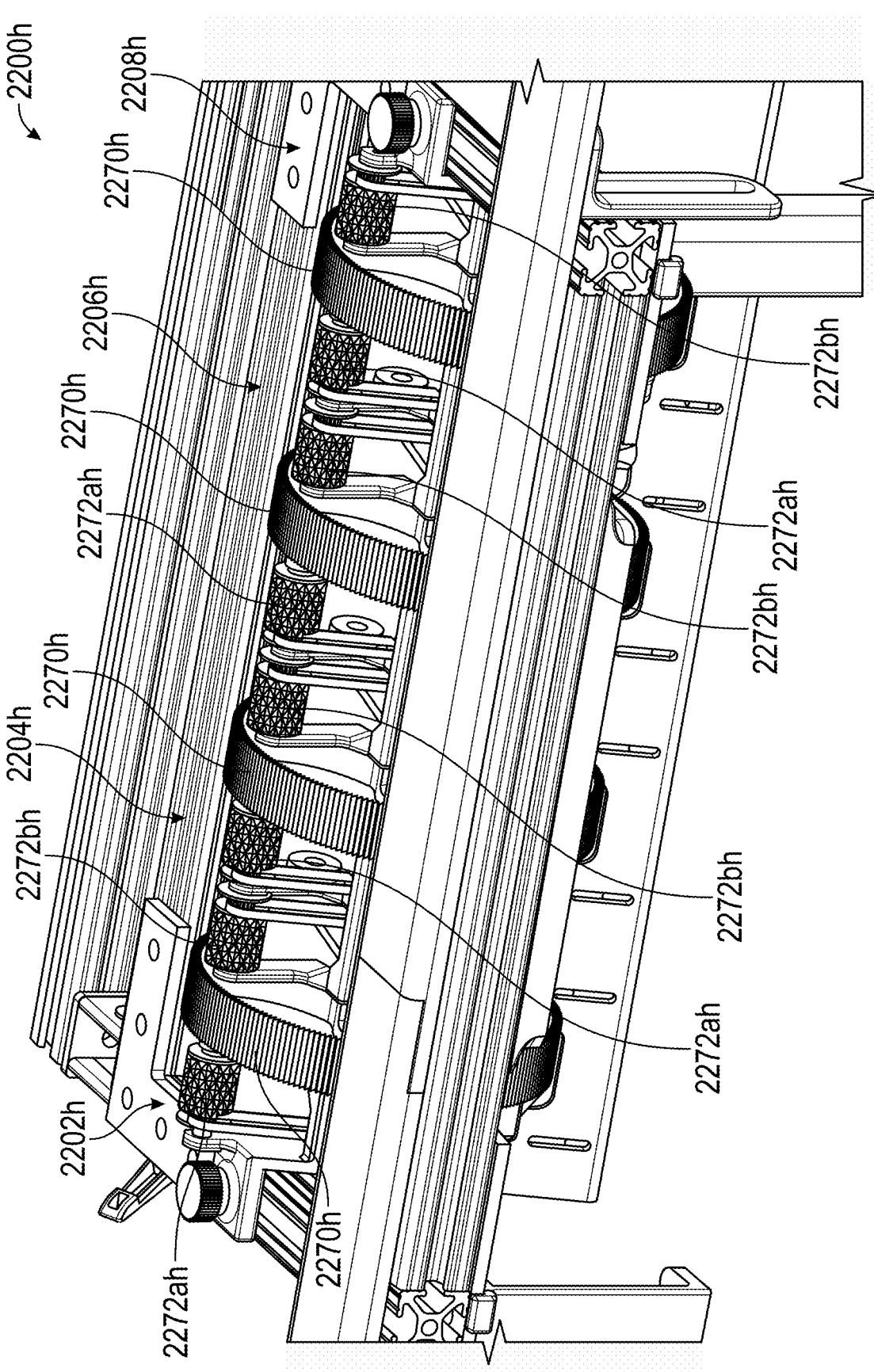
FIGS. 26A-26C illustrate an example control mechanism for manipulating interventional devices driven by respective hubs.
Figure 26B:
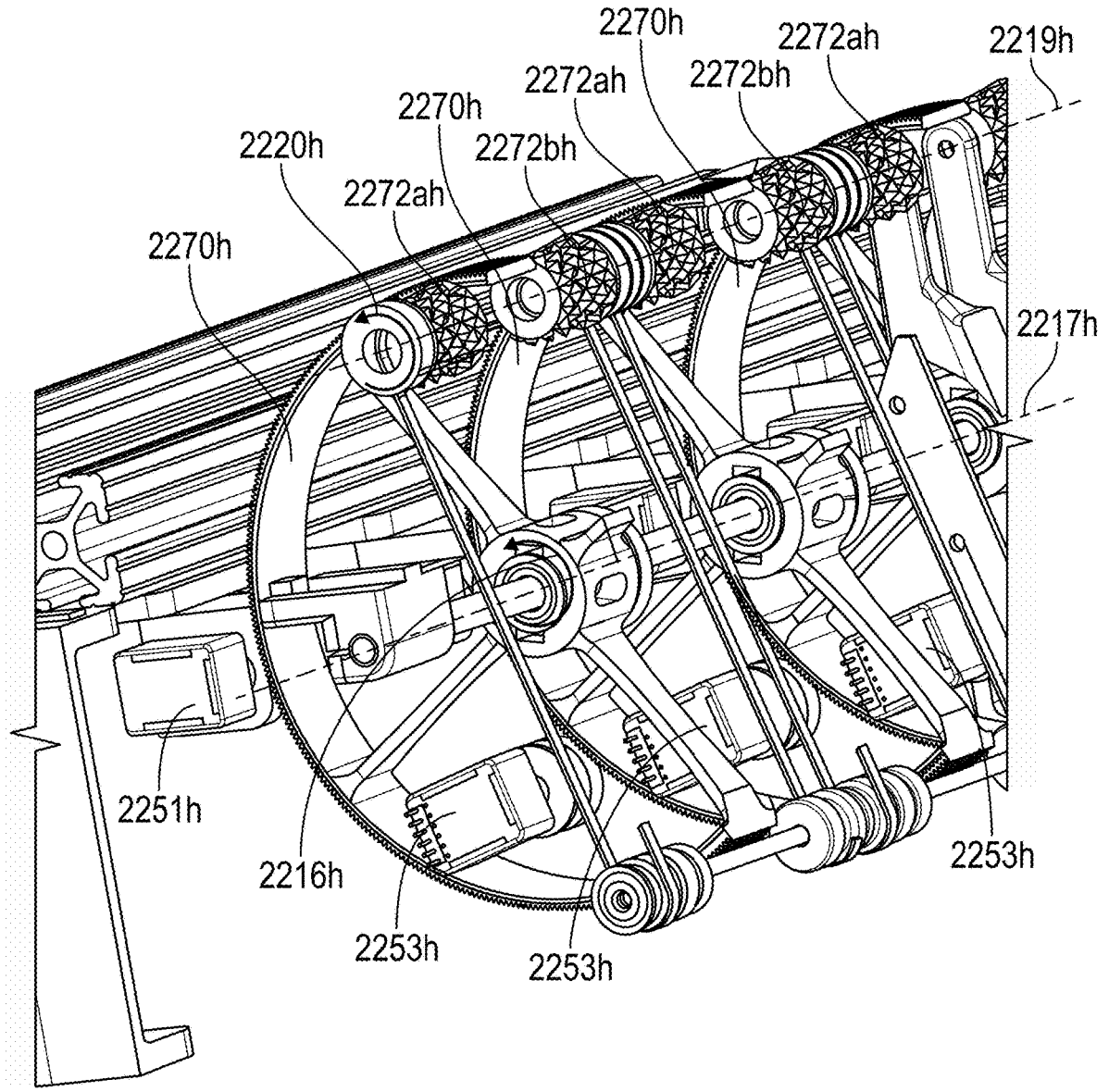

FIGS. 26A-26B illustrate another example of a control mechanism for manipulating interventional devices driven by (or otherwise associated with) respective hubs. The control mechanism of FIGS. 26A-26C may include any of the same or similar features and/or functions as any of the other control mechanisms described herein. In certain embodiments, each hub may be manipulated and/or otherwise moved using at least one control. Each control may be adapted to move a unique hub and associated interventional device during an interventional procedure. For example, each control movement may trigger a responsive movement in a corresponding hub and/or interventional device. In certain embodiments, at least some movements of each control may trigger a responsive movement in a corresponding carriage on the support table, which may in turn drive movement of a corresponding hub.

As shown in FIG. 26A, the control mechanism 2200h can include a first control 2202h, a second control 2204h, a third control 2206h, and a fourth control 2208h. More or fewer controls may be provided, depending upon the intended interventional device configuration. Each control can include spinning wheel 2270h and a plurality of knobs 2272ah, 2272bh. The plurality of knobs 2272ah, 2272bh can be coupled together. Beneficially, this may allow a user to control the plurality of knobs 2272ah, 2272bh using a right hand or a left hand. Each spinning wheel 2270h may rotate around a first axis 2217h, as indicated by arrow 2216h, to cause axial movement of a corresponding hub and/or interventional device. In addition, the plurality of knobs 2272ah, 2272bh may rotate about a second axis 2219h, as indicated by arrow 2220h to cause rotational movement of a corresponding hub and/or interventional device. Manipulating the spinning wheel 2270h and/or cither knob 2272ah, 2272bh can cause a corresponding hub and/or interventional device to move.

The control mechanism 2200h including the controls 2202h, 2204h, 2206h, 2208h may be positioned on or near to a patient support table having a set of hubs and catheters/interventional devices. In some implementations, the control mechanism may be positioned remote from the support table such as behind a radiation shield or in a different room or different geographical location in a telemedicine implementation.

Each control 2202h-2208h may correspond to and drive movement of a hub and/or a hub and/or interventional device. In certain embodiments, the control 2202h may be configured to move (e.g., axially and/or rotationally) an interventional device such as an 0.088 inch guide catheter (e.g., guide catheter 31 or guide catheter 2906), for example, by driving a hub (e.g., hub 30 or hub 2914) associated with the interventional device. Similarly, the control 2204*h* may be configured to move (e.g., axially and/or rotationally) an interventional device such as an 0.071 inch procedure catheter (e.g., catheter 29, catheter 120, or catheter 2904), for example, by driving a hub (e.g., hub 28, hub 122, or hub 2912) associated with the interventional device. The control 2206*h* may be configured to move (e.g., axially and/or rotationally) an interventional device such as a steerable access catheter (e.g., catheter 124 or catheter 2902), for example, by driving a hub (e.g., hub 126 or hub 2910) associated with the interventional device. The control 2208*h* may be configured to move (e.g., axially and/or rotationally) an interventional device such as a guidewire (e.g., guidewire 27 or guidewire 2907), for example, by driving a hub (e.g., hub 26 or hub 2909) associated with the interventional device.

In operation, if the user rotates the spinning wheel 2270*h* of the first control 2202*h* (by, for example, half a revolution (e.g., 180°)), a corresponding hub and/or interventional device may move axially in a corresponding direction by a same or scaled amount. For example, if the user rotates the spinning wheel 2270 counterclockwise, the corresponding hub and/or interventional device may move proximally and if a user rotates the spinning wheel 2270*h* in a clockwise direction, the corresponding hub may move distally. If the user rotates either knob 2272*ah*, 2272*bh* of the first control 2202*h* (e.g., clockwise or counterclockwise), the corresponding interventional device can be driven rotationally (e.g., by a corresponding hub) in the same direction and/or by a same or scaled amount. If the user rotates the spinning wheel 2270*h* of the first control 2202*h* and rotates either knob 2272*ah*, 2272*bh* of the first control 2202*h*, a corresponding coupled interventional device can responsively move rotationally by a same or scaled amount and axially in a corresponding direction by a same or scaled amount.

The control may be configured to move the corresponding hub and/or interventional device axially on a 1:1 basis, or on a non 1:1 scaled basis. For example, if the user rotates the wheel about 5 degrees, then the corresponding hub and/or interventional device may responsively move an axial distance of 5 mm.

The control may be configured to move the corresponding interventional device rotationally on a 1:1 basis, or on a non 1:1 scaled basis. For example, if the user rotates either knob 2072*ah*, 2072*bh* of the first control 2202*h* by 5 degrees, then the corresponding hub may responsively move an angular distance of 5 degrees.

The control mechanism 2200 can be configured to enable the clinician to adjust the scale of linear displacement and/or rotational displacement of the corresponding hub and/or interventional device relative to the movements of the controls. For example, distal advance of a procedure catheter and an access catheter through a guide catheter and up to the selected ostium may desirably be accomplished in a 'fast' mode. More distal travel into the neuro vasculature may desirably be accomplished in a relatively slow mode by actuation of a speed control. For example, for stages of a procedure where the clinician wishes to proceed in a "fast" mode, the clinician may adjust the control so that a 180° rotational movement of the spinning wheel 2270*h* causes the corresponding coupled hub and/or interventional device to move in the same direction by 50 mm. For stages of the procedure where the clinician wishes to proceed in a relatively slow mode, the clinician may adjust the control so that the same 180° rotational movement of the spinning wheel causes the corresponding coupled hub and/or interventional device to move in the same direction by 10 mm.

Figure 26C:
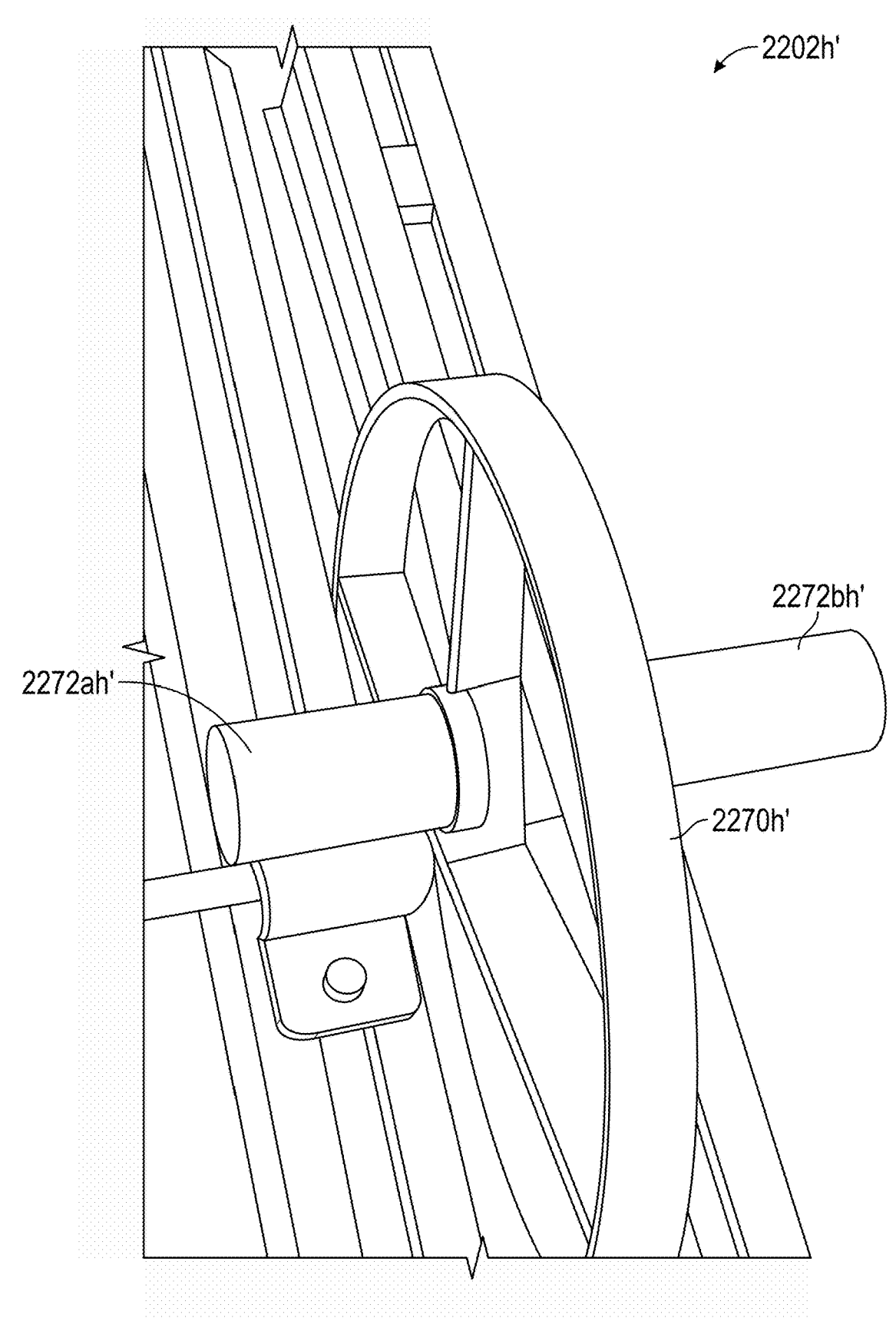

The control 2202*h*' shown in FIG. 26C, is an alternative embodiment of one of the controls 2202*h*-2208*h* shown in FIGS. 26A-26B. Like controls 2202*h*-2208*h*, control 2202*h*' can include a spinning wheel 2270*h*' and a plurality of knobs 2272*ah*', 2272*bh*'. The position of the plurality of knobs 2272*ah*', 2272*bh*' relative to the spinning wheel 2270*h*' can be different than the position of the plurality of knobs 2272*ah*, 2272*bh* relative to the spinning wheel 2270*h*.

One or more rotation sensors can be used to measure the rotational movement of the spinning wheel 2270*h* and the plurality of knobs 2272*ah*, 2272*bh*, as shown in FIG. 26B. For example, the one or more rotation sensors 2251*h*, 2253*h* can be configured to measure the rotational movement (e.g., 180 degree) of the spinning wheel 2270 and/or the plurality of knobs 2272*ah*, 2272*bh*. For example, the rotation sensor 2251*h* can be configured to measure the rotational movement of the spinning wheel 2270*h* while the rotation sensor 2253*h* can be configured to measure the rotational movement of the plurality of knobs 2272*ah*, 2272*bh*. The rotational distance and/or distal travel the corresponding hub and/or interventional device will move depends, among other things, on the rotational movement measured by the one or more rotation sensors 2251*h*, 2253*h*. The one or more rotation sensors can include, for example, a magnet, a magnet resistive element, an encoder, a potentiometer, a hall effect sensor, or a combination thereof.

While the foregoing describes example operations of the control 2202*h*, it will be understood by one of skill in the art that any of the controls 2204*h*, 2206*h*, and 2208*h* may be operated in the same manner. In certain embodiments, each of the controls 2202*h*, 2204*h*, 2206*h*, and 2208*h* can control axial and rotational movement of corresponding interventional devices. In other embodiments, one or more of the controls 2202*h*, 2204*h*, 2206*h*, and 2208*h* may control only axial movement or only rotational movement of a corresponding interventional device.

Figure 27:
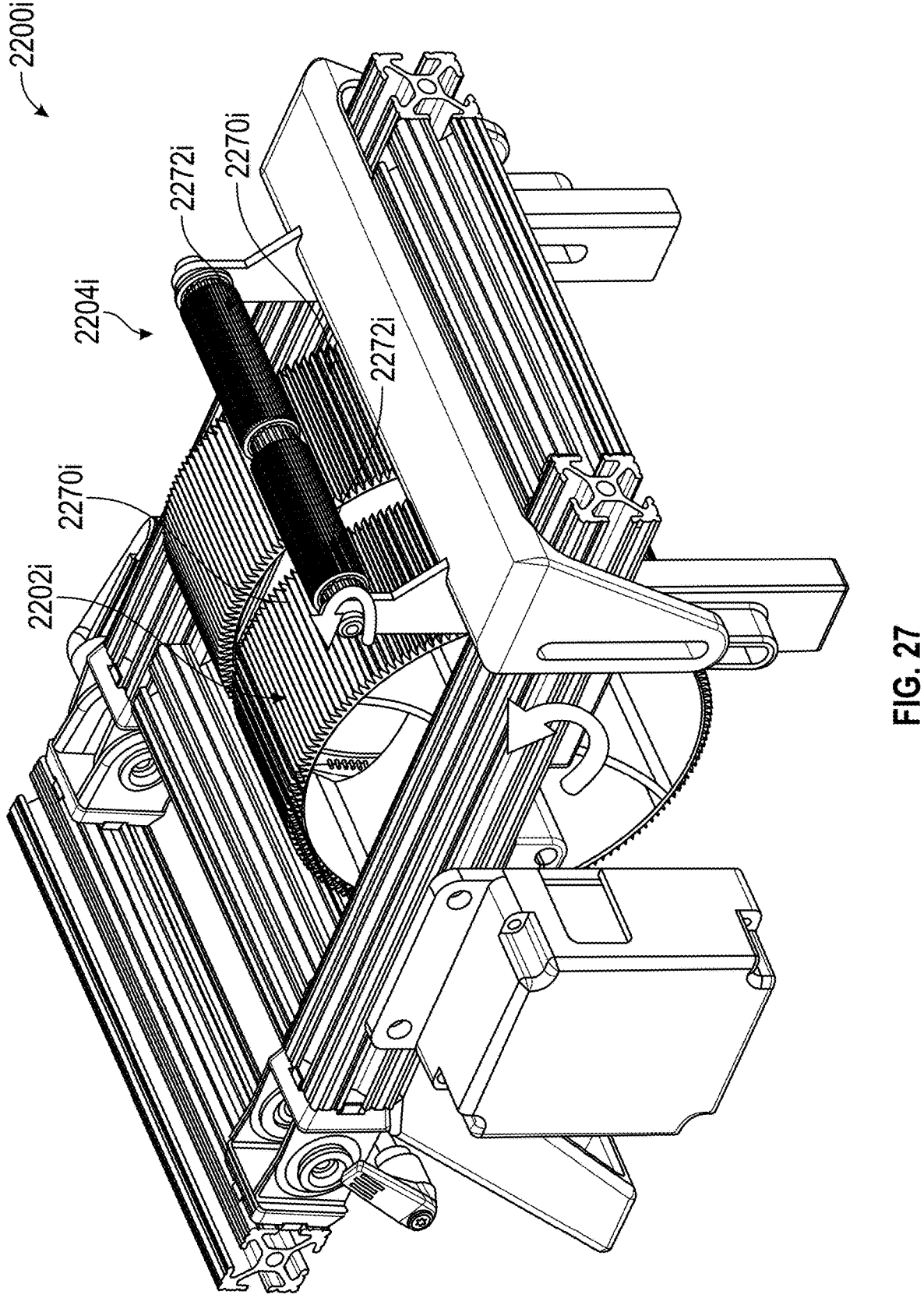
FIG. 27 illustrates an example control mechanism for manipulating interventional devices driven by respective hubs.

FIG. 27 illustrates another example of a control mechanism for manipulating interventional devices driven by (or otherwise associated with) respective hubs. The control mechanism 2200*i* shown in FIG. 27 is an alternative embodiment of the control mechanism shown in FIGS. 26A-26C. The control mechanism 2200*i* can include a first control 2202*i* and a second control 2204*i* for controlling at least two corresponding hubs and/or interventional devices. More or fewer controls may be provided, depending upon the intended interventional devices configuration. Each control can include spinning wheel 2270*i* and a knob 2272*i*. Manipulating the spinning wheel 2270*i* and/or knob 2272*i* can cause a corresponding hub and/or interventional device to move, as described for example, with respect to FIGS. 26A-C.

Figure 28A:
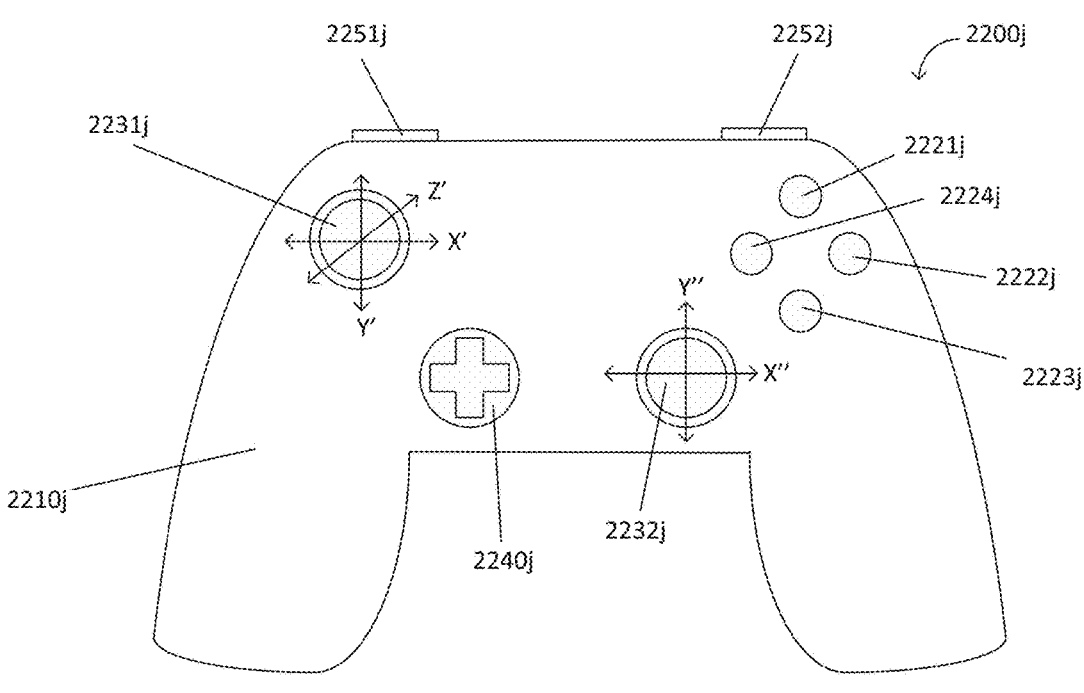
FIGS. 28A-28C illustrate an example control mechanism for manipulating interventional devices driven by respective hubs.
Figure 28B:
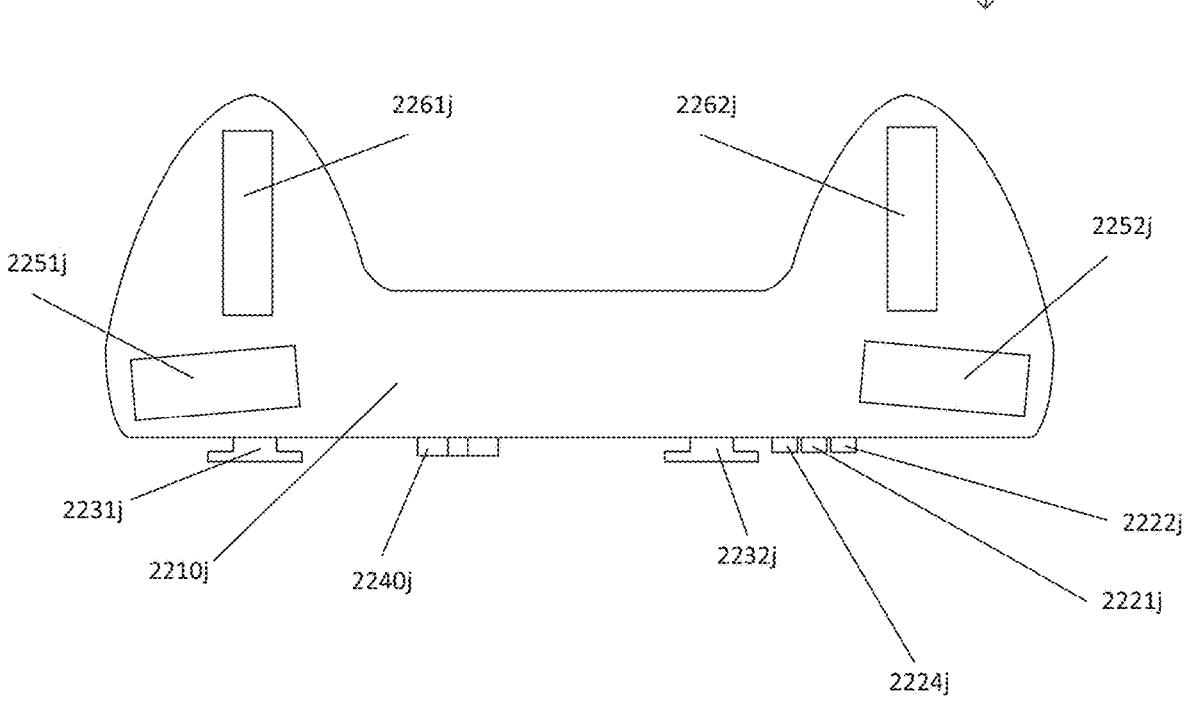

FIGS. 28A and 28B illustrate another example control mechanism 2200*j* for manipulating interventional devices driven by (or otherwise associated with) respective hubs. The control mechanism of FIGS. 28A-28B may include any of the same or similar features and/or functions as any of the other control mechanisms described herein. In some embodiments, the control mechanism can include a controller having one or more buttons, joysticks, and/or directional pads (d-pads). In some embodiments, each hub may be manipulated and/or otherwise moved using one or more of the buttons, joysticks, and/or d-pads. Each of the one or more joysticks can have a starting position. The control mechanism can be configured so that each of the one or more joysticks returns to its starting position when each of the one or more joysticks is not being manipulated by a user. In some embodiments, each of the buttons, joysticks, and/or a d-pad may be adapted to move a unique hub and associated interventional device during an interventional procedure.

The control mechanism 2200*j* can include a control 2210*j* having one or more buttons, joysticks, and/or a d-pad. More or fewer buttons, joysticks, and/or d-pads may be provided, depending upon the intended interventional devices configuration. For example, and as shown in FIGS. 28A and 28B, the control 2210*j* can include a plurality of buttons 2221*j*, 2222*j*, 2223*j*, 2224*j*, a first joystick 2231*j*, a second joystick 2232*j*, a d-pad 2240*j*, a first shoulder button or bumper button 2251*j*, a second shoulder button or bumper button 2252*j*, a first trigger 2261*j*, and/or a second trigger 2262*j*. Each of the buttons, joysticks, and/or d-pads can be manipulated by a user. For example, a joystick can be moved along one or more axes, and one or more of the joysticks, buttons, and d-pads can be pressed. Manipulation of one or more of the buttons, joysticks, and/or d-pads may trigger a responsive movement in a corresponding hub and/or interventional device. In certain embodiments, at least some movements of the buttons, joysticks, and/or d-pads may trigger a responsive movement in a corresponding carriage on the support table, which may in turn drive movement of a corresponding hub. The control mechanism 2200*j* may be positioned on or near to a patient support table having a set of hubs and catheters/interventional devices. In some implementations, the control mechanism 2200*j* may be positioned remote from the support table such as behind a radiation shield or in a different room or different geographical location in a telemedicine implementation.

One or more of the plurality of buttons, joysticks, and/or a d-pad of the control 2210*j* may correspond to and drive movement of a hub and/or interventional device. In certain embodiments, one or more buttons, joysticks, and/or a d-pad may be operated to link or assign control of a hub (e.g., control of axial and/or rotational movement) to another one of the plurality of buttons, joysticks, and/or d-pad of the control 2210*j*. For example, in certain embodiments, one of the plurality of buttons, joysticks, and/or a d-pad can be selected to assign control of a particular hub to the joystick 2231*j*, and another one of the plurality of buttons, joysticks, and/or a d-pad can be selected to assign control of a different particular hub to the joystick 2231*j*.

In some embodiments, button 2224*j* and the first joystick 2231*j* can be configured to move (e.g., axially and/or rotationally) an interventional device such as an 0.088 inch guide catheter (e.g., guide catheter 31 or guide catheter 2906), for example, by driving a hub (e.g., hub 30 or hub 2914) associated with the interventional device. For example, a user can enable translation and/or rotation of the corresponding drive hub (e.g., hub 30 or hub 2914) or interventional device (e.g., guide catheter 31 or guide catheter 2906) by pressing the button 2224*j*. When translation and/or rotation of the corresponding hub and/or interventional device is enabled, the user can manipulate the first joystick 2231*j* to control the corresponding drive hub and/or interventional device. Similarly, button 2222*j* and the first joystick 2231*j* can be configured to move (e.g., axially and/or rotationally) an interventional device such as an 0.071 inch procedure catheter (e.g., catheter 29, catheter 120, or catheter 2904), for example, by driving a hub (e.g., hub 28, hub 122, or hub 2912) associated with the interventional device. For example, a user can enable translation and/or rotation of the corresponding hub (e.g., hub 28, hub 122, or hub 2912) and/or interventional device (e.g., catheter 29, catheter 120, or catheter 2904) by pressing the button 2222*j*. When translation and/or rotation of the corresponding hub and/or interventional device is enabled, the user can manipulate the first joystick 2231*j* to control the corresponding hub and/or interventional device. The button 2223*j* and the first joystick 2231*j* can be configured to move (e.g., axially and/or rotationally) an interventional device such as a steerable access catheter (e.g., catheter 124 or catheter 2902), for example, by driving a hub (e.g., hub 126 or hub 2910) associated with the interventional device. For example, a user can enable translation and/or rotation of a corresponding hub (e.g., hub 126 or hub 2910) and/or interventional device (e.g., catheter 124 or catheter 2902) by pressing the button 2223*j*. When translation and/or rotation of the corresponding hub and/or interventional device is enabled, the user can manipulate the first joystick 2231*j* to control the corresponding hub and/or interventional device. The button 2221*j* and the first joystick 2231*j* can be configured to drive more than one hub at the same time and/or more than one interventional device at the same time. For example, a user can enable translation and/or rotation of a plurality of hubs (e.g., hubs 2910, 2912, and 2914) of a plurality of interventional devices (e.g., catheters 2902, 2904, and 2906) by pressing the button 2221*j*. When translation and/or rotation of the plurality of hubs and/or interventional devices is enabled, the user can manipulate the first joystick 2231*j* to control each of the plurality of hubs and/or plurality of interventional devices simultaneously.

In some cases, the second joystick 2232*j* can be configured to move (e.g., axially and/or rotationally) an interventional device such as a guidewire (e.g., guidewire 27 or guidewire 2907), for example, by driving a hub (e.g., hub 26 or hub 2909) associated with the interventional device. In some embodiments, one of the plurality of buttons, joysticks, and/or a d-pad can be selected to assign control of a particular hub to the joystick 2232*j*, and another one of the plurality of buttons, joysticks, and/or a d-pad can be selected to assign control of a different particular hub to the joystick 2232*j*, for example as described with respect to the joystick 2231*j*.

The control 2210*j* can be configured to enable the clinician to adjust the functionality of each or at least some of the buttons, joysticks, and/or d-pads. That is, each of the plurality of buttons, joysticks, and/or a d-pad can be configured by the clinician to perform different functions and/or enable control of different hubs.

In operation, if the user enables control of a drive hub by pressing the button 2222*j* and moves the first joystick 2231*j* in a direction along arrow X' (i.e., about axis 2219*j*), a corresponding coupled hub and/or interventional device may move responsively in a corresponding axial direction at a predefined linear velocity. The corresponding coupled hub and/or interventional device may continue to move in the same direction at the predefined linear velocity until the user releases (e.g., stops manipulating) the first joystick 2231*j* or further moves the first joystick 2231*j*. When the user stops manipulating the first joystick 2231*j*, the first joystick 2231*j* can return to its starting position. If the user moves the first joystick 2231*j* in a direction along arrow Y' (i.e., about axis 2217*j*), the corresponding coupled hub can drive the corresponding interventional device rotationally in a corresponding direction at a predefined angular velocity. When the user stops manipulating the first joystick 2231*j*, the first joystick 2231*j* can return to its starting position. In some cases, if the user moves the first joystick 2231*j* a direction having both X' and Y' components, (for example, diagonally in the direction along arrow Z'), the corresponding coupled interventional device can responsively move rotationally at a predefined angular velocity and axially at a predefined linear velocity. The corresponding coupled interventional device can continue to move rotationally at the predefined angular velocity and axially at the predefined linear velocity until the user releases (e.g., stops manipulating) the first joystick 2231*j* or further moves the first joystick 2231*j*. When the user stops manipulating the first joystick 2231*j*, the first joystick 2231*j* can return to its starting position. A clinician may control a different hub and/or interventional device, or more than one hub and/or interventional device at the same time by pressing one of the second, third, or fourth buttons 2221*j*, 2223*j*, 2224*j*, which can enable control of one more of the hubs and/or interventional devices, and operating the first and/or second joysticks 2231*j*, 2232*j*.

In some embodiments, if the user moves the second joystick 2232*j* in a direction along arrow Y", the corresponding coupled interventional device can responsively move rotationally at a predefined angular velocity. The corresponding coupled interventional device can continue to move rotationally at the predefined angular velocity until the user releases (e.g., stops manipulating) the second joystick 2232*j* or further moves the second joystick 2232*j*. When the user stops manipulating the second joystick 2232*j*, the second joystick 2232*j* can return to its starting position. If the user moves the second joystick 2232*j* in a direction along the arrow X", the corresponding coupled interventional device can responsively move axially at a predefined velocity. The corresponding coupled interventional device can continue to move axially at the predefined velocity until the user releases (e.g., stops manipulating) the second joystick 2232*j* or further moves the second joystick 2232*j*. When the user stops manipulating the second joystick 2232*j*, the second joystick 2232*j* can return to its starting position.

In some embodiments, the first and second triggers 2261*j*, 2262*j* can be used to articulate and/or relax an interventional device, such as access catheter. For example, pressing the first trigger 2261*j* can cause the access catheter to relax. In some cases, the access catheter will continue to relax until the user releases the first trigger 2261*j*. The access catheter can stay in a relaxed position even when the first trigger 2261*j* is released. The user can articulate the access catheter by pressing the second trigger 2262*j*. In some cases, the access catheter will continue to articulate until the user releases the second trigger 2262*j*.

Other axes and degrees of freedom may be defined to enable control 2210*j* to perform movements that may be translated to movement of hubs and/or interventional devices. For example, the control mechanism 2200*j* may be provided with one or more deflection controls configured to initiate a lateral deflection in a deflection zone on the corresponding interventional device.

Movement of the first and/or second joysticks 2231*j*, 2232*j* along arrows X', Y', Z', Y" can be configured to move the coupled hub on a 1:1 basis, or on a non 1:1 scaled basis. For example, if the user rotates the first joystick 2231*j* about 5 degrees along arrow X' (i.e., about axis 2219*j*), then the corresponding hub may responsively move at a predefined linear velocity of 5 mm/second in the same direction.

Movement of the first and/or second joysticks 2231*j*, 2232*j* along arrows X', Y', Z', Y" can be configured to rotate the coupled hub on a 1:1 basis, or on a non 1:1 scaled basis. For example, if the user rotates the first joystick 2231*j* about 5 degrees along arrow Y' (i.e., about axis 2217*j*), then the corresponding hub may responsively move at a predefined angular velocity of 5 degrees/second.

In some implementations, the scaled amount described herein may be determined using a scale factor. The scale factor may apply to one or both axial and rotational movement. In some implementations, a first scale factor is selected for translational movement and a second scale factor, different than the first scale factor, is selected for rotational movement. The axial scaling factor may drive proximal catheter movement at a faster speed than distal catheter movement for a given proximal or distal manipulation of the control.

The rotational scale factor may be 1:1 while the axial scale factor may move the hub by a greater distance than movement of the control such that hub travel to control travel is at least about 2:1 or 5:1 or 10:1 or more depending upon the desired axial length of the control assembly.

Figure 28C:
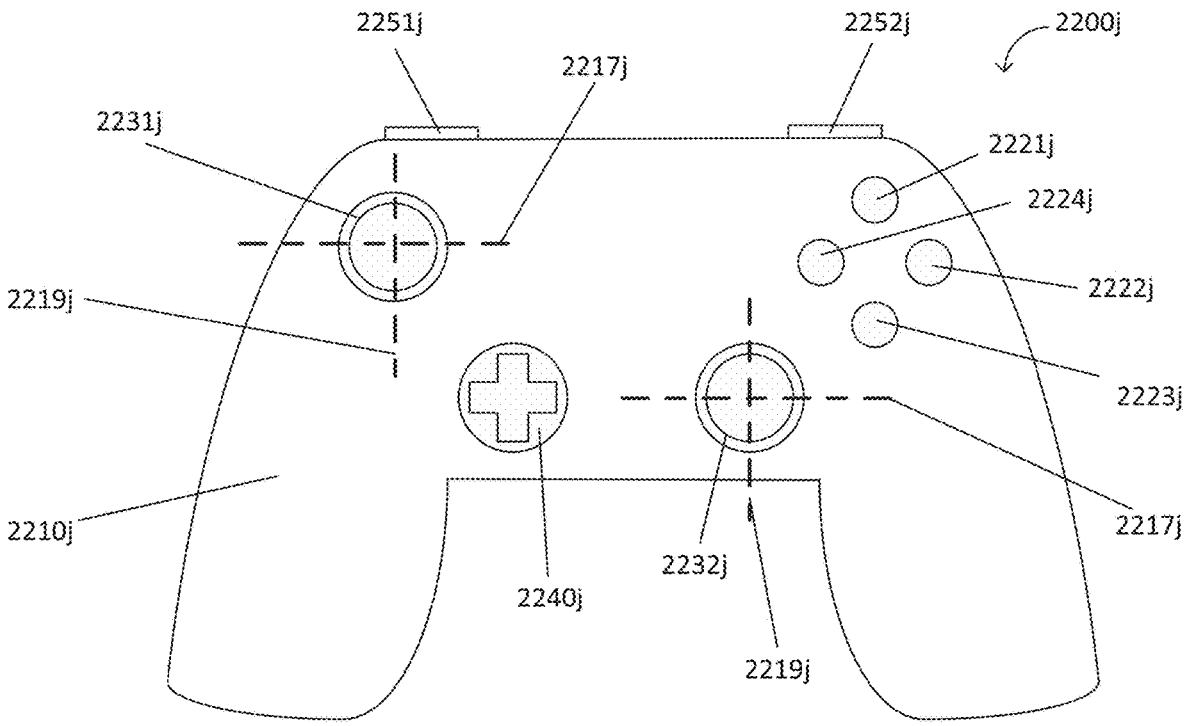

One or more rotation sensors can be used to measure the rotational movement of each joystick 2231*j*, 2232*j* about axis 2217*j* and/or axis 2219*j*, as shown in FIG. 28C, relative to the starting position of each control. For example, the one or more rotation sensors can be configured to measure the rotational movement (e.g., 5 degrees) of a control from its starting position. The linear velocity and/or predefined angular velocity at which the corresponding interventional device will move can depend on the measurement by the one or more rotation sensors. The one or more rotation sensors can include, for example, an encoder, a potentiometer, a hall effect sensor, or a combination thereof. In some cases, the control mechanism 2200*j* can include one or more rotation sensors for each joystick 2231*j*, 2232*j*.

The control mechanism 2200*j* can be configured to enable the clinician to adjust the scale factor for different parts of the procedure. For example, distal advance of a procedure catheter and an access catheter through a guide catheter and up to the selected ostium may desirably be accomplished in a 'fast' mode. More distal travel into the neuro vasculature may desirably be accomplished in a relatively slow mode by actuation of a speed control. For example, for stages of a procedure where the clinician wishes to proceed in a "fast" mode, the clinician may adjust the predefined linear velocity to 10 mm/second when the control moves 5 degrees along the arrow X' (i.e., about axis 2219*j*). For stages of the procedure where the clinician wishes to proceed in a relatively slow mode, the clinician may adjust the predefined linear velocity to 2 mm/second when the control moves 5 degrees along the arrow X'.

Any of the control mechanisms disclosed herein, including but not limited to control mechanisms 2200, 2200*a*, 2200*b*, 2200*c*, 2200*d*, 2200*e*, 2200*f*, 2200*g*, 2200*h*, 2200*i*, and 2200*j* can be configured to allow the user to manipulate two or more hubs and/or interventional devices simultaneously. For example, the control mechanisms can be configured to fix the relative positions (e.g., axial and/or rotational positions) of two or more hubs and/or interventional devices relative to one another. When the relative positions of two or more hubs and/or interventional devices are fixed, operation of a control as described herein can cause the two or more hubs and/or interventional devices to move axially and/or rotationally together as described herein. In other embodiments, the two or more hubs and/or interventional devices can be configured to move at different rates/distances when a user operates a single control. For example, moving a control by 2 mm can cause a first hub and/or interventional device to move 2 mm and cause a second a second hub and/or interventional device to move 1 mm.

In some embodiments, moving a hub close to an adjacent second hub can cause the second hub to start moving (e.g., to prevent collision). For instance, moving control 2202*a* so that a first hub moves in the direction of a second hub controlled by control 2204*a* can cause control the second hub to move to move (thereby causing the related interventional device to move) if the first hub gets within a predefined distance of the second hub. The predefined distance can be, for example, about 1 mm, about 2 mm, about 3 mm, about 4 mm, about 5 mm, etc. In some embodiments, moving a first hub close to an adjacent second hub can cause the first hub to stop moving. For instance, if a user moves control 2202*a* to move a first hub within a predefined distance of a second hub controlled by control 2204*a*, the user may be prevented from further advancing the first hub using the control 2202*a* in the direction of the second hub until control 2204*a* is moved to move the second hub further from the first hub.

Controlling the speed of the corresponding hubs either axially or both axially and rotationally may enhance the overall speed of the procedure. For example, advance of the various devices from the femoral access point up to the aortic arch may desirably be accomplished at a faster rate than more distal navigation closer to the treatment site. Also proximal retraction of the various devices, particularly the guidewire, access catheter and procedure catheter may be desirably accomplished at a relatively higher speeds than distal advance.

Any of the control mechanisms disclosed herein, including but not limited to control mechanisms 2200, 2200*a*, 2200*b*, 2200*c*, 2200*d*, 2200*e*, 2200*f*, 2200*g*, 2200*h*, 2200*i*, and 2200*j*, can be configured to allow the user to control movement (e.g., axial movement) of a telescoping drive table. For example, at least one control of a control mechanism can be configured to cause axial movement of the telescoping drive table in order to cause axial movement of a hub coupled to the telescoping drive table. For example, any of the control mechanisms disclosed herein, including but not limited to control mechanisms 2200, 2200*a*, 2200*b*, 2200*c*, 2200*d*, 2200*c*, 2200*f*, 2200*g*, 2200*h*, 2200*i*, and 2200*j*, may be used to control movement of the embodiments of a telescoping drive table and/or one or more hubs coupled thereto as described in U.S. Application No. 63/385, 761, filed Dec. 1, 2022, titled "TELESCOPING DRIVE TABLE," the entirety of which is hereby incorporated by reference herein.

Any of the control mechanisms disclosed herein, including but not limited to control mechanisms 2200, 2200*a*, 2200*b*, 2200*c*, 2200*d*, 2200*c*, 2200*f*, 2200*g*, 2200*h*, 2200*i*, and 2200*j*, may further be provided with one or more fluidics controls (e.g., a button, a joystick, and/or any of the other control embodiments described herein) for controlling components of a fluidics system, for example, to initiate and/or terminate the introduction of fluids to a catheter (e.g., saline, contrast, etc.) and/or to initiate and/or terminate aspiration of fluids from a catheter.

In some implementations, each control mechanism and/or additional controls (not shown) may be color coded, shaped coded, tactile coded, or other coding to indicate to the user 2230 which color is configured to move which hub or interventional device. In some implementations, the control color coding may also be applied to the hubs and/or interventional devices such that a user may visually match a particular hub/device with a particular control.

In some implementations, other control operations beyond translational movement and rotational movement may be carried out using any of the controls described herein. For example, the controls may be configured to drive a shape change and/or stiffness change of a corresponding interventional device. Controls may be toggled between different operating modes. For example, controls may be toggled between movement driven by acceleration and velocity to movement that reflects actual linear displacement or rotation.

In some implementations, the control mechanisms may be provided with a visual display or other indicator of the relative positions of the controls which may correspond the relative positions of the interventional devices. Such displays may depict any or all movement directions, instructions, percentage of movements performed, and/or hub and/or catheter indicators to indicate which device is controlled by a particular control. In some implementations, the display may depict applied force or resistance encountered by the catheter or other measurement being detected or observed by a particular hub or interventional component.

In some implementations, the control mechanism may include haptic components to provide haptic feedback to a user operating the controls. For example, if a control 2202*a* is triggering movement of a catheter and the catheter detects a large force at the tip, the control 2202*a* may generate haptic feedback to indicate to the user to stop or reverse a performed movement. In some implementations, haptic feedback may be generated at the control to indicate to the user to slow or speed a movement using the control. In some implementations, haptics may provide feedback on a large torsional strain buildup that might precede an abrupt rotation, or a large axial force buildup that may be a prelude to buckling of the catheter. Alternatively or additionally, feedback may be provided by one or more visual indicators (e.g., warning lights), audible indicators, etc.

The systems described herein may compare an actual fluoroscopic image position to an input displacement from the controller. A static fluoroscopic image of the patient may be captured in which the patient's vasculature is indexed relative to bony landmarks or one or more implanted soft tissue fiducial markers. Then a real time fluoroscopic image may be displayed as an overlay, aligned with the static image by registration of the fiducial markers. Visual observation of conformance of the real time movement with the static image, assisted by detected force data can help confirm proper navigation of the associated catheter or guidewire. The systems described herein can also display a comparison of an input proximal mechanical translation of a catheter or guidewire and a resulting distal tip output motion or lack thereof. A loss of relative motion at the distal tip may indicate shaft buckling, prolapse, kinking, or a similar outcome, either inside or outside the body. Such a comparison may be beneficial when the shaft buckling, prolapse, kinking, or similar outcome occurs outside of a current fluoroscopic view.

Figure 17:
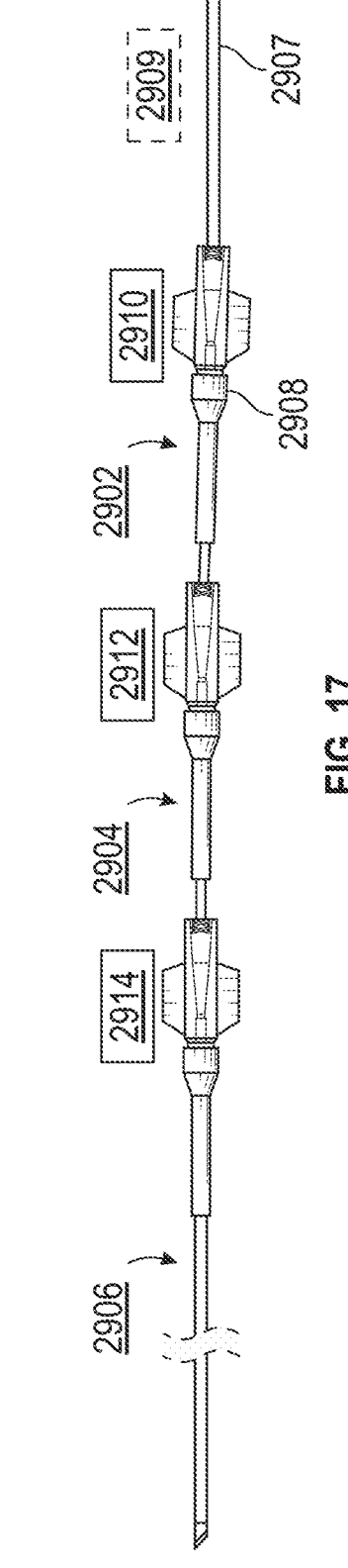
FIG. 17 illustrates a side elevational schematic view of an interventional device assembly for supra-aortic access and neuro-interventional procedures.

FIG. 17 illustrates a side elevational schematic view of a multi catheter interventional device assembly 2900 for combined supra-aortic access and/or neurovascular site access and procedure (e.g., aspiration), as described herein. The multi catheter assembly 2900 may be configured for either a manual or a robotic procedure.

The interventional device assembly 2900 includes an insert or access catheter 2902, a procedure catheter 2904, and a guide catheter 2906. Other components are possible including, but not limited to, one or more guidewires (e.g., optional guidewire 2907), one or more guide catheters, an access sheath and/or one or more other procedure catheters and/or associated catheter (control) hubs. In some embodiments, the assembly 2900 may also be configured with an optional deflection control 2908 for controlling deflection of one or more catheters of assembly 2900.

In operation, the multi-catheter assembly 2900 may be used without having to exchange hub components. For example, in the two stage procedure disclosed previously, a first stage for achieving supra-aortic access, includes mounting an access catheter, guide catheter and guidewire to the support table. Upon gaining supra aortic access, the access catheter and guidewire were typically removed from the guide catheter. Then, a second catheter assembly is introduced through the guide catheter after attaching a new guidewire hub and a procedure catheter hub to the corresponding drive carriage on the support table.

The single multi catheter assembly 2900 of FIG. 17 is configured to be operated without having to remove hubs and catheters and without the addition of additional assemblies and/or hubs. Thus, the multicomponent access and procedure configuration of assembly 2900 may utilize a guidewire 2907 manufactured to function as an access guidewire and a navigation guidewire to allow for sufficient access and support, and navigation to the particular distal treatment site. In a non-limiting example configured for robotic implementation, a catheter assembly may include a guidewire hub (e.g., guidewire hub 2909 or guidewire hub 26 positioned on a drive table and to the right of catheter 2902), an insert or access catheter hub 2910, a procedure catheter hub 2912, a guide catheter hub 2914 and corresponding catheters. In certain embodiments, one or more of the hubs may include or be coupled to a hemostasis valve (e.g., a rotating hemostasis valve) to accommodate introduction of interventional devices therethrough. In some embodiments, any of the control mechanisms described herein can include at least one control for opening and closing a hemostasis valve.

One or more of interventional device and hub combinations may further include fluidics connections for coupling to fluid sources and/or vacuum sources. For example, each of the insert or access catheter 2902, the procedure catheter 2904, and the guide catheter 2906 may be in fluid communication with a saline source, a contrast source, and/or a vacuum source. In some embodiments, any of the control mechanisms described herein can include at least one control for initiating and/or terminating the introduction of fluids to one or more of the catheters and/or aspiration of fluids from one or more of the catheters. For example, any of the control mechanisms described herein can include at least one control for opening and/or closing one or more valves to initiate the introduction of fluids to one or more of the catheters and/or aspiration of fluids from one or more of the catheters. For example, any of the control mechanisms described herein can be used to control various components (e.g., manifold valves, pumps, hemostatic valves, hubs, and/or catheters) of a fluidics systems as described in U.S. patent application Ser. No. 17/879,614, entitled Multi Catheter System With Integrated Fluidics Management, filed Aug. 2, 2022, the entirety of which is hereby incorporated by reference herein.

In some embodiments, the control mechanisms described herein amy allow a user to simultaneously control movement of a catheter (e.g., axial and/or rotational movement) and a fluidics system (e.g., for introduction of fluids and/or aspiration).

Once access above the aortic arch has been achieved, the insert or access catheter 2902 (associated with insert catheter hub 2910) may be parked in the vicinity of a carotid artery ostia and the remainder or a subset of the catheter assembly may be guided more distally toward a particular site (e.g., a clot site, a surgical site, a procedure site, etc.).

In some embodiments, other smaller procedure catheters may also be added and used at the site. As used herein for catheter assembly 2900, in a robotic configuration of assembly 2900, the catheter 2906 may function as a guide catheter. The catheter 2904 may function as a procedure (e.g., aspiration) catheter. In some embodiments, the catheter 2906 may function to perform aspiration in addition to functioning as a guide catheter, either instead of or in addition to the catheter 2904. The access catheter 2902 may have a distal deflection zone and can function to access a desired ostium. One of skill in the art will appreciate from FIGS. 18A-18E that either manual manipulation or robotic manipulation of the multi catheter stack are contemplated herein.

In some embodiments, the catheter assembly 2900 (or other combined catheter assemblies described herein) may be driven as a unit to a location. However, each catheter (or guidewire) component may instead be operated and driven independent of one another to the same or different locations.

In a non-limiting example, the catheter assembly 2900 may be used for a diagnostic angiogram procedure. In some embodiments, the assembly 2900 may include only the guidewire 2907 and access catheter 2902 (in the form of a diagnostic angiographic catheter) for performing the diagnostic angiogram procedure or only the guidewire 2907 and the access catheter 2902 may be utilized during the procedure. Alternatively, the guide catheter 2906 and procedure catheter 2904 may be retracted proximally to expose the distal end of the access catheter 2902 (e.g., a few centimeters of the distal end of the access catheter) to perform the diagnostic angiography.

As shown in FIG. 17, the guide catheter 2906, procedure catheter 2904, access catheter 2902, and guidewire 2907 can be arranged concentrically. In certain embodiments, the guide catheter 2906 may be a 'large bore' guide catheter or access catheter having a diameter of at least about 0.075 or at least about 0.080 inches in diameter. The procedure catheter 2904 may be an aspiration catheter having a diameter within the range of from about 0.060 to about 0.075 inches. The access catheter 2902 may be a steerable catheter with a deflectable distal tip, having a diameter within the range of from about 0.025 to about 0.050 inches. The guidewire 2907 may have a diameter within the range of from about 0.014 to about 0.020 inches. In one example, the guide catheter 2906 may have a diameter of about 0.088 inches, the procedure catheter 2904 about 0.071 inches, the access catheter 2902 about 0.035 inches, and the guidewire 2907 may have a diameter of about 0.018 inches.

FIGS. 18A-18E depict an example sequence of steps of introducing a multi-catheter assembly configured to achieve access all the way to the clot, either manually or robotically. FIGS. 18A-18E may be described using the interventional device assembly of FIG. 17. Other combinations of catheters may be substituted for the interventional device assembly, as will be appreciated by those of skill in the art in view of the disclosure herein.

Figures 18A, 18B, 18C:
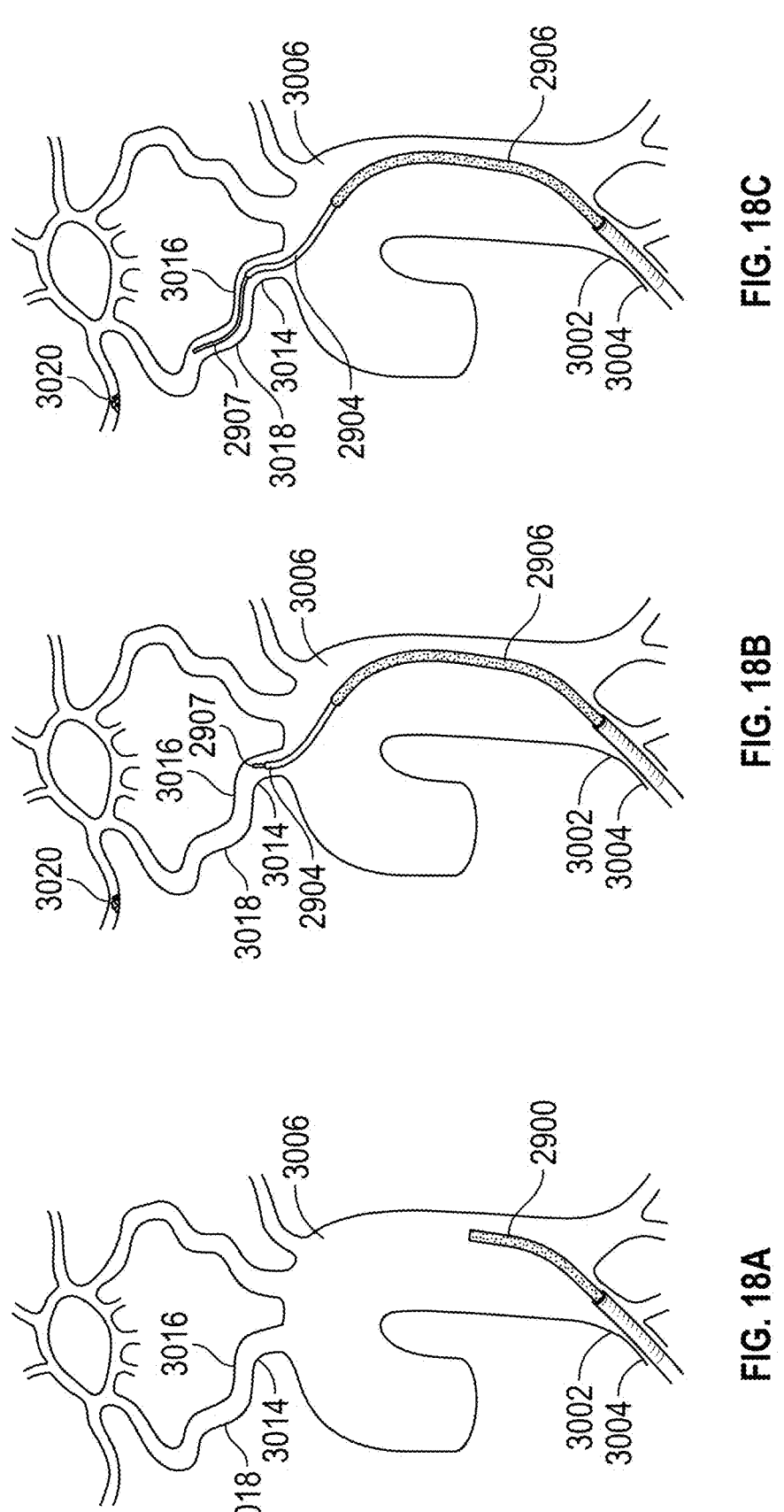
FIGS. 18A-18E depict an example sequence of steps of introducing a catheter assembly configured to achieve supra-aortic access and neurovascular site access.

Referring to FIG. 18A, the three catheter interventional device assembly 2900 is shown driven through an introducer sheath 3002, up through the iliac artery 3004 and into the descending aorta. Next, the access catheter 2902, the procedure catheter 2904 (e.g., 0.071 inch) and the guide catheter 2906 (e.g., 0.088 inch) are tracked up to the aortic arch 3006, as shown in FIG. 18B. Here, the distal end of the guide catheter 2906 may be parked below the aortic arch 3006 and the procedure catheter 2904, access catheter 2902 (positioned within the procedure catheter 2904 and not visible in FIG. 18B), and a guidewire 2907 can be driven into the ostium (e.g., simultaneously or separately). In some embodiments, the access catheter 2902 is advanced out of the procedure catheter 2904 and the guide catheter 2906 to engage the ostium first. After the distal end of the access catheter 2902 is positioned within the desired ostium, the guidewire 2907 can be advanced distally into the ostium to secure access. After the access catheter 2902 and guidewire 2907 are positioned within the desired ostium, the procedure catheter 2904 and/or guide catheter 2906 can be advanced into the ostium (and, in some embodiments, beyond), while using the support of the access catheter 2902 and/or guidewire 2907 to maneuver through the aorta and into the ostium. In the embodiment shown in FIG. 18B, the procedure catheter 2904 has been advanced into the ostium while the guide catheter 2906 has remained parked below the aortic arch 3006.

Referring to FIG. 18C, the guidewire 2907 may be distally advanced and the radiopacity of the guidewire 2907 may be used to confirm under fluoroscopic imaging that access through the desired ostia has been attained. The guidewire 2907 engages the origin of the brachiocephalic artery 3014. The guidewire 2907 is then advanced up to the petrous segment 3018 of the internal carotid artery 3016.

Figure 18E:
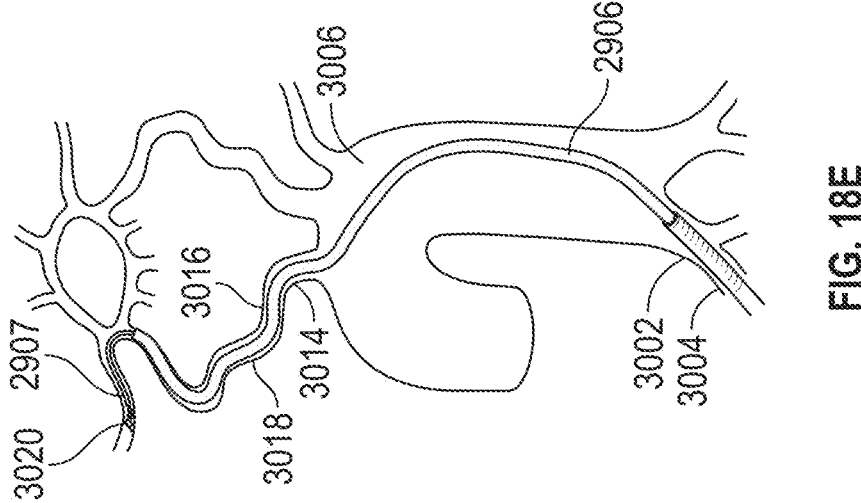
Figure 18D:
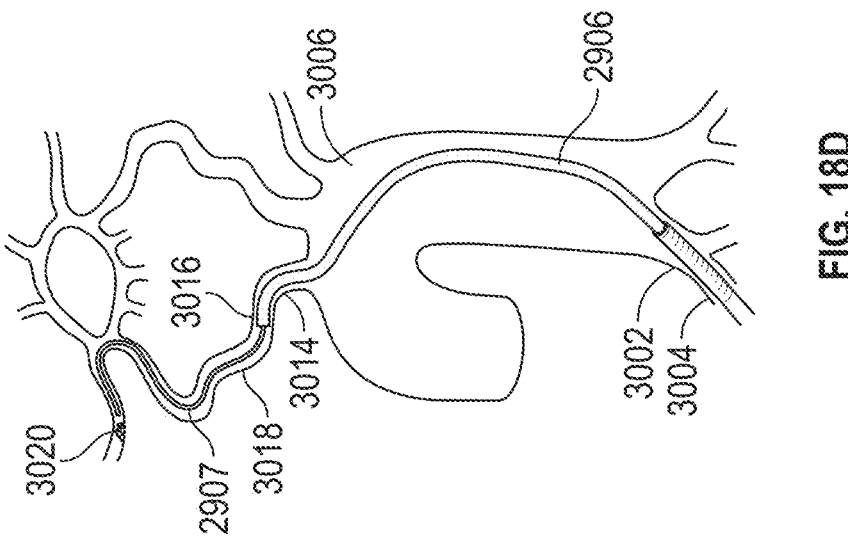

Referring to FIG. 18D, the guide catheter 2906 and the procedure catheter 2904 (positioned within the guide catheter 2906 and not visible in FIG. 18D) are both advanced (e.g., simultaneously or sequentially) over the guidewire 2907 and over the insert or access catheter 2902 (positioned within the procedure catheter 2904 and not visible in FIG. 18D) while the access catheter 2902 remains at the ostium for support. The guidewire 2907 may be further advanced past the petrous segment 3018 to the site of the clot 3020, such as the Ml segment.

Referring to FIG. 18E, the guide catheter 2906 and the procedure catheter 2904 (positioned within the guide catheter 2906 and not visible in FIG. 18E) are advanced (e.g., simultaneously or sequentially) to position the distal tip of the procedure catheter 2904 at the procedure site, for example on the face of the clot 3020. The guidewire 2907 and access catheter 2902 (positioned within the procedure catheter 2904 and not visible in FIG. 18E) are removed, and aspiration of the clot 3020 commences through the procedure catheter 2904. That is, the guidewire 2907 and the access catheter 2902 are proximally retracted to allow aspiration through the procedure catheter 2904. After aspiration of the clot, the procedure catheter 2904 and guide catheter 2906 can be removed (e.g., simultaneously or sequentially). For example, in some embodiments, the procure catheter 2904 may be removed before removing the guide catheter 2906.

The catheter assembly 2900 may be used to perform a neurovascular procedure, as described in FIGS. 18A-18E. For example, the neurovascular procedure may be a neurovascular thrombectomy. The steps of the procedure may include providing an assembly that includes at least a guidewire, an access catheter, a guide catheter, and a procedure catheter. For example, the catheter assembly 2900 includes a guidewire 2907, an access (e.g., insert) catheter 2902, a guide catheter 2906, and at least one procedure catheter 2904. The procedure catheter 2904 may include an aspiration catheter, an embolic deployment catheter, a stent deployment catheter, a flow diverter deployment catheter, a diagnostic angiographic catheter, a stent retriever catheter, a clot retriever catheter, a balloon catheter, a catheter to facilitate percutaneous valve repair or replacement, an ablation catheter, and/or an RF ablation catheter or guidewire.

The neurovascular procedure may further include steps of coupling the assembly to a non-robotic or a robotic drive system, and driving the assembly to achieve supra-aortic access. The steps may further include driving a subset of the assembly to a neurovascular site, and performing the neurovascular procedure using a subset of the assembly. The subset of the assembly may include the guidewire, the guide catheter, and the procedure catheter.

Each of the guidewire 2907, the access catheter 2902, the guide catheter 2906, and the procedure catheter 2904 is configured to be adjusted by a respective hub. For example, the guidewire 2907 may include (or be coupled to) a hub installed on one of the tray assemblies described herein. Similarly, the access catheter 2902 may be coupled to catheter hub 2910. The guide catheter 2906 may be coupled to the guide catheter hub 2914. The procedure catheter 2904 may be coupled to the procedure catheter hub 2912.

In general coupling of the assembly may include magnetically coupling a first hub 2909 on the guidewire 2907 to a first drive magnet, magnetically coupling a second hub 2910 on the access catheter 2902 to a second drive magnet, magnetically coupling a third hub 2912 on the procedure catheter 2904 to a third drive magnet, and magnetically coupling a fourth hub 2914 on the guide catheter 2906 to a fourth drive magnet. In general, the first drive magnet, the second drive magnet, the third drive magnet, and the fourth drive magnet are each independently movably carried by a drive table, as described with respect to tray assemblies and controls described herein. In some embodiments, the first drive magnet, the second drive magnet, the third drive magnet, and the fourth drive magnet are coupled (e.g., to their respective catheter hubs) through a sterile barrier (e.g., a sterile and fluid barrier) and independently movably carried by a drive table having a plurality of driven magnets. In some embodiments, two or more drive magnets can be tethered or otherwise coupled together to move as a unit in response to commands from a single controller tethered or otherwise coupled to one of the drive magnets.

In some implementations, the steps of performing the neurovascular procedure may include driving the assembly in response to movement of each of the hub adapters along a support table until the assembly is positioned to achieve supra-aortic vessel access. The hub adapters may include, for example, a coupler/carriage that acts as a shuttle by advancing proximally or distally along a track in response to operator instructions. The hub adapters described herein may each include at least one drive magnet configured to couple with a driven magnet carried by the respective hub. This provides a magnetic coupling between the drive magnet and driven magnet through the sterile barrier such that the respective hub is moved across the top of the sterile barrier in response to movement of the hub adapter outside of the sterile field (as described in detail in FIG. 4). Movement of the hub adapter is driven by a drive system carried by the support table in which the guidewire hub 2909, the guide catheter hub 2914, the procedure catheter hub 2912, and the access catheter hub 2910 are installed upon.

The steps may further include driving a subset of the assembly in response to movement of each of the hub adapters along the support table until the subset of the assembly is positioned to perform a neurovascular procedure at a neurovascular treatment site. The subset of the assembly may include the guidewire 2907, the guide catheter 2906, and the procedure catheter 2904.

In some embodiments, the guidewire 2907, the guide catheter 2906 and the procedure catheter 2904 are advanced as a unit through (with respect to the guidewire 2907) and over (with respect to the guide catheter 2906 and the procedure catheter 2904) at least a portion of a length of the access (e.g., insert) catheter 2902 after supra-aortic access is achieved.

In some embodiments, the catheter assembly 2900 may be part of a robotic control system for achieving supra-aortic access and neurovascular treatment site access, as described in FIGS. 18A-18E. In some embodiments, the catheter assembly 2900 may be part of a manual control system for achieving supra-aortic access and neurovascular treatment site access. In some embodiments, the catheter assembly 2900 may be part of a hybrid control system (with manual and robotic components) for achieving supra-aortic access and neurovascular treatment site access. For example, in such hybrid systems, supra-aortic access may be robotically driven while neurovascular site access and embolectomy or other procedures may be manual. Alternatively, in such hybrid systems, supra-aortic access may be manual while neurovascular site access may be robotically achieved. Still further, in such hybrid systems, any one or more of: the guidewire, access catheter, guide catheter, or procedure catheter may be robotically driven or manually manipulated.

An example robotic control system may include at least a guidewire hub (e.g., guidewire hub 2909) configured to adjust each of an axial position and a rotational position of a guidewire 2907. The robotic control system may also include an access catheter hub 2910 configured to adjust axial and rotational movement of an access catheter 2902. The robotic control system may also include a guide catheter hub 2914 configured to control axial movement of a guide catheter 2906. The robotic control system may also include a procedure catheter hub 2912 configured to adjust an axial position and a rotational position of a procedure catheter 2904.

In some embodiments, the procedure catheter hub 2912 is further configured to laterally deflect a distal deflection zone of the procedure catheter 2904.

In some embodiments, the guidewire hub 2909 is configured to couple to a guidewire hub adapter by magnetically coupling the guidewire hub to a first drive magnet. The access catheter hub 2910 is configured to couple to an access catheter hub adapter by magnetically coupling the access catheter hub 2910 to a second drive magnet. The procedure catheter hub 2912 is configured to couple to a procedure catheter hub adapter by magnetically coupling the procedure catheter hub 2912 to a third drive magnet. The guide catheter hub 2914 is configured to couple to a guide catheter hub adapter by magnetically coupling the guide catheter hub 2914 to a fourth drive magnet. In some embodiments, the first drive magnet, the second drive magnet, the third drive magnet, and the fourth drive magnet are independently movably carried by a drive table.

In some embodiments, the robotic control system includes a first driven magnet on the guidewire hub 2909. The first driven magnet may be configured to cooperate with the first drive magnet such that the first driven magnet is configured to move in response to movement of the first drive magnet. In some embodiments, the first drive magnet is configured to move outside of a sterile field separated from the first driven magnet by a barrier while the first driven magnet is within the sterile field. In some embodiments, a position of the first driven magnet is movable in response to manipulation of a procedure drive control on a control console associated with the drive table. Drive magnets and driven magnet interactions are described in detail with respect to FIG. 4 above.

In some embodiments, the robotic control system includes a second driven magnet on the access catheter hub 2910. The second driven magnet may be configured to cooperate with the second drive magnet such that the second driven magnet is configured to move in response to movement of the second drive magnet. In some embodiments, the second drive magnet is configured to move outside of a sterile field separated from the second driven magnet by a barrier while the second driven magnet is within the sterile field.

In some embodiments, the robotic control system includes a third driven magnet on the procedure catheter hub 2912. The third driven magnet may be configured to cooperate with the third drive magnet such that the third driven magnet is configured to move in response to movement of the third drive magnet. In some embodiments, the third drive magnet is configured to move outside of a sterile field separated from the third driven magnet by a barrier while the third driven magnet is within the sterile field.

In some embodiments, the robotic control system includes a fourth driven magnet on the guide catheter hub 2914. The fourth driven magnet may be configured to cooperate with the fourth drive magnet such that the fourth driven magnet is configured to move in response to movement of the fourth drive magnet. In some embodiments, the fourth drive magnet is configured to move outside of a sterile field separated from the fourth driven magnet by a barrier while the fourth driven magnet is within the sterile field. In some embodiments, there may be more than four driven magnets and corresponding catheter hubs for control of additional catheters.

User Interface

To facilitate control of any of the control mechanisms for interventional devices described herein, such as the control mechanisms described in relation to FIGS. 19A-28C, a user interface can be implemented along with the control mechanism. For instance, a user interface could beneficially allow clinicians to, among other things, visualize the position and movement of the interventional devices as the clinician manipulates the interventional devices using a control mechanism. This can also beneficially allow clinicians to observe the actual movement of the interventional devices as opposed to simply estimating the movement and position of the interventional devices inside the patient.

Figure 29A:
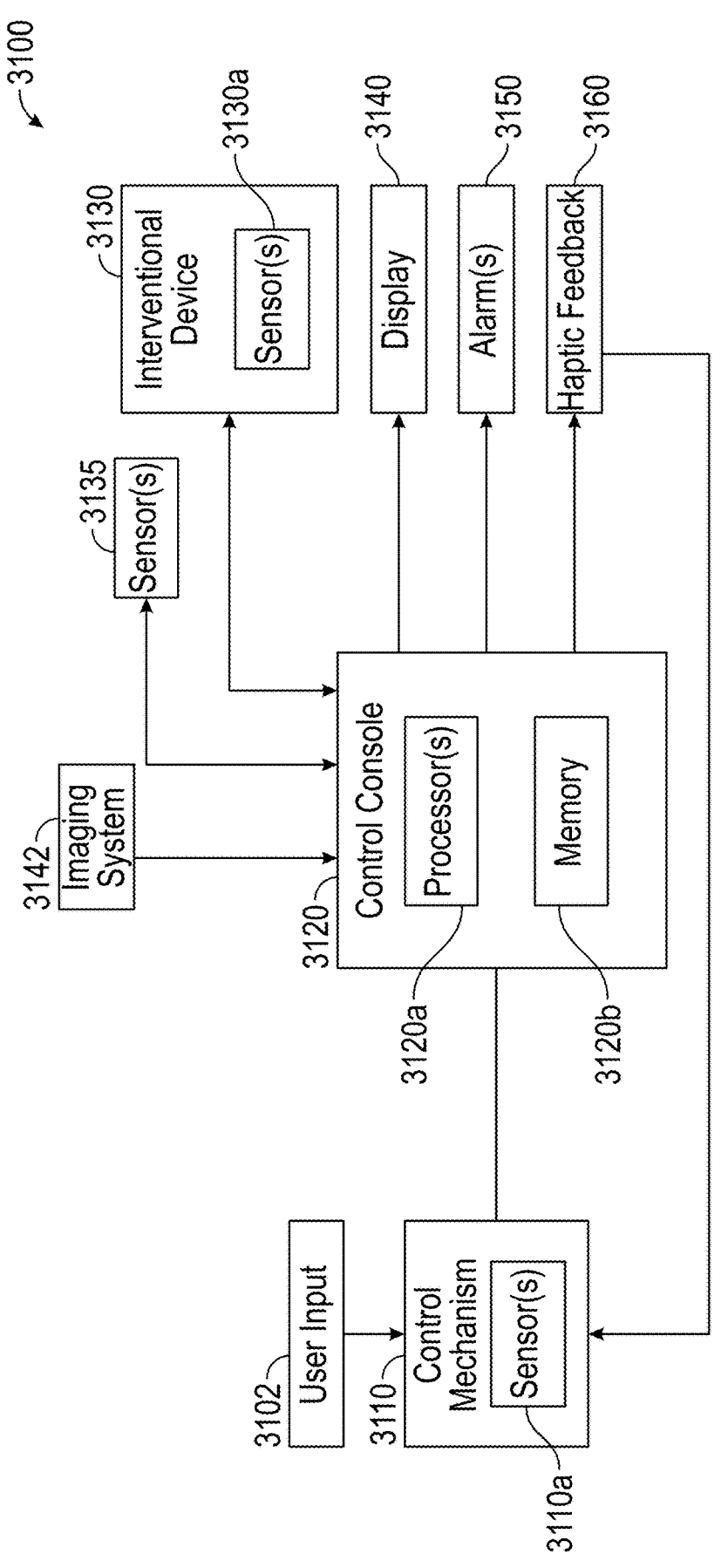
FIG. 29A is a simplified block diagram of a medical device operation environment.

FIG. 29A illustrates a simplified block diagram of a medical device operation environment 3100, according to an embodiment of the disclosure. The operation environment 3100 can include a control mechanism or controller 3110, a control system 3120, at least one interventional device 3130, and a display 3140. The control system 3120 can be a control station or control console, or be in communication with a control station or control console. The control system 3120 can be in communication with the control mechanism 3110, the at least one interventional device 3130, and the display 3140. Any of the components of the operation environment 3100 can be in wired or wireless communication through, for example, a connected cloud server, with each other. For example, as the sensors 3110a of the control mechanism 3110 can obtain information about the user's operation of the control mechanism 3110. For example, the sensors 3110a can detect how the control mechanism 3110 is manipulated by the clinician (e.g., can detect if the clinician moves a joystick, in what direction the joystick moves, if a button is pressed, etc.). The sensors 3110a can include any of the sensors described in FIGS. 19A-28C. The information obtained by the sensors 3110a can be transmitted to the control system 3120 through a cable or through a wireless connection.

The control system 3120 can receive information from the sensors 3110a of the control mechanism 3110. The control system 3120 can include a circuit having a processor 3120a, input ports for receiving the information from the sensors 3110a, a memory 3120b, and software stored in the memory 3120b in which can be executed by the processor 3120a. The processor 3120a can include digital signal processors, application specific integrated circuit (ASIC), a field program-mable gate array (FPGA) or other programmable logic device, discrete gate or transistor logic, discrete hardware components, or any combination thereof to perform the functions described herein. The processor 3120a can include electrical circuitry or digital logic circuitry configured to process computer-executable instructions. In some cases, the processor 3120a can include an FPGA or other program-mable device that performs logic operations without pro-cessing computer-executable instructions. The processor 3120a can also be implemented as a combination of com-puting devices, for example, a combination of a DSP and a microprocessor, a plurality of microprocessors, one or more microprocessors in conjunction with a DSP core, or any other such configuration.

The control system 3120 can process the signals from the sensors 3110a and utilize the display 3140 to show how the control mechanism 3110 is being manipulated and/or show the position of the interventional devices 3130 with respect to each other. The sensor information can include informa-tion from the sensors of any of the control mechanisms disclosed herein (e.g., any of the sensors from control mechanisms described in FIGS. 19A-28C.). The sensors 3110a of the control mechanism 3110 can detect the user input 3102 on the control mechanism 3110.

The control system 3120 can process the signals received from the sensors 3110a of the control mechanism 3110 and send signals to the interventional device. The signals to the interventional device can include instructions to the inter-ventional device to move according to the user input as detected by the sensors 3110a of the control mechanism 3110. The sensors 3110a of the one or more interventional devices 3130 can detect information relating to the position and movement of the interventional devices 3130. Position and motion information can be transmitted to the control system 3120.

The at least one interventional device 3130 can include sensors 3130a that can detect and/or track movement of the at least one interventional device 3130. For example, the sensors 3130a of the at least one interventional device 3130 can include one or more linear positions sensors and/or rotation sensors than can detect movement and/or track the position of the interventional device 3130 in real time, and/or any of the sensors described herein and in relation to FIGS. 12A-14 (e.g., pressure sensors, optical sensors, force sensors, positioning sensors, temperature sensors, oxygen sensors, and/or Fiber Bragg grating sensors). The sensors 3130a can include one or more of an inertial measurement unit sensor, an accelerometer, a gyroscope, a linear poten-tiometer, a linear variable differential transformer (LVDT) sensor, an ultrasonic sensor, a laser sensor, a hall effect sensor, a magnet, a magnet resistive element, an encoder, a rotary potentiometer, a rotary variable differential trans-former (RVDT) sensor, or a combination thereof to detect axial position, angular position, detect and/or measure linear movement, and/or detect and/or measure rotational move-ment of each of the interventional devices, hubs, and/or hub adapters.

The sensors 3130a of the at least one interventional device 3130 can monitor the operational status of the at least one interventional device 3130. The sensor information from the interventional device 3130 can be communicated to the control system 3120. Based at least in part on the sensor information received from the interventional device 3130, the control system 3120 can output information relating to the one or more interventional devices 3130 via a display 3140. The display 3140 can include, for example, display 23.

In some cases, the display 3140 can be carried on a portable, handheld device or desktop computer, and may be located in the same room as the patient, the same facility as the patient, or in a remote facility.

In some embodiments, the medical device operation envi-ronment 3100 can include one or more sensors 3135 con-figured to detect the coupling of an interventional device to a drive table. In some embodiments, the medical device operation environment 3100 can include one or more sen-sors 3135 configured to detect the identity of an interven-tional device coupled to the drive table. For example, the one or more sensors 3135 may detect a type of interventional device (e.g., a guide catheter, a procedure catheter, an access catheter, a guidewire, etc.), dimensions of the interventional device, a serial number of the interventional device, and/or if the interventional device is an authorized interventional device for using with the drive table. For example, in some embodiments, the sensor can read data from an RFID tag, bar code, and/or other machine readable data source of the interventional device to detect interventional device identify information. In some embodiments, a sensor or scanner 3135 for detecting and/or receiving the interventional device identity information can be positioned on or within the drive table, on or within a hub, on or within a hub adapter, on or within an interventional device, or at any other suitable location.

The sensor information from the sensor(s) 3135 can be communicated to the control system 3120. Based at least in part on the sensor information received from the sensor(s) 3135 the control system 3120 can output information relat-ing to the one or more interventional devices 3130 via a display 3140. The display 3140 can include, for example, display 23. In some cases, the display 3140 can be carried on a portable, handheld device or desktop computer, and may be located in the same room as the patient, the same facility as the patient, or in a remote facility. As described further herein, in some embodiments, a control system can output information from the sensors 3135 to a graphical user interface 5400 to associate interventional device identify information with one or more visual representations of interventional devices.

The control system 3120 can communicate with an imag-ing system 3142. In some cases, the imaging system 3142 can record, capture, and/or transmit fluoroscopic images and/or video. For instance, the imaging system 3142 can include a display for showing a live fluoroscopic video feed of a patient's vasculature and/or the interventional devices. The imaging data, as captured by the imaging system 3142, can be communicated to the control system 3120. The control system 3120 can process the imaging data of the imaging system 3142 and send it to the display 3140. The imaging data can be displayed on the display 3140. In some cases, the control system 3120 can mirror the image feed shown on the display of the imaging system 3142 and show it on a portion of the display 3140 (e.g., window 3210). The imaging system 3142 can beneficially allow clinicians to visualize the one or more interventional devices 3130 in the vasculature of a patient on the display 3140 as the interven-tional devices 3130 are advanced in and/or retracted from the body of the patient.

In some cases, the controller can process the sensor information obtained by the sensors 3110a of the control mechanism 3110 and/or the sensor information obtained by the sensors 3130a of the interventional devices 3130. The control system 3120 can determine, based on the motion and/or the position of the control mechanism 3110 and/or the interventional devices 3130 if the control mechanism 3110 and/or the interventional devices 3130 are operating correctly. For example, the control system 3120 can determine the interventional devices 3130 are not operating properly if movement of the interventional devices 3130 does not correspond to the user input 3102 on the control mechanism 3110. Upon detecting a faulty condition on either the control mechanism 3110 and/or the interventional devices 3130, the control system 3120 can emit an alert 3150. The alert 3150 can provide an indication to the clinician that the control mechanism 3110 and/or the interventional devices 3130 are not operating properly. In some cases, the alert 3150 can be displayed on the display 3140.

The control system 3120 can also process the sensor information from sensors 3110a and/or 3130a and send a signal to the control mechanism 3110. The signal can include haptic feedback 3160 which can cause operation of the control mechanism 3110 to change. For example, the haptic feedback 3160 can cause the components of the control mechanism 3110 to harden or soften, which may require a clinician to exert more force or less force to press or move a component. The haptic feedback 3160 can provide an indication to the clinician about the position of the one or more interventional devices. For example, the components of the control mechanism 3110 may require a clinician to exert more force as a first interventional device moves closer to a second interventional device. The components of the control mechanism 3110 may require a clinician to exert less force as a first interventional device moves away from a second interventional device.

In some embodiments, if the control mechanism 3110 is triggering movement of at least one interventional device 3130 and the sensors 3130a of the at least one interventional device 3130 detect a large force at the tip, the control system 3120 may cause actuators to generate haptic feedback 3160 to indicate to the user to stop or reverse a performed movement, and/or to otherwise cause the components of the control mechanism 3110 to adjust to reduce the force at the tip of the interventional device. In some implementations, haptic feedback 3160 may be generated at the control system 3120 to indicate to the user to reduce or increase a speed of a movement using the control mechanism 3110 or to reverse a movement or perform an alternative movement using the control mechanism 3110. In some implementations, haptic feedback 3160 may provide feedback on a large torsional strain buildup that might precede an abrupt rotation, or a large axial force buildup that may be a prelude to buckling of the catheter. Alternatively or additionally, feedback may be provided by one or more visual indicators (e.g., warning lights), audible indicators, etc.

FIG. 29B illustrates an embodiment of a process 3170 for displaying the position and movement of the interventional devices using a display and causing the interventional device to move according to user-provided input. In some cases, the process can be implemented by any of the control mechanisms, interventional devices, controllers, and displays described herein. In particular, the process 3170 can be implemented by one or more of the components of the medical device operation environment 3100. Advantageously, in certain embodiments, the process 3170 facilitates the generation of position and motion data based on information as obtained from the sensors of the control mechanism.

At block 3172, the user operates the control mechanism (e.g., control mechanism 3110 from FIG. 29A). At block 3174, the sensors (sensors 3110a from FIG. 29A) obtain motion and position information from the control mechanism. The information obtained by the sensors of the control mechanism can be transmitted to the controller (e.g., control system 3120 from FIG. 29A). At block 3176 the controller processes the information from the sensors and determines an instruction for the interventional devices (e.g., interventional device 3130 from FIG. 29A). When transmitted to the interventional devices at block 3178, the instruction can cause the interventional device to move according to the user-input on the control mechanism as detected by the sensors. At block 3180, the controller transmits a signal to a display (e.g., display 3140 of FIG. 29A) which causes the display to show a graphical representation of the interventional device's motion and position relative to each other. The graphical representation can include some or all of the elements described below in relation to FIGS. 30A-42.

Figure 30A:
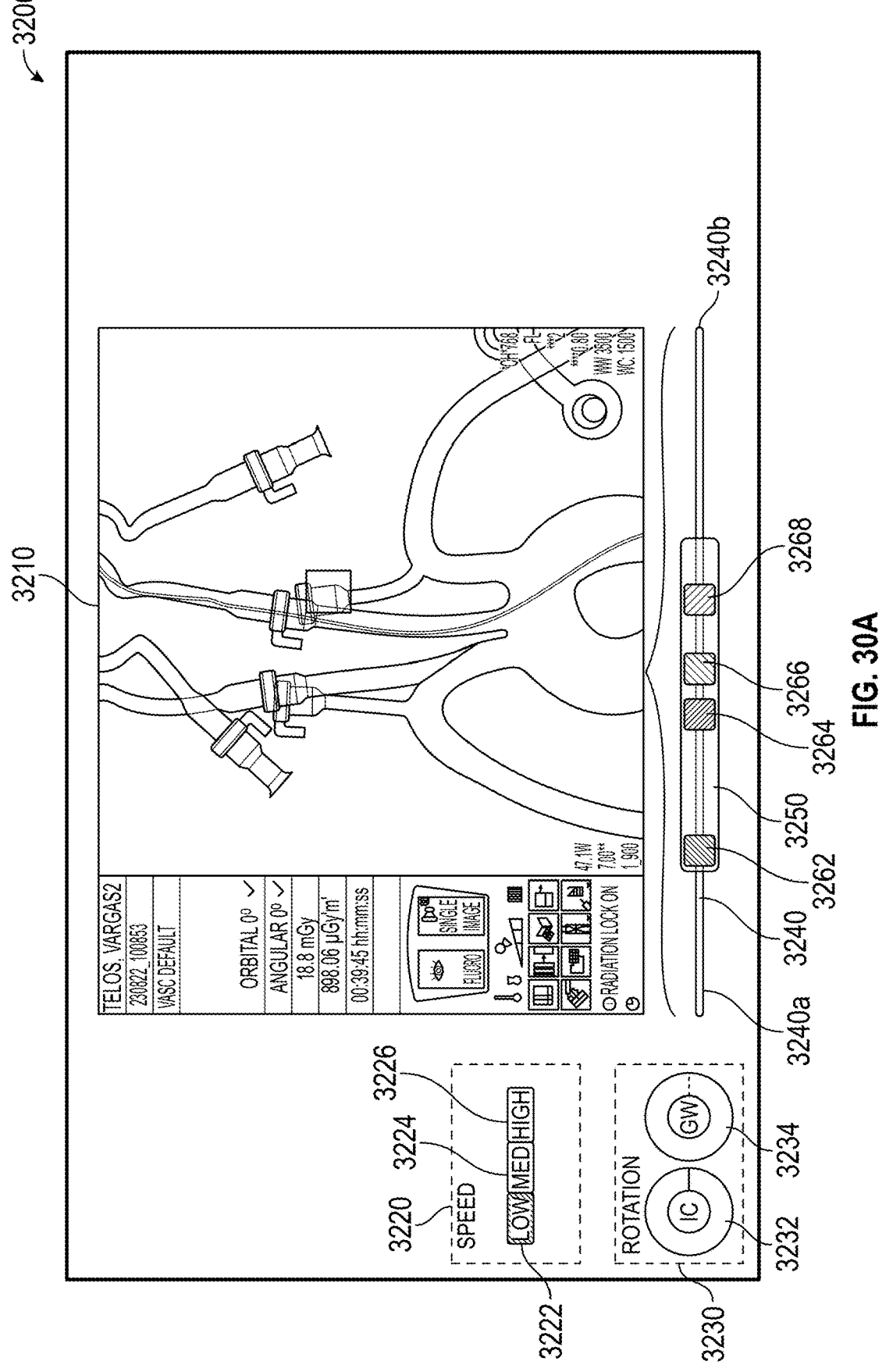

FIGS. 30A-30K illustrate embodiments of a user interface for controlling interventional devices. As shown in FIG. 30A, the user interface 3200 can include an imaging window 3210, a speed indicator 3220, a rotational indicator 3230, an axial position bar 3240, a telescopic position window 3250, and one or more axial position indicators 3262, 3264, 3266, and 3268. In some instances of the user interfaces, only some of the components shown in FIG. 30A are displayed. In some cases, the user interface 3200 can be displayed on a capacitive screen, a resistive screen, a touch pad, or other touch-based sensing device. This can beneficially allow users to interact with the visual elements displayed on the user interface 3200. For example, in addition to the user interface 3200 being displayed, users can adjust any of the parameters (e.g., speed, rotational direction, axial position) displayed on the user interface 3200 by interacting with the user interface 3200. Users can interact with the user interface 3200 by, for example, using basic gestures such as tapping, swiping, and/or dragging the components displayed on the capacitive screen, resistive screen, touch pad, or touch-based sensing device. Additionally or alternatively, the parameters displayed on the user interface 3200 can be adjusted by manipulating one or more physical buttons/components positioned adjacent the display in which the user interface 3200 is displayed.

In some cases, the imaging window 3210 can be configured to display a live feed of the images and/or video generated by the imaging system 3142 (as shown in FIG. 29A). The speed indicator 3220 can include one or more speed markers, 3222-3226 which can provide an indication to the clinician about the speed at which the control mechanism is being operated. The speed indicator 3220 can include more than or less than three speed markers 3222-3226.

The rotational indicator 3230 can include one or more rotational position indicators 3232, 3234. The rotational position indicators 3232, 3234 can provide a visual indication to the clinician operating the control mechanism 3110 about the rotational position of at least one interventional device 3130. In some cases, the rotational indicator includes less than or more than two rotational position indicators 3232, 3234. An axial position bar 3240 can provide a visual indication of the axial position of the one or more interventional devices 3130 with respect to each other. The axial position bar 3240 can include a first end 3240a and a second end 3240b. The length L of the axial position bar 3240 can provide a visual indication of the total axial space the one or more interventional devices 3130 can advance or retract.

Each of the interventional devices 3130 can be visually represented by an axial position indicator 3262-3268. The axial position indicators 3262-3268 can move along the length L of the axial position bar 3240 and/or the telescopic position window 3250 as the clinician moves the interventional devices 3130 using the control mechanism 3110. In some cases, the position of the telescopic position window 3250 along the axial position bar 3240 can provide an indication about the position of a telescoping drive table, for example, as shown and described in U.S. Application No. 63/385,761, filed Dec. 1, 2022, titled "TELESCOPING DRIVE TABLE," the entirety of which is hereby incorporated by reference herein. Movement of an axial position indicator 3262-3268 and/or the telescopic position window 3250 towards the first end 3240a of the axial position bar 3240 can provide an indication that the interventional device 3130 associated to the axial position indicator 3262-3268 is moving in a direction away from the patient. Movement of an axial position indicator 3262-3268 and/or the telescopic position window 3250 towards the second end 3240b of the axial position bar 3240 can provide an indication that the interventional device 3130 associated to the axial position indicator 3262-3268 is moving towards the patient (e.g., inside the patient). Movement of the axial position indicators 3262-3268 along the length L of the axial position bar 3240 and/or the telescopic position window 3250 can beneficially provide a visual indication to a clinician about the axial position of the interventional devices 3130 relative to each other and within the vasculature of a patient.

Figure 30B:
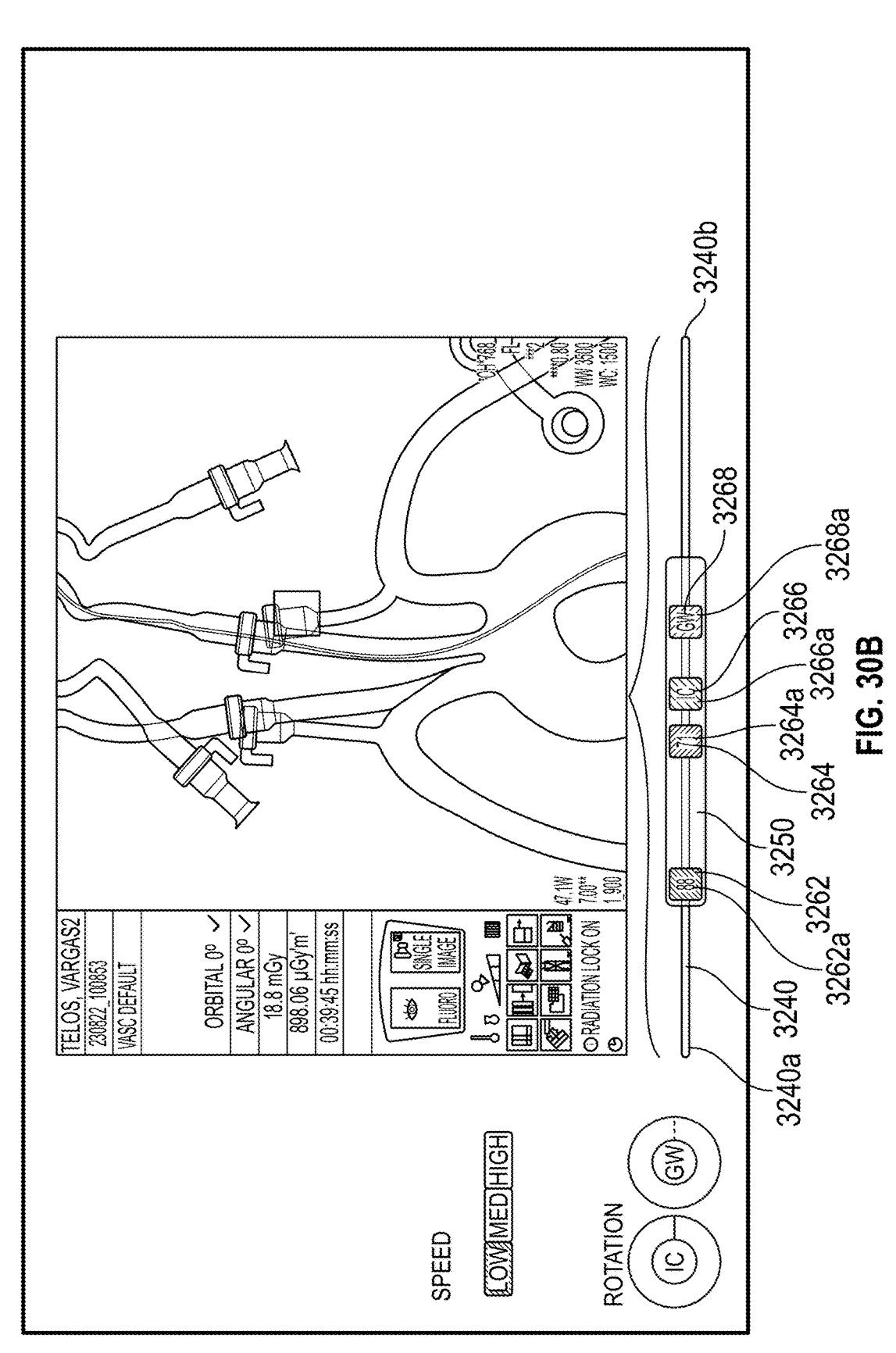

As illustrated in FIG. 30B, each of the axial position indicators 3262-3268 can include a marker 3262a, 3264a, 3266a, and/or -3268a. The markers 3262a-3268a can provide a visual indication of the specific interventional device 3130 the axial position indicators 3262-3268 are associated with. For example, marker 3262a can provide an indication that axial position indicator 3262 is associated to a 0.088 in. catheter (e.g., guide catheter 31). As another example, the marker 3264a can provide an indication that axial position indicator 3264 is associated to a 0.071 in. catheter (e.g., catheter 120). The markers 3262a-3268a can include any character, number, or combination thereof for providing an indication of the interventional device 3130 the axial position indicators 3262-3268 are associated with. Alternatively, or additionally, each axial position indicator 3262-3268 can include a color, as shown in FIG. 30B, which can provide an indication of the interventional device 3130 the axial position indicators 3262-3268 are associated with. In some cases, the markers 3262a-3268a can appear when the clinician operates the interventional device 3130 associated with an axial position indicator 3262-3268 and disappear if the clinician stops operating the interventional device 3130 for a predefined period of time (e.g., 1, 2, 3, 4, 5, 10, 60, seconds, etc.).

Figure 30C:
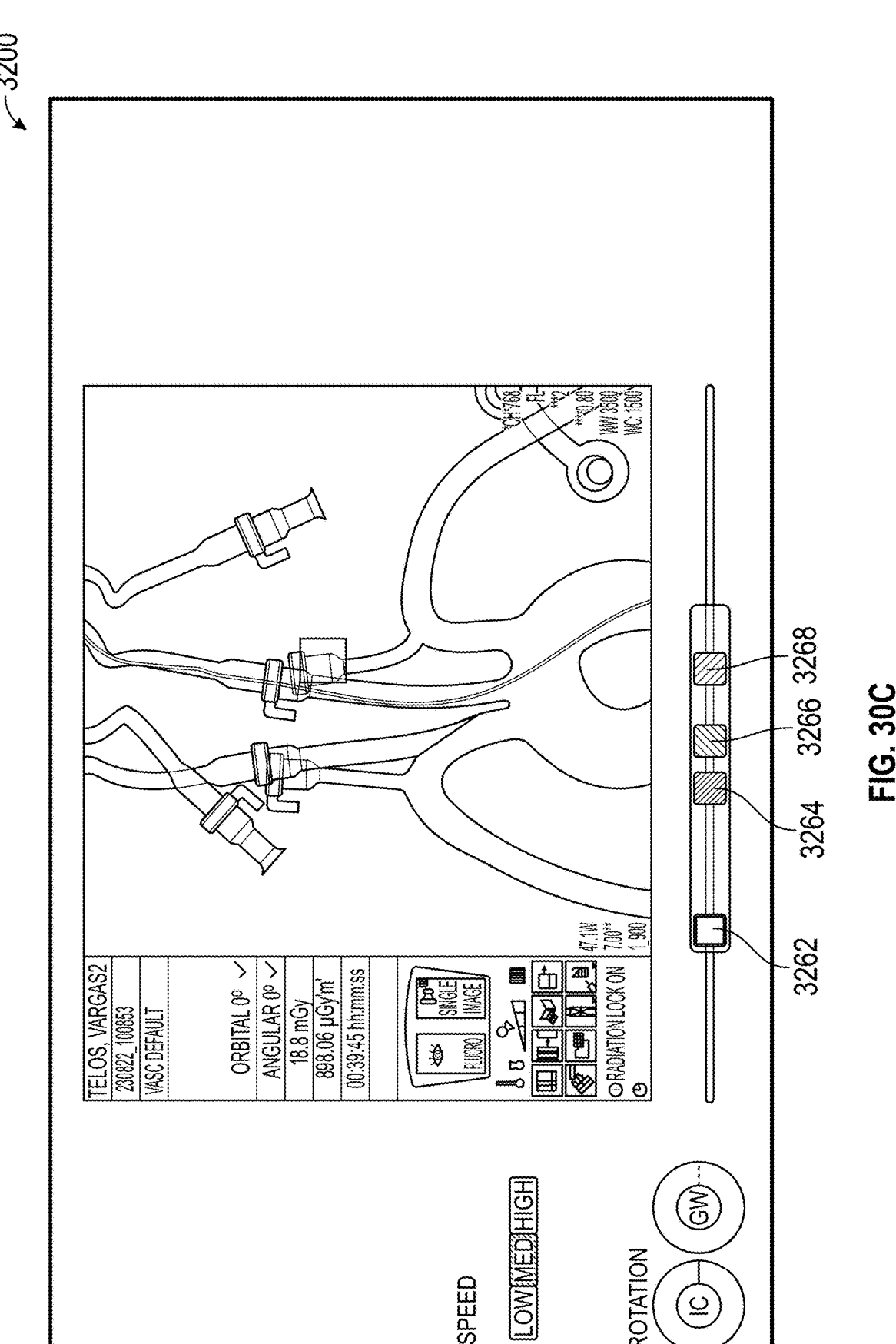
Figure 30D:
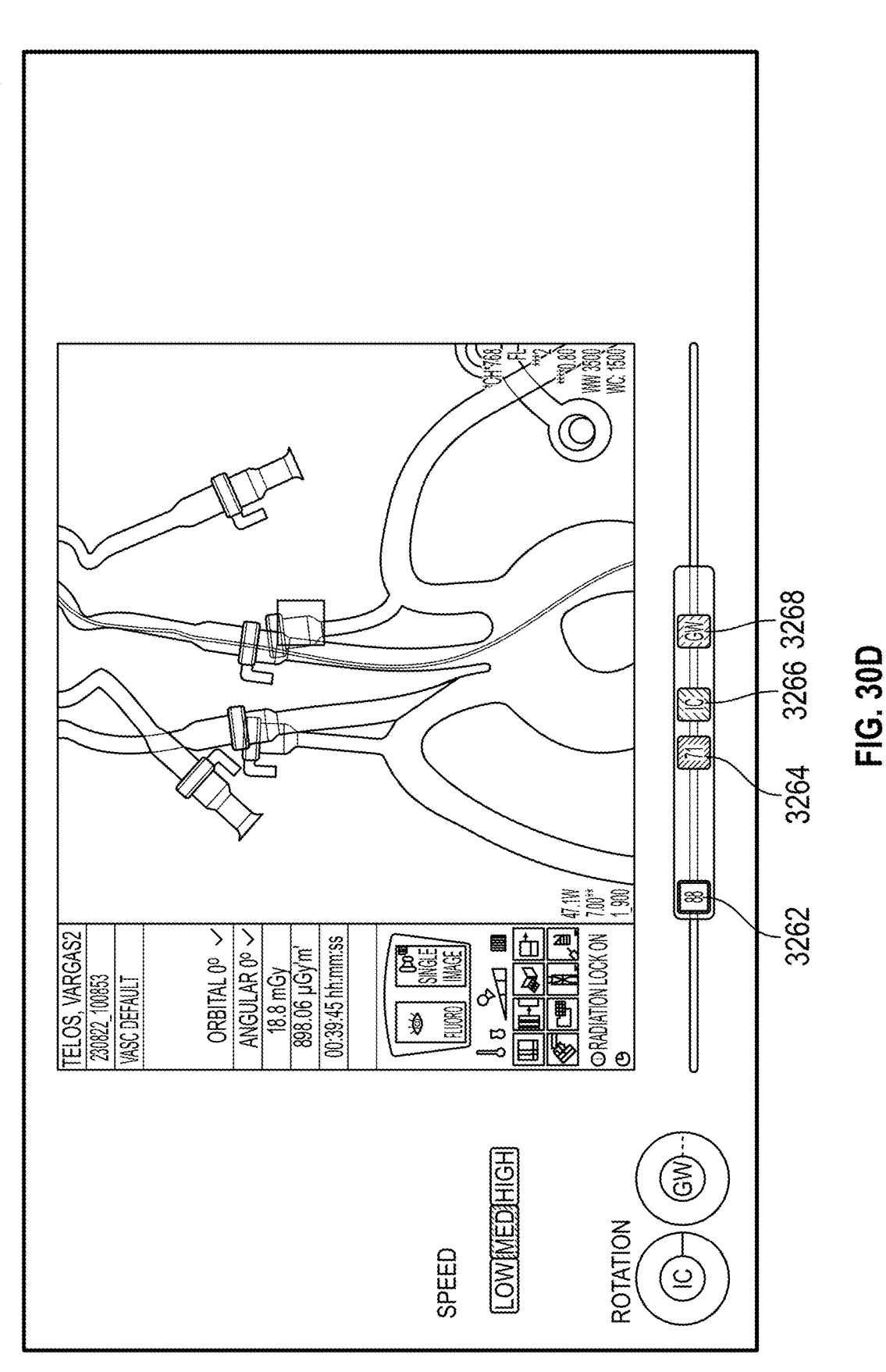

The user interface 3200 can provide alerts about the status of the interventional devices 3130. For example, the axial position indicators 3262-3268 can provide an indication that the interventional device 3130 they are associated with. In some cases, the color of the axial position indicators 3262-3268 can change if the one or more sensors 3130a of the interventional devices 3130 detect a condition. For example, the color of axial position indicator 3262 can transition from blue to black, as shown in FIGS. 30C-30D, if the sensors 3130a of the interventional device 3130 associated with the axial position indicator 3262 detect a condition. The condition can include, for example, malfunctioning and/or disconnection of the interventional device 3130.

Figure 30E:
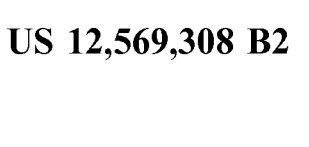

As shown in FIGS. 30E and 30F, the user interface 3200 can provide an indication about the operation of the one or more interventional devices 3130. For example, a force indicator 3269a, as shown in FIG. 30E, can provide an indication that the force applied to an interventional device 3130 associated with an axial position indicator 3262-3268, is below or above a threshold. The force indicator 3269a can appear near the axial position indicators 3262-3268. FIG. 30F shows an alternative embodiment of a force indicator 3269b.

Figure 30G:
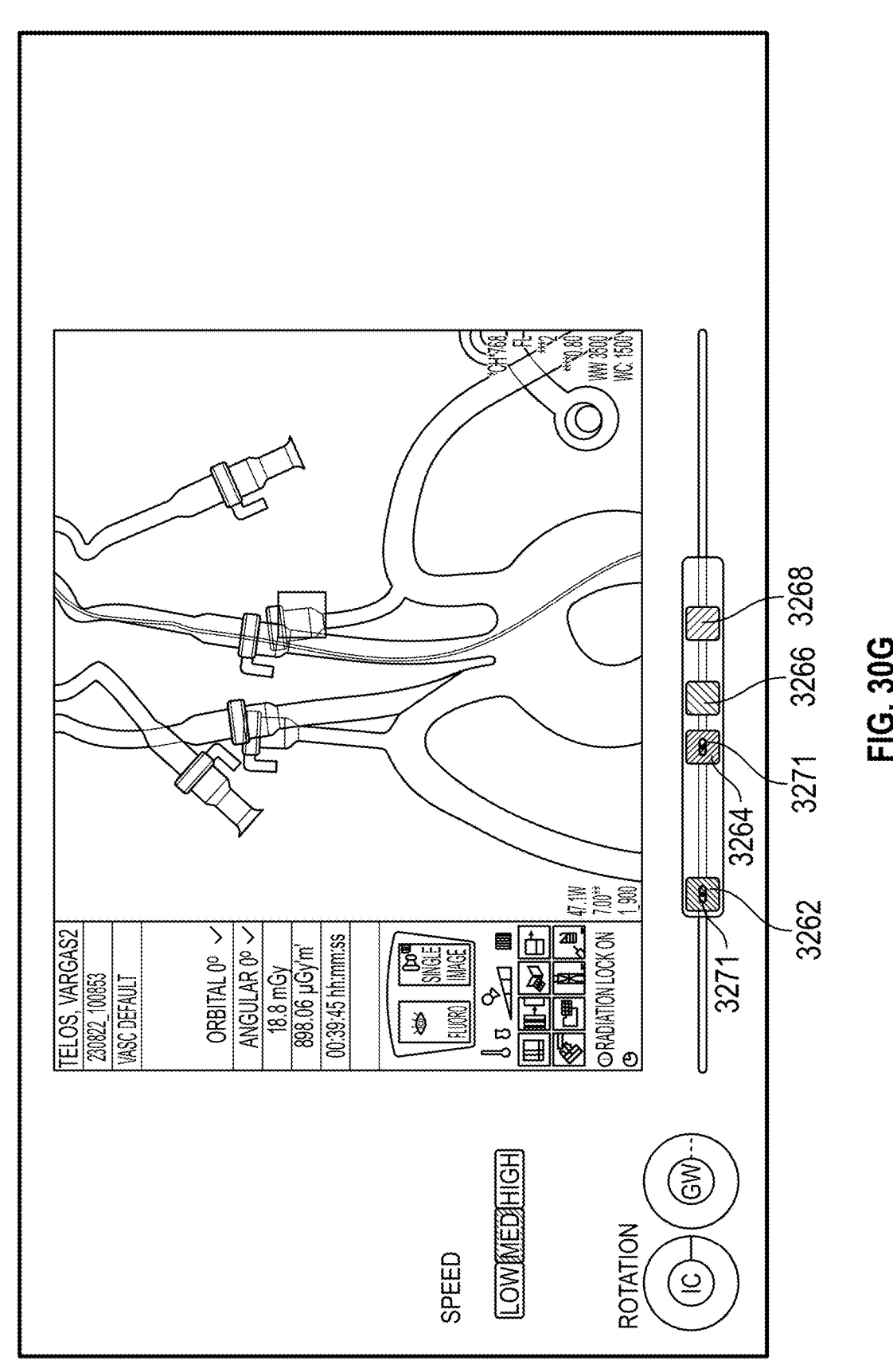
Figure 30H:
Figure 30I:
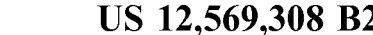

The user interface 3200 can also provide an indication that two or more interventional devices 3130 are linked. When linked, two or more interventional 3130 devices can move simultaneously if the clinician moves at least one of the linked interventional devices 3130 using the control mechanism 3110. As shown in FIGS. 30G-30I, the axial position indicators 3262-3268 can include a link marker 3271 on those axial position indicators 3262-3268 whose associated interventional devices 3130 are linked to each other. For example, and as shown in FIGS. 30G and 301, a link marker 3271 is displayed on axial position indicator 3262 and axial position indicator 3264. The link markers 3271 can provide an indication to the clinician that the interventional devices 3130 associated with axial position indicators 3262 and 3264 are linked. As another example, and as shown in FIG. 30H, a link marker 3271 is displayed on axial position indicators 3262-3268. The link markers 3271 can provide an indication to the clinician that the interventional devices 3130 associated with axial position indicators 3262-3268 are. The user interface 3200 can display a link marker 3271 for each linked interventional device 3130 (e.g., two, three, four, etc.).

In some cases, the control mechanism 3110 can be used to link two or more interventional devices 3130. For example, a predefined movement and/or a button combination can be executed by a clinician to link two or more interventional devices 3130 (e.g., pressing or moving the controls associated to two or more interventional devices 3130 at the same time can link the two or more interventional devices 3130). In some cases, however, two or more interventional devices 3130 can link when one of the interventional devices contacts another interventional device 3130. For example, if a first hub (e.g., hubs 26, 28, or 30 of FIG. 5A) of a first interventional device 3130 (e.g., an aspiration catheter) contacts a second hub of a second interventional device 3130 (e.g., and access catheter), the first and second interventional may link and an indication can be provided to the clinician using a link marker 3271.

Figure 30J:
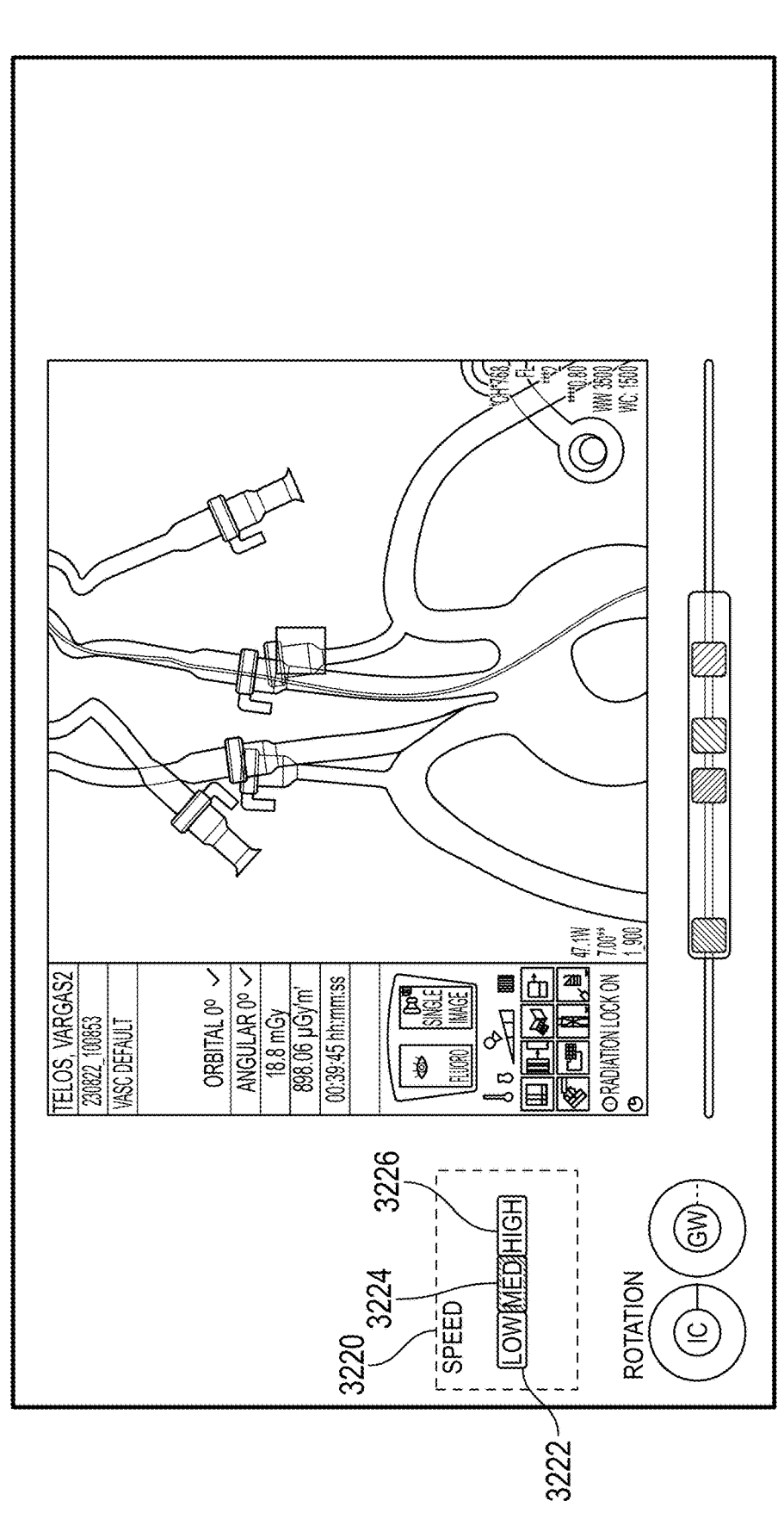
Figure 30K:
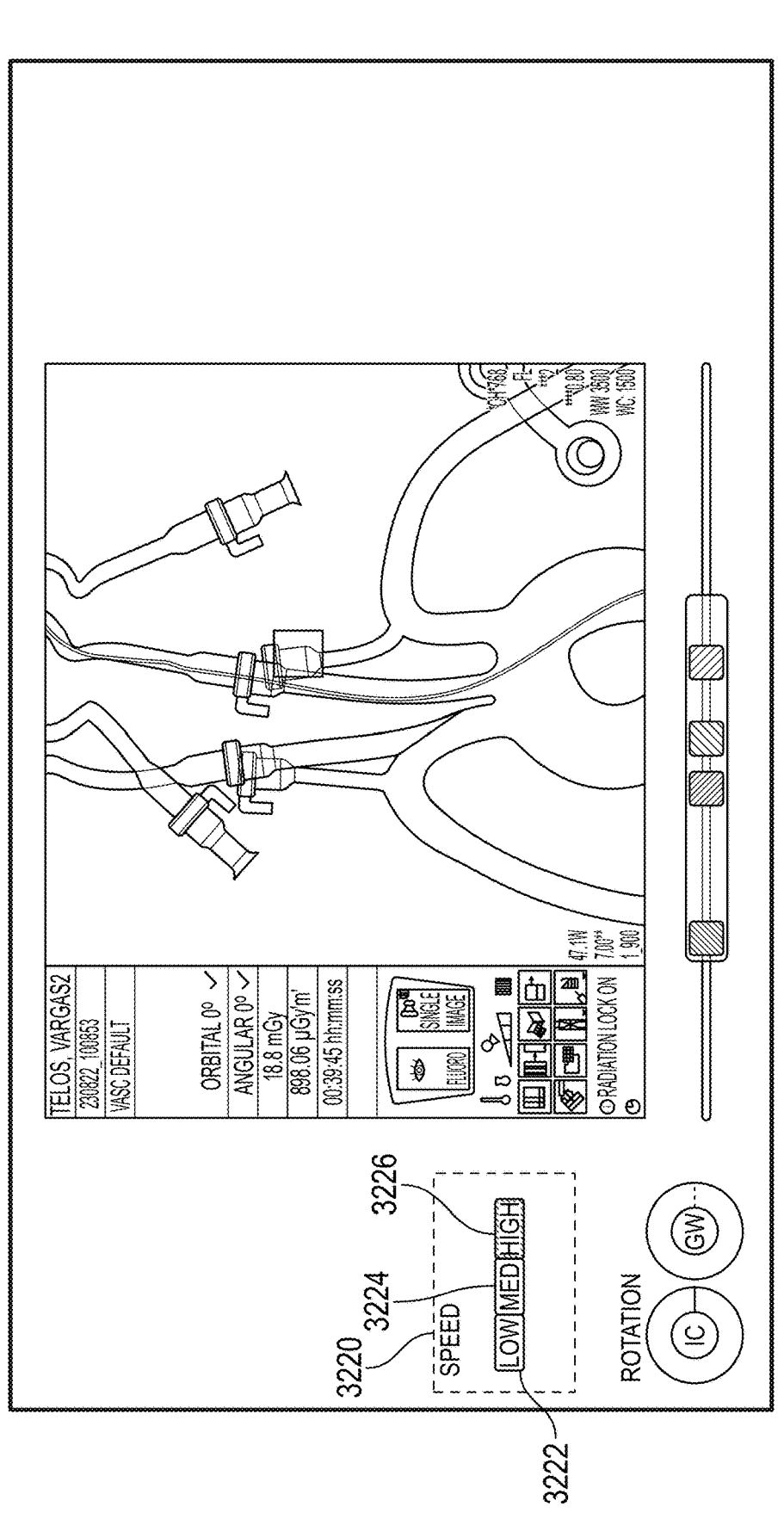

As shown in FIG. 30J-30K, the speed indicator 3220 can include one or more speed markers 3222-3226. The visual markers 3222-3226 can provide an indication of the speed at which the one or more interventional devices 3130 are operating. For example, as shown in FIG. 30J, the speed marker 3224 can include a color different than a color of the speed markers 3222 and 3226 thereby indicating that the interventional devices are operating at the speed setting indicated by speed marker 3224 (e.g., medium speed).

Figure 32:
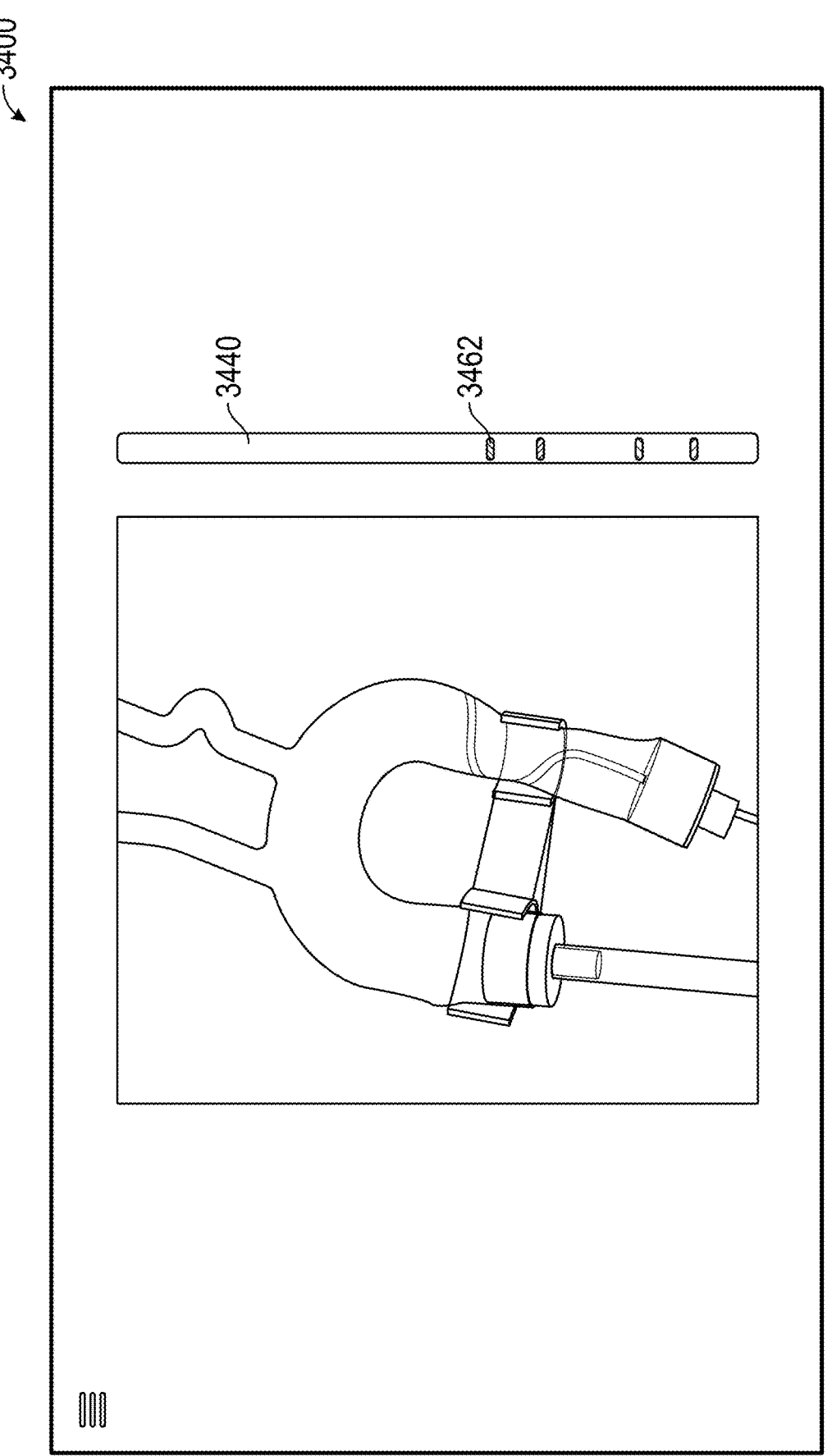

FIGS. 31-42 show examples of alternative user interfaces and components thereof. FIG. 31 shows an alternative user interface 3300 including a vertical axial position bar 3340 and axial position indicators 3362. The axial position indicators can include a marker 3362a. The marker 3362a can provide an indication that the interventional device associated to the axial position indicator 3362 is applying aspiration. The axial position indicators 3362 can also include a rotational marker 3366a which can provide an indication about the rotational position of the interventional device associated to each of the axial position indicators 3362. FIG. 32 shows an alternative user interface 3400 including a vertical axial position bar 3440 and axial position indicators 3462.

Figure 33:
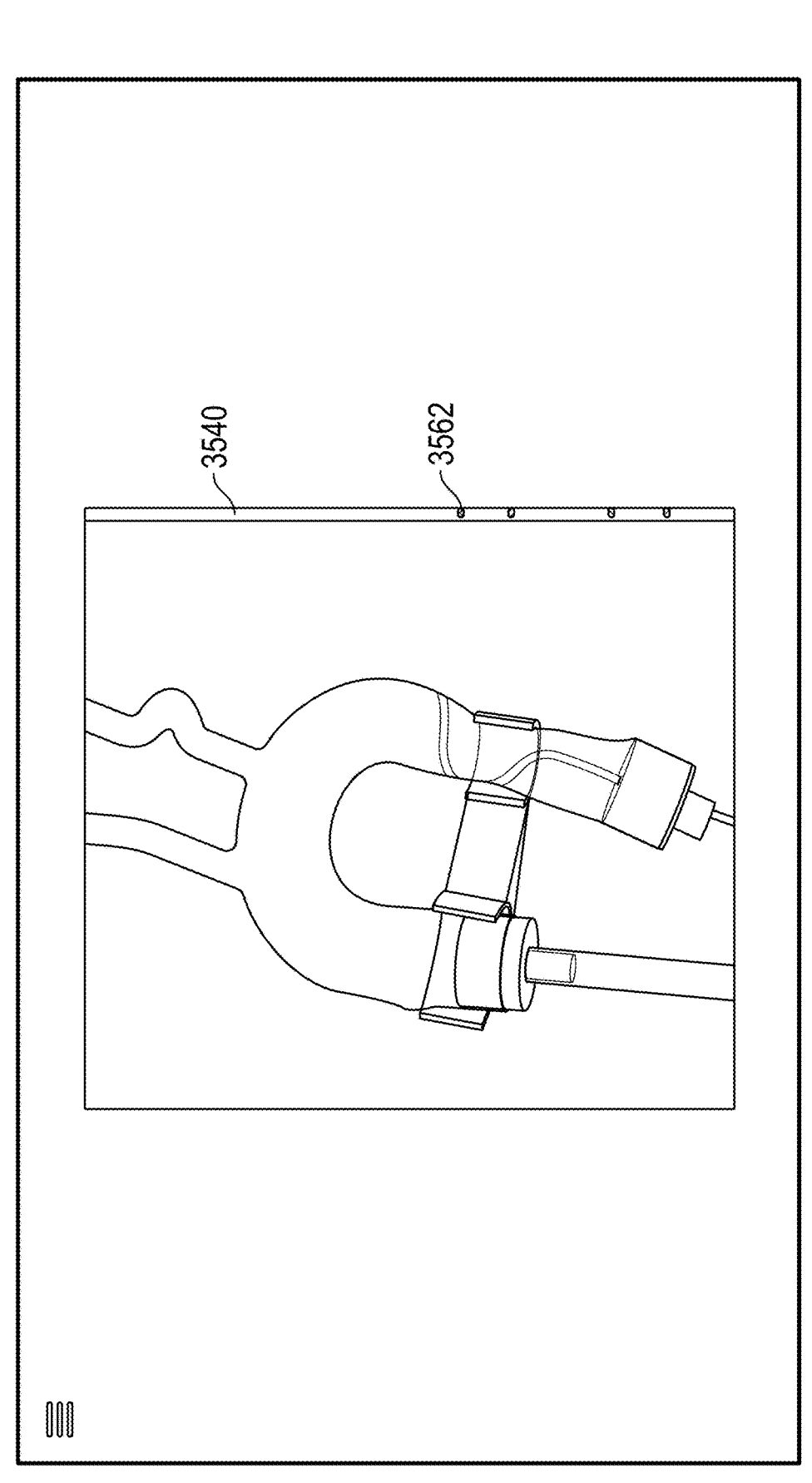
Figure 34:
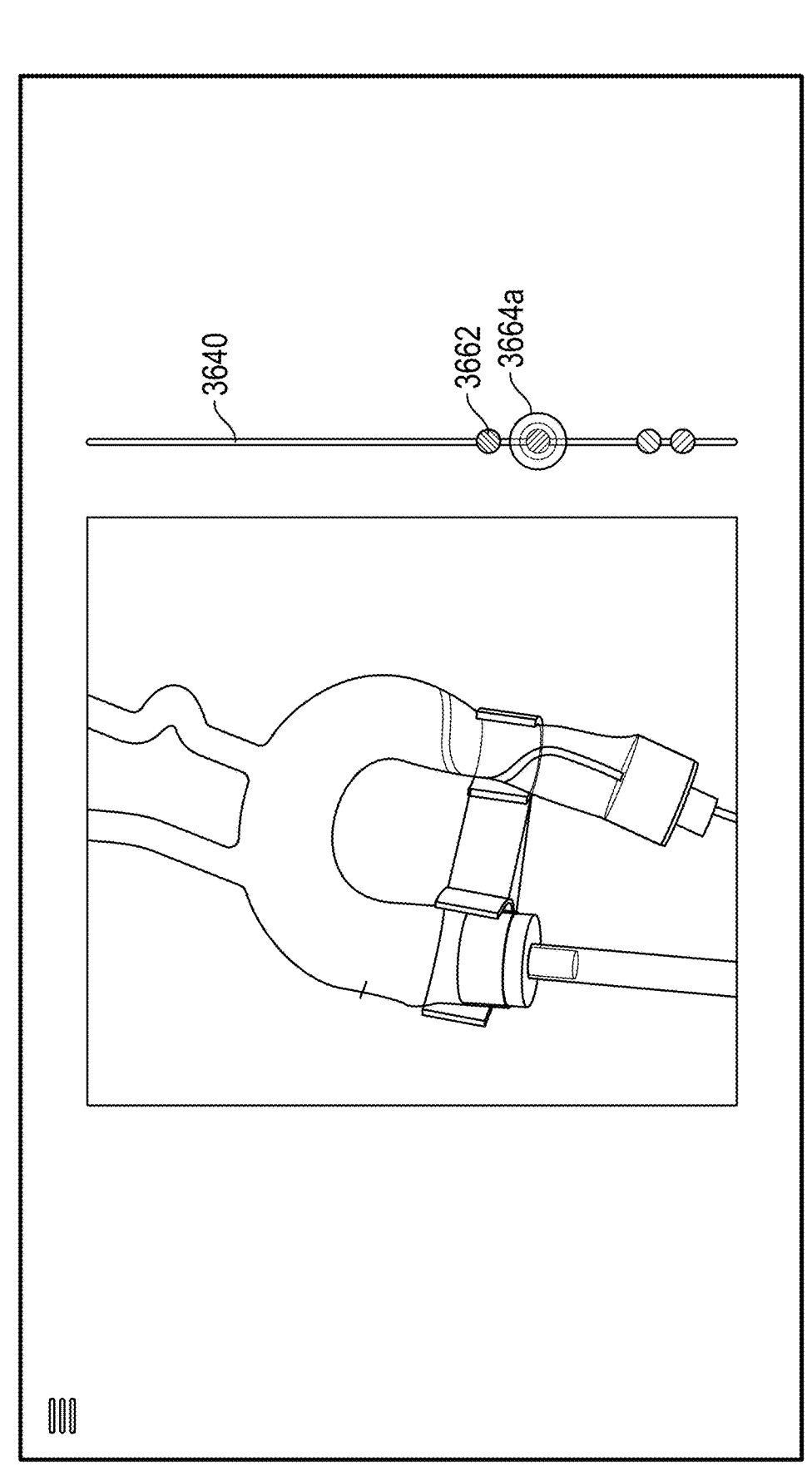

FIG. 33 shows an alternative user interface 3500 including a vertical axial position bar 3540 and axial position indicators 3562. FIG. 34 shows an alternative user interface 3600 including a vertical axial position bar 3640 and axial position indicators 3662. Any of the axial position indicators 3662 can include a marker 3664*a*. The marker 3664*a* can provide an indication to the clinician that a contrast solution and/or a saline solution is being applied to the interventional device associated to each of the axial position indicators 3662.

Figure 35:
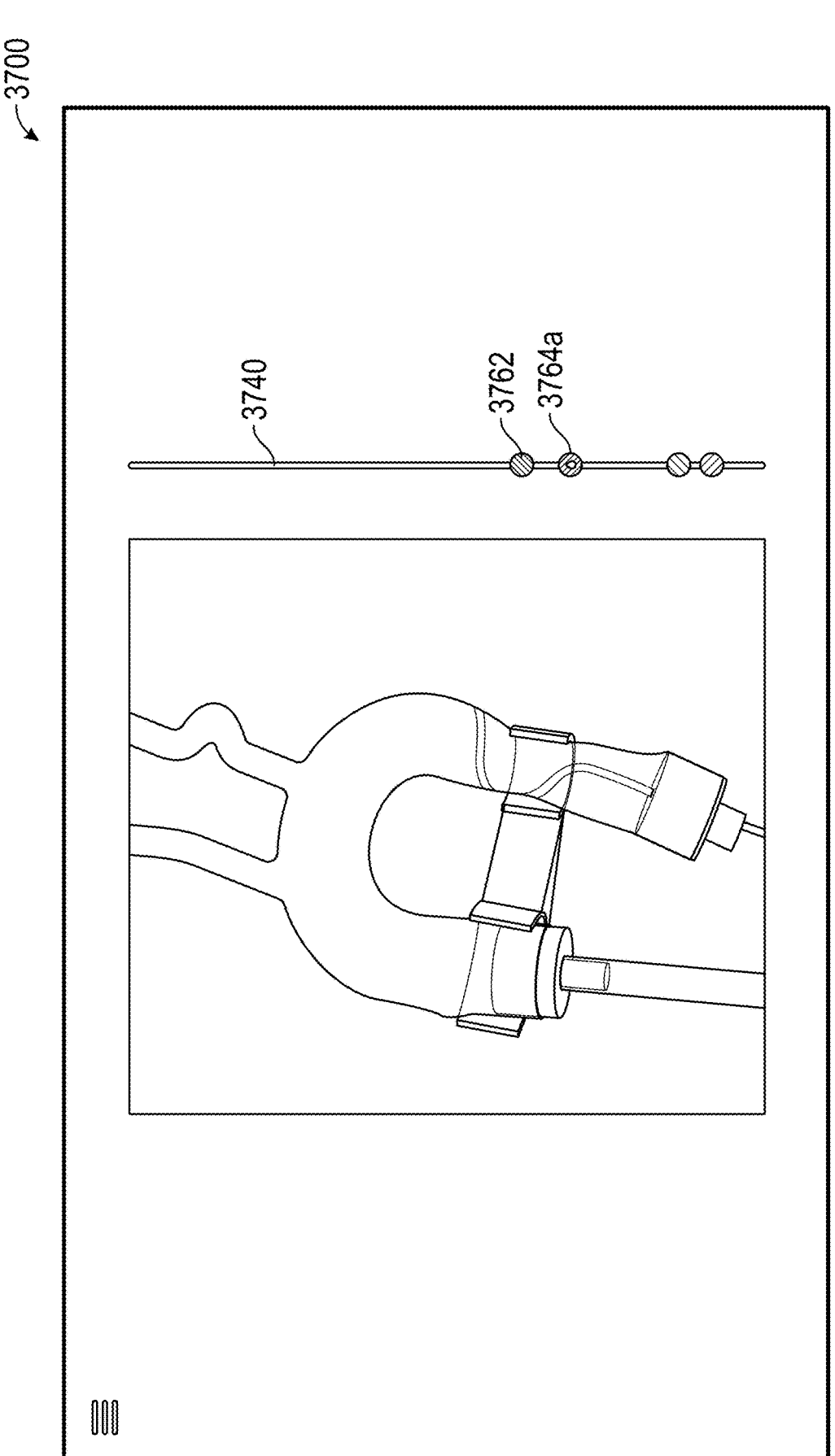
Figure 36:
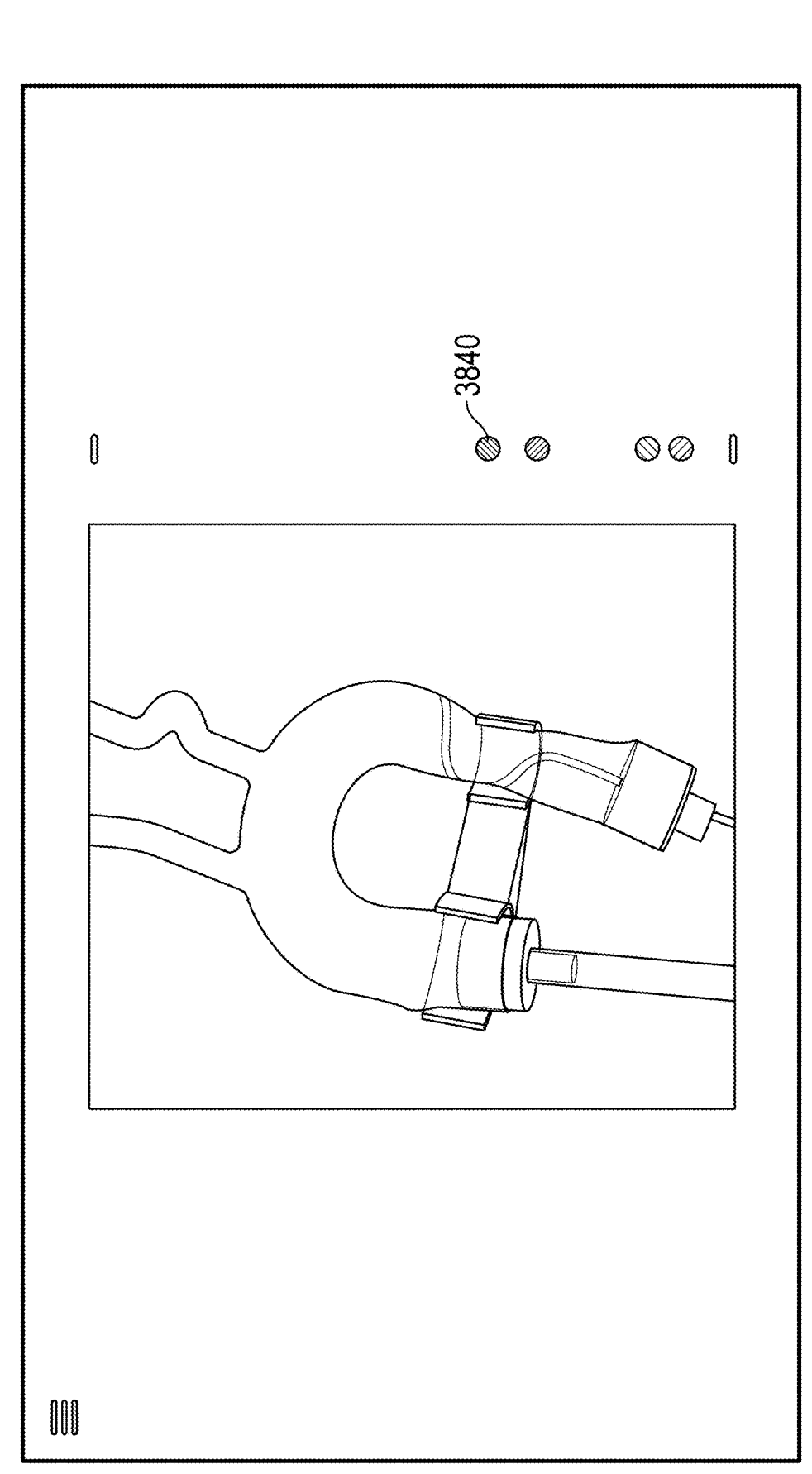
Figure 37:
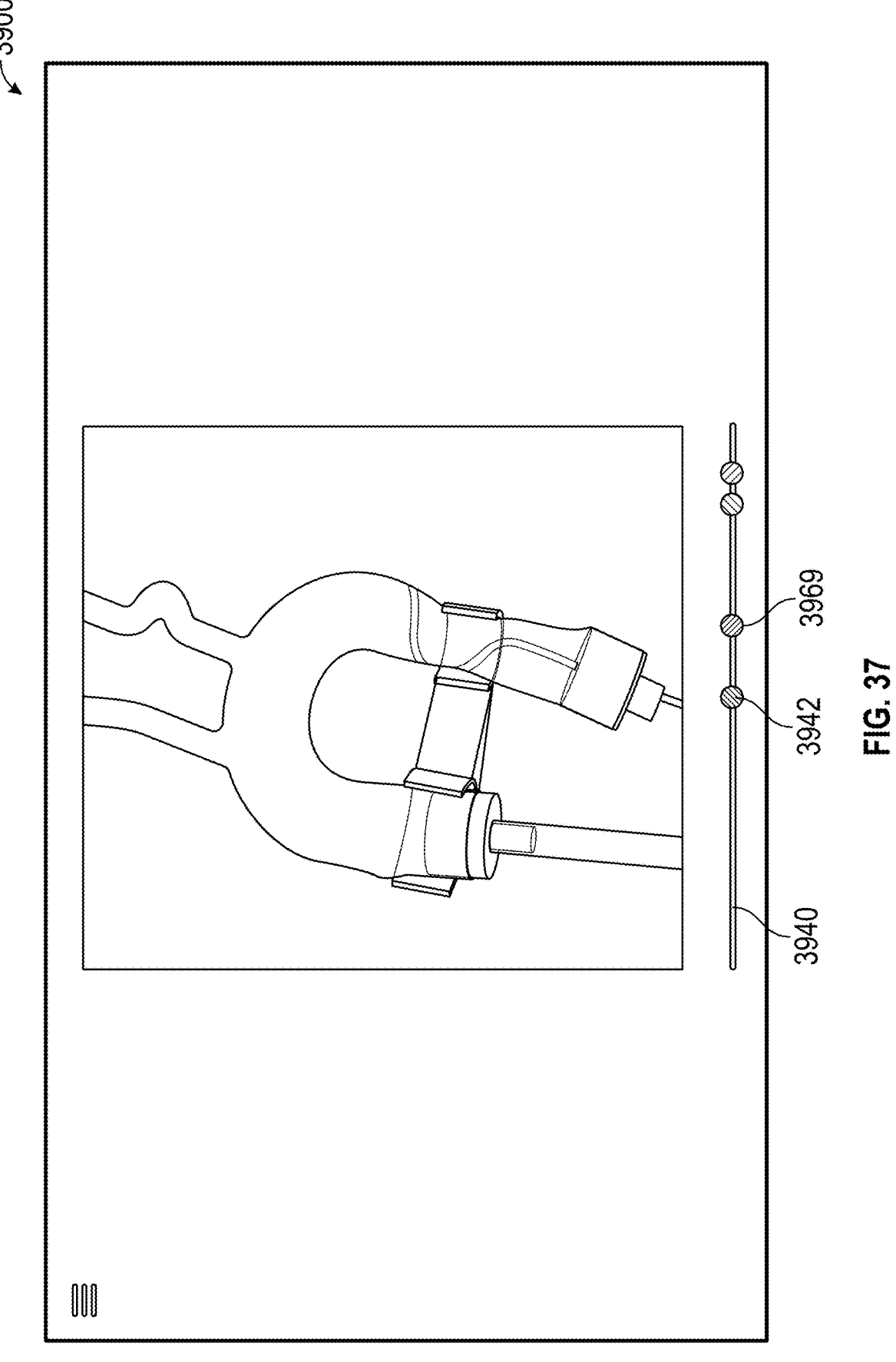

FIG. 35 shows an alternative user interface 3700 including a vertical axial position bar 3740 and axial position indicators 3762. Any of the axial position indicators 3762 can include a marker 3764*a*. The marker 3764*a* can provide an indication to the clinician that a contrast solution and/or a saline solution is being applied to the interventional device associated to each of the axial position indicators 3762. FIG. 36 shows an alternative user interface 3800 including axial position indicators 3840. FIG. 37 shows an alternative user interface 3900 including an axial position bar 3940, axial position indicators 3942, and force indicators 3969.

Figure 38A:
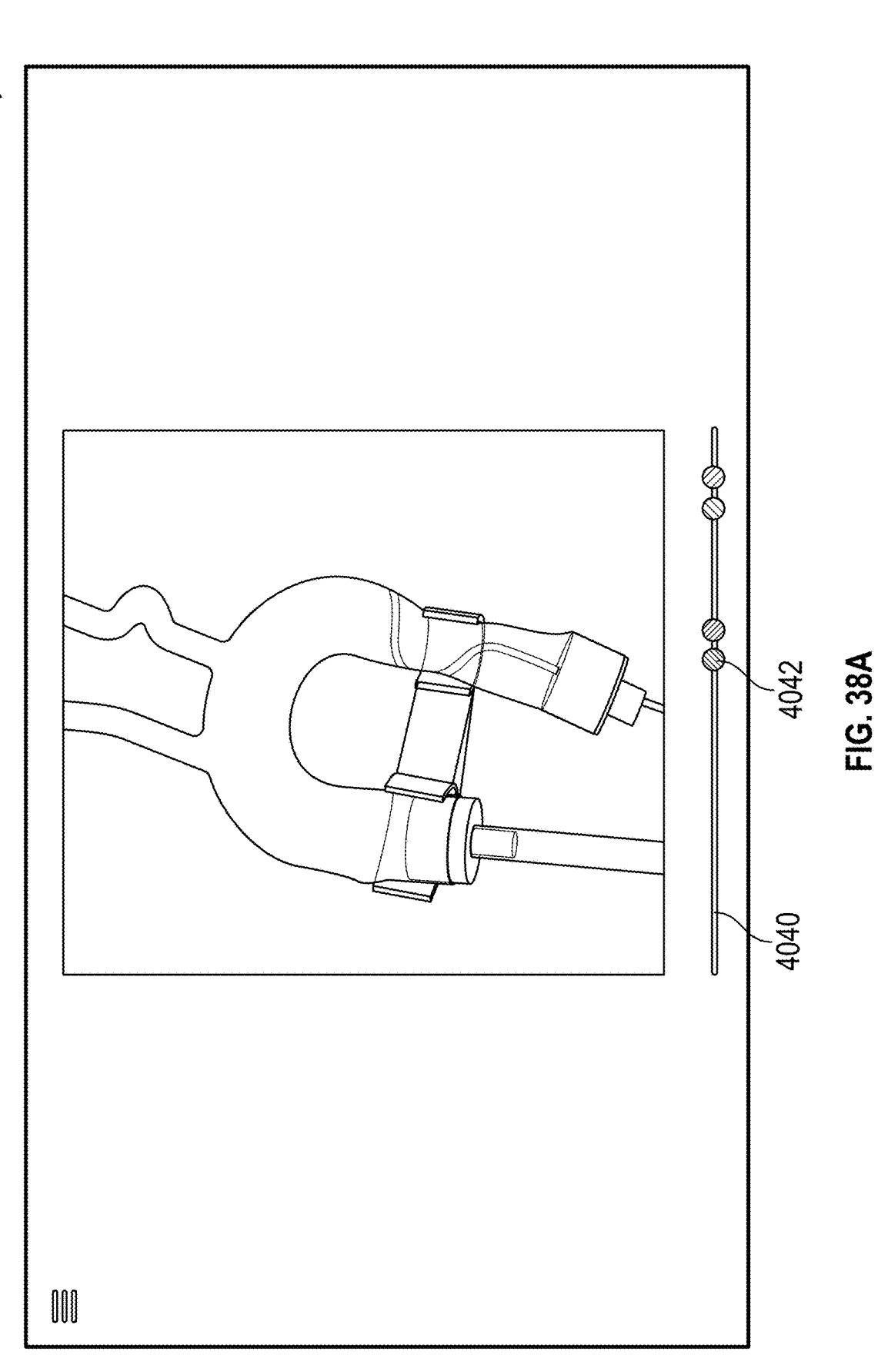
Figure 38B:
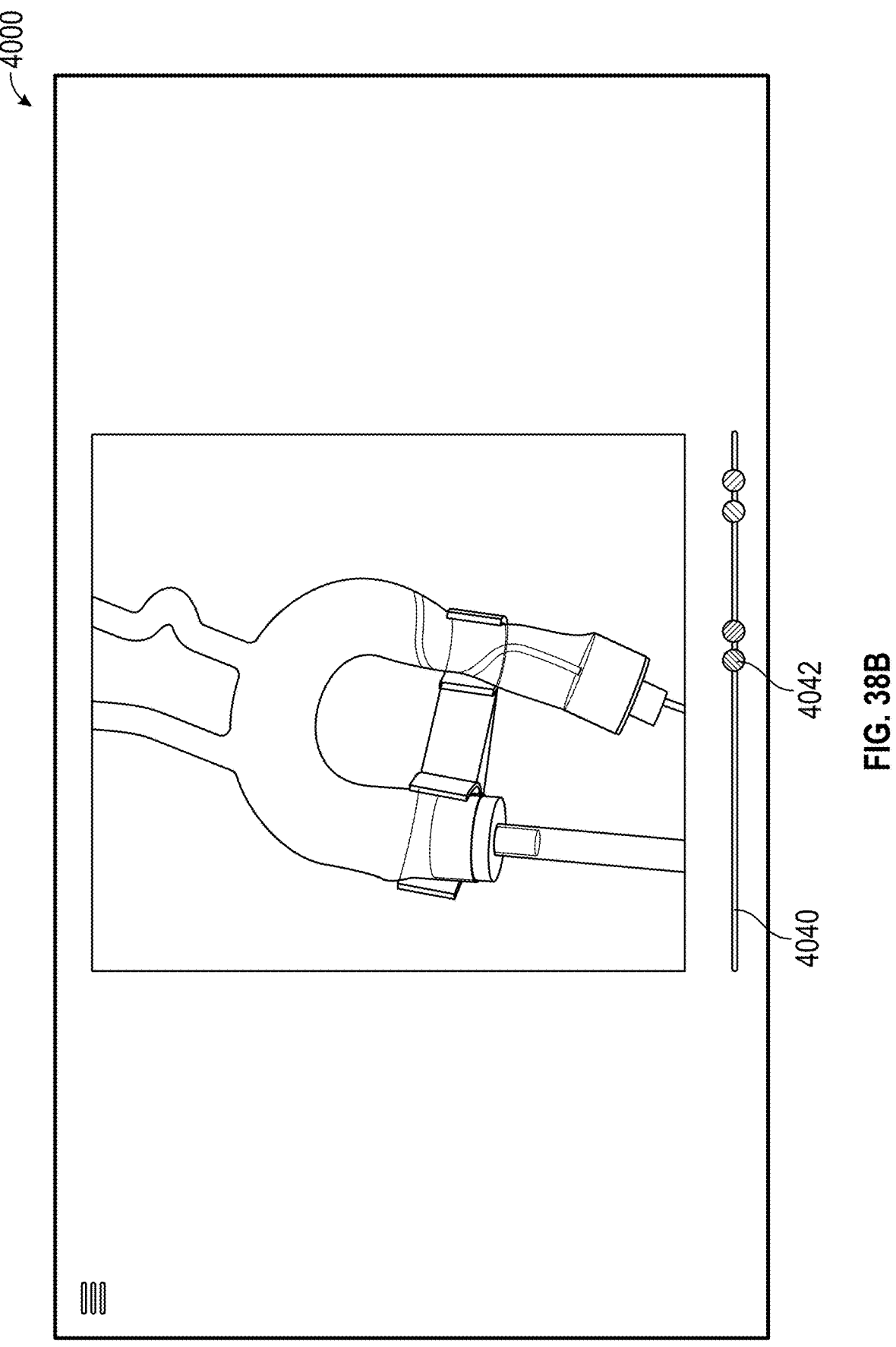
Figure 39:
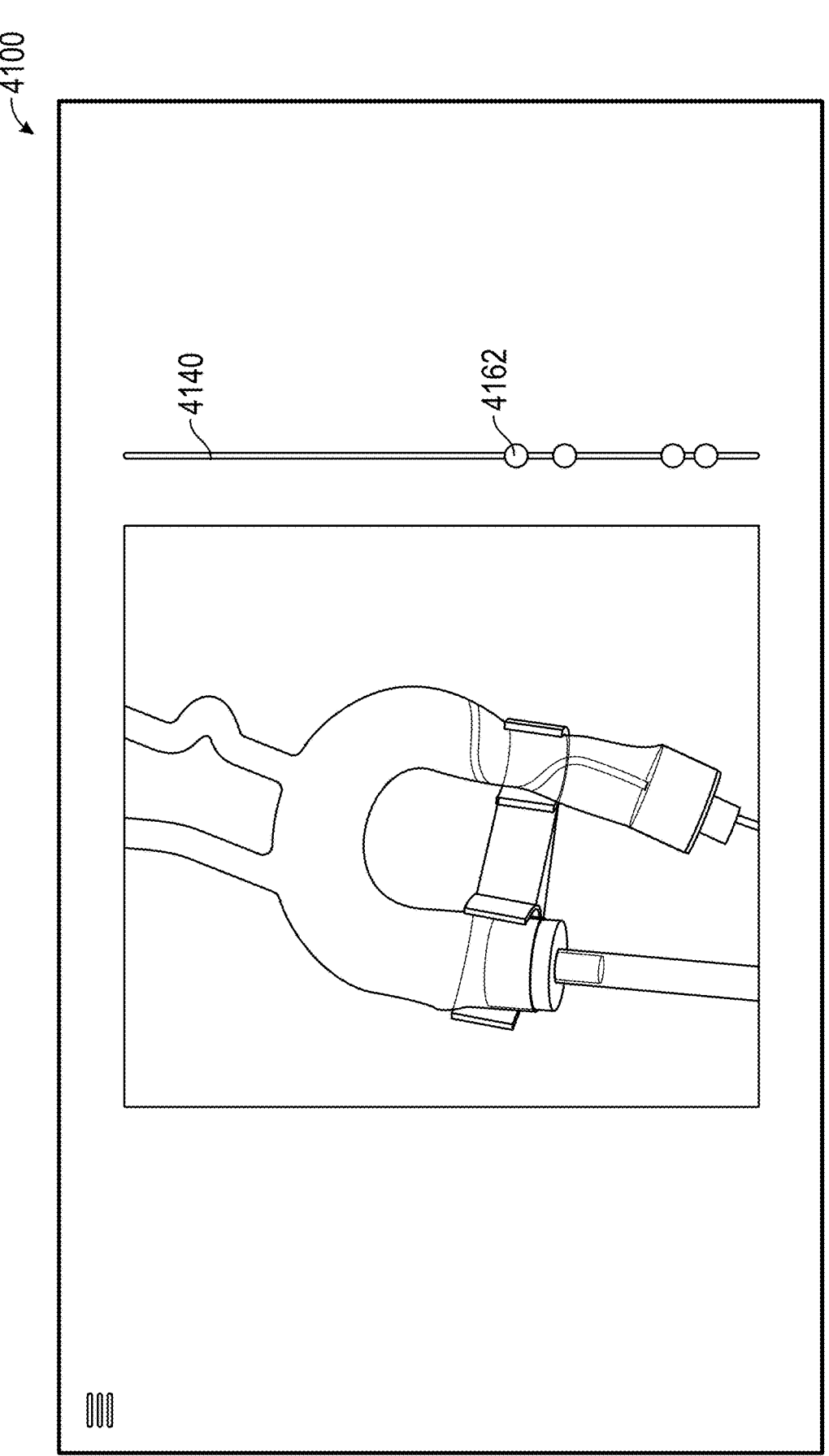
Figure 40:
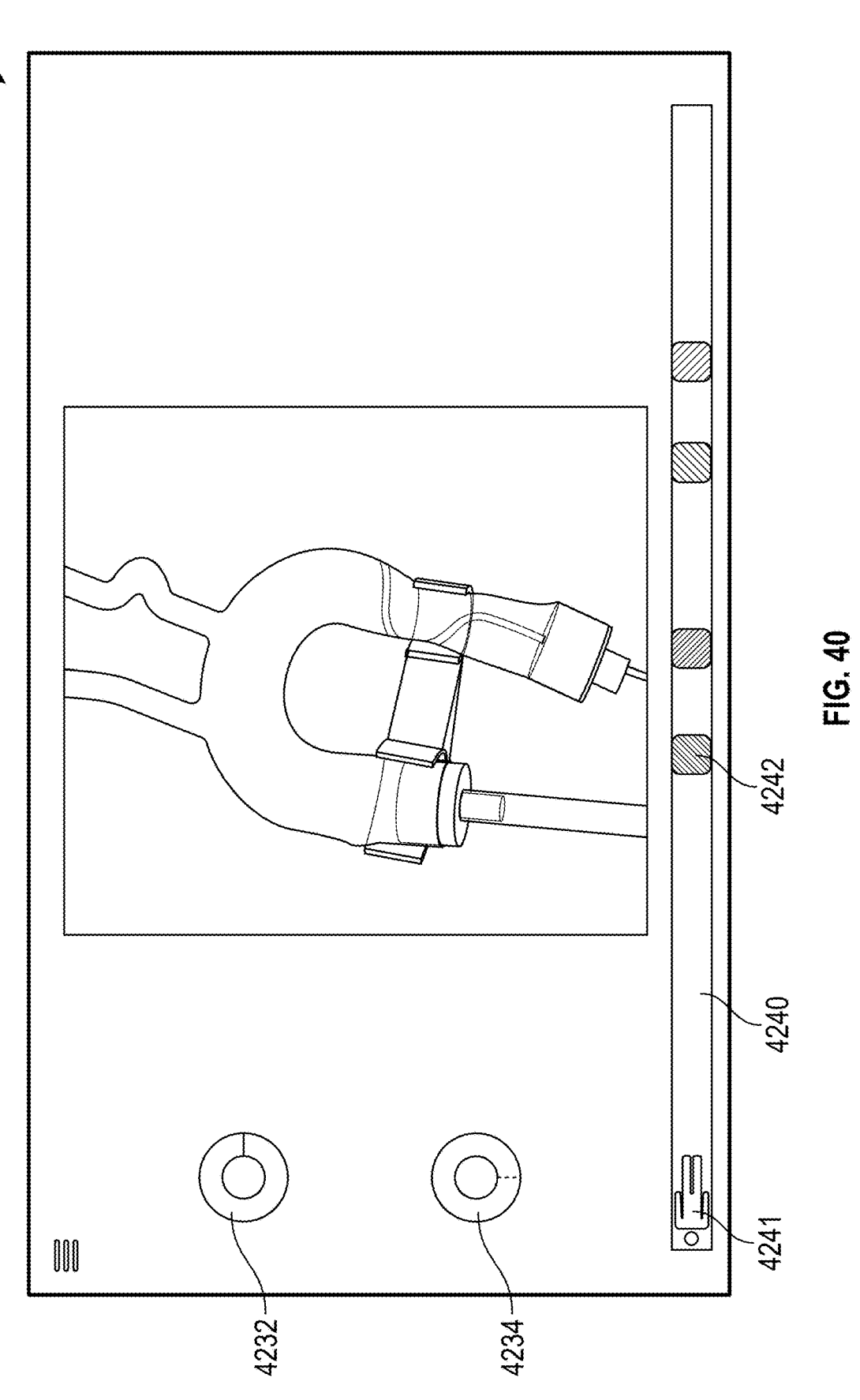
Figure 41:
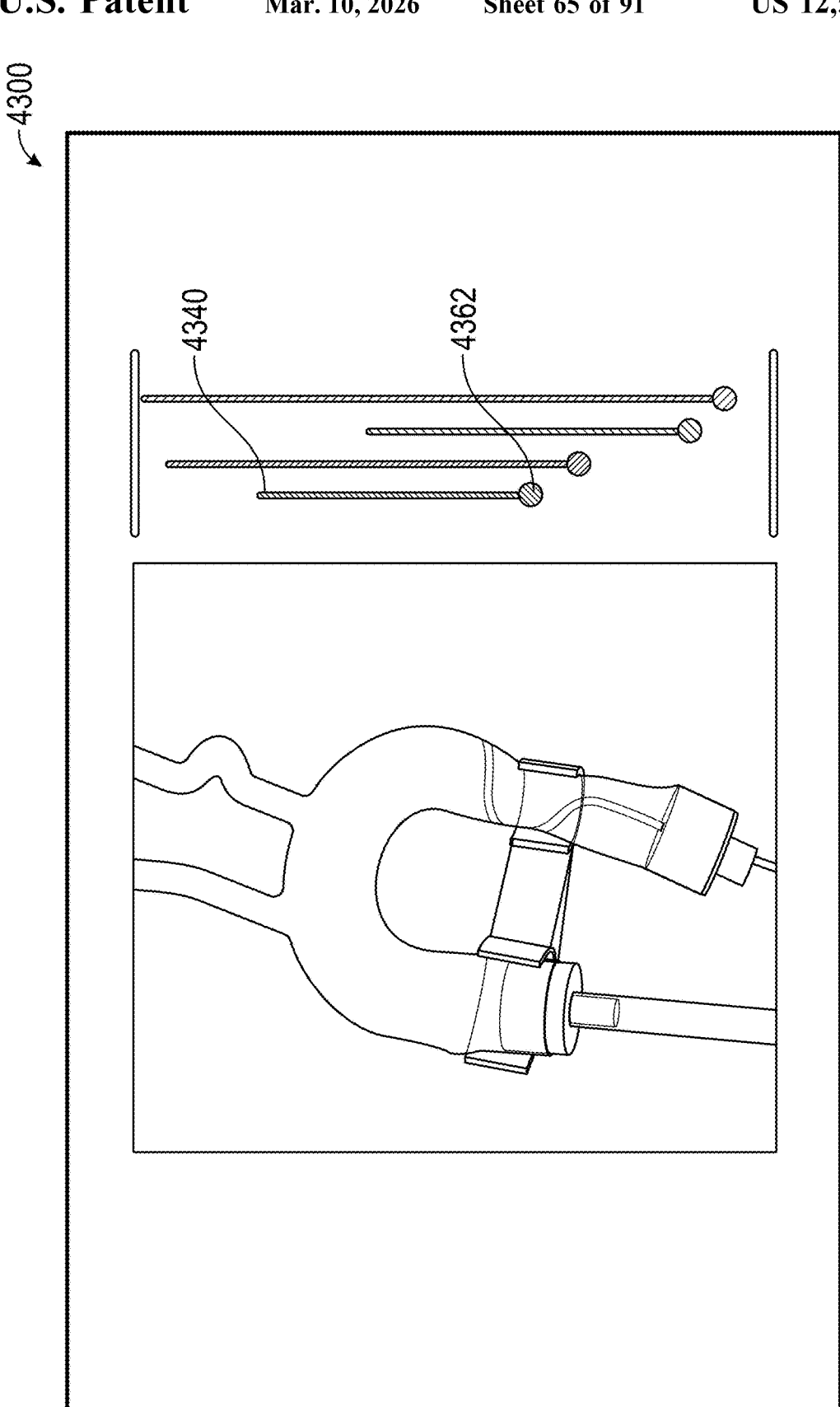
Figure 42:
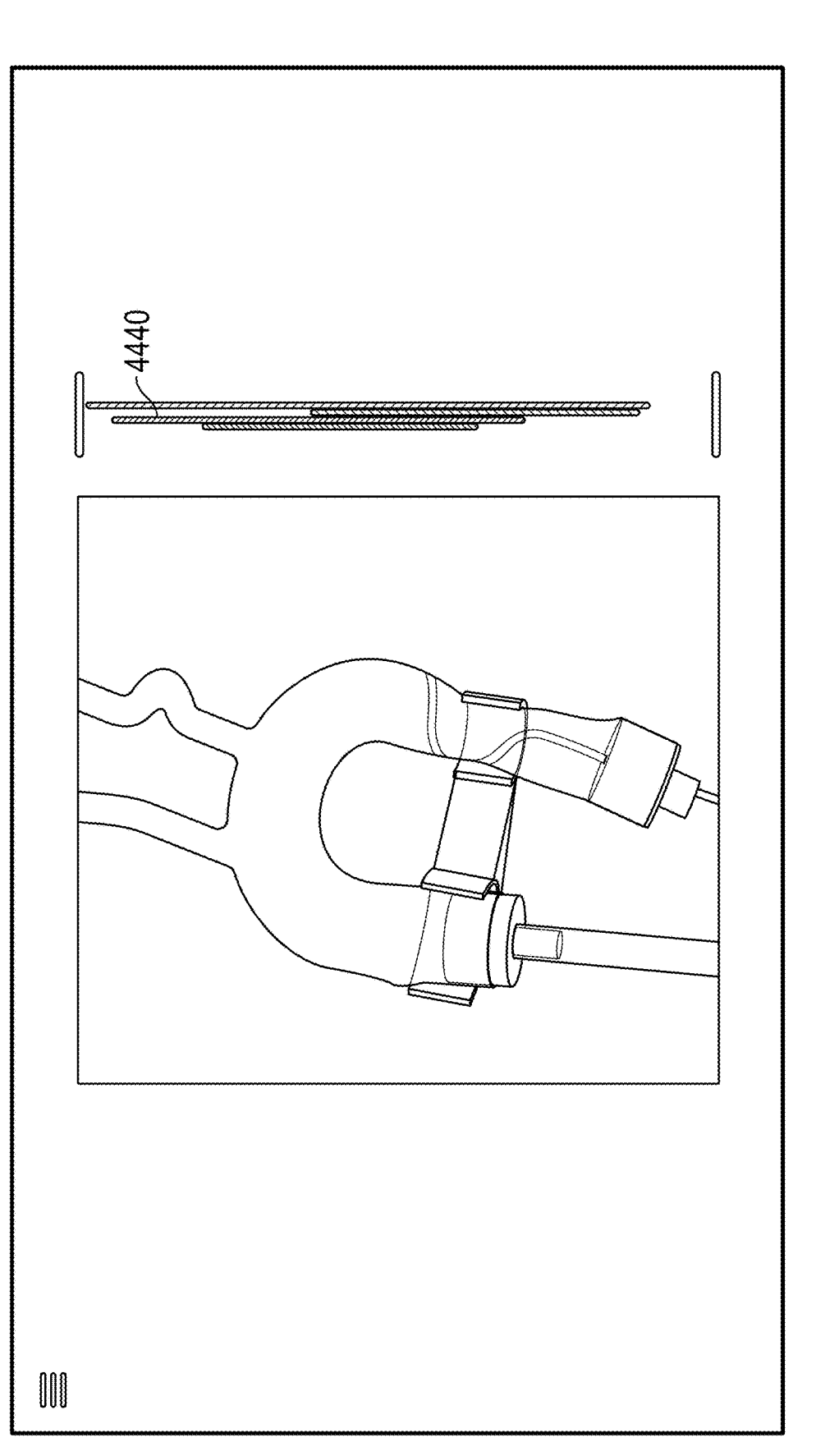

FIGS. 38A-38B show an alternative user interface 4000 including an axial position bar 4040 and axial position indicators 4042. As shown in FIG. 38B, the axial position indicators 4042 can fade if the interventional device associated to an axial position indicator is not detected. FIG. 39 shows an alternative user interface 4100 including an axial position bar 4140 and axial position indicators 4162. FIG. 40 shows an alternative user interface 4200 including an axial position bar 4240, axial position indicators 4242, rotational position indicators 4232, 4234, and a patient position marker 4241. The patient position marker 4241 can provide an indication about the position of the patient with respect to the interventional devices associated to the axial position indicators 4242. FIG. 41 shows an alternative user interface 4300 including a vertical axial position bar 4340 for each axial position marker 4362. FIG. 42 shows an alternative user interface 4400 including a vertical axial position bar 4440 for each interventional device.

In certain embodiments, a control, such as a joystick, knob, button, etc., can be selectively linked to control a particular hub and/or interventional device, e.g., by a user making a selection (e.g., by actuating one or more other controls of a controller) corresponding to the particular hub and/or interventional device so that movement of the control controls movement of the particular hub and/or interventional device. A user may change the particular hub and/or interventional device linked to the control by making an alternate selection.

Figure 43A:
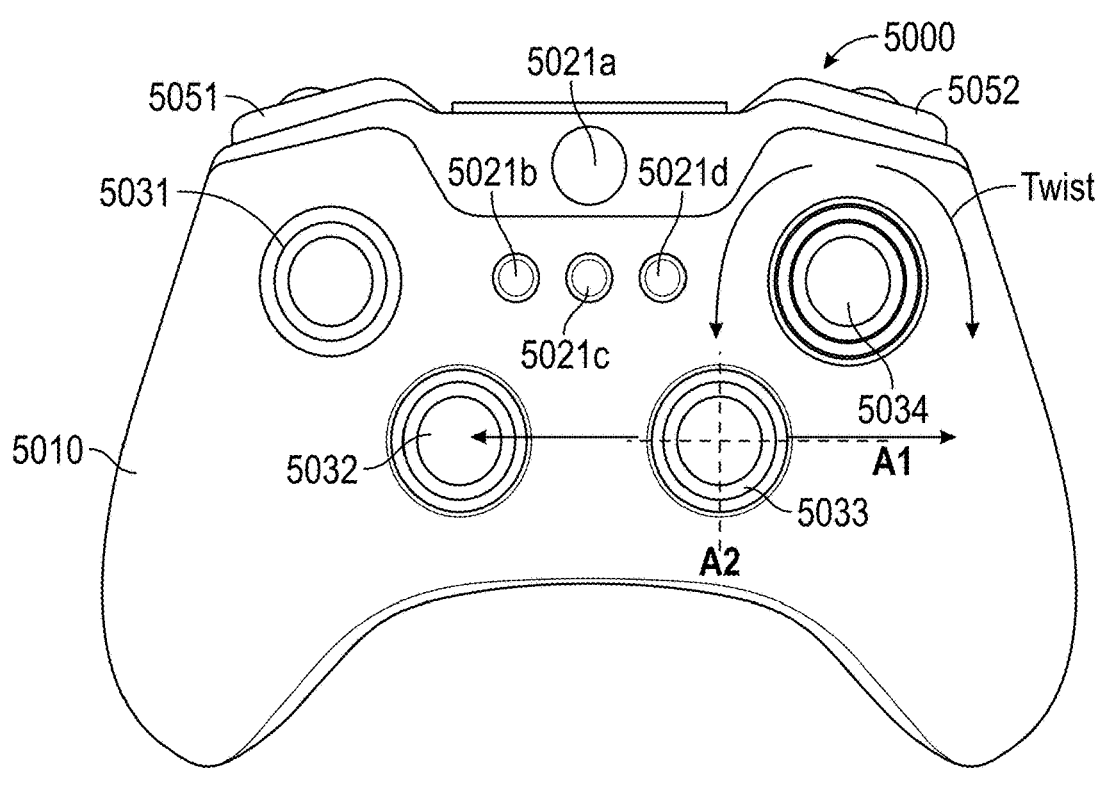
FIGS. 43A-43C illustrate an example control mechanism for manipulating interventional devices driven by respective hubs.
Figure 43B:
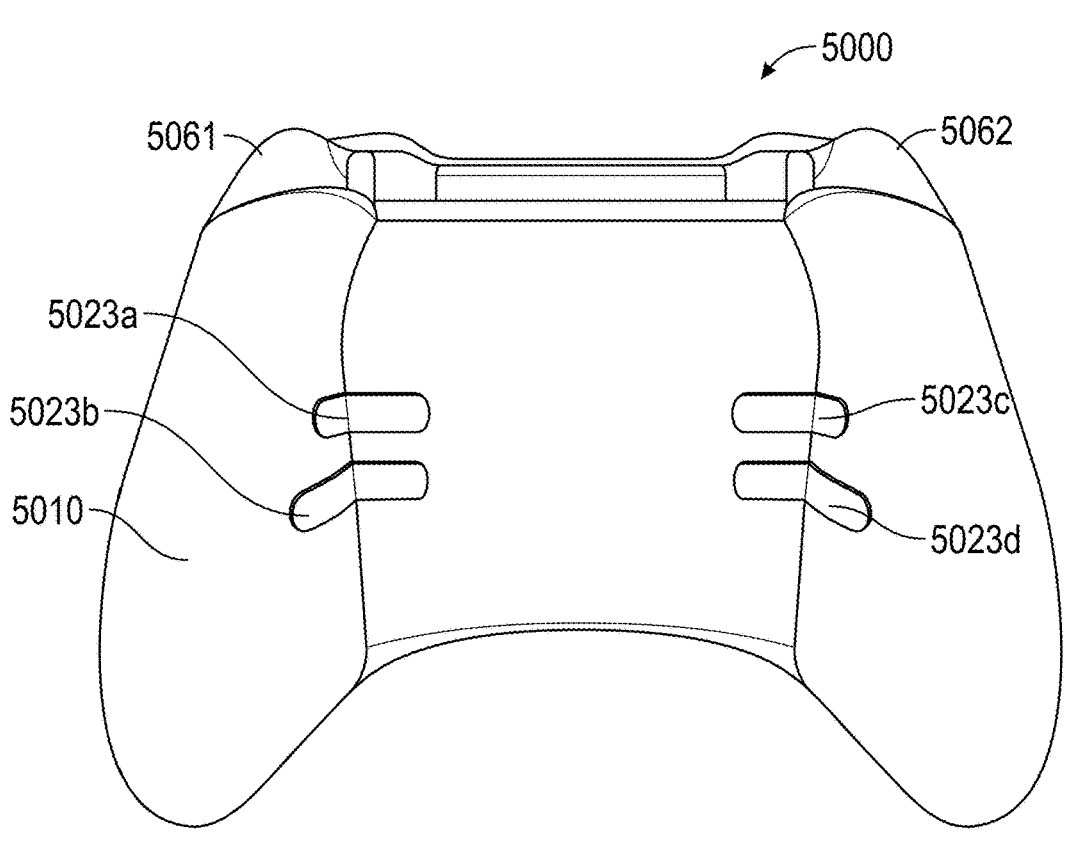
Figure 43C:
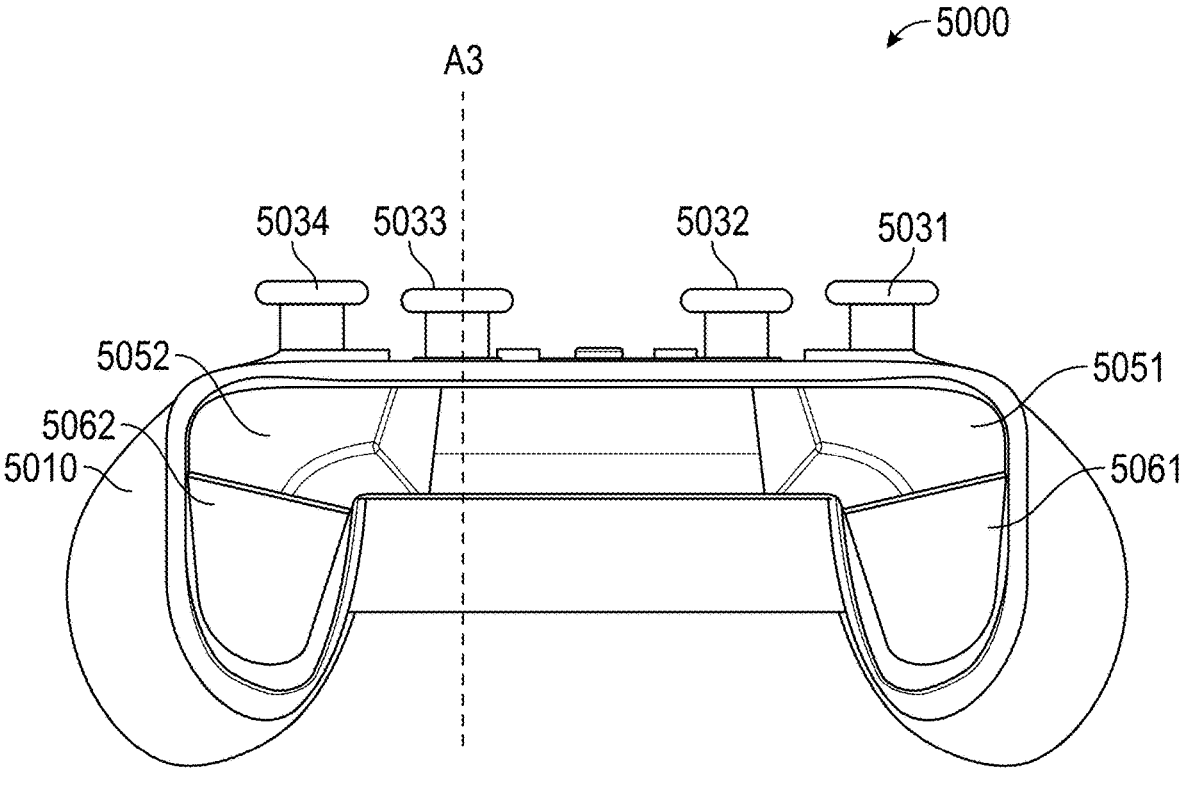

FIGS. 43A-43C illustrate another example control mechanism 5000 for manipulating interventional devices driven by (or otherwise associated with) respective hubs. The control mechanism 5000 of FIGS. 43A-43C may include any of the same or similar features and/or functions as any of the other control mechanisms described herein. For example, the control mechanism 5000 can be similar to the control mechanism 2200*j*, which is described in relation to FIGS. 28A-28C. In some embodiments, the control mechanism 5000 can include a controller having one or more controls, which may be in the form of one or more buttons and/or joysticks or any other suitable actuators. As shown in FIGS. 43A-43C, the control mechanism 5000 can include four joysticks. In some embodiments, each hub and/or interventional device may be manipulated and/or otherwise moved using one or more of the buttons and/or joysticks. For example, in certain embodiments, each hub and/or interventional device may be manipulated and/or otherwise moved using one of the one or more joysticks. In some embodiments, each of the one or more joysticks may be configured to control a unique hub and/or interventional device.

Each of the one or more joysticks can have a default position. The control mechanism 5000 can be configured so that each of the one or more joysticks returns to its default position when each of the one or more joysticks is not being manipulated by a user. In some embodiments, each or at least some of the buttons and/or joysticks can be adapted to move a unique hub and/or associated interventional device during an interventional procedure.

The control mechanism 5000 can include a handheld controller 5010 having one or more controls, which amy be in the form of one or more buttons and/or joysticks any other suitable actuators. More or fewer controls may be provided, depending upon the intended interventional devices configuration. For example, and as shown in FIG. 43A, the handheld controller 5010 can include a plurality of buttons 5021*a*, 5021*b*, 5021*c*, 5021*d* positioned on a front side of the handheld controller 5010, a plurality of buttons or paddles 5023*a*, 5023*b*, 5023*c*, 5023*d* positioned on a back side of the handheld controller 5010, a first joystick 5031, a second joystick 5032, a third joystick 5033, a fourth joystick 5034, a first shoulder button or bumper button 5051, a second shoulder button or bumper button 5052, a first trigger button 5061, and/or a second trigger button 5062. Each of the buttons and/or joysticks can be manipulated by a user. For example, a joystick can be moved along one or more axes, and one or more of the joysticks and/or buttons can be pressed.

Manipulation of one or more of the buttons and/or joysticks may trigger a responsive movement in a corresponding hub and/or interventional device. In certain embodiments, at least some movements of the buttons and/or joysticks may trigger a responsive movement in a corresponding hub adapter on the support table, which may in turn drive movement of a corresponding hub.

The control mechanism 5000 may be positioned on or near to a patient support table having a set of hubs and interventional devices coupled to the hubs. In some implementations, the control mechanism 5000 may be positioned remote from the support table such as behind a radiation shield or in a different room or different geographical location in a telemedicine implementation.

Each joystick 5031-5034 may correspond to and drive movement of a unique hub and/or interventional device. In certain embodiments, the first joystick 5031 may be configured to move (e.g., axially and/or rotationally) a first interventional device, such as a guide catheter (e.g., guide catheter 31 or guide catheter 2906), for example, by driving a hub (e.g., hub 30 or hub 2914) associated with the interventional device. Similarly, the second joystick 5032 may be configured to move (e.g., axially and/or rotationally) a second interventional device, such as a procedure catheter (e.g., catheter 29, catheter 120, or catheter 2904), for example, by driving a hub (e.g., hub 28, hub 122, or hub 2912) associated with the interventional device. The third joystick 5033 may be configured to move (e.g., axially and/or rotationally) a third interventional device, such as an access catheter (e.g., catheter 124 or catheter 2902), for example, by driving a hub (e.g., hub 126 or hub 2910) associated with the interventional device. The fourth joystick 5034 may be configured to move (e.g., axially and/or rotationally) a fourth interventional device, such as a guidewire (e.g., guidewire 27 or guidewire 2907), for example, by driving a hub (e.g., hub 26 or hub 2909) associated with the interventional device. In other embodiments, one or more of the joysticks 5031-5034 may be able to control multiple interventional devices, either simultaneously or at different times.

In operation, the corresponding coupled hubs and/or interventional devices can move axially and/or rotationally in response to actuation (e.g., movement) of the joysticks 5031-5034. Using the third joystick 5033 as an example, if the user moves the third joystick 5033 in a direction along an axis A1, a corresponding coupled hub and/or interventional device may move responsively in a corresponding axial direction at a predefined linear velocity. The corresponding coupled hub and/or interventional device may continue to move in the same or a corresponding direction at the predefined linear velocity until the user releases (e.g., stops manipulating) the third joystick 5033 or moves the third joystick 5033 further along the axis A1. The predefined linear velocity can change based on the extent of movement of the joystick 5033 along the axis A1. For example, further movement away from the default position may result in an increase in velocity. When the user stops manipulating the third joystick 5033, the third joystick 5033 can return to its default position. In some embodiments, the third joystick 5033 may be configured so that movement of the joystick along any of a plurality of different axis may cause axial movement of the corresponding coupled hub and/or interventional device. For example, in some embodiments, moving the third joystick 5033 in a direction along axis A2 can cause the corresponding coupled hub and/or interventional device to move responsively in a corresponding axial direction at a predefined linear velocity. This can beneficially allow users to advance and/or retract the coupled hub and/or interventional device by moving the third joystick along axes A1 and/or A2.

The corresponding hubs and/or interventional devices can move rotationally when a joystick is rotated. For example, if the user twists or rotates the third joystick 5033 about an axis A3, the corresponding coupled hub can drive the corresponding interventional device rotationally in a corresponding direction at a predefined angular velocity. When the user stops manipulating the third joystick 5033, the third joystick 5033 can return to its default position. In some embodiments, twisting the third joystick 5033 can cause the corresponding hub and/or interventional device to rotate on a 1:1 basis, or on a non 1:1 scaled basis. For example, if the user twists the third joystick 5033 rotationally about 5 degrees, then the corresponding hub and/or interventional device may responsively move 5 degrees in a corresponding direction. Although reference is made to the third joystick 5033 controlling movement of a corresponding hub and/or interventional device, the first, second, and fourth joysticks 5031, 5032, 5034 can be actuated as described above to control axial and/or rotational movement of their corresponding hub and/or interventional device.

Movement of the joysticks 5031, 5032, 5033, and 5034 along axes A1 and/or A2 can be configured to move the corresponding coupled hubs and/or interventional devices on a 1:1 basis, or on a non 1:1 scaled basis. For example, if the user moves the third joystick 5033 5 mm along the axis A1, then the corresponding hub and/or interventional device may responsively move at a predefined linear velocity of 5 mm/second in the same or a corresponding direction.

In some embodiments, the first and second triggers 5061, 5062 can be used to articulate and/or relax an interventional device, such as access catheter. For example, pressing the first trigger 5061 can cause the access catheter to relax. In some cases, the access catheter will continue to relax until the user releases the first trigger 5061. The access catheter can stay in a relaxed position even when the first trigger 5061 is released. The user can articulate the access catheter by pressing the second trigger 5062. In some cases, the access catheter will continue to articulate until the user releases the second trigger 5062.

The one or more buttons of the handheld controller 5010 can include digital and/or analog controls. In some embodiments, the plurality of buttons 5021a, 5021b, 5021c, 5021d and the plurality of paddles 5023a, 5023b, 5023c, 5023d, can include digital controls. Digital controls can be configured to switch between a first position and a second position, and vice versa. For example, the first position can be a position in which a button (e.g., button 5021a) is not pressed and the second position can be position in which the button is pressed. Digital controls can be used to activate and/or deactivate one or more functions of any of the systems disclosed herein. For example, buttons 5021a-5021d and/or paddles 5023a-5023d including a digital control can be actuated (e.g., pressed/depressed) to link two or more catheter hubs and/or interventional devices so that movement of one of the two or more catheter hubs and/or interventional devices causes movement of the other of the two or more catheter hubs and/or interventional devices and/or unlink the two or more catheter hubs and/or interventional devices, turn aspiration on and/or off at one or more interventional devices, switch between user interfaces (e.g., the user interfaces shown in FIGS. 30A-42), enable and/or disable controller commands (e.g., activating/deactivating the joysticks 2031-2034), and/or change the speed the corresponding hubs and/or interventional devices translate at in response to movement of a joystick.

In some cases, the first and second shoulder or bumper buttons 5051, 5052, and the first and second triggers 5061, 5062 can include analog controls. Analog controls can be configured to activate and/or deactivate one or more functions of any of the systems disclosed herein and/or control their intensity. For example, the first and second triggers 5061, 5062 the first and second shoulder or bumper buttons 5051, 5052, and the first and second triggers 5061, 5062 can each include a moving magnet and a stationary hall effect sensor. The hall effect sensor can detect the proximity of the magnet by detecting the presence and/or magnitude of the magnetic field of the magnet. For example, the hall effect sensor of the first trigger 5061 can detect a stronger magnetic field when the first trigger 5061 is fully pressed and a weaker magnetic field when the trigger 5061 is not fully pressed and/or pressed at all. The intensity of the magnetic field as detected by the hall effect sensor can beneficially control the delivery of, for example, fluidics injections at variable rates. For example, fully pressing the first trigger 5061 can cause delivery of fluidics at a first rate, half-pressing the first trigger 5061 can cause delivery of fluidics at a second rate lower than the first rate, and not pressing the trigger 5061 can cause the delivery of fluidics to stop. Although reference is made to analog controls being capable of controlling the intensity and/or fluid flow rate of fluidics, analog controls can be used to control any parameters or aspects of the system where the parameter or aspect includes a variable operating range (e.g., axial movement speed; rotational movement speed; etc.).

Figure 44A:
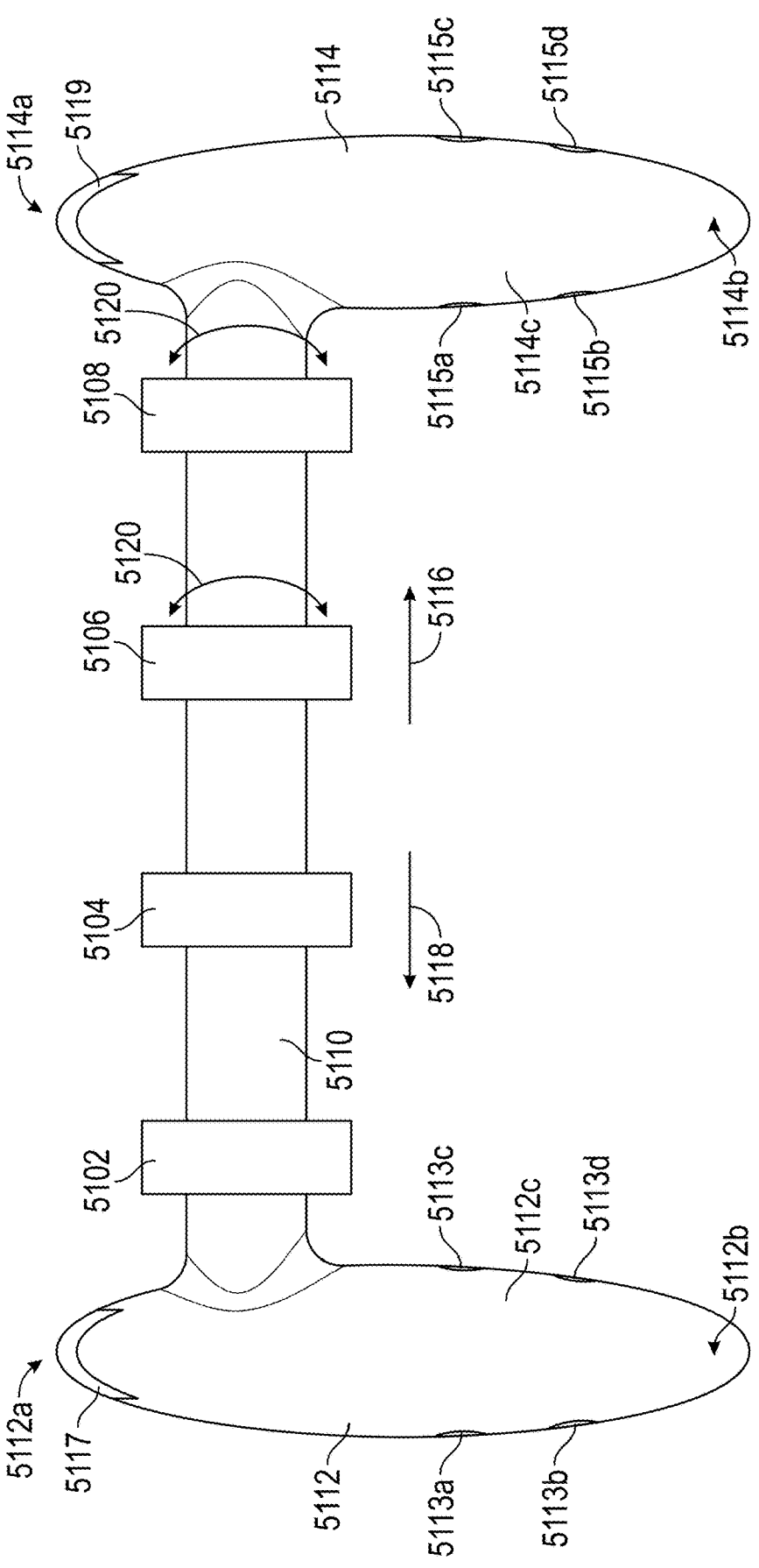
FIGS. 44A-44C illustrate an example control mechanism for manipulating interventional devices driven by respective hubs.
Figure 44B:
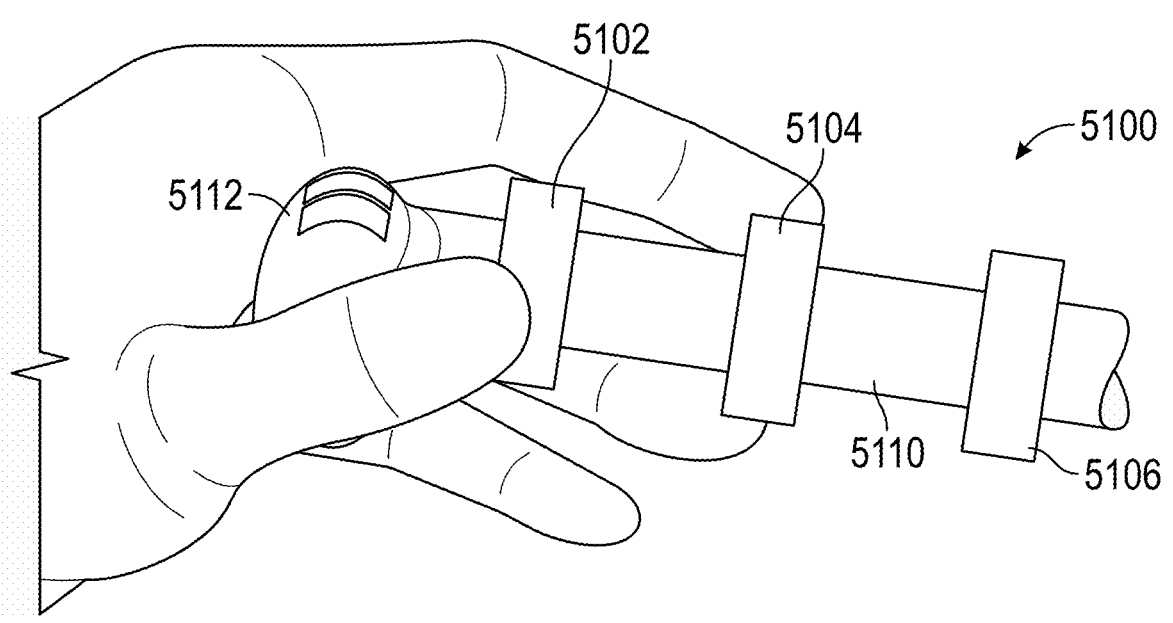
Figure 44C:
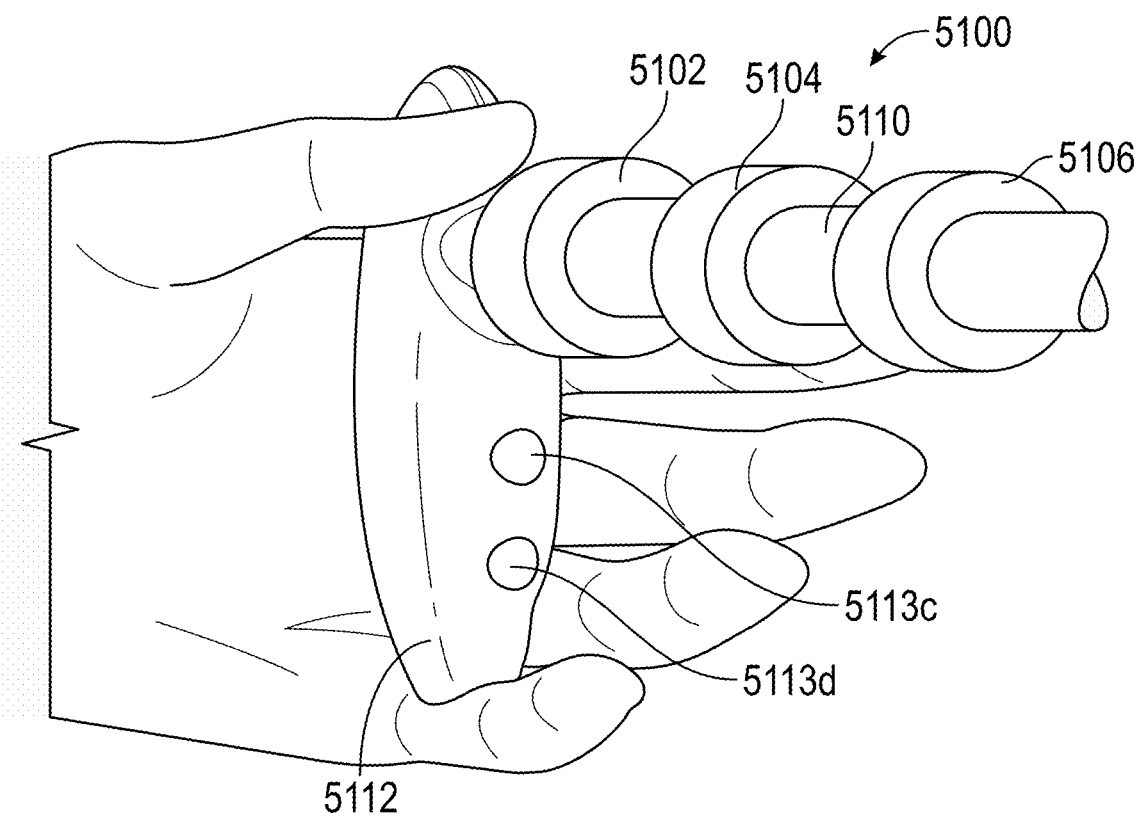

FIGS. 44A-44C illustrate another example control mechanism 5100 for manipulating interventional devices driven by (or otherwise associated with) respective hubs. The control mechanism of FIGS. 44A-44C may include any of the same or similar features and/or functions as any of the other control mechanisms described herein. For example, the control mechanism 5100 can be similar to the control mechanism 2200, which is described in relation to FIGS. 16A-16C. In some embodiments, the control mechanism 5100 can include a first control 5102, a second control 5104, a third control 5106, and a fourth control 5108. More or fewer controls may be provided, depending upon the intended interventional device configuration. Each control 5102-5108 can be movably carried on a shaft 5110. In certain embodiments, the shaft 5110 of the control mechanism 5100 can coupled to a proximal handle 5112 and to a distal handle 5114. The controls 5102-5108 may advance distally or retract proximally along the shaft 5110, as indicated by arrow 5116 and arrow 5118, respectively. Additionally or alternatively, each control 5102-5108 may be rotated about the shaft 5110, as indicated by arrow 5120. In operation, the control mechanism 5100 and/or controls 5102-5108 can manipulate interventional devices driven by (or otherwise associated with) respective hubs as described herein in relation to control mechanism 2200 (which is described in relation to FIGS. 16A-16C), control mechanism 2200a (which is described in relation to FIGS. 19A-19C), and/or control mechanism 2200e (which is described in relation to FIGS. 23A-23C).

Each control 5102-5108 may correspond to and drive movement of a hub and/or interventional device. In certain embodiments, the control 5102 may be configured to move (e.g., axially and/or rotationally) an interventional device such as a guide catheter (e.g., guide catheter 31 or guide catheter 2906), for example, by driving a hub (e.g., hub 30 or hub 2914) associated with the interventional device. Similarly, the control 5104 may be configured to move (e.g., axially and/or rotationally) an interventional device such as a procedure catheter (e.g., catheter 29, catheter 120, or catheter 2904), for example, by driving a hub (e.g., hub 28, hub 122, or hub 2912) associated with the interventional device. The control 5106 may be configured to move (e.g., axially and/or rotationally) an interventional device such as an access catheter (e.g., catheter 124 or catheter 2902), for example, by driving a hub (e.g., hub 126 or hub 2910) associated with the interventional device. The control 5108 may be configured to move (e.g., axially and/or rotationally) an interventional device such as a guidewire (e.g., guidewire 27 or guidewire 2907), for example, by driving a hub (e.g., hub 26 or hub 2909) associated with the interventional device.

The proximal handle 5112 can include a first end 5112a, a second end 5112b opposite the first end 5112a, a grip 5112c, and one or more buttons or other actuators 5113a, 5113b, 5113c, and/or 5113d. In some cases, the one or more buttons 5113a-d can be positioned on an anterior portion of the grip 5112c and/or a posterior portion of the grip 5112c. In some embodiments, the proximal handle 5112 can include one or more shoulder or bumper buttons 5117.

The distal handle 5114 can include a first end 5114a, a second end 5114b opposite the first end 5114a, a grip 5114c, and one or more buttons or other actuators 5115a, 5115b, 5115c, an/or 5115d. In some cases, the one or more buttons 5115a-d can be positioned on an anterior portion of the grip 5114c and/or a posterior portion of the grip 5114c. In some embodiments, the distal handle 5114 can include one or more shoulder or bumper buttons 5119.

In operation, a user can grasp the proximal handle 5112 with a first hand (e.g., left hand) and/or the distal handle 5114 with a second hand (e.g., right hand). As shown in FIGS. 44B and 44C, one or more of the controls, for example, controls 5102, 5104, and the buttons 5113a-d can be within reach of a user's hand (e.g., left hand). Similarly, one or more of the controls, for example, controls 5106, 5108, and the buttons 5115a-d can both be within reach of a user's hand (e.g., right hand). This can beneficially allow for easy and instant access to any of the controls 5102-5108 and/or the buttons 5113a-d, 5115a-d. The position of the controls 5102-5108 relative to the proximal handle 5112 and distal handle 5114 may provide for improved grasp and more precise movements in comparison to other locations.

The buttons or actuators 5113a-d, 5115a-d, 5117, and 5119 may be configured to perform various functions as described herein with respect to other buttons or other actuators (e.g., initiate a contrast injection, initiate aspiration, link/unlink movement of interventional devices with respect to each other, change axial velocity, change rotational velocity, etc.).

Figure 45A:
FIGS. 45A-45B illustrate an example control mechanism for manipulating interventional devices driven by respective hubs.
Figure 45B:
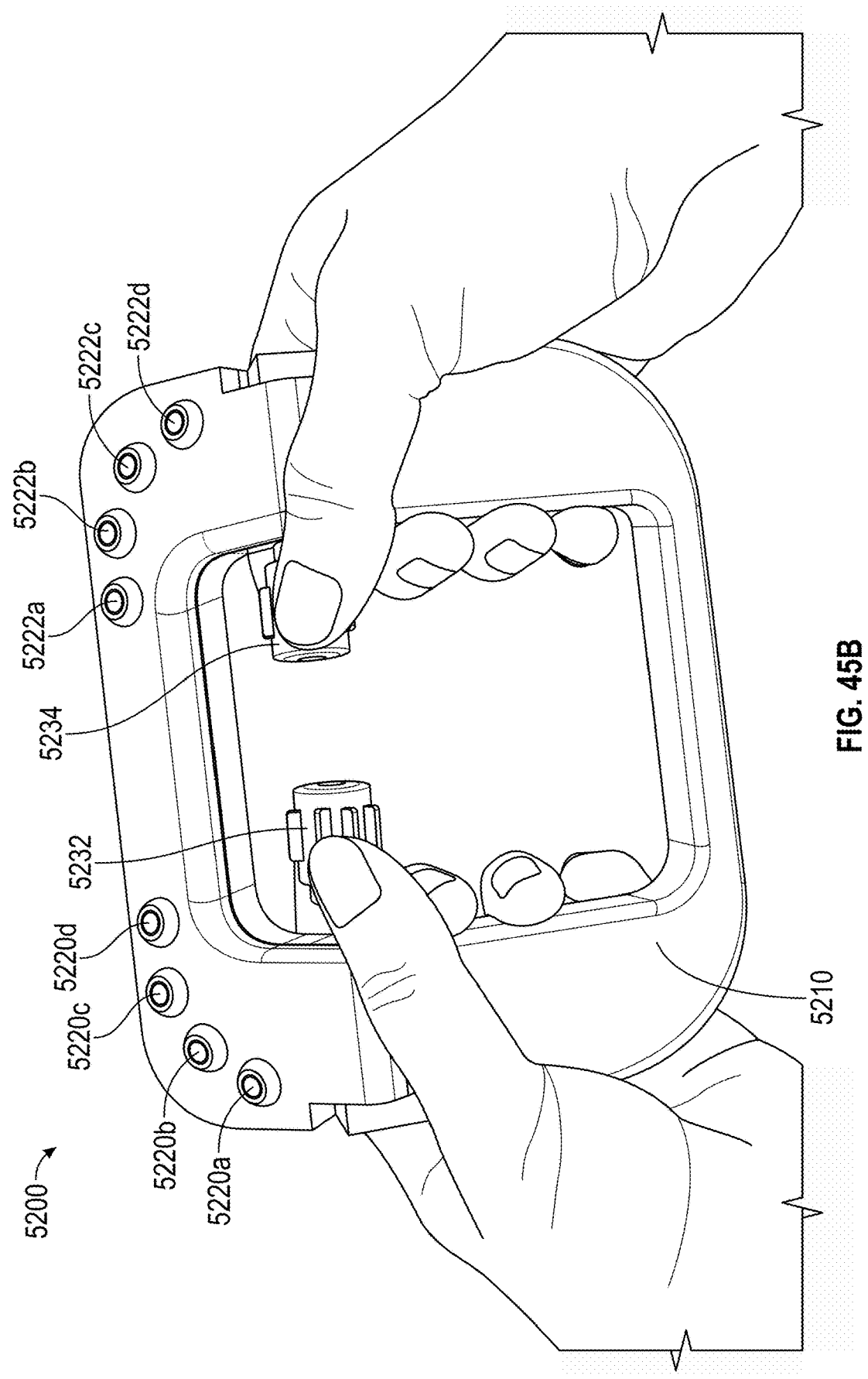

FIGS. 45A-45B illustrate another example control mechanism 5200 for manipulating interventional devices driven by (or otherwise associated with) respective hubs. The control mechanism of FIGS. 45A-45B may include any of the same or similar features and/or functions as any of the other control mechanisms described herein. The control mechanism 5200 can include a handheld controller 5210 having one or more controls, which may be in the form of buttons and/or knobs or any other suitable actuators. More or fewer buttons and/or knobs may be provided, depending upon the intended interventional devices configuration. For example, the handheld controller 5210 can include a first plurality of buttons 5220, a second plurality of buttons 5222, a first knob 5232, and a second knob 5234. Each of the buttons and/or knobs can be manipulated by a user. For example, the first and/or second knobs can be rotated around and/or translated along an axis to cause a corresponding hub and/or interventional device to move responsively in the same or a corresponding axial and/or rotational direction.

Each of the first knob 5232 and the second knob 5234 may correspond to and drive movement of a hub and/or interventional device. In some cases, the first knob 5232 and the second knob 5234 can be assignable to control different hubs/interventional devices. For example, the first knob 5232 can be linked to a first particular hub and/or interventional device by pressing one button of the first plurality of buttons 5220. The second knob can be linked to a second particular hub and/or interventional device by pressing one button of the second plurality of buttons 5222.

For example, pressing a first button 5220a of the first plurality of buttons 5220 can link the first knob 5232 to a first interventional device, such as a guide catheter (e.g., guide catheter 31 or guide catheter 2906), so that movement of the first knob 5232 controls movement of the first interventional device, and pressing a second button 5220b of the first plurality of buttons 5220 can link first knob 5232 to a second interventional device, such as a procedure catheter (e.g., catheter 29, catheter 120, or catheter 2904), so that movement of the first knob 5232 controls movement of the second interventional device. In some embodiments, pressing a third button 5220c of the first plurality of buttons 5220 can link first knob 5232 to a third interventional device, such as an access catheter (e.g., catheter 124 or catheter 2902), so that movement of the first knob 5232 controls movement of the third interventional device. In some embodiments, pressing a fourth button 5220d of the first plurality of buttons 5220 can link first knob 5232 to a fourth interventional device, such as a guidewire (e.g., guidewire 27 or guidewire 2907), so that movement of the first knob 5232 controls movement of the fourth interventional device.

In certain embodiments, pressing a first button 5222a of the second plurality of buttons 5222 can link the second knob 5234 to the first interventional device so that movement of the second knob 5234 controls movement of the first interventional device, and pressing a second button 5222b of the second plurality of buttons 5222 can link second knob 5234 to the second interventional device so that movement of the second knob 5234 controls movement of the second interventional device. In some embodiments, pressing a third button 5222c of the second plurality of buttons 5222 can link second knob 5234 to the third interventional device so that movement of the second knob 5234 controls movement of the third interventional device. In some embodiments, pressing a fourth button 5222d of the second plurality of buttons 5222 can link second knob 5234 to a fourth interventional device so that movement of the second knob 5234 controls movement of the fourth interventional device. In this way, the first plurality of buttons 5220 and the second plurality of buttons 5222 can beneficially allow the first knob 5232 and/or second knob 5234 to be linked to, and control, more than one corresponding hub/and or interventional device. For example, each button of the first and/or second plurality of buttons can be associated to a corresponding hub and/or interventional device (e.g., guide catheter 31 or guide catheter 2906; catheter 29, catheter 120, or catheter 2904; catheter 124 or catheter 2902; guidewire 27 or guidewire 2907) to allow control of the corresponding hub and/or interventional device via the first knob 5232 and/or second knob 5234. This can beneficially allow users to quickly and easily toggle between corresponding hubs and/or interventional devices. The two knobs may allow users to control two different hubs and/or interventional devices simultaneous by assigning one of the hubs/interventional devices to each knob so that axial and rotational movement of the two hubs and/or interventional devices can be controlled independently from one another at the same time.

In operation, if the user moves the first knob 5232 or the second knob 5234 along an axis A3 distally, as shown by arrow 5216, or proximally, as shown by arrow 5218, a corresponding coupled hub and/or interventional device may move responsively in the same direction at a predefined linear velocity. The predefined linear velocity can change based on the extent of movement of the first knob 5232 or the second knob 5234 along the axis A3. For example, further movement away from a default position may result in an increase in velocity. The corresponding coupled hub and/or interventional device can continue to move in the same direction at the predefined linear velocity until the user releases (e.g., stops manipulating) or further moves the first knob 5232 or the second knob 5234. When the user stops manipulating the first knob 5232 or the second knob 5234, the first knob 5232 or the second knob 5234 can return to a starting axial position.

If the user moves the first knob 5232 or the second knob 5234 rotationally about the axis A3 (e.g., clockwise, or counterclockwise), as shown by arrow 5219, the corresponding interventional device can be driven rotationally (e.g., by a corresponding hub) in the same direction at a predefined angular velocity. The predefined angular velocity can change based on the extent of rotational movement of the first knob 5232 or the second knob 5234 about the axis A3. For example, further movement away from a default position may result in an increase in velocity. The corresponding interventional device can continue to move in the same direction at the predefined angular velocity until the user releases (e.g., stops manipulating) or further rotates the first knob 5232 or the second knob 5234. When the user stops manipulating the first knob 5232 or the second knob 5234, the first knob 5232 or the second knob 5234 can return to their starting rotational position.

In some embodiments, the control mechanism 5200 may include one or more other actuators (e.g., buttons) configured to perform various functions as described herein with respect to other buttons or other actuators (e.g., initiate a contrast injection, initiate aspiration, link/unlink movement of interventional devices with respect to each other, change axial velocity, change rotational velocity, etc.).

In certain embodiments, a control, such as a joystick, knob, button, or any other suitable actuator, can be selectively linked to control a particular combination of two or more hubs and/or interventional devices, e.g., by a user making a selection (e.g., by actuating one or more other controls of a controller) corresponding to the particular combination of hubs and/or interventional devices so that movement of the control controls movement of the particular combination of hubs and/or interventional device. For example, when the control is linked to the particular combination of devices, movement of the control may cause corresponding axial and/or rotational movement of each hub and/or interventional device in the particular combination of hubs and or interventional devices (e.g., simultaneously or successively). A user may change the particular combination of hubs and/or interventional devices linked to the control by making an alternate selection.

In some embodiments, when the control is linked to the particular combination of devices, movements of the control that correspond to axial hub/interventional device motion may cause each of the hubs and/or interventional devices to move axially, but movements of the control that correspond to rotational interventional device motion may cause only a subset of the interventional devices to rotate (e.g., in embodiments in which at least some of the interventional devices do not rotate or rotation is not desired). For example, in some embodiments having a guide catheter, a procedure catheter, an access catheter, and a guidewire, the access catheter and guidewire may be configured to rotate, and the guide catheter and procedure catheter may not be configured to rotate. In such embodiments, for example, movements of a control linked to one or more of the guidewire and the access catheter and linked to one or more of the procedure catheter and the guide catheter that correspond to rotational interventional device motion may cause rotation of only the one or more of the guidewire and the access catheter without causing rotation of the one or more of the procedure catheter and the guide catheter.

In some embodiments, when the control is linked to the particular combination of devices, movements of the control that correspond to rotational interventional device motion may cause each of the interventional devices to rotate, but movements of the control that correspond to axial hub/interventional device motion may cause only a subset of the interventional devices to move axially.

Figure 46A:
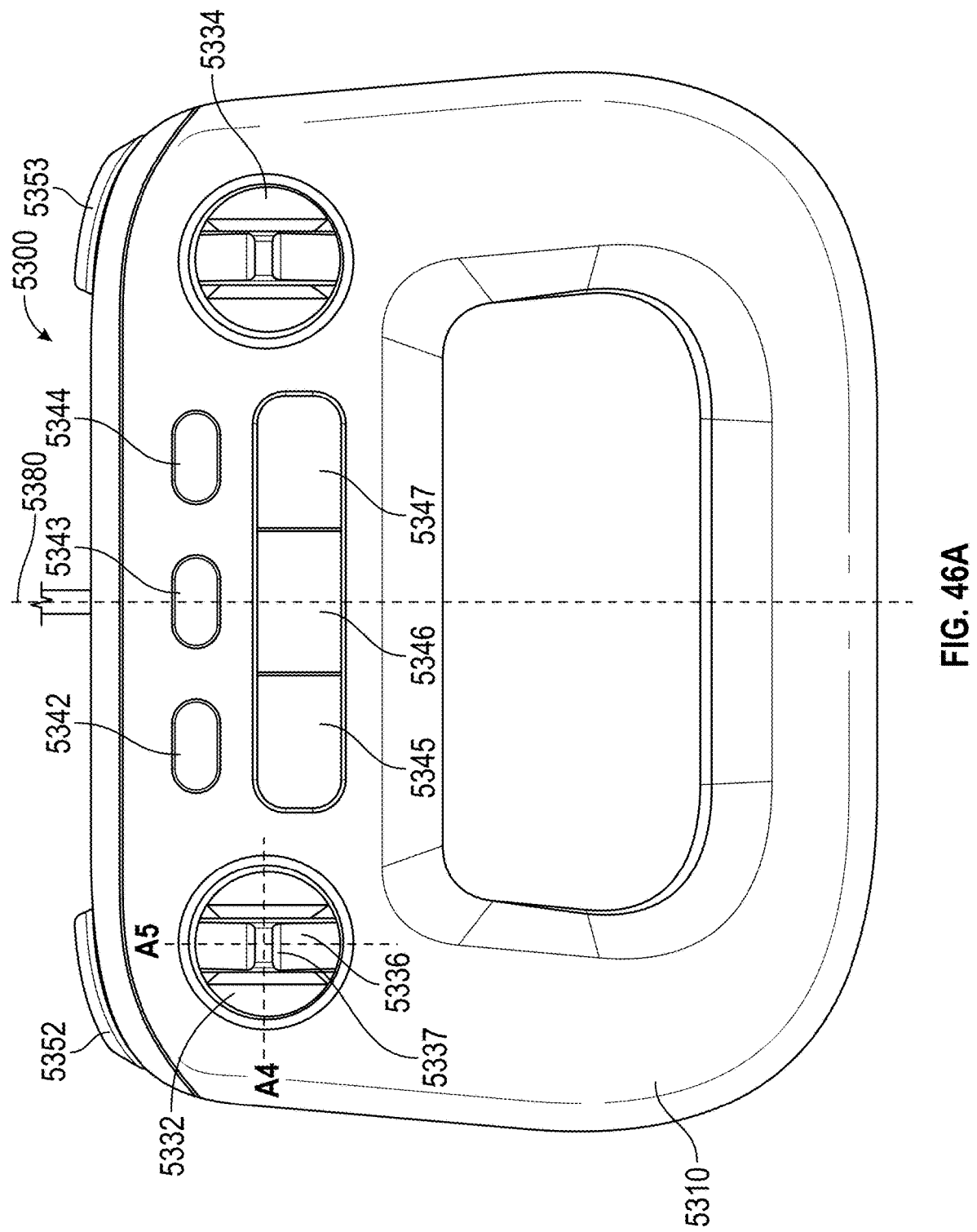
FIGS. 46A-46B illustrate an example control mechanism for manipulating interventional devices driven by respective hubs.
Figure 46B:
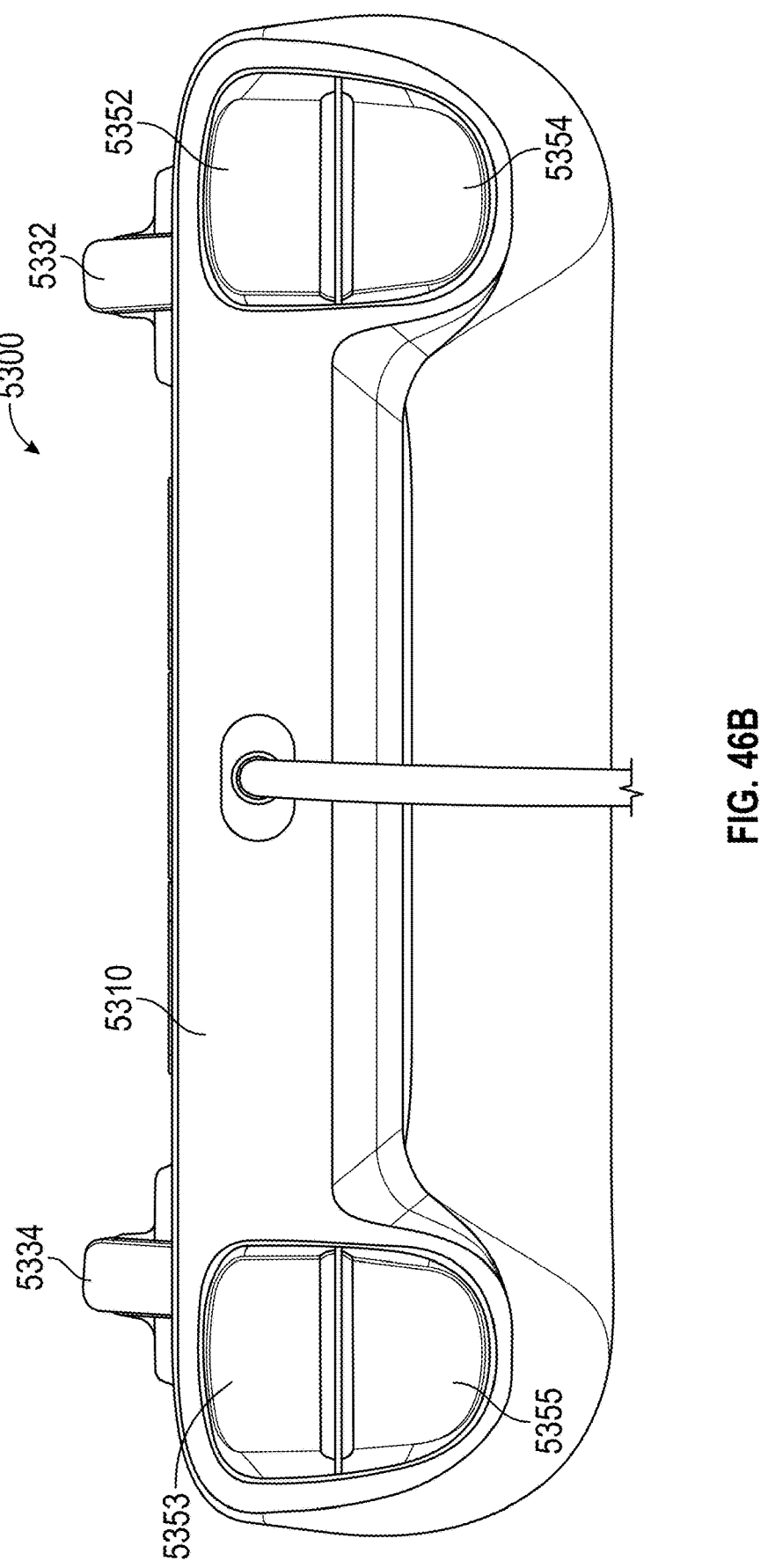

FIGS. 46A-46B illustrate another example control mechanism 5300 for manipulating interventional devices driven by (or otherwise associated with) respective hubs. As shown in FIGS. 46A-46B, the control mechanism 5300 can be in the form of a handheld controller. The control mechanism may include any of the same or similar features and/or functions as any of the other control mechanisms described herein.

As shown in FIGS. 46A-46B, the control mechanism 5300 can include a handheld controller 5310 having one or more controls, which may be in the form of buttons and/or joysticks or any other suitable actuators. As shown, the control mechanism 5300 can include a first control or first joystick 5332. The control mechanism 5300 can include a second control or second joystick 5334. The control mechanism can include a plurality of buttons 5342, 5343, 5344, 5345, 5346, 5347, and a plurality of shoulder or bumper buttons 5352, 5353, 5354, 5355.

Each of the first joystick 5332 and the second joystick 5334 may correspond to and drive movement of a hub and/or interventional device. In some cases, each of the first joystick 5332 and the second joystick 5334 can be assignable to control different hubs and/or interventional devices. For example, the first joystick 5332 can be selectively linked to a first particular hub and/or interventional device, for example, by a user making a selection on the controller 5310 (e.g., by pressing one or more buttons). The second joystick 5334 can be selectively linked to a second particular hub and/or interventional device, for example, by a user making a selection on the controller 5310 (e.g., by pressing one or more buttons). In some embodiments, the first joystick 5332 and/or the second joystick 5334 can be selectively linked to a combination of hubs and/or interventional devices, for example, by a user making a selection on the controller 5310 (e.g., by pressing one or more buttons). For example, the first joystick 5332 and/or the second joystick 5334 can be selectively linked to a combination of two hubs and/or interventional devices, three hubs and/or interventional devices, or four hubs and/or interventional devices to simultaneously control at least certain movements (e.g., axial/linear movement and/or rotational movement) of each hub and/or interventional device in the combination. In certain embodiments, the joystick 5332 or joystick 5334 can correspond to and drive movement of a hub and/or interventional device by driving movement of a hub adapter associated with the interventional device.

The control mechanism 5300 can include one or more drive modes in which the first joystick 5332 and the second joystick 5334 are each linked to, and can control, one or more corresponding hubs and/or interventional devices. In some embodiments, in different drive modes, the first joystick 5332 and/or the second joystick 5334 can be configured to control different hubs and/or interventional devices or different combinations of hubs and/or interventional devices.

In some embodiments, the control mechanism 5300 can toggle between drive modes (e.g., in response to a user input). In some embodiments, in different drive modes, the first joystick 5332 and/or the second joystick 5334 can control different subsets of corresponding hubs and/or interventional devices. In some embodiments, in different drive modes, one or both of the first joystick 5332 and/or the second joystick 5334 can control corresponding hubs and/or interventional devices at different axial and/or rotational velocities.

In some embodiments, the control mechanism 5300 can be selectively configured in a first drive mode, which is also referred to herein as a first operation mode, a first stage mode, and/or an access stage mode. As described in further detail herein, in the first drive mode, the control mechanism 5300 can be configured to control a plurality of hubs and/or interventional devices to drive interventional devices to achieve supra-aortic access.

In some embodiments, the control mechanism 5300 can be selectively configured in a second drive mode, which is also referred to herein as a second operation mode, a second stage, and/or a procedure stage mode. As described in further detail herein, in the second drive mode, the control mechanism 5300 can be configured to control one or more hubs and/or interventional devices to drive the interventional devices to a procedure site (e.g., a neurovascular procedure site, such as a thrombectomy site) after supra-aortic access has been achieved. In some embodiments, in the second drive mode, the control mechanism 5300 can be configured to control the plurality of hubs and/or interventional devices to perform a procedure (e.g., a neurovascular procedure, such as a thrombectomy).

In some embodiments, one or more hubs and/or interventional devices may be driven to retract the interventional devices from the procedure site using the control mechanism 5300 in the second drive mode. In some embodiments, one or more hubs and/or interventional devices may be driven to retract the interventional devices from the procedure site using the control mechanism 5300 in the second drive mode until the interventional devices are withdrawn from the supra-aortic vessels. In some embodiments, after the interventional devices are withdrawn from the supra-aortic vessels, the hub and/or interventional devices can be driven to retract the interventional devices in the first drive mode. In other embodiments, there may be one or more additional drive modes for retracting the interventional devices from the procedure site and/or after withdrawal from the supra-aortic vessels.

In some embodiments, in the first drive mode, the first joystick 5332 can be linked to an interventional device such as a guidewire (e.g., guidewire 27 or guidewire 2907), and the second joystick 5334 can be linked to a combination of corresponding hubs and/or international devices. The combination of corresponding hubs and/or international devices can include a guide catheter (e.g., guide catheter 31 or guide catheter 2906), a procedure catheter (e.g., catheter 29, catheter 120, or catheter 2904), and/or an access catheter (e.g., catheter 124 or catheter 2902). In certain embodiments, the first drive mode may be used to drive the hubs and/or interventional devices to achieve supra-aortic access as described herein.

In some embodiments, in the second drive mode, the first joystick 5332 can be linked to an interventional device such as a guidewire (e.g., guidewire 27 or guidewire 2907), and the second joystick 5334 can be linked to a combination of corresponding hubs and/or international devices including a guide catheter (e.g., guide catheter 31 or guide catheter 2906), and/or procedure catheter (e.g., catheter 29, catheter 120, or catheter 2904). As described herein, in certain embodiments, the second drive mode may be used to drive the hubs and/or interventional devices to navigate the interventional devices to a procedure site and/or perform a procedure.

Although reference is made to the control mechanism 5300 including two drive modes, the control mechanism 5300 can include a single drive mode and or more than two drives modes, with each of the first joystick 5332 and the second joystick 5334 linked to one or more corresponding hubs and/or interventional devices in each drive mode. Additionally, as described herein, a user may change which hubs and/or interventional devices are driven by each of the first joystick 5332 and second joystick 5334 while operating in a particular drive mode, for example, by making a selection using the control mechanism 5300 (e.g., by pressing one or more buttons on the control mechanism 5300).

In certain embodiments, users can toggle between drives modes by making a user input via the control mechanism 5300 (e.g., by pressing one of the buttons of the control mechanism 5300). For example, users can toggle between the first drive mode and the second drive mode by pressing the button 5344. As way of example, if the control mechanism 5300 is in the first drive mode, pressing the button 5344 once can cause the control mechanism to switch to the second drive mode. In other embodiments, a user may press a first button to activate the first drive mode and a second button to activate the second drive mode.

In some embodiments in which a plurality of interventional devices is linked with one of the joysticks 5332 and 5334, movement of the joystick 5332 or 5334 can cause the linked interventional devices to move different axial distances relative to one another and/or at different axial velocities relative to one another.

For example, in some embodiments, it may be desirable for the distal ends of a plurality of interventional devices to be arranged at particular positions relative to one another for a particular step of a surgical procedure. In some embodiments, it may be desirable that the distal ends of the plurality of interventional devices may be arranged at different particular positions relative to one another at a different step of the surgical procedure. In some embodiments, a plurality of interventional devices linked to a single joystick 5332 or 5334 can be driven from a first set of positions to a second set of positions in which at least some of the interventional devices are at different relative positions to one another in comparison to the first set of positions (e.g., by moving the linked interventional devices different distances relative to one another and/or at different axial velocities relative to one another).

For example, in certain embodiments, the distal ends of the guide catheter, access catheter, and procedure catheter may be parallel or almost parallel upon initial insertion into the patient access point (e.g., femoral access point). The guide catheter, access catheter, and procedure catheter may be linked to the joystick 5334 (e.g., in the first drive mode), and can be axially driven by the joystick 5334 to desired positions for achieving supra-aortic access (e.g., desired positions within the aortic arch) in which the relative positions of the guide catheter, access catheter, and procedure catheter are different than the relative positions upon initial insertion. This may be achieved, for example, by driving the guide catheter, access catheter, and procedure catheter at different velocities from their positions at initial insertion to the desired positions for achieving supra-aortic access in response to movement of the joystick 5334. For example, in some embodiments, it may be desirable for the access catheter to extend further distally than the procedure catheter and the guide catheter for achieving supra-aortic access. In some embodiments, it may be desirable for the procedure catheter to extend further distally than the guide catheter for achieving supra-aortic access.

Similarly, after supra-aortic access is achieved, the distal ends of the guide catheter and the procedure catheter may be arranged at a first set of positions. The guide catheter and procedure catheter may be linked to the joystick 5334 (e.g., in the second drive mode), and can be axially driven by the joystick 5334 to a second set of positions for performing a procedure in which the relative positions of the guide catheter and the procedure catheter are different than the relative positions at the first set of positions. This may be achieved, for example, by driving the guide catheter and procedure catheter at different velocities from the first set of positions to the second set of positions.

In certain embodiments in which multiple interventional devices linked to a joystick 5332 or 5334 move at different velocities, movement of the joystick may correspond to a velocity of one of the interventional devices (e.g., a leading or distal most interventional device, or an interventional device intended to have a distal most position at the end of a current procedure step), and the velocities of the other interventional devices relative to movement of the joystick may be reduced proportionally (e.g., to correspond to their intended positions at the end of the current procedure step).

In certain embodiments, the interventional devices linked to a joystick 5332 or 5334 may move at different relative velocities until a desired set of second positions is reached for a particular procedure step, and then may all move at the same relative velocity. In other embodiments, after the desired set of second positions is reached. The interventional devices may move at a different set of relative velocities, for example, to reach a third set of relative positions different from the second set of relative positions.

In some embodiments, different interventional devices can be associated with different axial and/or rotational velocity profiles. The velocity profiles may be stored in one or more parameter files which can be stored in a memory and can be accessed and implemented by a control system. In certain embodiments, a user may be able to customize the velocity profiles associated with one or more interventional devices and/or joysticks. In certain embodiments, the user can create a user profile that includes such customized velocity profiles. The user profile may be stored in a memory and accessed and implemented by the control system.

In some embodiments, users can selectively link at least one of the first joystick 5332 and the second joystick 5334 to a single corresponding hub and/or interventional device, for example, when the control mechanism 5300 is in a drive mode (e.g., first and/or second drive mode). In some such embodiments, only the interventional device temporarily linked to the joystick may move in response to movement of the joystick, and not any other interventional devices assigned to the joystick in the particular drive mode in the absence of a temporary linkage. This can beneficially allow clinicians to operate (e.g., translate) a hub and/or interventional device independently during any stage of a procedure (or operate two hubs and/or interventional devices independently when each of the first joystick 5332 and the second joystick 5334 is linked with only a single corresponding hub and/or interventional device). For example, while the control mechanism is in a particular drive mode (e.g., the first drive mode or second drive mode), a user can temporarily link the first joystick 5332 to a corresponding hub and/or interventional device, such as a guide catheter (e.g., guide catheter 31 or guide catheter 2906), by pressing and holding one of the plurality of buttons (e.g., one of the shoulder or bumper buttons 5352, 5353, 5354, 5355). For example, in some embodiments, a user can temporarily link the first joystick 5332 to a guide catheter by pressing and holding the button 5352. In certain embodiments, while the bumper button 5352 is pressed, translation of the first joystick 5332 can cause guide catheter to translate accordingly. When the first bumper button 5352 is released, the first joystick 5332 can be automatically linked again to the corresponding hub and/or interventional device according to the particular drive mode.

In certain embodiments, if an interventional device is linked the first joystick 5332 in a particular drive mode and a user input is made to temporarily link the interventional device to the second joystick 5334, the interventional device can be temporarily unlinked from the first joystick 5332 while temporarily linked to the second joystick 5334. Similarly, in certain embodiments, if an interventional device is linked the second joystick 5334 in a particular drive mode and a user input is made to temporarily link the interventional device to the first joystick 5332, the interventional device can be temporarily unlinked from the second joystick 5334 while temporarily linked to the first joystick 5332.

As another example, while the control mechanism is in a particular drive mode or operated without a particular drive mode, a user can temporarily link the second joystick 5334 to a corresponding hub and/or interventional device, such as a procedure catheter (e.g., catheter 29, catheter 120, or catheter 2904) or an access catheter (e.g., catheter 124 or catheter 2902), by pressing and holding one of the buttons of the control mechanism (e.g., one of the plurality of shoulder or bumper buttons 5353, 5354, 5355). For example, the user can temporarily link the second joystick 5334 to a procedure catheter by pressing and holding the bumper button 5353 and link the second joystick 5334 with the access catheter by pressing and holding bumper button 5355. While the bumper button 5353 or bumper button 5355 is pressed, translation of the second joystick 5334 can cause the procedure catheter or the access catheter, respectively, to translate accordingly. When the bumper button 5353 or the bumper button 5355 are released, the second joystick 5334 can be automatically linked again to the corresponding hubs and/or interventional devices according to the particular drive mode.

In some embodiments, a user can select to link one of the first joystick 5332 and the second joystick 5334 with a plurality of hubs and/or interventional devices that differ from the default hubs and/or interventional devices for a current drive mode. For example, while the control mechanism is in a particular drive mode, a user can temporarily link the second joystick 5334 to a combination of different hubs and/or interventional devices, such as a procedure catheter (e.g., catheter 29, catheter 120, or catheter 2904) and an access catheter (e.g., catheter 124 or catheter 2902) by pressing and holding both the bumper button 5353 and the bumper button 5355 at the same time. While the bumper button 5353 and bumper button 5355 are pressed, translation of the second joystick 5334 can cause the procedure catheter and the access catheter to translate accordingly. When the bumper button 5353 and the bumper button 5355 are released, the second joystick 5334 can be automatically linked again to the corresponding hubs and/or interventional devices according to the first and/or second drive modes.

While the above examples describe linkage of particular hubs and/or interventional devices to a joystick by pressing and holding buttons, such as bumper buttons, in other embodiments, a particular hub and/or interventional device may be linked with a particular joystick after pressing and releasing a button, for example, until the button is pressed again or another button is pressed.

While the above examples, describe particular drive modes, in other embodiments, there may not be separate selectable drive modes. Instead, users may select which hubs and/or interventional devices are assigned to each of the joystick 5332 and joystick 5334 as described herein, for example, by pressing and/or holding one or more buttons on the control mechanism 5300. In some embodiments, the joystick 5332 and the joystick 5334 may each have default hubs and/or interventional devices or combinations of hubs and/or interventional devices linked thereto.

In operation, the corresponding coupled hubs and/or interventional devices linked to the first joystick 5332 or the second joystick 5334 can move axially and/or rotationally in response to actuation (e.g., movement) of the first joystick 5332 or the second joystick 5334.

Using the first joystick 5332 as an example, if the user moves (e.g., rolls) the first joystick 5332 in a direction along an axis A5, one or more hubs and/or interventional devices linked to the first joystick 5332 may move responsively in a corresponding axial direction, for example, at a predefined linear velocity. A user can advance and/or retract the linked hubs and/or interventional devices by moving the first joystick along the axis A5. In certain embodiments, movement of the joystick 5332 along the axis A5 may be referred to as forward and backward movement. For example, movement along the axis A5 in the direction of the button 5352 may be referred to as forward movement, and movement along the axis A5 in the direction opposite of the button 5352 may be referred to as backward movement. In some embodiments, forward movement of the joystick 5332 can correspond to distal movement or insertion of a linked interventional device. Backward movement of the joystick 5332 can be referred to as proximal movement or retraction of a linked interventional device.

In some embodiments, the predefined linear velocity can vary according to the extent of movement of the joystick 5332. For example, further movement of the joystick 5332 along the axis A5 from a starting position or neutral position can result in greater linear velocities. In other embodiments, the linear velocity may not vary as a result of the extent of movement of the joystick 5332.

In some embodiments, the linear velocity of one or more interventional devices linked with the joystick 5332 can be mapped linearly to the joystick (e.g., so that the linear velocity corresponds linearly to the throw of the joystick 5332. In other embodiments, the linear velocity of one or more of the interventional devices linked with the joystick 5332 can be mapped to the joystick 5332 using a non-linear cubic function, a step function, a combination of step and linear mapping, or other non-linear functions.

In some embodiments, one of the plurality of buttons of the control mechanism 5300, for example, button 5342, can be actuated to change (e.g., increase, decrease) the predefined linear velocity of the linked hubs and/or interventional devices. For example, pressing the button 5342 can toggle between two or more predefined linear velocities. In some embodiments in which the predefined linear velocity can vary according to the extent of movement of the joystick 5332, it may be possible for a user to change a range of predefined linear velocities over which movement of the joystick 5332 can cause the linked hubs and/or interventional devices to translate (e.g., by pressing a button). For example, a first range of linear velocities may be between 0-10 mm/second and a second range may be between 10-20 mm/second. A button, such as button 5342 may be pressed to change the range of linear velocities from the first range to the second range. In some embodiments, the same or a different button may be selected to change from the second range to the first range. In some embodiments, a third range of linear velocities (e.g., between 20-30 mm/second) may also be selectable (e.g., by pressing the button 5342 when the control mechanism is already operating within the second range of linear velocities). The control mechanism may be configured to operate using any suitable number of ranges of linear velocities. In some embodiments, the predefined linear velocities and/or ranges of linear velocities may change in response to a change in drive mode.

In some embodiments, the linked hubs and/or interventional devices may continue to move in the same direction at the predefined linear velocity until the user releases (e.g., stops manipulating) the first joystick 5332 or further moves the joystick along the axis A5.

In some embodiments, if the user moves (e.g., rolls) the first joystick 5332 in a direction along axis A4, one or more hubs and/or interventional devices linked to the first joystick 5332 can move responsively. For example, one or more interventional devices linked to the first joystick can move in a corresponding rotational direction, for example, at a predefined rotational velocity. In some embodiments, movement of the first joystick 5332 along axis A4 can cause a corresponding movement of a torque element of a hub (e.g., a gear or gear train) that can cause rotational movement of any interventional device coupled thereto. A user can rotate linked interventional devices by moving the first joystick 5332 along axis A4. In some embodiments, movement of the joystick along the axis A4 may be referred to as sideways or left/right movement. For example, movement along the axis A4 in the direction towards a central axis 5380 can be referred to as rightward movement and movement of the joystick along the axis A4 in the direction away from central axis 5380 can be referred to as leftward movement. With respect to the second joystick 5334, movement along the axis A4 away from the central axis 5380 may be referred to as rightward movement, and movement along the axis A4 towards the central axis 5380 may be referred to as leftward movement. In certain embodiments rightward movement of the joystick may correspond to clockwise rotation and leftward movement may correspond to counterclockwise rotation.

In some embodiments, the predefined rotational velocity can vary according to the extent of movement of the joystick 5332. For example, further movement of the joystick 5332 along the axis A4 from a starting position can result in greater rotational velocities. In other embodiments, the rotational velocity may not vary as a result of the extent of movement of the joystick 5332.

In some embodiments, one of the plurality of buttons (e.g., 5342, 5343, 5344, 5345, 5346, 5357) can change (e.g., increase, decrease) the predefined rotational velocity of the linked hubs and/or interventional devices. In some embodiments, the same button that changes the linear velocity may change the rotational velocity. In other embodiments, a different button may change the rotational velocity. For example, in some embodiments, pressing the button 5342 can toggle between two or more predefined rotational velocities. In some embodiments in which the predefined rotational velocity can vary according to the extent of movement of the joystick 5332, it may be possible for a user to change a range of predefined rotational velocities over which movement of the joystick 5332 can cause the linked interventional devices to rotate (e.g., by pressing a button). For example, a first range of rotational velocities may be between 0-5 degrees/second and a second range may be between 5-10 degrees/second. A button, such as button 5342 may be pressed to change the range of rotational velocities from the first range to the second range. In some embodiments, the same or a different button may be selected to change from the second range to the first range. In some embodiments, a third range of rotational velocities (e.g., between 10-15 degrees/second) may also be selectable (e.g., using the button 5342). The control mechanism may be configured to operate using any suitable number of ranges of rotational velocities. In some embodiments, the predefined rotational velocities and/or ranges of rotational velocities may change in response to a change in drive mode.

In some embodiments, the linked interventional devices may continue to move in the same direction at the predefined rotational velocity until the user releases (e.g., stops manipulating) the first joystick 5332 or further moves the joystick along the axis A4.

In some embodiments, only certain interventional devices may be configured to rotate. For example, in some embodiments, a guidewire and an access catheter may be configured to rotate, but a guide catheter and a procedure catheter may not rotate. In such embodiments, if an interventional device that is configured to rotate and an interventional device that is not configured to rotate are both linked to a joystick, movement of the joystick along the axis A4 may cause rotation of only the interventional device that is configured to rotate.

While embodiments in which movement of the joystick 5332 along the axis A5 causes axial movement and movement of the joystick 5332 along the axis A4 causes rotational movement are described herein, in other embodiments, movement of the joystick 5332 along the axis A4 can cause axial movement and movement of the joystick 5332 along the axis A5 can cause rotational movement.

In certain embodiments, the joystick 5332 can be shaped, textured, dimensioned, or otherwise configured to prevent undesired movement along one of the axis A4 and the axis A5 during movement along the other of the axis A4 and the axis A5 (e.g., to prevent unintended rotation when translation is desired or vice versa). For example, as shown the joystick 5332 can have an elongate protruding band 5336 extending parallel and colinear with the axis A5 and perpendicular with the axis A4. The joystick 5332 may have an additional protrusion 5337 protruding from the band 5336. The protrusion 5337 may extend parallel and colinear with axis A4 when the joystick is in a starting position, as shown in FIG. 46A. In certain embodiments, when the joystick 5332 is in the starting position, a center of the protrusion 5337 may be positioned at the intersection of the axis A4 and the axis A5. In certain embodiments, in use, a user may push the protrusion 5337 to move the joystick 5332 along the axis A5 to translate one or more interventional devices. A user may push a side surface of the protrusion 5337 or of the protruding band 5336 to move the joystick 5332 along the axis A4 to rotate one or more interventional devices. The shape of the joystick 5332 may reduce the likelihood that a user will inadvertently move the joystick 5332 along an axis offset from either the axis A4 or the axis A5.

In some embodiments, simultaneous axial movement and rotational movement of an interventional device may be desirable. The joystick 5332 may be configured to move in a direction having directional components along both the axis A4 and the axis A5 (e.g., along an axis offset from both the axis A4 and the axis A5) to allow for both axial movement and rotational movement simultaneously. While a description of the first joystick 5332 has been provided herein, one of skill in the art would understand that the second joystick 5334 can have any of the same or similar features and/or functions. Additionally, in some embodiments, the first joystick 5332 and/or second joystick 5334 may be other types of controls (e.g., dials, buttons, scroll wheels, touch pads, etc.).

In some embodiments, the control mechanism 5300 may be provided with one or more fluidics controls for controlling components of a fluidics system, for example, to initiate and/or terminate the introduction of fluids to a catheter (e.g., saline, contrast, etc.). For example, the controller can include one or more contrast controls (e.g., button 5345, button 5347) that when actuated cause contrast media to be injected through one of the interventional devices linked to the control mechanism. In some embodiments, the buttons 5345 and 5347 may be associated with particular interventional devices and/or particular hubs so that actuation will cause contrast injection through any interventional device coupled to those hubs. In some embodiments, contrast injection may be linked to the hubs and/or interventional devices associated with a particular joystick such that actuation of a contrast injection button (e.g., button 5345 and 5347) can cause contrast injection via the hubs and/or interventional devices linked with the particular joystick. In some embodiments, a selection of a particular interventional device may be performed prior to actuation of the contrast controls. For example, a user may press and/or hold a button associated with a particular interventional device (e.g., button 5355 associated with an access catheter) and then actuate the contrast control (e.g., button 5345 or 5347) to cause contrast injection through the particular interventional device. In certain embodiments, the system may be configured to supply contrast through an inner most catheter upon actuation of a contrast control.

In some embodiments, the control mechanism 5300 can include one or more aspiration controls (e.g., button 5346). For example, pressing the button 5346 can initiate aspiration, and pressing the button 5346 again may end aspiration through one or more of the hubs and/or interventional devices. In some embodiments, the button 5346 may be associated with a particular hub and/or interventional device, such as a procedure catheter hub and/or procedure catheter. In some embodiments, aspiration may be linked to the hubs and/or interventional devices associated with a particular joystick such that actuation of an aspiration control (e.g., button 5346) can cause contrast injection via the hubs and/or interventional devices linked with the particular joystick. In some embodiments, a selection of a particular interventional device may be performed prior to actuation of the aspiration control. For example, a user may press and/or hold a button associated with a particular interventional device (e.g., button 5353 associated with a procedure catheter) and then actuate the aspiration control (e.g., button 5353) to cause aspiration through the particular interventional device. In certain embodiments, the system may be configured to supply aspiration through an inner most catheter upon actuation of an aspiration control.

In an example procedure using the control mechanism 5300, a user may begin with the control mechanism 5300 in the first drive mode or may select the first drive mode, for example, by pressing button 5344. In the present example, in the first drive mode, the joystick 5332 is linked with a guidewire and the joystick 5334 is linked with an access catheter, a procedure catheter, and a guide catheter.

The user may control the first joystick 5332 to advance the guidewire from a femoral access point into the aortic arch and adjacent a desired ostium. Next, the user may control the second joystick 5334 to advance the access catheter, procedure catheter, and guide catheter from the femoral access point into the aortic arch and adjacent the desired ostium.

After the guidewire, access catheter, procedure catheter, and guide catheter are positioned adjacent the desired ostium, the user may control the first joystick 5332 to rotate the guidewire so that the guidewire enters the desired ostium.

After the guidewire is positioned within the desired ostium, the use can control the second joystick 5334 to advance the access catheter, procedure catheter, and guide catheter into the desired ostium.

In some embodiments, the access catheter may be driven separately out of procedure catheter and guide catheter to engage the ostium first. For example, the user may press and/or hold the shoulder button 5355 so that the second joystick 5334 controls movement of the access catheter. In some embodiments, the user may control the second joystick 5334 to rotate the access catheter to enter the desired ostium. In some embodiments, after the access catheter is positioned within the desired ostium, the user may control the first joystick 5332 to advance the guidewire distally into the ostium to secure access. After the access catheter and guidewire are positioned within the desired ostium, the user can control the procedure catheter and/or the guide catheter to advance the procedure catheter and/or guide catheter into the ostium (and, in some embodiments, beyond), while using the support of the access catheter and/or guidewire to maneuver through the aorta and into the ostium. For example, in some embodiments, the user may press and/or hold the shoulder button 5352 to link the first joystick 5332 with the guide catheter and/or press and/or hold the shoulder button 5353 to link the second joystick 5334 with the procedure catheter. The user may then advance the guide catheter and/or the procedure catheter using the first and/or second joysticks.

In some embodiments, in the first drive mode, a user may press and/or hold the shoulder button 5352 so that the first joystick controls only the guide catheter. In certain embodiments, when the first joystick controls only the guide catheter when the control mechanism is in the first drive mode, the second joystick 5334 can control the procedure catheter and the access catheter. In some embodiments, the user may choose to advance the procedure catheter and access catheter together into the desired ostium prior to the guide catheter.

In certain embodiments, after supra-aortic access is achieved, the control mechanism can be switched to the second drive mode, for example, by a user pressing button 5344. In the present example, in the second drive mode, the first joystick 5332 is linked with the guidewire and the second joystick 5334 is linked with the procedure catheter and the guide catheter.

In certain embodiments, the user can control the first joystick 5332 to advance the guidewire to a procedure site. The user can control the second joystick 5334 to advance the procedure catheter and guide catheter to the procedure site while the access catheter remains by the ostium for support. In some embodiments, the guidewire and procedure catheter and guide catheter can be advanced to the procedure site in stages. For example, the guidewire may be advanced up to the petrous segment. The procedure catheter and guide catheter may then be advanced up to the petrous segment. The guidewire may then be advanced to the procedure site, and then the procedure catheter and guide catheter may be advanced up to the procedure site.

In some embodiments, it may be desirable to advance the guide catheter and procedure catheter separately to the procedure site. Additionally, in some embodiments, it may be desirable to advance only the procedure catheter all the way to the procedure site, while the guide catheter may be advanced only partially to the procedure site. In certain embodiments, the user may press and/or hold the shoulder button 5352 so that the first joystick 5332 controls only the guide catheter. In certain embodiments, when the first joystick 5332 controls only the guide catheter when the control mechanism is in the second drive mode, the second joystick 5334 can control only the procedure catheter.

In certain embodiments, if additional support is desired while advancing the procedure catheter and/or guide catheter to the procedure site, the access catheter can be advanced further distally towards the procedure site. For example, the user can press and/or hold the button 5355 to link the access catheter with the second joystick 5334, and can control the second joystick 5334 to advance the access catheter.

After the guide catheter and/or procedure catheter are positioned at the procedure site, the guidewire and the access catheter may be removed. For example, the user can control the first joystick 5332 to withdraw the guidewire. The user may press and/or hold the button 5355 to link the access catheter with the second joystick 5334 and control the second joystick 5334 to withdraw the access catheter.

After the guidewire and access catheter are withdrawn, the user can actuate button 5353 to apply aspiration through the procedure catheter, for example, to remove a clot at the procedure site. In certain embodiments, actuating the button 5353 may additionally apply aspiration through the guide catheter. In other embodiments, a second button may be actuatable to apply aspiration through the guide catheter. In some embodiments, a second aspiration control may be provided on a user interface, such as user interface 3200, instead of on the control mechanism 5300.

In some embodiments, it may be desirable to remove the procedure catheter from the treatment site prior to removing the guide catheter, for example, to perform additional aspiration using only the guide catheter. In those embodiments, the user may control only the procedure catheter, for example, by pressing and/or holding the button 5353 to link the procedure catheter with the second joystick 5334 so that movement of the second joystick controls movement of the procedure catheter. Alternatively, while in the second drive mode, the user may press and/or hold the shoulder button 5352 so that the first joystick 5332 controls only the guide catheter. As described above, in the second drive mode, when the first joystick 5332 controls only the guide catheter, the second joystick 5334 can control only the procedure catheter.

After aspiration is complete, the user may remove both the guide catheter and the procedure catheter (if the procedure catheter has not previously been removed), either together by controlling the second joystick 5334 when both the procedure catheter and guide catheter are linked thereto, or separately, for example, by pressing and holding the shoulder button 5352 so that the first joystick controls only the guide catheter and the second joystick controls only the procedure catheter.

In some embodiments, as the interventional devices are driven through the anatomy, tension can build between adjacent interventional devices. In some embodiments, it may be desirable to release the tension by controlling the adjacent interventional devices to drive in opposite directions. For example, a user may link a first of the adjacent interventional devices with the first joystick 5332 and a second of the adjacent interventional devices with the second joystick 5334 (if neither are already linked by themselves with their respective joysticks), and can operate the first joystick 5332 and the second joystick 5334 to move the first interventional device and the second interventional device in opposite directions (e.g., moving one proximally and one distally).

As described above, multiple hubs and/or interventional devices can be linked to a single control, such as the joystick 5332 and the joystick 5334. In certain embodiments, when multiple hubs and/or interventional devices are linked to a control, operation of the control to cause axial movement of the multiple hubs and/or interventional devices can cause the multiple hubs and/or interventional devices to move in in parallel. In other embodiments, the multiple hubs and/or interventional devices may move in series. For example, a first linked interventional device may move axially over a particular distance corresponding to the operation of the control, and then a second linked interventional device can move over the same distance. In other embodiments, the second linked interventional device may move over a scaled distance.

Figure 61:
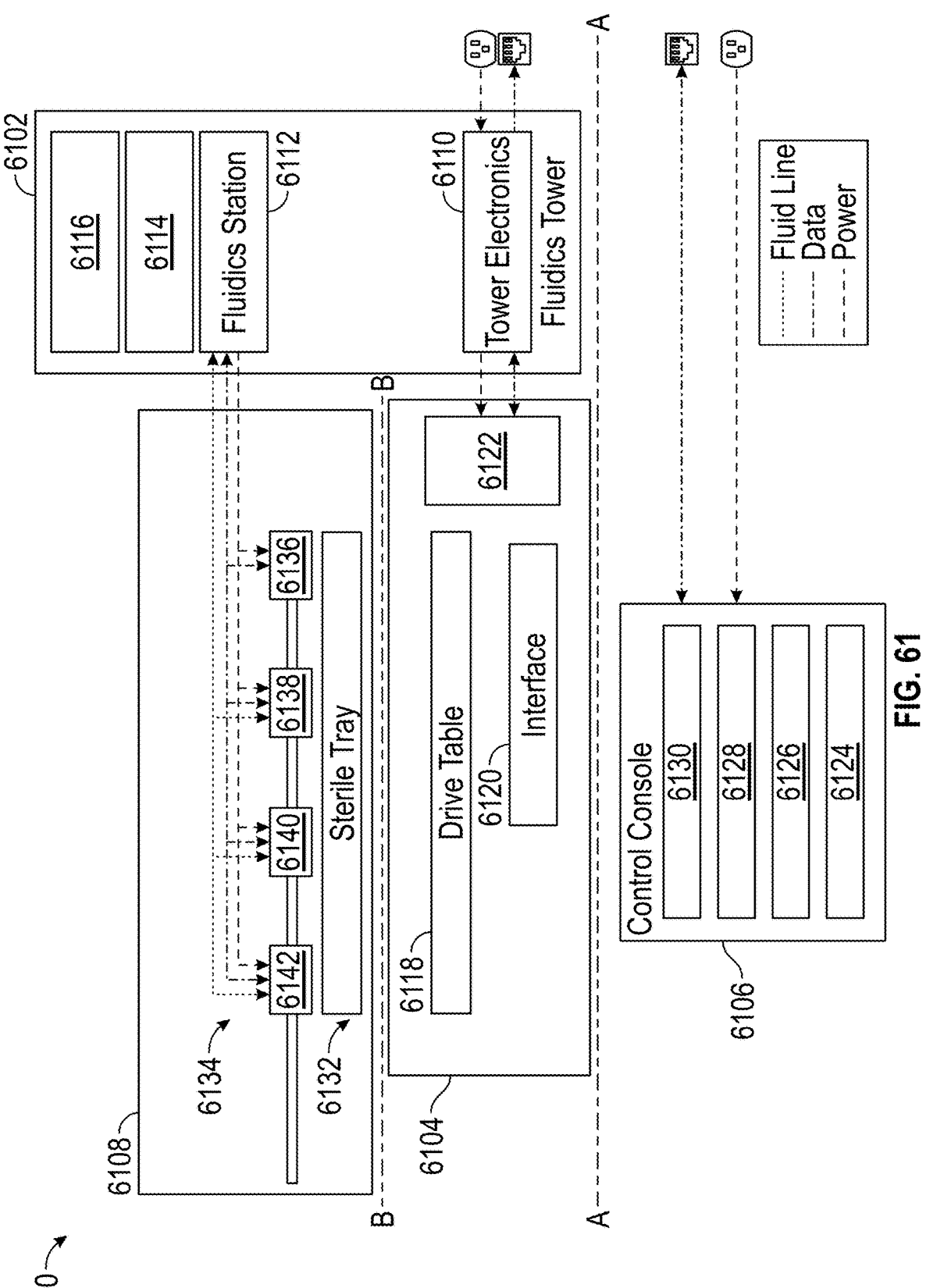
FIG. 61 illustrates a system diagram of an embodiment of a control system.

FIG. 61 illustrates a system diagram of an example of a medical device operation system 6100. The system diagram shows fluid and electrical connectivity between the subsystems of the medical device operation system 6100. The medical device operation system 6100 may comprise a fluidics tower 6102, a robotic drive system 6104, a control system 6106, and one or more interventional devices 6108.

The fluidics tower 6102 may be a housing or console comprising a fluidics management system for controlling the administration or removal of contrast, saline and/or bodily fluids to and/or from an interventional device. The fluidics tower 6102 may further comprise an electronics tower 6110, a fluidics station (or "system") 6112, a monitor 6114, and one or more communication devices 6116. Although illustrated in FIG. 61 as part of the fluidics tower 6102, in other embodiments the electronics tower 6110 may be housed separately from the fluidics tower 6102 while still being in communication with the fluidics tower 6102, the interventional devices 6108, the robotic drive system 6104, and the control console system.

The electronics tower 6110 may be a housing configured to contain system electronics such as one or more processors and memory. The one or more processors and memory may be organized into one or more computer devices. The electronics tower 6110 may comprise a power cord configured to be operatively coupled to a power source, such as a battery, a generator, or an outlet. In some embodiments, the electronics tower 6110 may draw power from a source providing 110/220 volts of alternating current (VAC) power.

The system electronics may be a central hub for the medical device operation system 6100 interconnecting the electronic devices from other components as described in greater detail below. The system electronics of the electronics tower 6110 may be configured to transmit and receive electronic signals and/or data to operate components of the medical device operation system 6100. The electronics tower 6110 may comprise means for connecting to other devices. The electronics tower 6110 may transmit and/or receive electronic signals and/or data wirelessly or over a wired connection. In some embodiments, the electronics tower 6110 may comprise an ethernet port for connecting the system electronics to a network. In some embodiments, the electronics tower 6110 may include one or more ports for tethering to nearby electronic devices via a wired connection. For example, the electronics tower 6110 may have ports to run cables between the fluidics tower 6102 and the robotic drive system 6104 and/or control system 6106. Alternatively, the electronics tower 6110 may be configured to connect wirelessly to nearby electronic devices. For example, the electronics tower 6110 may include a personal area network (PAN) module, such as Bluetooth®, or other network capabilities to transmit data wirelessly.

In some embodiments, electronic signals and/or data may comprise instructions for a system, subsystem, component, or device to perform a particular task. Additionally and/or alternatively, electronic signals and/or data may comprise indicators or data measured from sensors for processing by a computing device.

In some embodiments, the electronics tower 6110 may connect to other devices over a communication network ("network"). The network may cover a small geographic area such as a particular room or building, a medium geographic area such as a city, or a large geographic area so long as there is access to a network. For example, the network may be a local area network (LAN) or wireless local area network (WLAN) comprising a series of devices linked together to form a network within a hospital or clinic.

Alternatively, the network may be a wide-area network (WAN) comprising a series of devices linked together to form a network within a medical campus comprising two or more buildings. Alternatively, the network may be an intranet or internet for providing global connectivity. Connecting over the network advantageously connects the operating room to physicians located around the world, including experts located across the nation or in other countries, without requiring the physician to travel to the operating room. This advantageously connects patients to physicians without the time or cost required for the physician to physically travel to the operating room. In some procedures, every minute of delay before a procedure is performed can increase the chance of a bad outcome, and thus such surgical systems can help mitigate damage to the patient due to a delay in starting the surgical procedure.

The fluidics system 6112 may comprise one or more subsystems comprising one or more containers, one or more tubes, and one or more pumps. The subsystems may be divided and organized into a contrast subsystem, a saline subsystem, and/or an aspiration (or "vacuum") subsystem. The fluidics system 6112 may be the fluidics system described above.

A contrast subsystem may be configured for supplying contrast to a patient. The contrast subsystem may comprise one or more containers for storing and supplying contrast, one or more fluid communication channels ("tubes"), one or more valves, and a high-pressure pump.

A saline subsystem may be configured for supplying saline to a patient. The saline subsystem may similarly comprise one or more containers for storing and supplying saline, one or more tubes, one or more valves, and one or more pumps.

An aspiration subsystem may be configured for removing biological material from a patient. The aspiration subsystem may comprise one or more containers, one or more tubes, one or more valves, and a vacuum pump.

The one or more pumps and containers of the contrast, saline, and aspiration subsystems may be contained with the fluidics tower 6102. The one or more tubes of the contrast, saline, and aspiration subsystems may extend out of the fluidics tower 6102 for interacting with and coupling to other devices.

The monitor 6114 may be any electronic visual computer display (or displays) that includes a screen and circuitry configured to interpret electronic signals to display one or more images. For example, the monitor 6114 may comprise an imaging window, a speed indicator, a rotational indicator, an axial position bar, a telescopic position window, one or more axial position indicators, and/or other graphical user interfaces or windows. In some embodiments, the monitor 6114 may be configured to display fluoroscopic images, catheter data, fluidics information (e.g., information relating to a contrast injection subsystem including its current operation status, information relating to a saline subsystem including its current operation status, and/or information relating to a aspiration subsystem including its current operation status) including current state information) providing saline, providing vacuum for aspiration), and patient data including vital signs. In some embodiments, the monitor 6114 may be the display 23 described above.

The one or more communication devices 6116 may be one or more microphones, one or more cameras, and/or one or more audio output devices such as a speaker and/or a headset.

The fluidics system 6112, the monitor 6114, and the one or more communication devices 6116 may be electrical communication with the electronics tower 6110 and configured to receive and/or transmit electronic signals and/or data therebetween. In some embodiments, the electronic signals and/or data may include instructions to activate one or more pumps and/or one or more valves of the fluidics system 6112. For example, the instructions may direct the fluidics system 6112 to provide saline and/or contrast to the one or more interventional devices 6108. In some embodiments, the data may include video and/or audio inputs and audio outputs for the monitor 6114 and one or more communication devices 6116. For example, the data may be one or more images to be displayed on the monitor 6114 and/or audiovisual data captured by the one or more communication devices 6116.

The fluidics tower 6102 may be further configured to be operatively coupled with the one or more interventional devices 6108. In some embodiments, the fluidics system 6112 may be mechanically coupled to and/or in fluid communication with the one or more interventional hubs 6134. Accordingly, activating the fluidics system 6112 may provide contrast, saline, and/or suction to the interventional hubs 6134 and corresponding interventional devices.

The robotic drive system 6104 may include a plurality of components to drive one or more access systems such as catheters and guidewires during a procedure. The robotic drive system 6104 may be the drive system 18 described above. The robotic drive system 6104 may comprise a drive table 6118, an interface 6120, and a joint setup 6122.

The drive table 6118 may support the one or more disposable devices 6108 (e.g., a catheter) configured to be advanced to access a patient for performing a surgical procedure and/or for introducing saline, contrast media or therapeutic agents, or providing aspiration. The drive table 6118 may further support a sterile barrier.

The drive table 6118 may be the support table 20 described above. The drive table 6118 may be positioned over or alongside a patient, and configured to axially advance, retract, and in some cases rotate two or three or more different concentrically oriented intravascular devices of an interventional device assembly. The drive table 6118 may comprise electronics and motors for controlling the location of the interventional devices and actuation of fluidics components.

In some embodiments, the drive table 6118 may comprise one or more hub adapters. The one or more hub adapters may comprise the drive magnets described above. Movement of the drive magnets may be driven by a drive system carried by the drive table 6118. Movement of the drive magnets may be configured to drive one or more interventional hubs 6134 of the one or more disposable devices 6108. The drive table 6118 and the one or more disposable devices 6108 may be separated such that the one or more interventional hubs 6134 may not mechanically couple to the drive table 6118 as shown by axis B-B.

The interface 6120 may be any device configured to interact with and/or display information to personnel locally situated within an operating room during a procedure, such as a bedside user. For example, a bedside user may be nurse or surgical technician staffed within the operating room. The interface 6120 may comprise an imaging window, a speed indicator, a rotational indicator, an axial position bar, a telescopic position window, and/or one or more axial position indicators. The interface 6120 may be the display 23 described above configured to display fluoroscopic images, catheter data, pressure values of the fluidics system, and/or other patient data. In some embodiments, the interface 6120 may be a touchscreen device such as a tablet computer. The interface 6120 may display information to a bedside user. The information displayed to the bedside user may include directions and/or prompts for the bedside user to follow. For example, the information may describe what steps to perform next, how to position the robotic drive system 6104, when to deploy the drapes, whether the system is malfunctioning or whether an error is detected, and/or prompt the bedside user to otherwise interact with the system. In some embodiments, the interface 6120 is configured to accept user input to control one or more components, for example, position of the drive table.

The interface 6120 may be in communication with one or more portions of the medical device operation system 6100 (for example, the robotic drive system 6104, the fluidics tower 6102, the disposable devices 6108, etc.). In some embodiments, the interface 6120 may be mechanically coupled to the robotic drive system 6104, be housed separately, or be mechanically coupled to another part of the medical device operation system 6100. The interface 6120 may control the setup joint 6122 of the robotic drive system 6104. For example, the interface 6120 may control the transition processes between a storage position and a deployed position, engaging a priming sequence, or controlling fine motor adjustments for providing minor adjustments to the positions of the interventional hubs. Controlling the setup joint 6122 and motors with the interface 6120 advantageously provides greater precision and setup before an operation by individuals present in the operating room.

The interface 6120 may advantageously provide a backup control mechanism to interact with and provide input to control the medical device operation system 6100, for example, in the event that the control system 6106 is rendered incapable of performing an operation.

The joint setup 6122 may comprise a plurality of joints and motors for controlling the positioning and movements of the robotic drive system 6104. In some embodiments, the joint setup 6122 may initialize the robotic drive system 6104 into a starting position. The initialization process may include transitioning the robotic drive system 6104 from a storage position to a deployed position and vice versa. For example, the joint setup 6122 may be configured to transition the robotic drive system 6104 from a storage position the robotic drive system 6104 to a deployed position such that at least a portion of the robotic drive system 6104 transitions from a compact state to a position where at least a portion of the robotic drive system 6104 is positioned either over or alongside a patient.

Within the robotic drive system 6104, the drive table 6118 may be mechanically coupled with the interface 6120 and the setup joint 6122. The setup joint 6122 may also be electrically connected to the drive table 6118 and the interface 6120. The robotic drive system 6104 may be configured for the setup joint 6122 to transmit electronic signals and data to the drive table 6118 and the interface 6120. Additionally and/or alternatively, the robotic drive system 6104 may be configured for the setup joint 6122 to receive electronic signals and data from the drive table 6118 and the interface 6120.

The control system 6106 may be a collection of components configured to control and operate the robotic control system described above. In some embodiments, the control system is a control console or is coupled to a control console. The control system 6106 may further comprise an operator controller 6124, an interface 6126, a monitor 6128, and one or more communication devices 6130. The control system 6106 may be locally positioned or remotely positioned. For example, in some embodiments, the control system 6106 may be located in the operating room with the fluidics tower 6102, the robotic drive system 6104, and the one or more disposable devices 6108. Alternatively, the control system 6106 may be located remotely (e.g., in a control room) as illustrated by line A-A. The control system 6106 may include system electronics comprising one or more processors and one or more memory components ("memory"). The system electronics may be configured to electrically connect the controller 6124, the interface 6126, the monitor 6128, and the one or more communication devices 6130.

The control system 6106 may comprise means for connecting to other devices. The control system 6106 may transmit and/or receive electronic signals and/or data wirelessly or over a wired connection. In some embodiments, the control system 6106 may comprise an ethernet port for connecting the system electronics to a network. In some embodiments, the control system 6106 may include one or more ports for tethering to nearby electronic devices via a wired connection. For example, the control system 6106 may have ports to run cables between the control system 6106 and the fluidics tower 6102 and/or robotic drive system 6104. Alternatively, the control system 6106 may be configured to connect wirelessly to nearby electronic devices. For example, the control system 6106 may include a Bluetooth® module or other network capabilities to transmit data wirelessly.

In some embodiments, the control system 6106 may connect to other devices over a network as described above.

The controller 6124 may be any device configured to enable a surgeon to control portions of the medical device operation system 6100 in the same location as the patient. For example, the controller 6124 may be any of the control mechanisms or controllers described herein (e.g., controller 5310). The controller 6124 may enable a user to control portions of the fluidics tower 6102, the interventional devices 6108, and the robotic drive system 6104. For example, the controller 6124 may be configured to move the to desired positions to perform a procedure on a patient as described herein.

The controller 6124 may be part of the control system 6106 or connected, wirelessly or via a wired connection, to the control system 6106.

The interface 6126 may be configured to display information to the surgeon. The interface 6126 may be the display 23 described above configured to display fluoroscopic images, catheter data, or other patient data. The interface 6126 may be a touchscreen device. The interface 6126 be a graphical user interface as described, for example, with respect to FIGS. 47-59.

The monitor 6128 may include one or more electronic displays. The monitor 6128 may be any electronic visual computer display that includes a screen and circuitry configured to interpret electronic signals to display one or more images. The monitor may display the interface 6126. In some embodiments, the monitor 6128 may be configured to display fluoroscopic images, catheter data, or other patient data. Alternatively, the monitor 6128 may be configured to display one or more views of the operating room. For example, the monitor 6128 may be configured to display the working area during a procedure by displaying only the surgical site. In another example, the monitor 6128 may display the entire operating room including the surgical technicians. In another example, the monitor 6128 may display more than one view. Displaying a plurality of views to capture the entire operating room may advantageously enhance communication and understanding between the physician and the technicians and/or assistants located in the operating room thereby increasing the efficiency and safety of procedures.

The one or more communication devices 6130 may be any one or more microphones, one or more cameras, and/or one or more audio output devices.

As shown in FIG. 61, the fluidics tower 6102, the 6104, the control system 6106, and the one or more disposable devices 6108 are connected to a power source. In some embodiments, the fluidics tower 6102 and the control system 6106 may be directly connected to a power source such as an outlet. In some embodiments, the robotic drive system and the one or more disposable devices 6108 may indirectly connect to a power source. For example, the robotic drive system 6104 and the one or more disposable devices 6108 may receive power from the fluidics tower 6102. In such embodiments, the joint setup 6122 of the robotic drive system 6104 may be electrically connected to the electronics tower 6110 of the fluidics tower and the interventional hubs 6134 of the one or more disposable devices 6108 may be electrically connected to the fluidics system 6112 of the fluidics tower 6102 such that power may be transmitted therebetween.

Furthermore, as shown in FIG. 61, the fluidics tower 6102, the robotic drive system 6104, the control system 6106, and the one or more disposable devices 6108 may be electrically connected and configured to share electrical signals and/or data. In some embodiments, the fluidics tower 6102 may be electrically connected and configured to share electrical signals and/or data with the robotic drive system 6104, the control system 6106, and the one or more disposable devices 6108. For example, the electronics tower 6110 of the fluidics tower 6102 may be electrically connected with the joint setup 6122 of the robotic drive system 6104 and the control system 6106 while the fluidics system 6112 of the fluidics tower 6102 may be electrically connected with the one or more interventional hubs 6134 of the one or more disposable devices 6108. In some embodiments, the electronics tower 6110 may be electrically connected with the control system 6106 via a network, as shown in FIG. 61.

The one or more interventional hubs 6134 may include a first interventional hub 6136, a second interventional hub 6138, a third interventional hub 6140, and a fourth interventional hub 6142. In some embodiments, the one or more interventional hubs 6134 may be aligned sequentially such that the first interventional hub 6136 may be positioned at a first end and the fourth interventional hub 6142 may be positioned at a second end opposite the first end. In some embodiments the first end may be a proximal end closest to a patient and the second end may be a distal end furthest from the patient. A sterile tray 6132 may separate the one or more interventional hubs 6134 and corresponding interventional devices from a support table. In some embodiments, the sterile tray 6132 forms a sterile barrier, such as the sterile barrier 32 described above.

In some embodiments, the first interventional hub 6136 may be a guidewire hub, such as the guidewire hub 26 described above; the second interventional hub 6138 may be a first catheter hub, such as the access catheter hub 2910 described above; the third interventional hub 6140 may be a second catheter hub configured to engage with and guide a procedure catheter, such as the procedure catheter hub 2912 described above; and the fourth interventional hub 6142 may be a third catheter hub configured to engage with and guide a guide catheter, such as the guide catheter hub 2914. In some embodiments, the guide catheter may extend distally from the fourth interventional hub 6142.

The fluidics tower 6102 may be electrically connected to the robotic drive system 6104, the control system 6106, and the one or more disposable devices 6108 wherein electrical signals and/or data may be transmitted between therebetween as discussed in greater detail below. The local system may transmit information about the fluidics system 6112, the robotic drive system 6104, and the plurality of interventional devices 6108 to the control system 6106 via the fluidics tower 6102.

The one or more communication devices 6130 may be in electrical communication with a power source. The one or more communication devices 6130 may further be in electrical communication with the electronics tower 6110 and configured to receive and/or transmit electronic signals and/or data therebetween. In some embodiments, the one or more communication devices 6130 is in electrical communication with the electronics tower 6110 via a network. For example, the one or more communication devices 6130 may be electrically coupled to an ethernet cable configured to connect the one or more communication devices 6130 to a network, wherein the electronics tower 6110 may be electrically coupled to the network.

FIGS. 47-59 illustrate embodiments of a user interface coupled to or part of a control system (e.g., control system 6106, control system 3120) for controlling one or more interventional devices. In some embodiments, the user interface can be coupled to or part of a control console. In some embodiments, information regarding user inputs from a controller (e.g., controller 5310) may be provided (e.g., from one or more sensors of a sensor system, such as sensors 3110a) to the control system and used (e.g., by one or more hardware processors, such as processor(s) 3120a) to generate a user interface. In some embodiments, information regarding the interventional devices, hubs, hub adapters, and/or drive table may be provided from one or more subsystems or components (e.g., fluidics tower 6102, robotic drive system 6104, interventional devices 6108, etc.) to the control system and/or control console and used (e.g., by one or more hardware processors) to generate a user interface. For example, in some embodiments, information regarding the interventional devices, hubs, hub adapters, and/or drive table may be provided from one or more sensors of a sensor system (e.g., sensors 3135 and sensors 3130a) to the control system and/or control console and used (e.g., by one or more hardware processors) to generate a user interface. As used herein, "sensor system" may refer collectively to the one or more sensors (e.g., sensors 3110a, sensors 3135, and/or sensors 3130a) that may be provide information regarding a medical procedure as described herein. The sensor system can include one or more linear position sensors, such as a linear potentiometer, a linear variable differential transformer (LVDT) sensor, an ultrasonic sensor, a laser sensor, and/or a hall effect sensor, to measure axial movement of each of the interventional devices 3130. In some cases, the sensor system can include a magnet, a magnet resistive element, an encoder, a potentiometer, a hall effect sensor, rotary variable differential transformer (RVDT) sensor, or a combination thereof to detect an angular position and/or measure a rotational movement of each of the interventional devices.

Figure 47:
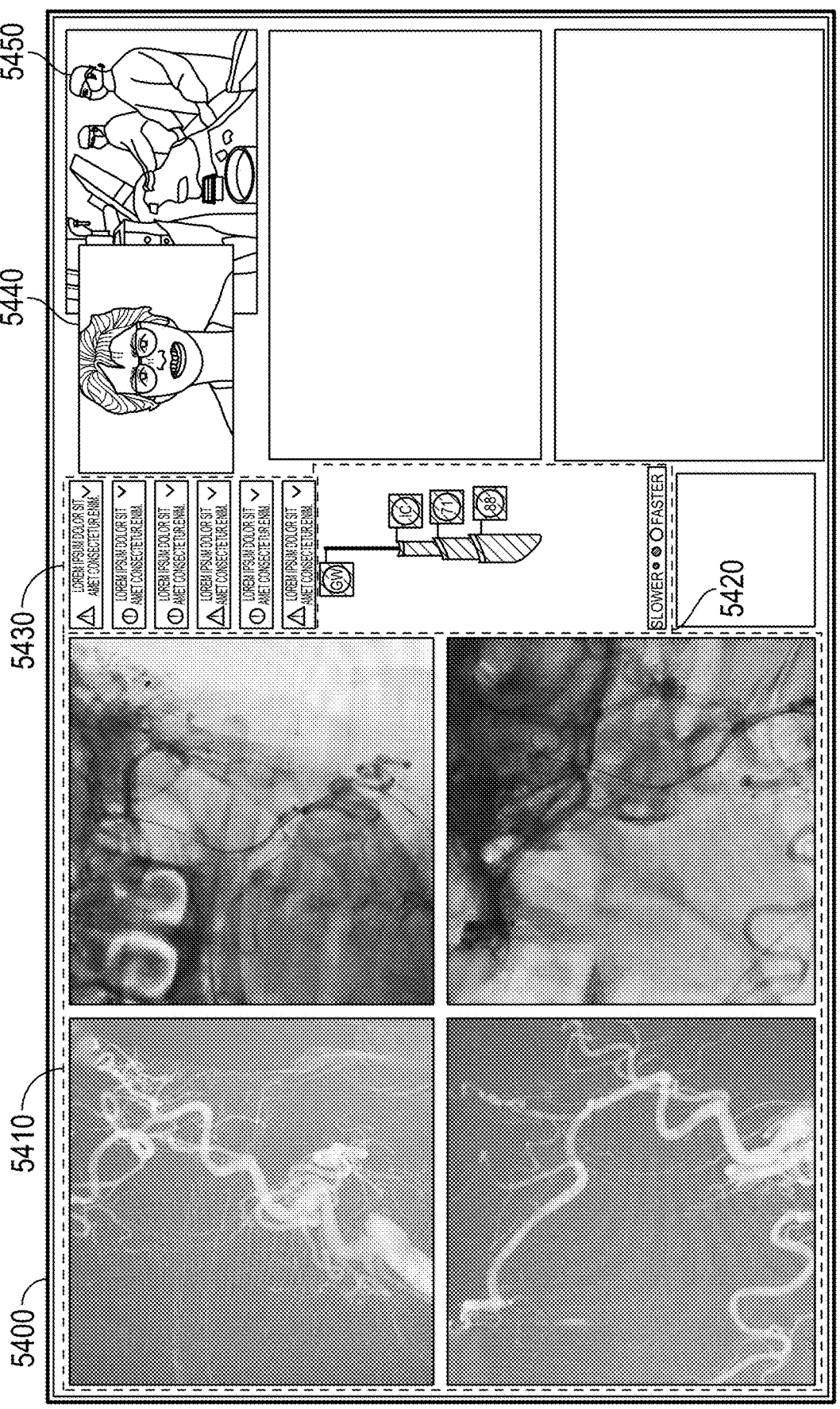

As shown in FIG. 47, the user interface 5400 can include a plurality of windows. For instance, the user interface 5400 can include an imaging window 5410, an instrument window 5420, a notification window 5430, a first video feed window 5440, a second video feed window 5450. In some instances of the user interfaces, only some of the components shown in FIG. 47 are displayed. In some cases, the user interface 5400 can be displayed on a capacitive screen, a resistive screen, a touch pad, or other touch-based sensing device. This can beneficially allow users to interact with the visual elements displayed on the user interface 5400. For example, in some embodiments, in addition to the user interface 5400 being displayed, users can adjust each of a plurality of parameters (e.g., speed, rotational direction, axial position) displayed on the user interface 5400 by interacting with the user interface 5400. As further described below, the plurality of parameters can be displayed on the instrument window 5420. Users can interact with the user interface 5400 by, for example, using basic gestures such as tapping, swiping, and/or dragging the components displayed on the capacitive screen, resistive screen, touch pad, or touch-based sensing device. Additionally or alternatively, the parameters displayed on the user interface 5400 can be adjusted by manipulating one or more physical buttons/components positioned adjacent the display in which the user interface 5400 is displayed. In some cases, at least one window of the plurality of windows of the user interface 5400 can display a patient's vital signs (e.g., body temperature, pulse rate, respiration rate, blood pressure, blood oxygen, etc.). In some embodiments, at least one window of the plurality of windows can include user profiles and/or settings. In some cases, instructions on how to move and/or operate the interventional devices associated with the user interface 5400 can be shown on the user interface 5400.

In some cases, the imaging window 5410 can be configured to display a live feed of the images and/or video generated by the imaging system 3142 (as shown in FIG. 29A). The imaging window 5410 can include more than one live feed. For instance, the imaging window 5410, can include four live feeds of the images and/or video generated by the imaging system 3142. Each of the live feeds of the imaging window 5410 can include a live feed showing fluoroscopic imaging of different parts of the body patient and/or taken from different angles. Although reference is made to the imaging window 5410 having four live feeds, the imaging window 5410 can display more than or less than four live feeds. The first video feed window 5440 and the second video feed window 5450 can each provide live feed of, for example, the clinician performing the procedure, the location where the procedure is taking place, the medical devices used in the operating room, and/or the control mechanism used for the procedure. In some embodiments, more live feeds may be available than are displayed by the imaging window 5410. In such embodiments, the user interface may change the live feeds shown in the window 5410, for example, in response to a user selection. In certain embodiments, one or more of the live feeds may also be expanded over a larger portion of the window 5410, for example, in response to a user input. In some cases, in response to a user selecting a point on the imaging window 5410 corresponding to a location along a vasculature of a patient as represented by the fluoroscopic imaging, one or more of the interventional devices associated with the instrument window 5420 may be automatically driven to the location along the vasculature.

Figures 48A, 48B, 48C:
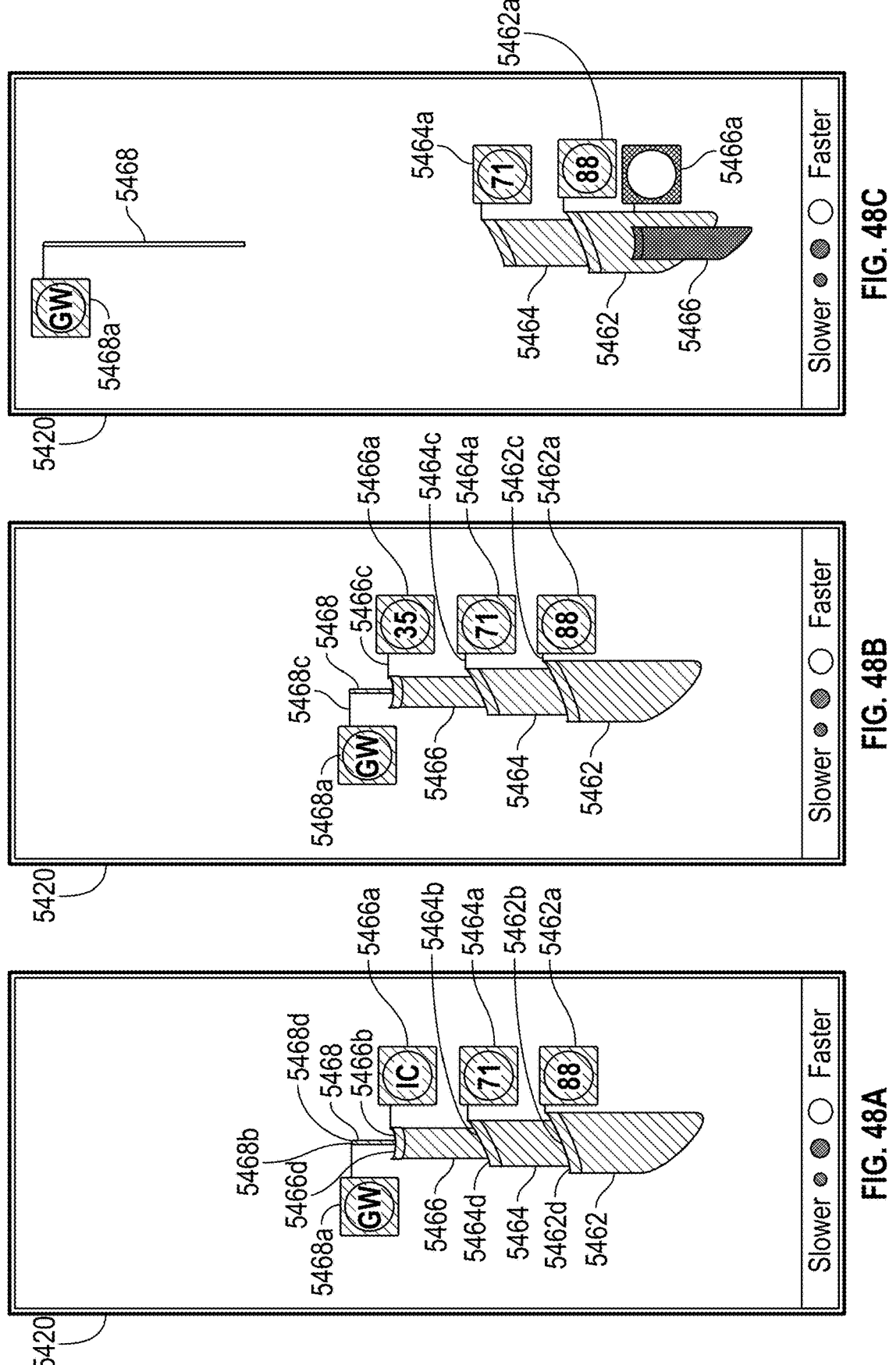

The instrument window 5420 can provide a visual indication of the status of one or more interventional devices. For example, the instrument window 5420 can display what interventional devices, if any, are active and/or associated to respective hubs of the drive system (e.g., drive system 18). This can beneficially allow clinicians to easily identify which interventional devices are available and the position of the interventional devices relative to each other. As shown in FIGS. 48A-48C, the instrument window 5420 can include a plurality of interventional device representations 5462, 5464, 5466 and 5468. In some embodiments, each of the plurality of interventional device representations can represent a particular interventional device coupled to a drive table in communication with the user interface (e.g., via a control system or control console). In certain embodiments, the control system or control console may receive information, related to the particular interventional devices (e.g., identify information, shape and/or size information, axial and/or rotational position of the interventional devices, information regarding an order of devices, axial and/or rotational velocity of the interventional devices, magnitudes and/or directions of axial and/or rotational movement, etc.) via a sensor system including one or more sensors (e.g., sensors 3135, sensors 3130a). The received information can be used (e.g., by one or more hardware processors) to generate a user interface providing information about the particular interventional devices. For example, the identify information can be used (e.g., by one or more hardware processors) to provide an indication of the particular interventional devices represented by the interventional device representations (e.g., by generating a user interface including the identify information).

In certain embodiments, each of the interventional device representations 5462, 5464, 5466 and 5468 may have visual characteristics that correspond to characteristics of the interventional devices to which they correspond. For example, each interventional device representation 5462, 5464, 5466 and 5468 may be shaped and/or sized (e.g., on a scaled or proportional basis) to correspond to the shape and/or size of the interventional device to which it corresponds or a portion of the interventional device to which it corresponds (e.g., a distal section). In some embodiments, the interventional device representations 5462, 5464, 5466 and 5468 may be displayed in relative positions corresponding to the relative positions of the interventional devices to which they correspond. For example, a distance between the distal ends of two interventional device representations may correspond (e.g., on a 1:1 or scaled basis) to a distance between the distal ends of the two interventional devices to which the interventional device representations correspond.

Each of the plurality of interventional device representations 5462, 5464, 5466 and 5468 can include a marker 5462a, 5464a, 5466a, 5468a. The markers 5462a, 5464a, 5466a, 5468a can provide an indication of the specific interventional devices each of the plurality of interventional device representations 5462, 5464, 5466 and 5468 are associated with. For example, each marker can include a character or set of characters identifying the interventional device its respective interventional device representation is associated with.

For example, as shown in FIGS. 48A-48C, the marker 5462a can provide an indication (e.g., the label "88") that the interventional device representation 5462 is associated with a guide catheter (e.g., guide catheter 31), which may be a guide catheter having a 0.088 inch inner diameter. As another example, the marker 5464a can provide an indication (e.g., the label "71") that the interventional device representation 5464 is associated with a procedure catheter (e.g., catheter 120), which may be a procedure catheter having a 0.071 inch inner diameter. In some embodiments, the marker 5466a can provide an indication (e.g., the label "IC" as shown in FIG. 48A) that the interventional device representation 5466 is associated with an insert catheter (e.g., insert or access catheter 2902). In some embodiments, the marker 5466a can provide an indication (e.g., the label "35" as shown in FIG. 48B) that the interventional device representation 5466 is associated with a second procedure catheter (e.g., catheter 124), which may have a 0.035 inch inner diameter. The marker 5468a can provide an indication (e.g., the label "GW") that the interventional device representation 5468 is associated to a guidewire (e.g., guidewire 27 or guidewire 2907).

Each of the interventional device representations 5462, 5464, 5466 and 5468 can include a visual indication 5462b, 5464b, 5466b, and 5468b of a distal end of the interventional device representation, as shown in FIG. 48A. Each of the visual indications 5462b, 5464b, 5466b, and 5468b can include a shape corresponding to a distal shape of the interventional device associated with the interventional device representations 5462, 5464, 5466 and 5468. The shape may include a distal tip or edge 5462d, 5464d, 5466d, 5468d. The edge 5462d, 5464d, 5466d, 5468d may be a rounded (e.g., semi-circular) top edge, a flat edge, or a beveled edge. In certain embodiments, the shape of the visual indication 5462b, 5464b, 5466b, and 5468b can include a beveled surface, which can correspond to a shape of the distal end of the interventional device (e.g., a guide catheter) associated with the interventional device representation 5462. As another example, the shape of the visual indication 5466b can include a surface which can be substantially perpendicular with a longitudinal axis of the interventional device representation 5466.

In some embodiments, a distance between a distal tip or edge 5462d, 5464d, 5466d, 5468d of a first visual indication 5462b, 5464b, 5466b, and 5468b and a distal tip or edge 5462d, 5464d, 5466d, 5468d of a second visual indication 5462b, 5464b, 5466b, and 5468b can provide an indication about the distance between the distal end of the interventional device associated with the first visual indication and the interventional device associated with the second visual indication. In some embodiments, a distance between a point 5462e, 5464c, 5466c, and 5468e along the shape of a first visual indication 5462b, 5464b, 5466b, and 5468b and a point 5462c, 5464c, 5466e, and 5468e along the shape of a second visual indication 5462b, 5464b, 5466b, and 5468b can provide an indication about the distance between the distal end of the interventional device associated with the first visual indication and the interventional device associated with the second visual indication.

In some embodiments, at least some of the points 5462c, 5464c, 5466c, and 5468e are aligned along a longitudinal axis parallel with the axis 5480. In some embodiments, at least some of the points 5462e, 5464c, 5466e, and 5468e are positioned along the central longitudinal axis 5480. In some embodiments, at least some of the points 5462c, 5464c, 5466c, and 5468e are position along the distal tip or edge 5462d, 5464d, 5466d, and 5468d of the visual indications. In some embodiments, at least some of the points 5462e, 5464c, 5466c, and 5468c are positioned along a top most or distal most portion of the shapes of the visual indication 5462b, 5464b, 5466b, and 5468b. In some embodiments, at least some of the points 5462c, 5464c, 5466c, and 5468e are positioned at a distal most location along the distal tip or edge 5462d, 5464d, 5466d, and 5468d of the shape of the visual indication 5462b, 5464b, 5466b, and 5468b.

The distance between at least two of the visual indications 5462b, 5464b, 5466b, and 5468b can be measured from a point 5462c, 5464c, 5466c, and 5468e along the shape of one of the visual indications and a point 5462e, 5464c, 5466e, and 5468e along the shape of another one of the visual indications. For instance, the distance can be measured from between a point on a top-most or distal most portion of a shape of a first visual indication and a point on a top-most or distal most portion of a shape of a second visual indication (e.g., along a central axis, such as axis 5480). In some cases, the distance can be measured from points on a distal-most portion of the shapes which are not along the central axis. In some embodiments, the distance is an axial distance between the two points measured along the axis 5480.

The distance between a point along the shape of a first visual indication 5462b, 5464b, 5466b, and 5468b and a point along the shape of a second visual indication 5462b, 5464b, 5466b, and 5468b can represent a scaled and/or a non-scaled distance between the distal end of a first interventional device associated with a first interventional device representation 5462, 5464, 5466 and 5468 having the first visual indication 5462b, 5464b, 5466b, and 5468b and the distal end of a second interventional device associated with a second interventional device representation 5462, 5464, 5466 and 5468 having the second visual indication 5462b, 5464b, 5466b, and 5468b. For example, a non-scaled distance can provide an indication that the distance between the points of the first visual indication and the second visual indication is the actual distance between the distal ends of the interventional devices associated with the first visual indication and the second visual indication. A scaled distance can provide an indication that the distance between the points of the first visual indication and the second visual indication represents a proportional distance of the actual distance between the distal ends of the interventional devices associated with the first visual indication and the second visual indication. For example, using a 2:1 scale, a distance of 2 cm between the points can provide an indication that the actual distance between the distal ends of the interventional devices associated with the first visual indication and the second visual indication is 1 cm. Although reference is made to a 2:1 scale, other scales can be used (e.g., 1:2; 1:3; 1:4; 1:10; 2:1; 3:1; 4:1; 10:1; etc.).

In some embodiments, the distance between a point along the shape of the first visual indication 5462b, 5464b, 5466b, and 5468b and a point along the shape of a second visual indication 5462b, 5464b, 5466b, and 5468b can represent an estimated scaled and/or a non-scaled distance between the distal end of a first interventional device associated with a first interventional device representation 5462, 5464, 5466 and 5468 having the first visual indication 5462b, 5464b, 5466b, and 5468b and the distal end of a second interventional device associated with a second interventional device representation 5462, 5464, 5466 and 5468 having the second visual indication 5462b, 5464b, 5466b, and 5468b. In some embodiments, the positions of the distal end of the first interventional device and the distal end of the second interventional device may be estimated based on detected positions (e.g., by the sensor system) of the hubs and/or hub adapters corresponding to the first interventional device and the second interventional device.

In some embodiments the visual indications 5462b, 5464b, 5466b, and 5468b can provide a visual indication about the position of the distal end of the interventional devices associated with the interventional device representations 5462, 5464, 5466 and 5468 with respect to each other. This can beneficially allow clinicians to identify the position of the interventional devices associated with the interventional device representations 5462, 5464, 5466 and 5468 with respect to each other during the interventional procedure.

In some cases, the instrument window 5420 can include a plurality of pointers 5462c, 5464c, 5466c, 5468c, as shown in FIG. 48B. Each of the plurality of pointers 5462c, 5464c, 5466*c*, 5468*c* can be positioned between one of the plurality of interventional device indicator representations 5462, 5464, 5466 and 5468 and one of the plurality of markers 5462*a*, 5464*a*, 5466*a*, 5468*a*. For instance, each of the plurality of pointers 5462*c*, 5464*c*, 5466*c*, 5468*c* can include a line extending between an interventional device representation 5462, 5464, 5466 and 5468 and interventional device markers 5462*a*, 5464*a*, 5466*a*, 5468*a*. Using the pointer 5462*c* as an example, the pointer 5462*c* can extend between the interventional device representation 5462 and the interventional device marker 5462*a*. In some cases, one end of the pointer 5462*c* can be connected to the interventional device representation 5462 and the other end can be connected to the interventional device marker 5462*a*. This can beneficially allow clinicians to identify which interventional device marker 5462*a* the interventional device representation is associated with, and vice versa. As will be discussed in further detail below, this can beneficially allow clinicians to identify the operational status and/or identity of each of the plurality of interventional device representations 5462, 5464, 5466 and 5468.

The markers 5462*a*, 5464*a*, 5466*a*, 5468*a* can include any character(s) (e.g., letters, numbers, or combination thereof) for providing an indication of the interventional device the interventional device representations 5462, 5464, 5466 and 5468 are associated with. Alternatively, or additionally, each of the interventional device representations 5462, 5464, 5466 and 5468 and/or the markers 5462*a*, 5464*a*, 5466*a*, 5468*a* can include a color, which can provide an indication of the interventional device the interventional device representations 5462, 5464, 5466 and 5468 are associated with. In some cases, the markers 5462*a*, 5464*a*, 5466*a*, 5468*a* may be empty (e.g., not show a color, letters, numbers, etc.) to provide an indication that an interventional device is not associated with an interventional device representations 5462, 5464, 5466 and/or 5468 (e.g., an interventional device is not installed to a respective hub or hub adapter of the drive system). For example, as shown in FIG. 48C, the marker 5466*a* can display an empty box to indicate that the interventional device representation 5466 is not associated to any interventional device.

Figure 49B:
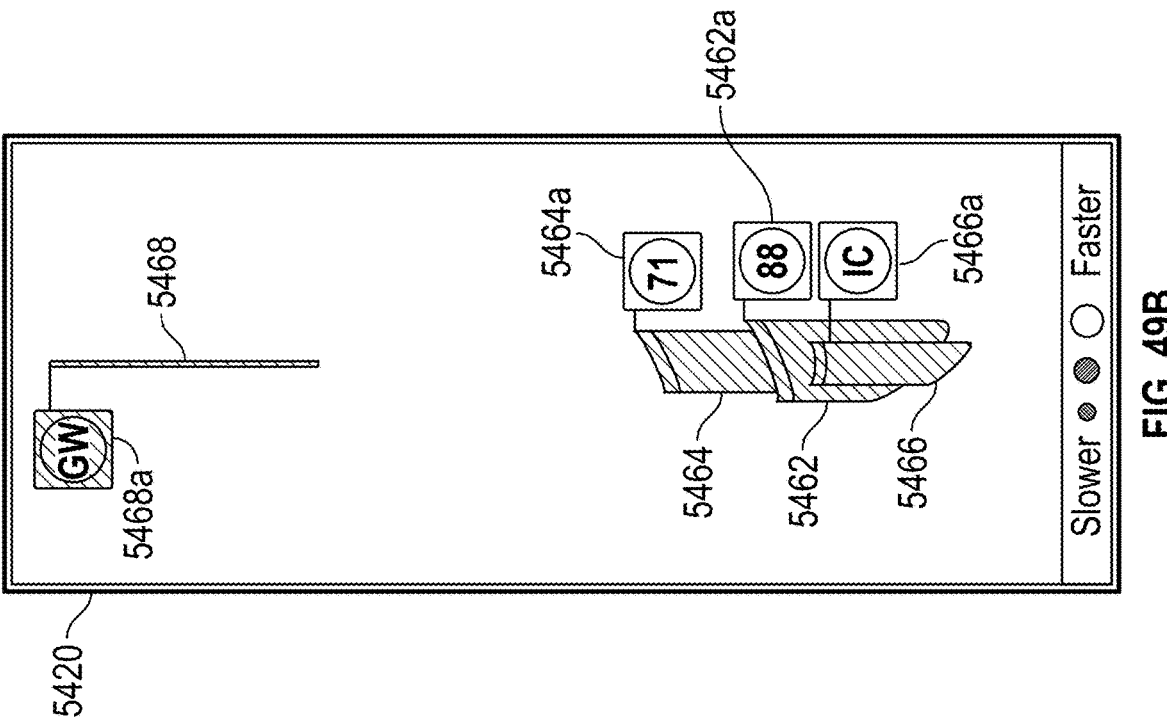
Figure 49A:
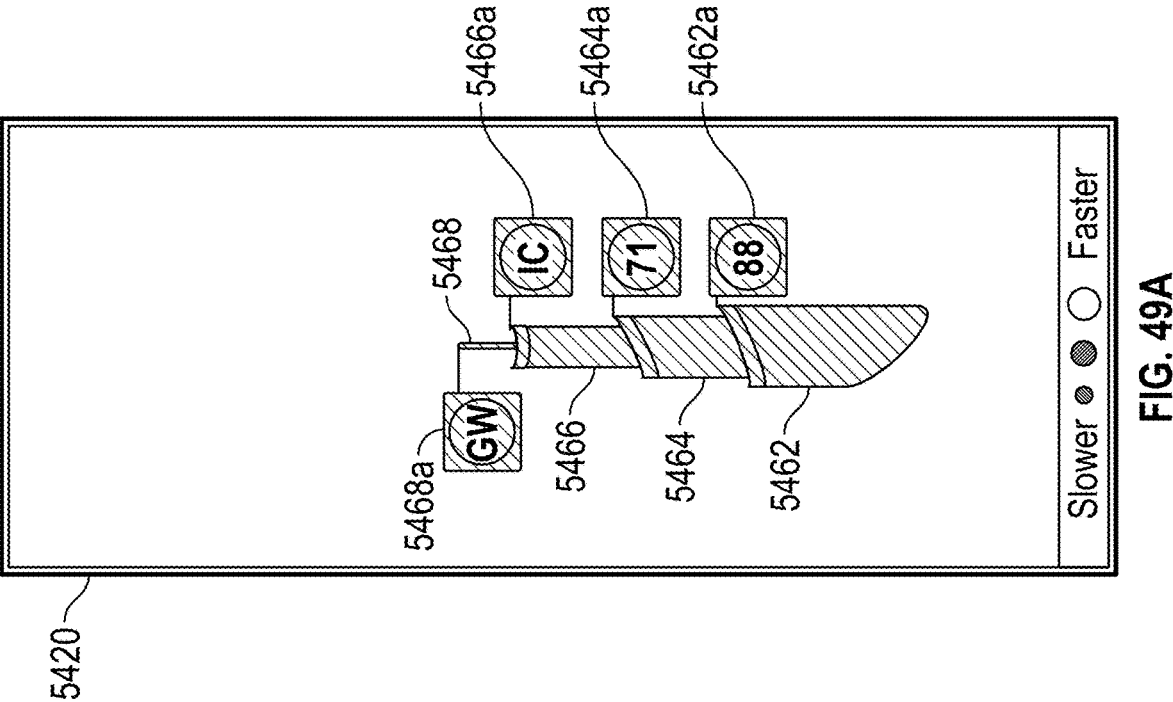

The instrument window 5420 can provide a visual indication of the axial position of the interventional device representations 5462, 5464, 5466 and 5468 with respect to each other. This can beneficially allow clinicians to assess the available range of motion for each interventional device associated with the interventional device representations 5462, 5464, 5466, 5468. As shown in FIG. 49A, the interventional device representations 5462, 5464, 5466, 5468 can be displayed so that a position of a distal end of each of the interventional device representations is shown. The visual indications 5462*b*, 5464*b*, 5466*b*, and 5468*b* of the interventional device representations 5462, 5464, 5466, 5468 can provide an indication of the position of the distal ends of the interventional devices corresponding to the interventional device representations with respect to each other. For example, the visual indication 5468*b* of the interventional device representation 5468 can provide an indication that the distal end of the interventional device associated with the interventional device representation 5468 (e.g., a guidewire) extends beyond a distal end of the interventional devices associated with the interventional device representations 5462, 5464 and/or 5466. The visual indications 5462*b*, 5464*b*, 5466*b*, and 5468*b* may provide an indication of relative distances between the interventional devices corresponding to the interventional device representations 5462, 5464, 5466, 5468 relative to each other. In some embodiments, as the interventional devices move relative to one another, the interventional device representations 5462, 5464, 5466, 5468 can move relative to one another so that the visual indications 5462*b*, 5464*b*, 5466*b*, and 5468*b* provide an indication of the relative positions of the distal ends of corresponding interventional devices as the interventional devices move. For example, as the guidewire associated to the interventional device representation 5468 is advanced though the vasculature of a patient, the position of the interventional device representation 5468 with respect to the interventional device representations 5464, 5466, 5468 may change to show the guidewire extended farther away from the interventional device representations 5464, 5466, 5468, as shown in FIG. 49B. In certain embodiments, information regarding the positions of the interventional devices and/or movement of the interventional devices (e.g., axial and/or rotational velocity, magnitude and/or direction of movement, etc.) may be received from one or more sensors (e.g., sensors 3135 and/or sensors 3130*a*) of a sensor system.

The instrument window 5420 can indicate whether an interventional device is positioned within another interventional device (e.g., in a nested configuration). In some embodiments, the interventional device representations 5462, 5464, 5466, 5468 can be shown in a transparent or semi-transparent appearance to allow other interventional device representations to be displayed and/or visualized through the semi-transparent interventional device representations. For example, as shown in FIG. 49B, the interventional device representation 5466 can be visualized through the interventional device representations 5462 and 5464 to indicate that the interventional device associated with the interventional device representation 5466 is positioned within the interventional devices associated with the interventional device representations 5462, 5464 but proximal to the distal ends of the interventional devices associated with the interventional device representations 5462.

Figure 50B:
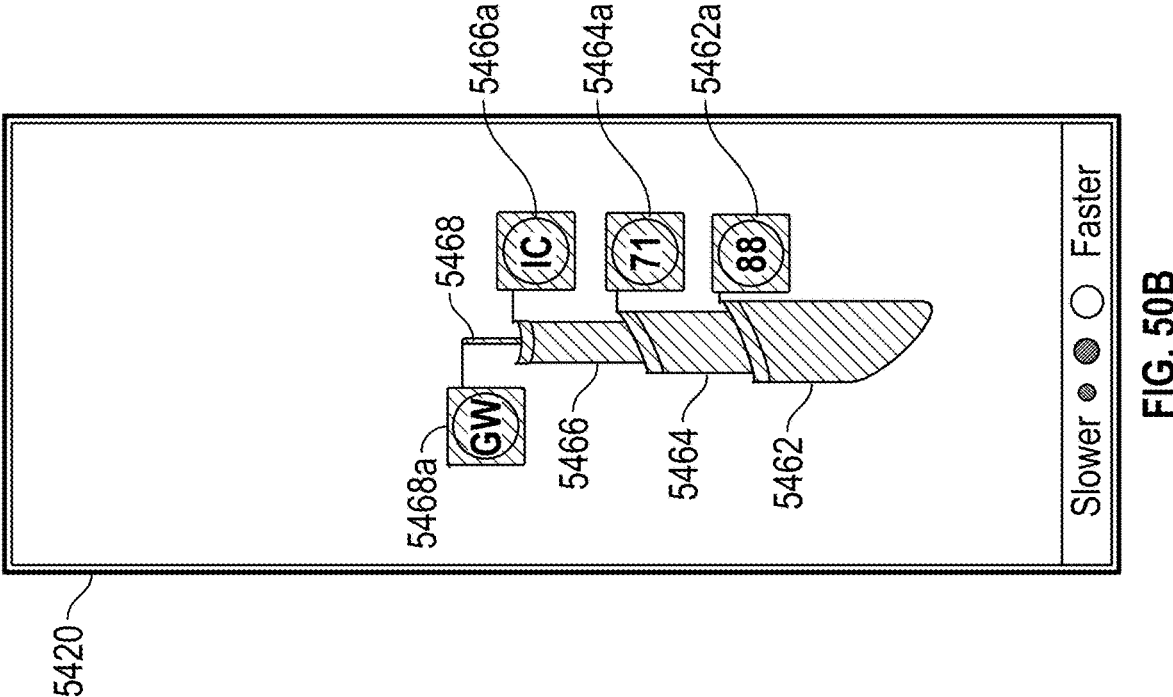
Figure 50A:
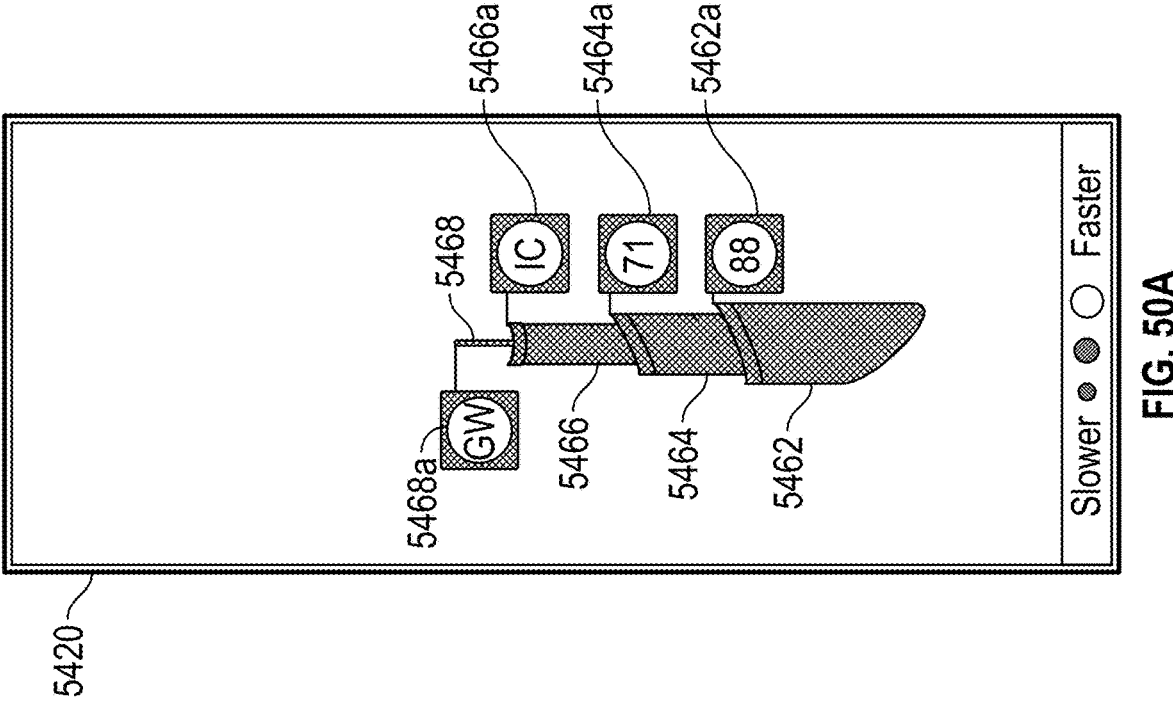

The interventional device representations 5462, 5464, 5466, 5468 and/or the interventional device markers 5462*a*, 5464*a*, 5466*a*, 5468*a* can provide an indication of whether the interventional devices associated to the interventional device representations 5462, 5464, 5466, 5468 are enabled. For instance, the interventional device representations 5462, 5464, 5466, 5468 and/or the interventional device markers 5462*a*, 5464*a*, 5466*a*, 5468*a* may be displayed in a first color (e.g., gray, transparent, etc.), shade (e.g., darker in comparison to when the devices are enabled), texture, pattern, etc. to indicate that the interventional devices associated to the interventional device representations 5462, 5464, 5466, 5468 are disabled, as shown in FIG. 50A. This can beneficially allow clinicians to easily identify which interventional devices are available and ready for use. The interventional device representations 5462, 5464, 5466, 5468 and/or the interventional device markers 5462*a*, 5464*a*, 5466*a*, 5468*a* can be displayed in a second color, shade (e.g., lighter in comparison to when the devices are disabled), texture, pattern, etc. to indicate that the interventional devices associated to the interventional device representations 5462, 5464, 5466, 5468 are enabled, as shown in FIG. 50B.

The instrument window 5420 can provide an indication of whether the interventional devices associated with the interventional device representations 5462, 5464, 5466, 5468 are selectively configured in a drive mode, which is also referred to herein as an operation mode, and/or stage mode. As described in relation to FIGS. 46A-46B, any of the control mechanisms described herein (e.g., the control mechanism 5300) can be configured to control two or more hubs and/or interventional devices simultaneously. For example, in a first drive mode, the hubs and/or interventional devices can be advanced to achieve supra-aortic access as described herein. In some embodiments, the instrument window 5400 can provide a visual indication of a current drive mode of the interventional devices. For example, in some embodiments, the instrument window 5420 can display all of the interventional device representations 5462, 5464, 5466, 5468 and/or all of the interventional device markers 5462a, 5464a, 5466a, 5468a with a particular visual appearance (e.g., color, shade, texture, pattern, etc.) to indicate that the interventional devices associated with the device representations 5462, 5464, 5466, 5468 are in a first drive mode (e.g., access mode). The instrument window 5420 can display one or more of the interventional device representations 5462, 5464, 5466, 5468 and/or the interventional device markers 5462a, 5464a, 5466a, 5468a with a different particular visual appearance to indicate that the interventional devices associated with one or more of the representations 5462, 5464, 5466, 5468 are in a second drive mode.

Figure 51B:
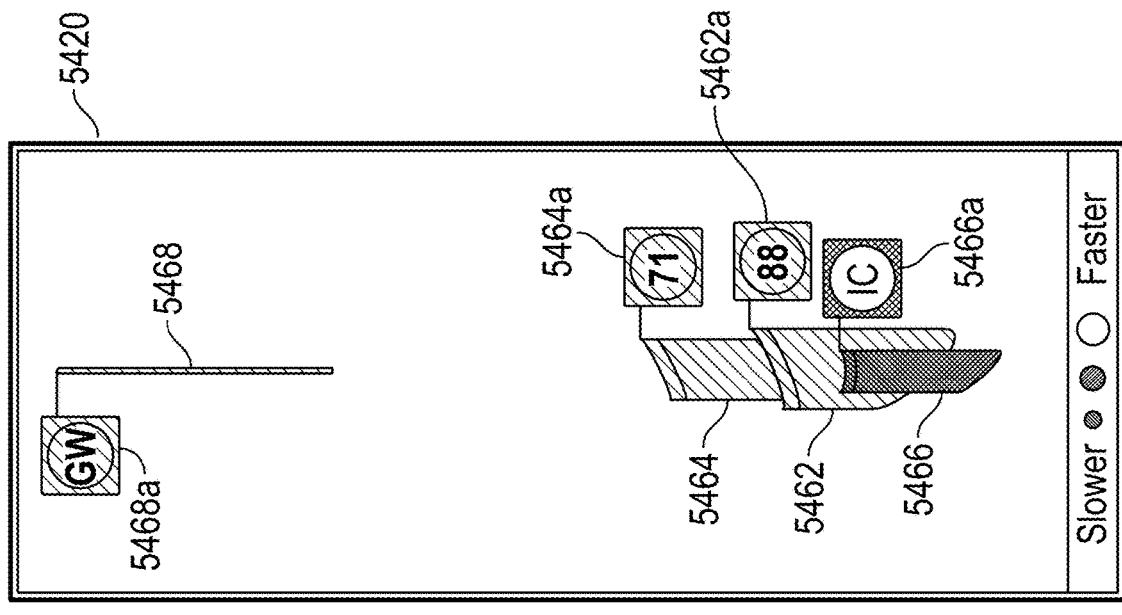
Figure 51A:
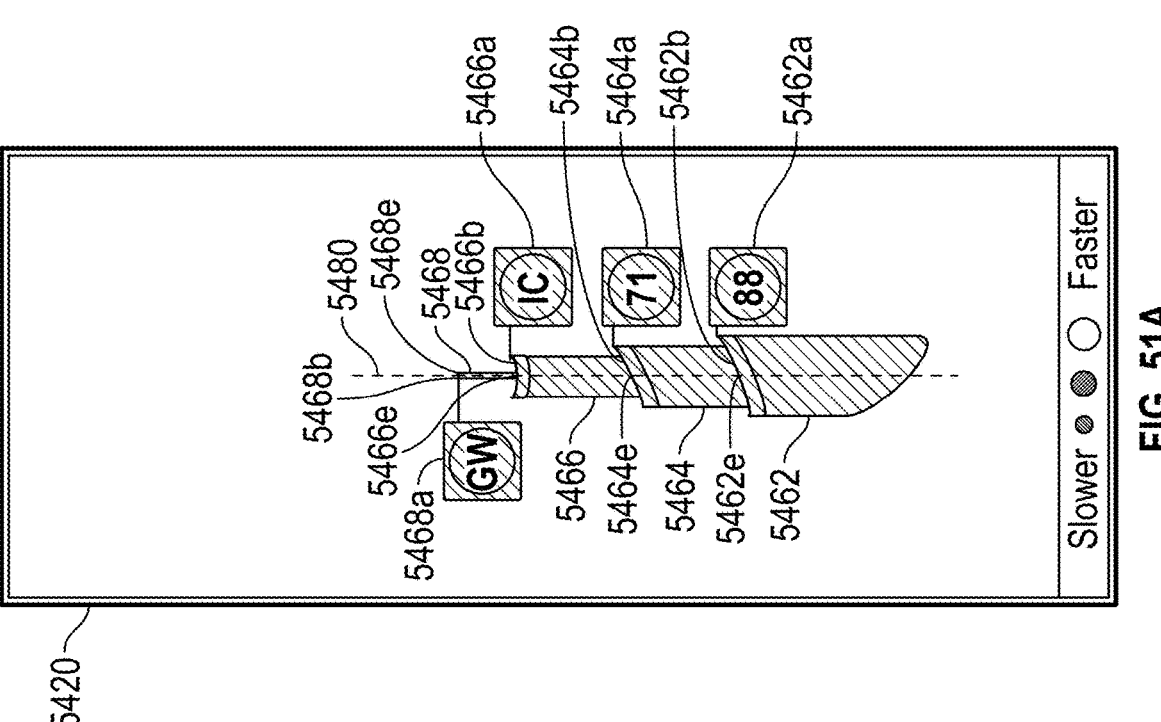

In certain embodiments, the instrument window 5420 can provide a visual indication of which devices are currently active (e.g., available for movement by one or more controls, such as joysticks 5332 and 5334) and which devices are inactive (e.g., not available for movement by one or more controls). Interventional devices may be inactive, for example, if they are not linked to be controlled by a control of a controller (e.g., controls 5332 and 5334), for example, in a particular drive mode or in response to a temporary linkage of particular interventional devices to the controls. In certain embodiments, the instrument window 5420 can display all active interventional device representations 5462, 5464, 5466, 5468 and/or all interventional device markers 5462a, 5464a, 5466a, 5468a in a first color, texture, pattern, etc. (as shown, for example, in FIG. 51A) and all inactive interventional device representations 5462, 5464, 5466, 5468 and/or all interventional device markers 5462a, 5464a, 5466a, 5468a in a second color, texture, pattern, etc. The first color, texture, and/or pattern, can be different than the second color, texture, and/or pattern. For example, as shown in FIG. 51B, the interventional device representation 5466 and/or the interventional device marker 5466a can be shown in a color, texture, pattern, different than that of the interventional device representations 5462, 5464, 5468 and/or all interventional device markers 5462a, 5464a, 5468a to indicate that the interventional device associated with the interventional device representation 5466 is not active. In some embodiments, by assessing which interventional devices are active and/or inactive, clinicians can beneficially identify whether the interventional devices associated with the interventional device representations 5462, 5464, 5466, 5468 are in a drive mode and/or what drive mode the interventional device representations 5462, 5464, 5466, 5468 are in. FIG. 51A may be an example of an instrument window 5420 during a first drive mode, as described herein, wherein a first control (e.g., joystick 5332) is linked to control a guidewire (corresponding to representation 5468), and a second control is linked to control an access catheter (corresponding to representation 5466), a procedure catheter (corresponding to representation 5464), and a guide catheter (corresponding to representation 5462). FIG. 51B may be an example of the instrument window 5420 during a second drive mode, as described herein, wherein a first control (e.g., joystick 5332) is linked to control a guidewire (corresponding to representation 5468), a second control (e.g., joystick 5334) is linked to control a procedure catheter (corresponding to representation 5464) and a guide catheter (corresponding to representation 5462), and neither the first control nor the second control is linked to control an access catheter (corresponding to representation 5466) such that the access catheter is considered inactive.

Figures 51C, 51D, 51E:
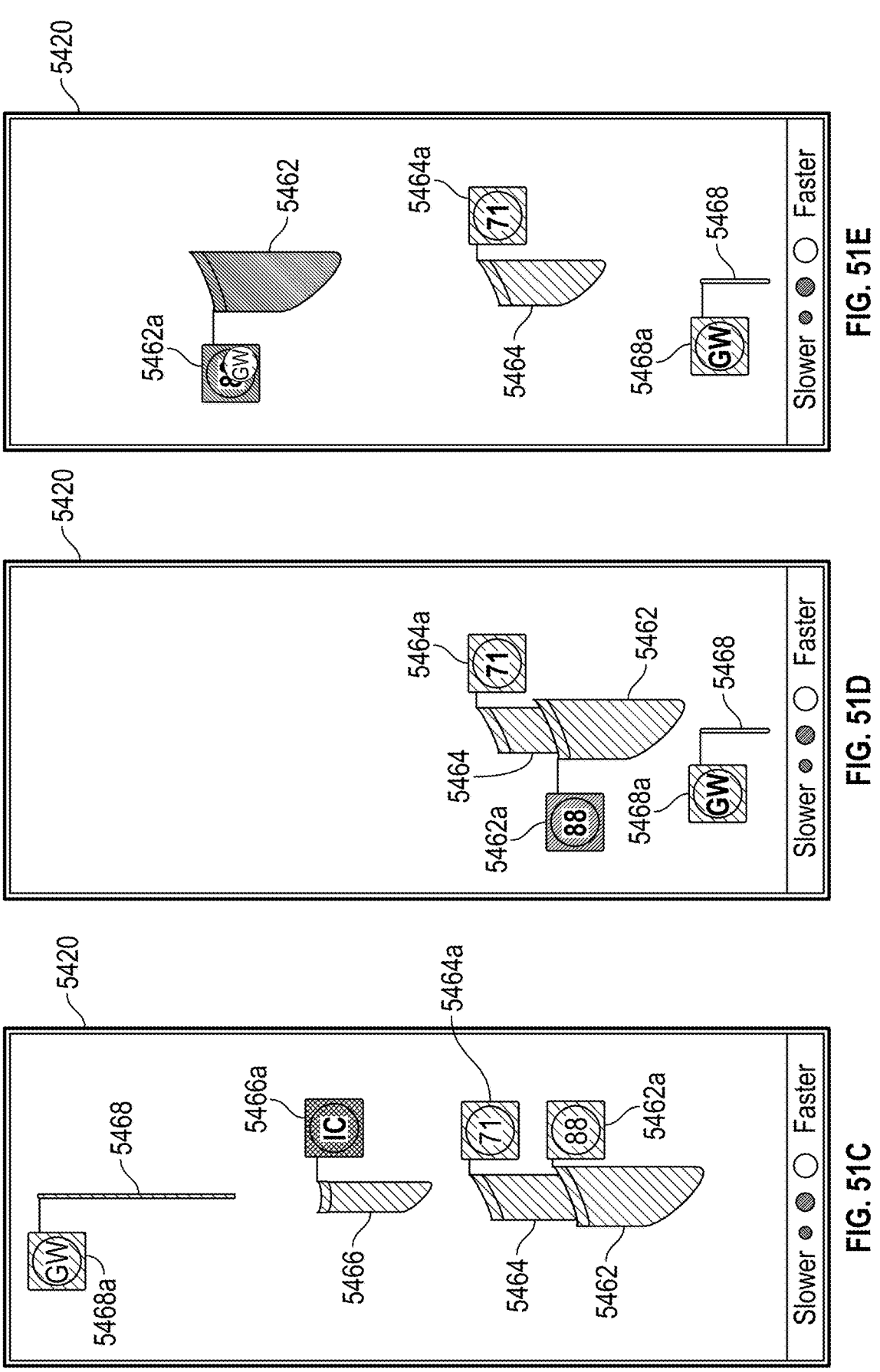

As shown in FIGS. 51C-51D, the instrument window 5420 can provide an indication of any active interventional device. Any of the interventional device markers 5462a, 5464a, 5466a, 5468a can provide a visual indication when the interventional device associated with the interventional device markers 5462a, 5464a, 5466a, 5468a is being driven or is not being driven. For example, the interventional device marker 5466a can include a color contrast and/or highlight to indicate that the interventional device (e.g., an insert catheter) associated with the marker 5466a is being driven, as shown in FIG. 51C. As another example, the interventional device marker 5462a can include a color contrast and/or highlight to indicate that the interventional device (e.g., 0.088 in. catheter; guide catheter 31) associated with the marker 5462a is being driven, as shown in FIG. 51D.

In some embodiments, one or more of the interventional device representations may change in appearance to indicate which interventional devices are being driven and/or which interventional devices are not being driven. For example, in certain embodiments, if an interventional device is being driven, the interventional device representation corresponding to the interventional device being driven can become brighter in appearance. In some embodiments, the interventional device representations corresponding to the interventional devices not being driven can become duller in appearance while an interventional device is being driven.

The interventional device representations 5462, 5464, 5466, 5468 can extend along a central longitudinal axis 5480, as shown in FIG. 51A. For instance, the interventional device representations 5462, 5464, 5466, 5468 can be centered along the central longitudinal axis 5480. The interventional device markers 5462a, 5464a, 5466a, 5468a can include at least two configurations and/or positions. In some cases, the interventional device markers 5462a, 5464a, 5466a, 5468a can extend away from the central longitudinal axis when the interventional devices associated with the interventional device representations 5462, 5464, 5466, 5468 are being driven. For example, the interventional device marker 5462a can move laterally or horizontally relative to the axis 5480 from a first position to a second position (e.g., further from the central axis 5480) to indicate that the interventional device associated with the interventional device representation 5462 is being driven.

The plurality of interventional device pointers 5462c, 5464c, 5466c, 5468c can additionally or alternatively provide a visual indication that the interventional devices associated with the interventional device representations 5462, 5464, 5466, 5468 are being driven. In some cases, the length of the plurality of interventional device pointers 5462c, 5464c, 5466c, 5468c can change from a first length to a second length to indicate whether an interventional device is being driven. Using the interventional device pointer 5462c as an example, a length of the pointer 5462c may transition from a first length to a second length larger than the first length to indicate that the interventional device associated with the interventional device representation 5462 and/or the interventional device marker 5462a is being drive. In some cases, the pointer 5462c may return to its original length when the interventional device is not being driven any more. The transition of the plurality of pointers 5462c, 5464c, 5466c, 5468c from a first state to a second state can beneficially allow clinicians to easily identify which interventional devices are being driven. Information regarding which interventional devices are being driven may be received from one or more sensors of a sensor system as described herein.

For example, the first position of the interventional device marker 5462a can be closer to the central longitudinal axis 5480 than the second position such that it is easily apparent to a user that the particular interventional device is in fact active and moving. In some instances, the interventional device representation corresponding to the driven interventional device can ungroup from the other representations. In some instances, the movement away from central axis improves a user's ability to operate the interventional device. For example, it can reduce errors and save time because a user doesn't have to think about or keep in their mind which interventional device are they moving. There might also not be a lot of available space on the user interface to indicate using text which device is moving. Accordingly, in some instances, the inventors realized that movement of the representations with respect to an axis can be used to convey important information about the status of operation.

The instrument window 5420 can provide an indication that two or more interventional devices associated with the interventional device representations 5462, 5464, 5466, 5468 are linked so that the two or more interventional devices move together in a same direction by a same magnitude and/or velocity regardless of whether the two or more interventional devices are linked to the same control of the controller. In some embodiments, when linked, two or more interventional devices can move simultaneously if the clinician moves at least one of the linked interventional devices using any control mechanism. In other embodiments, linked interventional devices can include a primary device and one or more secondary devices. Movement of a control to move the primary device can cause movement of the secondary device in the same direction by the same magnitude and/or velocity. Movement of a control to move the secondary device, but not the primary device, may not cause the primary device to move. Interventional devices may be so linked when controlled movements of one or more of the interventional devices would result in relative positions between the interventional devices, interventional device hubs, and/or hub adapters at distances greater than a total available separation distance (e.g., due to the length of the drive surface of the drive table or due to a length of a shuttle along which hub adapters translate) as described, for example, with respect to the telescoping table 6000. In some embodiments, movement of a control to move the secondary device, but not the primary device, in a direction that would increase a separation distance between the primary device and the secondary device may result in no movement of either the primary device or the secondary device. In some embodiments, movement of a control to move the secondary device, but not the primary device, in a direction that would decrease the separation distance between the primary device and the secondary device may cause the secondary device to move without movement of the primary device and/or may unlink the secondary device from the primary device.

As shown in FIG. 51E, an interventional device marker 5462a can include a first character set (e.g., number(s), letter(s) or combination thereof) and a second character set (e.g., number(s), letter(s), or combination thereof) to indicate that two interventional devices are linked to each other. For example, the interventional device marker 5462a can include a first character set (e.g., "88") and a second character set (e.g., "GW"). The first character set can be associated with the interventional device (e.g., a guide catheter) associated with the interventional device representation 5462. As shown, the second character set ("GW") is the same as the character ("GW") shown by marker 5468a, indicating that the interventional device (e.g., a guidewire) associated with the representation 5468 associated with the marker 5468a is linked to the interventional device associated with the first character set (e.g., the guide catheter). As shown, the first character set may correspond to the primary interventional device. The second character set may correspond to the secondary interventional device. The character set for the primary interventional device may be larger than the character set for the secondary interventional device. In some embodiments, the character set for the primary interventional device can be positioned within the marker of the interventional device representation associated with the same interventional device as the character set for the primary interventional device. The character set for the secondary interventional device can be positioned in the same marker as the character se for the primary interventional device, but may be smaller in size or otherwise different in appearance to indicate that it is the character set for the secondary interventional device. Although first and second characters sets are described herein, in some embodiments, different symbols or identifiers may be used to identify the linked devices (e.g., primary and secondary devices).

Figures 52A, 52B, 52C:
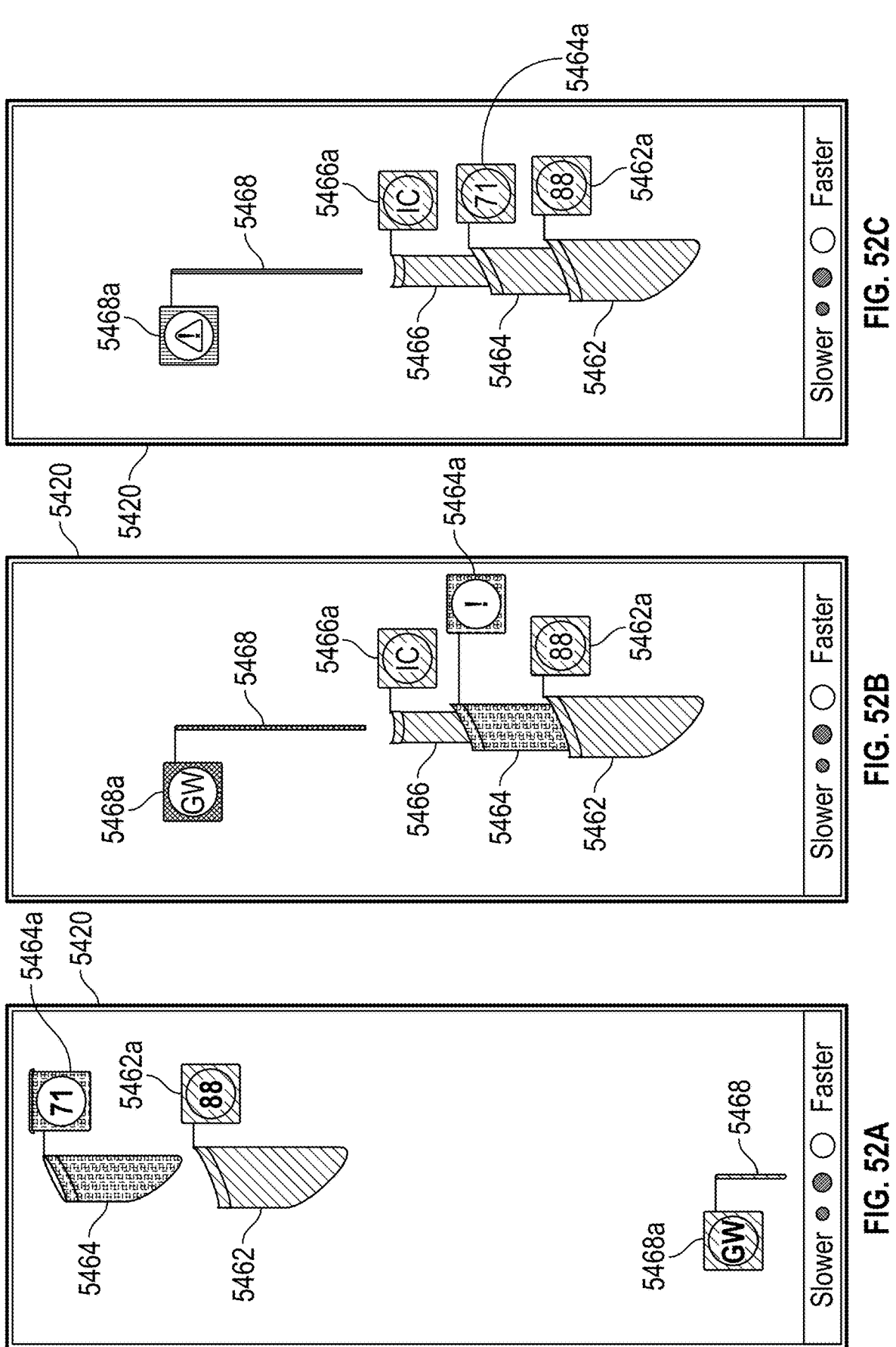

The instrument window 5420 can provide an indication about the status of the interventional devices associated with the interventional device representations 5462, 5464, 5466, 5468. In some cases, each of the interventional device markers 5462a, 5464a, 5466a, 5468a can be displayed in a color, texture, or pattern, etc. to indicate a status of the interventional device associated with the interventional device markers 5462a, 5464a, 5466a, 5468a. For example, the interventional device representation 5464 and/or the interventional device marker 5464a can transition from a first a first color (e.g., purple), texture, or pattern to a second color (e.g., yellow), texture, or pattern to indicate that the status of the interventional device associated with the interventional device representation 5464 and/or the interventional device marker 5464a has changed, as shown in FIG. 52A. In some embodiments, the status may indicate that the interventional device associated with the interventional device representation 5464 and/or the interventional device marker 5464a has reached a driving limit. An interventional device may reach its driving limit if the interventional device cannot move any further in a distal direction or a proximal direction. For example, an interventional device may reach its driving limit in a particular direction if further movement of the interventional device in that particular direction would cause a hub associated with that interventional device to collide with a hub of a second interventional device. An interventional device may reach a distal driving limit when the hub associated with the international device is positioned at a distal most point along a drive surface. An interventional device may reach a proximal driving limit when the hub associated with the interventional device is positioned at a proximal most point along a drive surface. An interventional device may reach a distal driving limit if a hub adapter associated with the interventional device is positioned at a distal most possible position within the drive table (e.g., at a distal most point along a shuttle as described with respect to telescoping table 6000). An interventional device may reach a proximal driving limit if a hub adapter associated with the interventional device is positioned at a proximal most possible position within the drive table (e.g., at a proximal most point along a shuttle as described with respect to telescoping table 6000).

The interventional device markers 5462a, 5464a, 5466a, 5468a can display a symbol, character, number, or combination thereof to indicate the status of an interventional device. For example, as shown in FIG. 52B, the device marker 5464a can display an exclamation mark ("!") in a first color (e.g., yellow), texture or pattern, to indicate a warning. In some cases, the warning may indicate that there is problem with the interventional device associated with the interventional device markers 5462a, 5464a, 5466a, 5468a (e.g., that the interventional device and/or hub associated with the interventional device may be experiencing a high force and/or resistance). As another example, and as shown in FIG. 52C, the device marker 5468a can display an exclamation mark ("!") in a second color (e.g., red), texture, or pattern to indicate that there is an error with the interventional device associated with the interventional device markers 5462a, 5464a, 5466a, 5468a (e.g., that the interventional device has disconnected, is not working properly, etc.).

Figures 53, 54A, 54B:
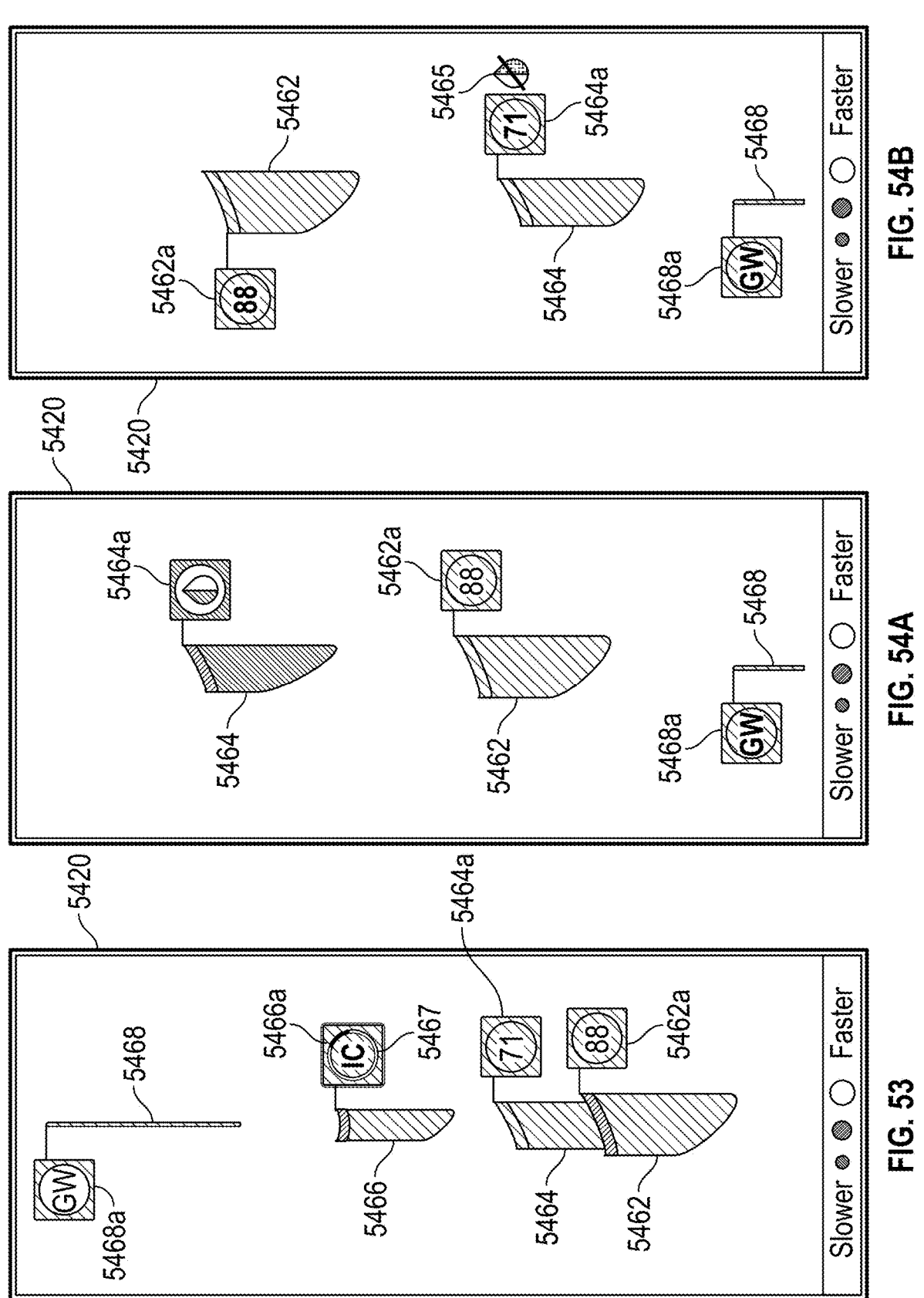

The interventional device representations 5462, 5464, 5466, 5468 and/or the interventional device markers 5462a, 5464a, 5466a, 5468a can include an indication about the rotational position or state of the interventional devices associated with the interventional device representations 5462, 5464, 5466, 5468. For example, as shown in FIG. 53, the interventional device marker 5466a can include a rotational indicator 5467 (e.g., a radial progress indicator). The rotational indicator 5467 can provide visual indication of a degree of rotation of an interventional device relative to a threshold of the interventional device about the longitudinal axis. For example, the threshold can represent a full revolution. In some embodiments, the rotational indicator can provide a visual indication of a direction of rotation. For example, in some embodiments, the rotational indicator may demonstrate clockwise movement to indicate clockwise rotation of a corresponding interventional device and counterclockwise movement to demonstrate counterclockwise movement of the corresponding interventional device.

The rotational indicator 5467 can be displayed inside the interventional device marker 5466a. In some cases, the rotational indicator 5467 can include a ring or circular shaped progress bar, but the rotational indicator 5467 can include other shapes (e.g., triangular, square, etc.). When the interventional device associated with the interventional device representation 5466 is rotated (e.g., the rotational position of the interventional device is changed), the rotational indicator 5467 (e.g., progress bar) may start to fill to indicate how much the interventional device has been rotated. In some cases, the rotational indicator 5467 can fill in its entirety to indicate that the interventional device has been rotated one full revolution. Upon completing a full revolution, the rotational indicator 5467 may reset. In some cases, the rotational indicator 5467 may fill in a clockwise direction and/in a counterclockwise direction to indicate which rotational direction the interventional device is moving in.

The ring shaped progress bar of the rotational indicator 5467 can be filled to indicate the degree and/or direction of rotation of an interventional device. For example, in some embodiments, the ring shaped progress bar of the rotational indicator 5467 can be filled by about 25% in a clockwise direction to indicate that the interventional device has been rotated, from a starting position, one quarter of a revolution in a clockwise direction. As another example, the ring shaped progress bar of the rotational indicator 5467 can be filled by about 50% in a counterclockwise direction to provide a visual indication that the interventional device has been rotated, from a starting position, half a revolution in a counterclockwise direction. The ring shaped progress bar of the rotational indicator 5467 may reset (e.g., be empty and/or shown at 0%) when the interventional device completes a full revolution.

The instrument window 5420 can provide an indication of whether contrast injection, and/or other fluid delivery is being delivered via the interventional devices associated with the interventional device representations 5462, 5464, 5466, 5468. For example, the interventional device representations 5462, 5464, 5466, 5468 and/or the interventional device markers 5462a, 5464a, 5466a, 5468a may change from a first color (e.g., purple), texture, or pattern to a second color (e.g., blue), texture or pattern to indicate that contract injection and/or other fluid delivery (e.g., saline) is active in one or more of the interventional devices. As shown, in FIG. 54A, the interventional device marker 5464a can display a symbol (e.g., a droplet) to indicate that the interventional device associated with the interventional device marker 5464a is delivering contrast. In some cases, the contrast symbol in the interventional device marker 5464a can replace the symbol, number, and or character that indicates the interventional device associated with the interventional device marker 5464a. The instrument window 5420 can also provide an indication of whether contrast is unavailable. For example, the instrument window 5420 can display a symbol 5465, as shown in FIG. 54B. The symbol 5465 can be displayed next to an interventional device marker (e.g., interventional device marker 5464a). The symbol 5465 can provide an indication that contrast is unavailable for the interventional device associated with the interventional device marker where the symbol is displayed. The same or additional symbols may be used to provide information regarding the delivery of other fluids.

Figure 55B:
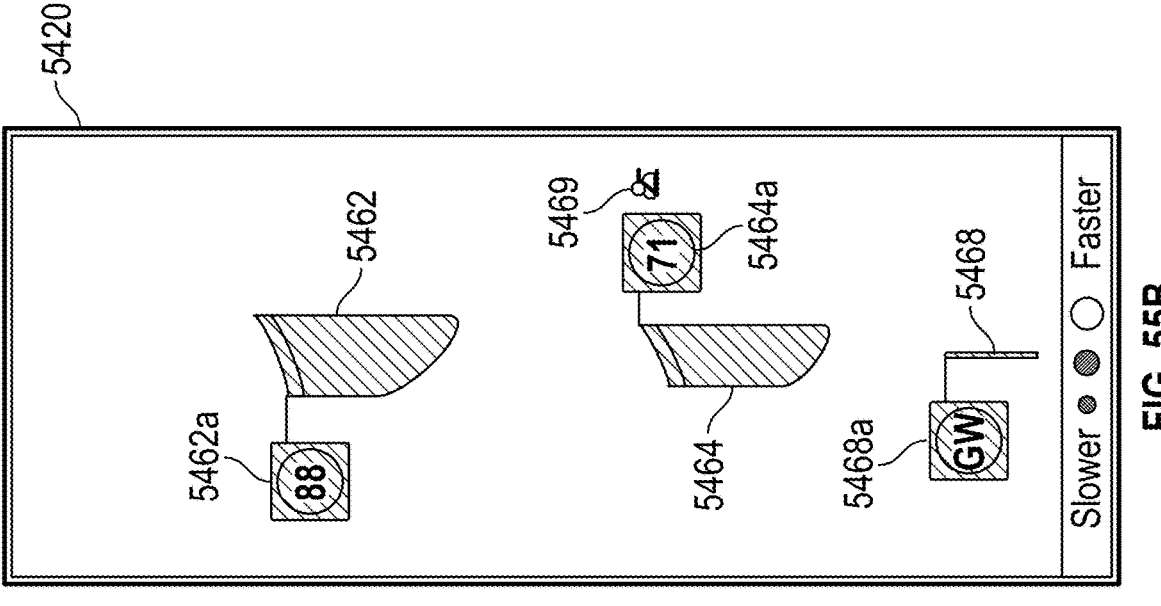
Figure 55A:
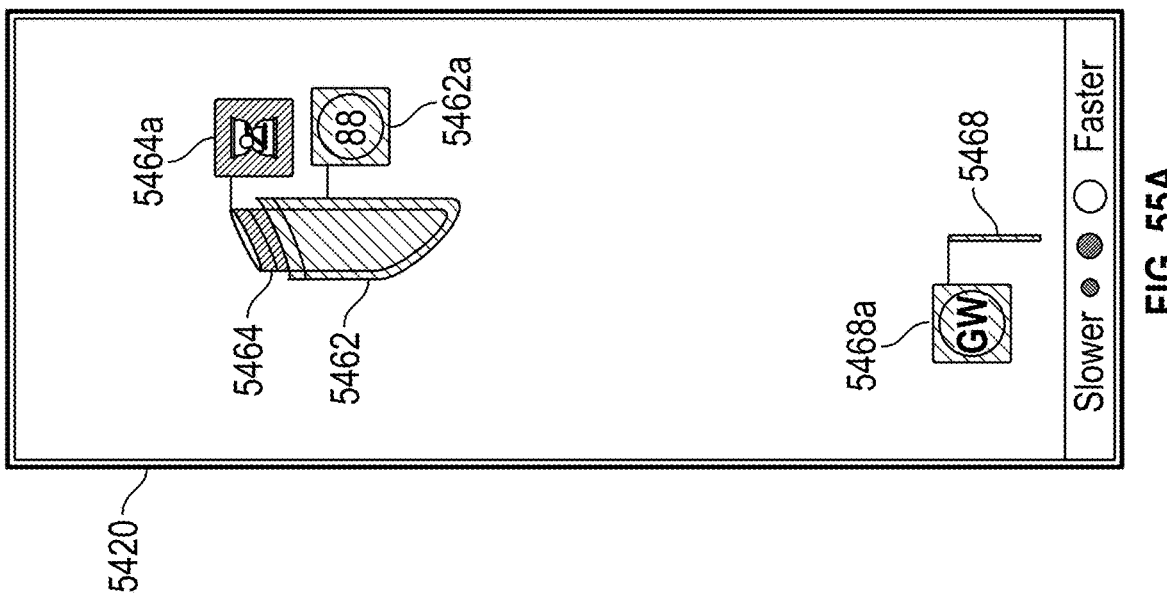

The instrument window 5420 can provide an indication of whether aspiration is being applied via the interventional devices associated with the interventional device representations 5462, 5464, 5466, 5468. For example, the interventional device representations 5462, 5464, 5466, 5468 and/or the interventional device markers 5462a, 5464a, 5466a, 5468a may change from a first color (e.g., purple), texture, or pattern to a second color (e.g., green), texture or pattern to indicate that aspiration is active and/or available in one or more of the interventional devices. As shown, in FIG. 55A, the interventional device marker 5464a can display a symbol (e.g., an aspiration icon) to indicate that the interventional device associated with the interventional device marker 5464a is applying aspiration and/or that aspiration is available in that interventional device. In some cases, the aspiration symbol in the interventional device marker 5464a can replace the symbol, number, and or character that indicates the interventional device associated with the interventional device marker 5464a. The instrument window 5420 can also provide an indication of whether aspiration is unavailable. For example, the instrument window 5420 can display a symbol 5469, as shown in FIG. 55B. The symbol 5469 can be displayed next to an interventional device marker (e.g., interventional device marker 5464a). The symbol 5469 can provide an indication that aspiration is unavailable for the interventional device associated with the interventional device marker where the symbol is displayed.

Information regarding fluidics (e.g., the status and/or availability of contrast injection, other fluid delivery, and/or aspiration) may be received from a sensor system including one or more sensors (e.g., in the fluidics system, interventional devices, hubs, drive table, etc.).

Figures 56A, 56B, 56C:
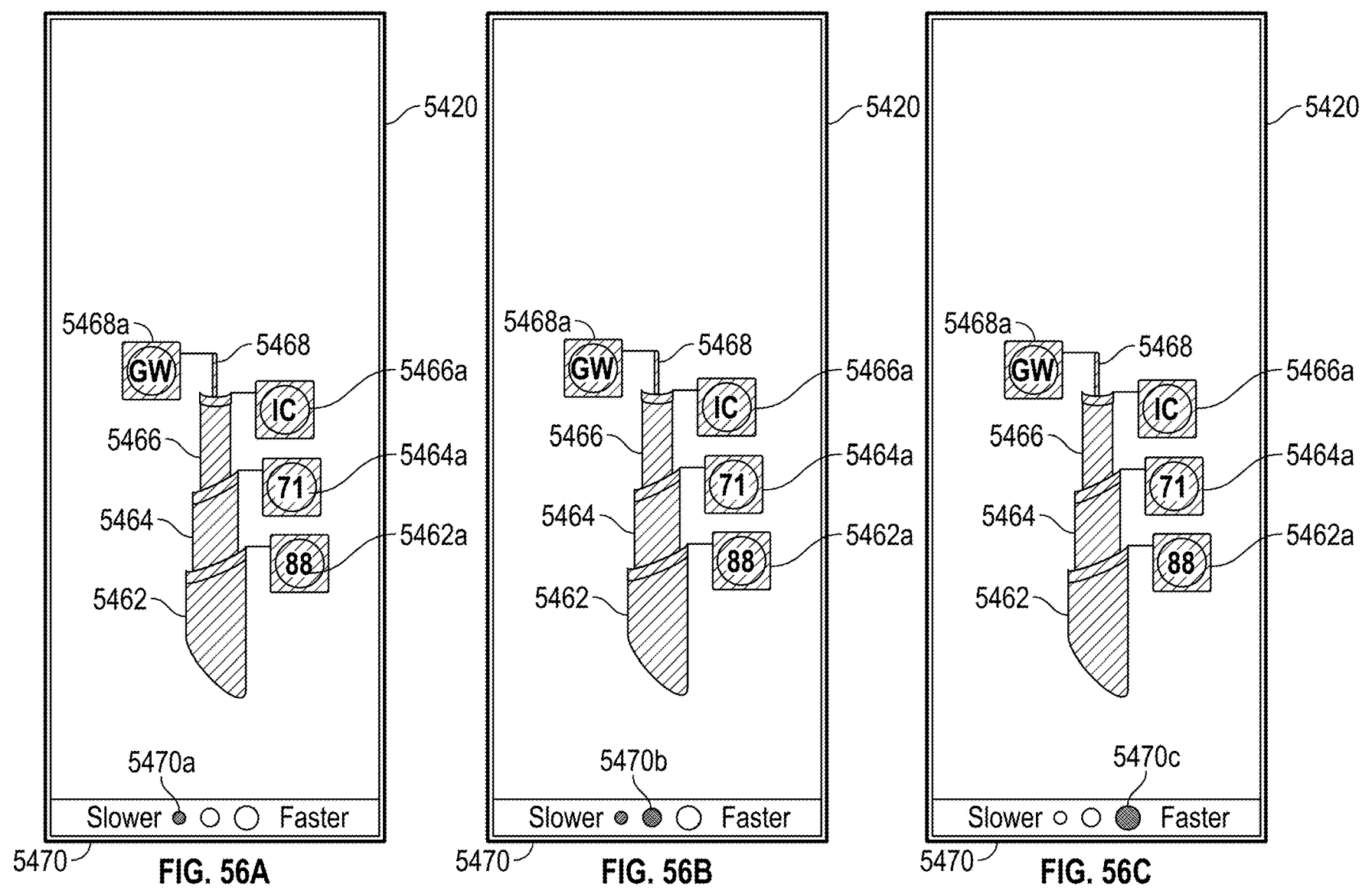

In cases where the interventional devices associated with the interventional device representations 5462, 5464, 5466, 5468 and/or the interventional device markers 5462a, 5464a, 5466a, 5468a can be operated at different speeds, the instrument window 5420 can provide an indication of the speed setting the interventional devices. For example, as shown in FIGS. 56A-56C, the instrument window 5420 can include a speed indicator 5470. The speed indicator 5470 can include one or more speed markers. In some cases, the speed indicator 5470 can include three speed markers, 5470a, 5470b, 5470c. The speed markers, 5470a, 5470b, 5470c can provide an indication about the speed at which the interventional devices associated with the interventional device representations 5462, 5464, 5466, 5468 are being operated. Each of the speed markers 5470a, 5470b, 5470c can be associated to a range of speeds (slow, medium, fast, etc.) over which the interventional device may be moved (axially and/or rotationally, in response to movement of a control (e.g., joystick 5332 or joystick 5334) of a controller (e.g., controller 5310).

The position of the interventional device markers 5462a, 5464a, 5466a, 5468a relative to the central longitudinal axis 5480 can provide an indication about which button, joystick, etc. of a control mechanism (e.g., control mechanism 5300) is controlling the interventional device associated with the interventional device markers 5462a, 5464a, 5466a, 5468a. In some embodiments, the position of the button, joystick, etc. (e.g., the first joystick 5332) relative to the central axis 5380 of the control mechanism 5300 can correspond to the positioning of the interventional device marker relative to the central longitudinal axis 5480 on the instrument window 5420. For example, as shown in FIGS. 56A-56C, the interventional device marker 5468a can be displayed left of the interventional device representation 5468 and the central longitudinal axis 5480 to indicate that the interventional device associated with the interventional device marker 5468a is being controlled and/or can be controlled by a left joystick (e.g., the first joystick 5332) of a control mechanism (e.g., handheld controller 5310). As another example, the interventional device markers 5462a, 5464a, 5466a can be displayed right of the interventional device representations 5462, 5464, 5466 to indicate that the interventional devices associated with the interventional device markers 5462a, 5464a, 5466a are being controlled and/or can be controlled by a right joystick (e.g., the second joystick 5334) of a control mechanism (e.g., handheld controller 5310). In some embodiments, the controller and user interface can be configured such that if a central axis of the controller (e.g., axis 5380) is aligned with a central axis of the interventional device representations (e.g., axis 5480), at least some movement of the joysticks can cause the interventional device representations to move in the same direction as the joysticks on the user interface. For example, forward or rearward movement of one of the joysticks can result in movement of the corresponding representations (due to movement of the corresponding interventional devices) in the same direction that the user moves the joystick. For example, with respect to FIG. 46, upward movement of the joystick 5332 along the axis A5 towards the button 5352 can cause a corresponding interventional device representation to move upward along the axis 5480 (e.g., towards the notification window 5430 in FIG. 47).

In some embodiments, as described herein, a user can operate a controller (e.g., controller 5310) to link an interventional device with a particular control of the controller (e.g., joystick 5332 or joystick 5334), for example, to temporarily change which interventional devices are controlled by which controls in a particular drive mode. In some embodiments, if a particular interventional device is linked to one of a first control and a second control, and is then subsequently linked to the other of the first control and the second control, the interventional device marker and/or pointer corresponding to the particular interventional device may switch from one side of the central axis 5480 to the other side of the central axis 5480. This change in appearance may make it easier for a user to see that a linkage has occurred.

In some embodiments, at the time a particular interventional device becomes linked with a particular control (e.g., in response to a user input), the interventional device representation, interventional device marker, and/or pointer corresponding to the particular interventional device may change in appearance (e.g., shape, pattern, texture, position, etc.) to indicate that the particular interventional device is linked to the particular control. For example, in certain embodiments, any of the same visual indications to indicate that an interventional device is currently being drive may (at least temporarily) be provided to indicate the link of the particular interventional device to the particular control. This change in appearance may make it easier for a user to see that a linkage has occurred.

For example, as described herein, FIG. 51A may be an example of an instrument window 5420 during a first drive mode, wherein a first control (e.g., joystick 5332) is linked to control a guidewire (corresponding to representation 5468), and a second control is linked to control an access catheter (corresponding to representation 5466), a procedure catheter (corresponding to representation 5464), and a guide catheter (corresponding to representation 5462). In response to a user input (e.g., actuation of a button 5352 of controller 5310), the guide catheter may be temporarily linked to the first control (e.g., joystick 5332). At the time the guide catheter is linked to the first control, the interventional device marker 5462a may move from the side of the axis 5480 associated with the second control (e.g., the right side of the central axis 5480 as shown in FIG. 51A) to the side of the axis 5480 associate with the first control (e.g., the left side of the central axis 5480). Additionally, in some embodiments, one or more of the marker 5462a, representation 5462, and pointer 5462c may change in appearance, at least temporarily, at the time the guide catheter becomes linked to the first control. The changes in appearance may be the same as or similar to any of the change in appearance that takes place when the guide catheter is driven. For example, the marker 5462a and or representation 5462 may change in appearance (e.g., including a color contrast or highlight relative to the other markers and/or representations) to indicate the linkage of the first control. In some embodiments, the other representations 5464, 5466, and 5468 and/or other markers 5464a, 5466a, and 5468a may additionally or alternatively change in appearance (e.g., including a color contrast (for example to be duller in color than representation 5462 and/or marker 5462a) or highlight relative to the representation 5462 and/or marker 5462a) to indicate the linkage of the first control. In some embodiments, the marker 5462a may move laterally away from the central axis 5480 to indicate the linkage of the guide catheter to the first control. In some embodiments, the pointer 5462c can extend or elongate between the representation 5462 and the marker 5462a to indicate the linkage of the guide catheter to the first control.

Figures 57, 58:
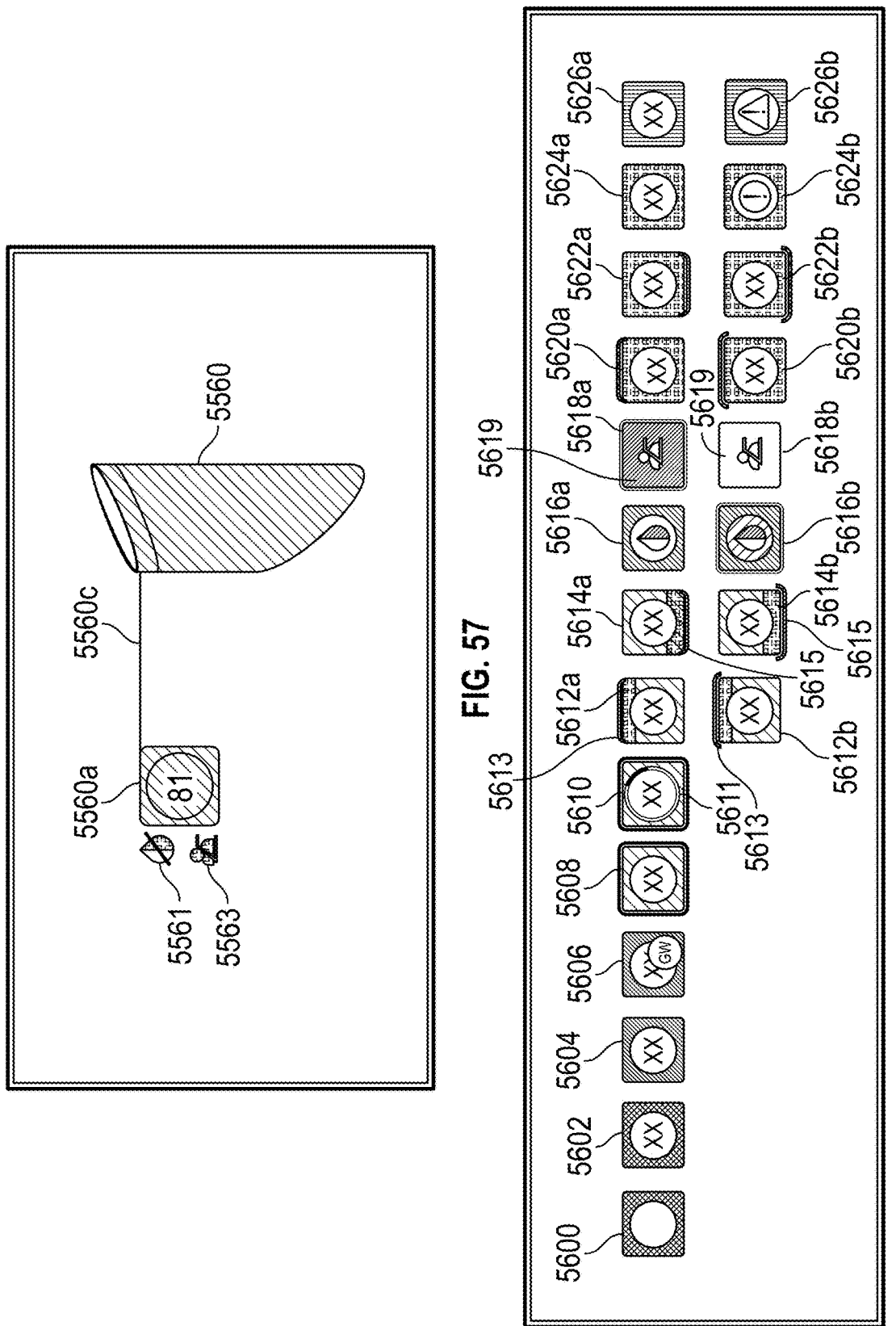

FIG. 57 shows another example of an interventional device representation 5560, an interventional device marker 5560*a*, an interventional device pointer 5560*c*, and symbols 5561, 5563 that can be displayed on the instrument window 5420. As previously described, the interventional device marker 5560*a* can provide an indication about the interventional device associated with the interventional device representation 5560. For example, as shown in FIG. 57, the interventional device marker 5560*a* can provide an indication that the interventional device representation 5560 is associated (e.g., linked) with a catheter (e.g., a 0.081 French catheter). The symbols 5561 and 5563 can provide an indication about the status of aspiration, contrast injection and/or other fluid delivery. For example, as shown in FIG. 57, the symbol 5561 can provide an indication that injection, and/or fluid delivery is disabled and/or unavailable. The symbol 5563 can provide an indication that aspiration is disabled and/or unavailable.

FIG. 58 shows examples of interventional device markers or appearances of interventional device markers that can be displayed on the instrument window 5420. The appearance of the interventional device markers can change to indicate a change in the status of the interventional devices associated with the interventional device markers. For example, one or more of the interventional device markers described herein with respect to FIGS. 48-57 may change in appearance to include the features of the markers shown in FIG. 58 to indicate a change in the status of the interventional devices associated with the interventional device markers. In some embodiments, any of the interventional device marker appearances shown in FIG. 58 can include a first animation state and a second animation state. The interventional device markers can transition from the first animation state to the second animation state to provide a visual indication of a change in the operation status of the interventional device associated with the interventional device markers. In some embodiments, the interventional device markers can include a first color (e.g., gray, transparent, purple, blue, green, yellow, red, etc.), texture, or pattern to indicate the status of the interventional device associated with the interventional device marker. The interventional device markers can also display a character set, symbol, and/or combination thereof to provide an indication of the interventional device associated with the interventional device markers and/or to provide an indication of the operational mode of the interventional device (e.g., active, inactive, enabled, disabled, aspiration on/off, fluid delivery on/off, etc.).

In some cases, an interventional device marker 5600 can be shown in a first color (e.g., gray), texture, or pattern to indicate that the interventional device associated with the interventional device marker 5600 is disabled. The interventional device marker 5600 may not include a character set, symbol, etc. to indicate that an interventional device is not associated (e.g., linked) with the interventional device marker 5600. Upon installation of an interventional device, the interventional device marker can display one or more character sets, symbols, etc. to provide an indication about the interventional device installed (e.g., as represented by "XX" in interventional device marker 5602). An interventional device marker 5604 can be shown in a second color (e.g., light purple), texture, or pattern to indicate that the interventional device associated with the interventional device marker 5604 is enabled. An interventional device marker 5606 can include a first character set or symbol (e.g., represented by "XX" in the interventional device marker 5606) and a second character set (e.g., "GW") to indicate that a first interventional device (e.g., a guide catheter and a second interventional device (e.g., a guidewire) are linked to each other.

An interventional device marker 5608 can be shown in a color (e.g., dark purple), texture, or pattern to indicate that the interventional device associated with the interventional device marker 5608 is being driven (e.g., being moved). As described in relation to FIG. 53, an interventional device marker 5610 can include a rotational indicator 5611 displayed inside the interventional device marker 5610. The rotational indicator 5611 can provide an indication about the rotational position of the interventional device associated with the interventional device marker 5610. For example, the rotational indicator 5611 can include a ring shaped progress bar. As the interventional device associated with the interventional device marker 5610 is rotated, the ring shaped progress bar may start filling in a clockwise and/or counterclockwise directions to provide a visual indication about the direction in which the interventional device has rotated and/or the degree of rotational motion of the interventional device. For example, and as shown by the interventional device marker 5610, the ring shaped progress bar of the rotational indicator 5611 can be filled by about 25% in a clockwise direction to indicate that the interventional device has been rotated, from a starting position, one quarter of a revolution in a clockwise direction. As another example, the ring shaped progress bar of the rotational indicator can be filled by about 50% in a counterclockwise direction to provide a visual indication that the interventional device has been rotated, from a starting position, half a revolution in a counterclockwise direction. The ring shaped progress bar of the rotational indicator 5611 may reset (e.g., be empty) when the interventional device complete a full revolution.

Any of the interventional device markers described herein can provide an alert when the interventional device associated with the interventional device marker (and/or the hub associated with the interventional device) is nearing a proximal end and/or a distal end of their motion range. In some embodiments, the appearance of the interventional device markers can change to indicate a particular state and/or status of the interventional device. An interventional device marker can transition from a first animation state to a second animation state to provide a visual indication about the status and/or operation state of the interventional device associated with an interventional device marker and/or interventional device representation. For example, in a first animation state, an interventional device marker 5612*a* can display a color (e.g., yellow), texture, or pattern on a top portion of the interventional device marker 5612*a* to indicate that that the interventional device associated with the interventional device marker 5612*a* is nearing a distal drive limit (e.g., nearing a maximum allowable distal position or nearing a hub positioned distally to the hub of the associated interventional device). When the interventional device associated with the interventional device marker 5612*a* gets closer to the distal drive limit, the interventional device marker 5612*a* can transition to a second animation state, as represented by the interventional device marker 5612*b*.

In the second animation state, a portion of the second interventional device marker 5612*b* can be different than the interventional device marker 5612*a*. For example, an indicator 5613 along a top portion of the interventional device marker 5612*b* can extend out of the top edge of the interventional device marker 5612*b*. In the first animation state, the indicator 5613 can be shown bounded within the top edge of the of the interventional device marker 5612*a*. The transition of the interventional device markers from the first animation state to the second animation state can be progressive, as opposed to just switching from the interventional device marker 5612a to the interventional device marker 5612b. This can beneficially allow clinicians to assess how far or close the interventional device associated with the interventional device markers 5612a, 5612b is from the distal drive limit.

The interventional device markers can also provide an indication of whether the interventional device (and/or the hub associated with the interventional device) associated with an interventional device marker is nearing a proximal drive limit (e.g., nearing a maximum allowable proximal position or nearing a hub positioned proximally to the hub of the associated interventional device). In a first animation state, an interventional device marker 5614a can display a color (e.g., yellow), texture, or pattern on a bottom portion of the interventional device marker 5614a to indicate that that the interventional device associated with the interventional device marker 5614a is nearing a proximal drive limit. When the interventional device associated with the interventional device marker 5614a gets closer to the proximal drive limit, the interventional device marker 5614a can transition to a second animation state, as represented by the interventional device marker 5614b.

In the second animation state, a portion of the second interventional device marker 5614b can be different than the interventional device marker 5614a. For example, an indicator 5615 along a bottom portion of the interventional device marker 5614b can extend out of the bottom edge of the interventional device marker 5614b. In the first animation state, the indicator 5615 can be shown bounded within the bottom edge of the of the interventional device marker 5614a. The transition of the interventional device markers from the first animation state to the second animation state can be progressive, as opposed to just switching from the interventional device marker 5614a to the interventional device marker 5614b. This can beneficially allow clinicians to assess how far or close the interventional device associated with the interventional device markers 5614a, 5614b is from the proximal drive limit.

In some cases, any of the interventional device markers described herein can be shown in a color (e.g., blue), texture, or pattern to indicate that contrast injection and/or other fluid delivery is available and/or active at the interventional device associated with the interventional device markers. In some cases, the interventional device markers can transition from a first animation state to a second animation state to provide a visual indication about the status and/or operation state of the interventional device and/or the application of contrast injection and/or other fluid delivery. For example, in a first animation state, an interventional device marker 5616a can include a symbol and/or a picture (e.g., a water drop) to indicate, for example, that contrast injection and/or other fluid delivery is available at the interventional device associated with the interventional device marker 5616a. In a second animation state, the interventional device marker 5616b can include a color contrast and/or highlight around its edge to indicate that contrast injection and/or other fluid delivery is active on the interventional device associated with the interventional device marker 5616b.

In some cases, the interventional device markers can show an action being undertaken by an interventional device and/or the progression of the action. An interventional device marker 5618a can be shown in a color (e.g., green), texture, or pattern to indicate that aspiration is available and/or active at the interventional device associated with the interventional device marker 5618a. The interventional device markers can transition from a first animation state to a second animation state to provide a visual indication about the status of aspiration in the interventional devices associated with the interventional device markers. For example, in a first animation state, the interventional device marker 5618a can include an aspiration indicator 5619. The aspiration indicator 5619 can provide a visual indication about the amount of aspiration time available in the interventional device associated with the interventional device marker 5618a. In the first animation state, the aspiration indicator 5619 can be represented by a bar in a full position, as shown by the interventional device marker 5618a. As aspiration is applied and the availability of aspiration decreases, a height of the of the bar of the aspiration indicator 5619 may start decreasing until aspiration at the interventional device is no longer available. When aspiration is no longer available and/or expired, the interventional device marker 5618a can transition to a second animation state, as represented by the interventional device marker 5618b. In the second animation state, the bar of the aspiration indicator may disappear to indicate that aspiration is not available at the aspiration catheter associated with the interventional device marker 5618b. As aspiration is restored in the interventional device, the bar of the aspiration indicator 5619 may transition from the first animation state to a second animation state, to provide an indication that aspiration at the interventional has been restored. In some cases, the interventional device marker 5618a can include a color contrast and/or highlight around its edge to indicate that aspiration is active on the interventional device associated with the marker 5618a.

The interventional device markers described herein can provide an alert when the interventional devices (and/or the hubs associated with the interventional devices) associated with the interventional device markers have reached a proximal drive limit and/or a distal drive limit. In some cases, the interventional device markers can include two or more animations states to indicate an event and/or action being undertaken by the interventional device. For example, in a first animation state, an interventional device marker 5620a can display a color (e.g., yellow), texture, or pattern on a top portion of the interventional device marker 5620a to indicate that that the interventional device associated with the interventional device marker 5620a has reached a distal drive limit (e.g., cannot be advanced any more). In a second state, at least a portion of the interventional device marker 5620b can extend outside a top edge of the interventional device marker 5620b when a clinician attempts to extend the interventional device beyond the distal drive limit of the interventional device (e.g., after the first animation state has already been displayed).

The interventional device markers can transition from a first animation state to a second animation state to indicate that the intervention devices have reached a proximal drive limit. For example, in a first animation state, an interventional device marker 5622a can display a color (e.g., yellow), texture, or pattern on a bottom portion of the interventional device marker 5622a to indicate that that the interventional device associated with the interventional device marker 5622a has reached a proximal drive limit (e.g., cannot be retracted any more). In a second state, at least a portion of the interventional device marker 5622b can extend outside a bottom edge of the interventional device marker 5622b when a clinician attempts to retract the interventional device beyond the proximal drive limit of the interventional device (e.g., after the first animation state has already been displayed).

In some cases, in a first animation state, an interventional device marker 5624a can be shown in a color (e.g., yellow), texture, or pattern to provide a warning about the device associated with the interventional device marker 5624a (e.g., that the interventional device and/or hub associated with the interventional device may be experiencing a high force and/or resistance). In a second animation state, an interventional device marker 5624b can also display a warning sign. In a first animation state, an interventional device marker 5626a can be shown in a color (e.g., red), texture, or pattern to indicate that there is an error with the device associated with the interventional device marker 5626a (e.g., that the interventional device has disconnected, is not working properly, etc.). In a second state, an interventional device marker 5626b can display can also display a warning sign.

While the appearances of the markers in FIG. 58 are described with respect to examples of different markers, one of skill in the art would understand that any of the markers described herein may change appearance to include features of any of the markers described in FIG. 58 to provide information to a user regarding the status of the interventional devices and/or other features of the drive system.

Figure 59:
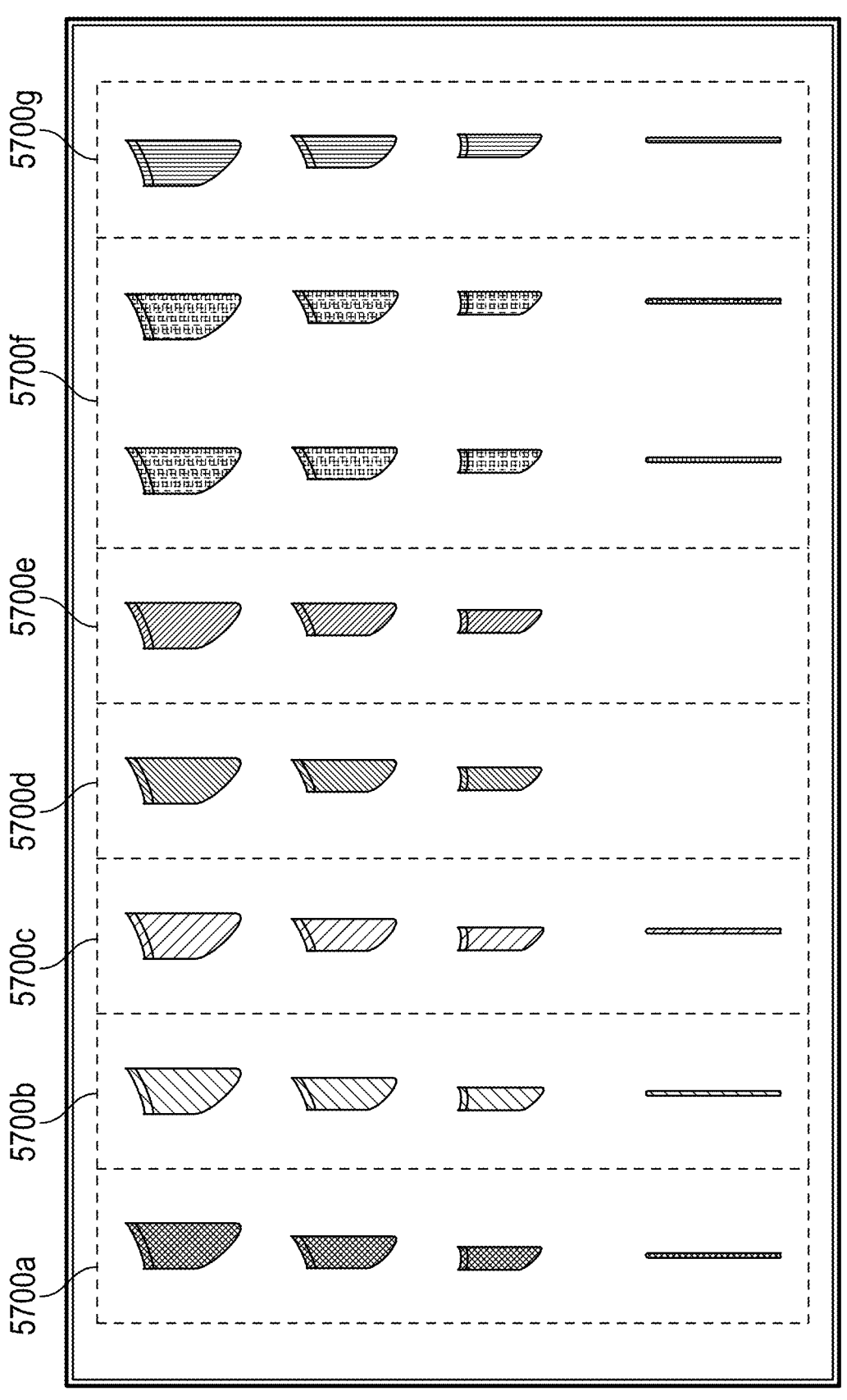

FIG. 59 shows examples of interventional device representations that can be displayed on the instrument window 5420. The interventional device representation can include a first color (e.g., gray, transparent, purple, blue, green, yellow, red, etc.), texture, or pattern to indicate the status of the interventional device associated with the interventional device representation.

In some cases, the interventional device representation 5700a can be shown in a first color (e.g., gray), texture, or pattern to indicate that the interventional device associated with the interventional device representation 5700a is disabled. The interventional device representation 5700b can be shown in a second color (e.g., light purple), texture, or pattern to indicate that the interventional device associated with the interventional device representation 5700b is enabled. The interventional device representation 5700c can be shown in a third color (e.g., dark purple), texture, or pattern to indicate that the interventional device associated with the interventional device representation 5700c is being driven (e.g., being moved). In some cases, the interventional device representation 5700d can be shown in a fourth color (e.g., blue), texture, or pattern to indicate that contrast injection and/or other fluid delivery is available and/or active at the interventional device associated with the interventional device representation 5700d. The interventional device representation 5700e can be shown in a fifth color (e.g., green), texture, or pattern to indicate that aspiration is available and/or active at the interventional device associated with the interventional device representation 5700e. In some cases, the interventional device representation 5700f can be shown in a sixth color (e.g., yellow), texture, or pattern to provide a warning about the device associated with the interventional device representation 5700f (e.g., that the interventional device and/or puck associated with the interventional device may be experiencing a high force and/or resistance). The interventional device representation 5700g can be shown in a seventh color (e.g., red), texture, or pattern to indicate that there is an error with the device associated with the interventional device representation 5700g (e.g., that the interventional device has disconnected, is not working properly, etc.).

Any of the embodiments of controllers and control systems described herein can be used to control a telescoping drive table and/or a drive table configured to move axially to cause axial movement of a hub adapter coupled to the drive table. For example, in certain embodiments, when a control (e.g., control 5332 or control 5334) is actuated to cause a corresponding axial movement of a particular hub and/or interventional device coupled to that hub, the corresponding axial movement of the particular hub and/or interventional device can be effectuated by an axial movement of the drive table itself or a component within the drive table (e.g., a shuttle) to which one or more hub adapters are coupled, alternatively or in addition to axial movement of the hub adapter to which the particular hub and/or interventional device is coupled along the drive table or component within the drive table.

Figure 60A:
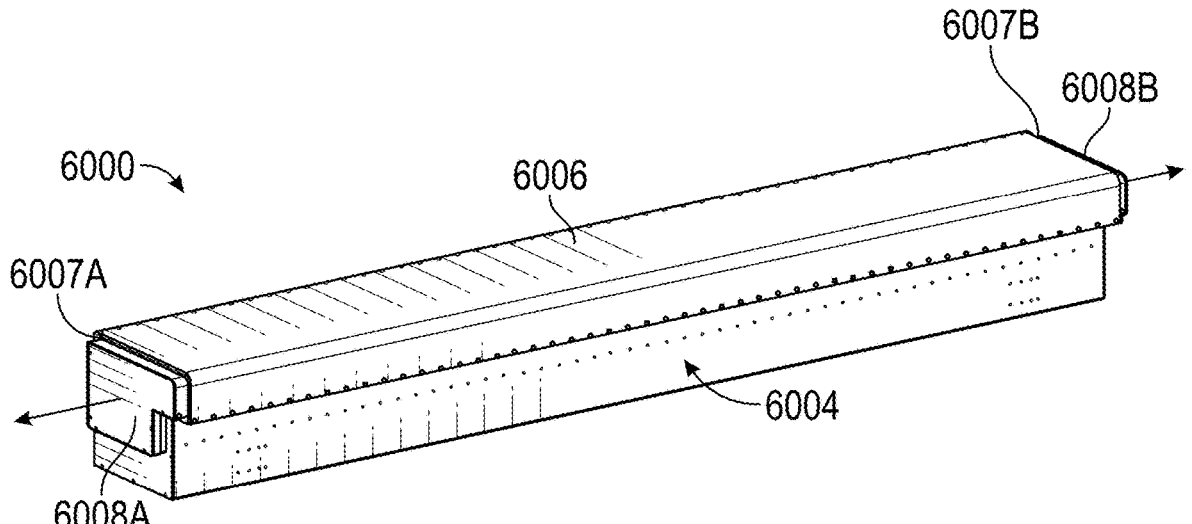
FIGS. 60A-60D illustrate an embodiment of a telescoping drive table.

FIGS. 60A-60D illustrate an embodiment of a telescoping drive table 6000. FIG. 60A illustrates a front perspective view of a telescoping drive table 6000. As shown in FIG. 24A, the telescoping drive table 6000 can include a main body 6004 and one or more telescoping members 6008A, 6008B. The telescoping members 6008A, 6008B may also be referred to as arms, extensions, extending members, table segments, or actuating beams. The main body 6004 can further include a support surface 6006 and one or more openings 6007A, 6007B. In some embodiments, the support surface 6006 may be a sterile barrier or form at least a portion of a sterile barrier. In some embodiments, the telescoping drive table 6000 may further include a separate sterile barrier.

The telescoping drive table 6000 can be the same or similar to any of the drive tables described herein. For example, the telescoping drive table 6000 may have any of the same or similar features and/or functions as the support table 20 described above. The telescoping drive table 6000 can transition between two or more lengths. In some embodiments, the one or more telescoping members 6008A, 6008B may extend from the main body 6004 (e.g., in a proximal and/or distal direction). The extension of the one or more telescoping members 6008A, 6008B from the main body 6004 may increase the longitudinal length of the telescoping drive table 6000 from a first length to a second length. The second length may include the length of the main body 6004 and at least a portion of the one or more telescoping members 6008A, 6008B. In some embodiments, the second length may include the sum of the length of the main body 6004 and the lengths of the one or more telescoping members 6008A, 6008B.

The main body 6004 can form an outer shell or housing of the telescoping drive table 6000 for housing internal components. For example, the main body 6004 may include one or more actuators, such as linear actuator assemblies. The main body 6004 can be defined by one or more exterior walls defining an interior cavity. The main body 6004 can have a longitudinal length. The longitudinal length of the main body 6004 can be fixed. The longitudinal length of the main body 6004 can be between 3 feet and 5 feet. For example, in some embodiments, the main body 6004 may have a longitudinal length of 4 feet. The main body 6004 can have a first end and a second end. In some embodiments, the first end may be positioned at a first longitudinal end of the main body 6004 and the second end may be positioned at a second longitudinal end of the main body 6004 opposite the first end.

The support surface 6006 can be a surface configured to support one or more hubs and/or interventional devices. In some embodiments, the support surface 6006 may be the superior or upper surface of the main body 6004.

The one or more openings 6007A, 6007B can provide access to an internal cavity of the main body 6004. The internal cavity can be defined by the main body 6004. In some embodiments, the one or more openings 6007A, 6007B may be sized to receive at the one or more telescoping members 6008A, 6008B. For example, in certain embodiments, the main body 6004 may include a single opening 6007A or 6007B configured to receive a single telescoping member 6008A or 6008B. In other embodiments, the main body can include a first opening 6007A configured to receive a first telescoping member 6008A and a second opening 6007B configured to receive a second telescoping member 6008B. In some embodiments, the one or more openings 6007A, 6007B may be positioned on lateral ends of the main body 6004. In some embodiments, the one or more openings 6007A, 6007B may be shaped to correspond to the profile of the one or more telescoping members 6008A, 6008B.

The one or more telescoping members 6008A, 6008B can transition between a collapsed state and a deployed state. The transition of the one or more telescoping members 6008A, 6008B between the collapsed state and the deployed state can adjust the overall length of the telescoping drive table 6000. Each of the one or more telescoping members 6008A, 6008B can be sized relative to the main body 6004. In some embodiments, each of the one or more telescoping members 6008A, 6008B may be sized to fit within the main body 6004. In some embodiments, the one or more telescoping members 6008A, 6008B may have the same structure or can share one or more of the same dimensions. For example, each of the one or more telescoping members 6008A, 6008B may have the same longitudinal length. In some embodiments, the one or more telescoping members 6008A, 6008B may have a longitudinal length up to half the length of the main body 6004. In some embodiments, the telescoping drive table 6000 may include two telescoping members 6008A, 6008B. In some embodiments, the one or more telescoping members 6008A, 6008B may have a first telescoping member 6008A and a second telescoping member 6008B. In some embodiments, the first telescoping member 6008A may extend from a first end of the main body 6004 and the second telescoping member 6008B may extend from a second end of the main body 6004.

The main body 6004 can slidably receive the one or more telescoping members 6008A, 6008B through the one or more openings 6007A, 6007B, respectively. Each of the one or more telescoping members 6008A, 6008B can be coupled to a corresponding linear actuator assembly housed within the main body 6004. The one or more telescoping members 6008A, 6008B may be configured to extend linearly along an axis between a collapsed state and deployed state. In the collapsed state, the one or more telescoping members 6008A, 6008B can be contained entirely within the main body 6004 such that the overall length of the telescoping drive table 6000 can be the length of the main body 6004. In other embodiments, the one or more telescoping members 6008A, 6008B can be partially contained within the main body in the collapsed state. For example, as shown in FIG. 60A, the one or more telescoping members 6008A, 6008B can be substantially contained within the main body 6004. In the deployed state, the one or more telescoping members 6008A, 6008B can extend linearly away from the main body 6004. In some embodiments, the one or more telescoping members 6008A, 6008B may be simultaneously controlled such that the effective length (e.g., the length of the one or more telescoping members 6008A, 6008B extending outside of the main body 6004) of each of the one or more telescoping members 6008A, 6008B is the same. In some embodiments, the one or more telescoping members 6008A, 6008B may be independently controlled such that the effective length of one of the one or more telescoping members 6008A, 6008B is independent of the effective length of the other one or more telescoping members 6008A, 6008B.

In some embodiments, the collapsed state may be used for storing the telescoping drive table 6000. In some embodiments, the deployed state may be used during an operation to provide a greater length to drive one or more hubs and/or interventional devices.

In some embodiments, a sterile barrier may be positioned along or form a top surface (e.g., support surface 6006) of the telescoping drive table 6000. The sterile barrier may be configured to prevent contamination of a surgical area. The sterile barrier may be a deployable or extendable (e.g., telescoping) sterile barrier. In some embodiments, the sterile barrier may be configured to extend with the one or more telescoping members 6008A, 6008B. In a collapsed state, the sterile barrier may have a length of the main body 6004. In a deployed state, the sterile barrier may have a length corresponding to the sum of the length of the main body 6004 and the deployed length of the one or more telescoping members 6008A, 6008B. Accordingly, the sterile barrier may extend along the combined length of the telescoping drive table 6000. The sterile barrier may advantageously allow a hub to transition from a position on the main body 6004 to a position on one of the one or more telescoping members 6008A, 6008B and vice versa.

The telescoping drive table 6000 can be controlled either manually or automatically via a control system. In some embodiments, the telescoping drive table 6000 may be in a collapsed position until activated prior to a surgical procedure. For example, the telescoping drive table 6000 may transition from the collapsed state to the deployed state before a patient enters the operating room. Alternatively, the telescoping drive table 6000 may transition from the collapsed state to the deployed state after a patient is prepped for surgery and positioned on an operating table. The telescoping drive table 6000 may thus advantageously conserve space within an operating room when not in use and advantageously expand when needed during a surgical procedure.

Figure 60B:
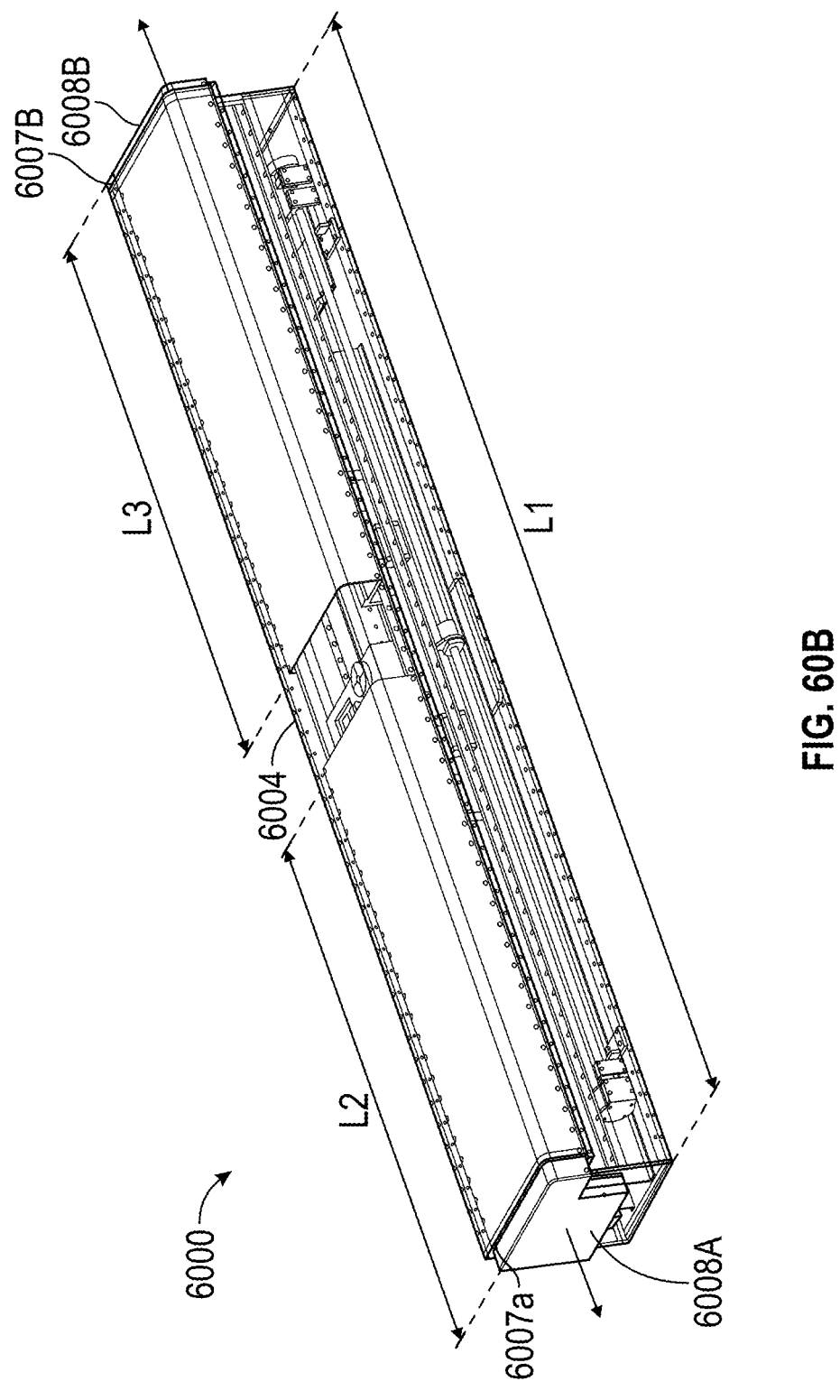

FIG. 60B illustrates a front perspective view of the interior components of the telescoping drive table 6000 in a collapsed state.

As further illustrated in FIG. 60B, the main body 6004 can have a longitudinal length shown in FIG. 60B as a first length L1. In some embodiments, the first length L1 of the main body 6004 may be between 3 feet and 5 feet. For example, the first length L1 may be 4 feet.

As further illustrated in FIG. 60B, the one or more telescoping members 6008A, 6008B can each have a longitudinal length represented by a second length L2 and a third length L3, respectively. In some embodiments, the second length L2 and the third length L3 may be half as long as the first length L1. For example, the second length L2 and the third length L3 may be 2 feet when the first length L1 is 4 feet. In some such embodiments, the one or more telescoping members 6008A, 6008B may be completely contained within the main body 6004 in the collapsed state. Additionally, the one or more telescoping members 6008A, 6008B can double the overall length of the telescoping drive table 6000 in the deployed state. In some embodiments, the second length L2 of the one or more telescoping members 6008A, 6008B is less than half of the first length L1 of the main body 6004 (e.g., ⅓ of the length L1, ¼ of the length L1, or any other suitable length. In some embodiments, a total length of the table 6000 when the telescoping members 6008A and 6008B are fully extended can be between 1 meter and 2.7 meters.

Figure 60C:
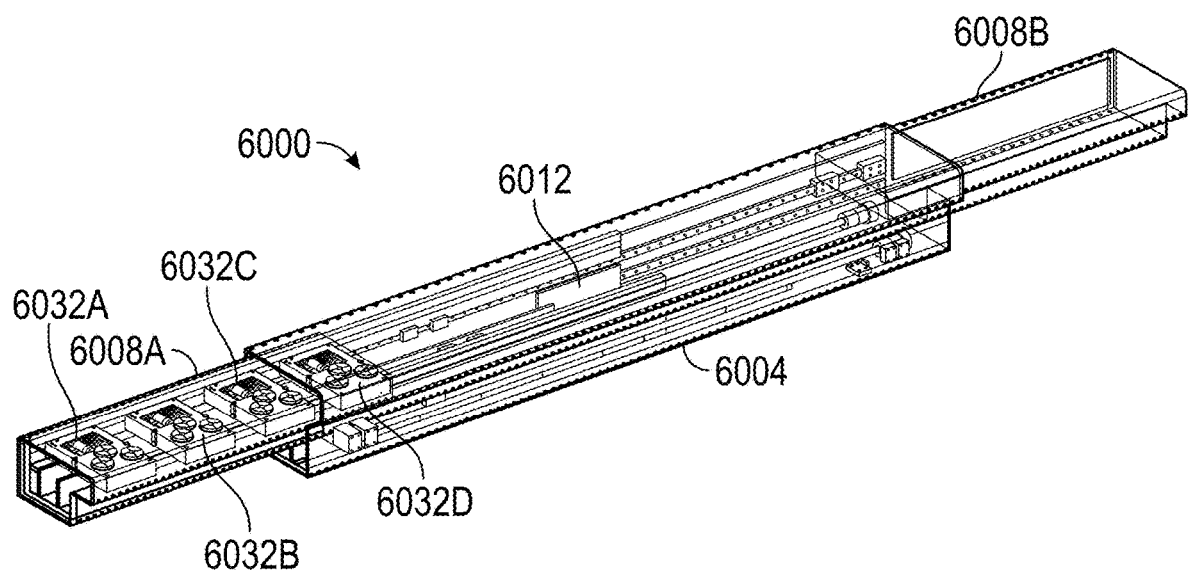
Figure 60D:
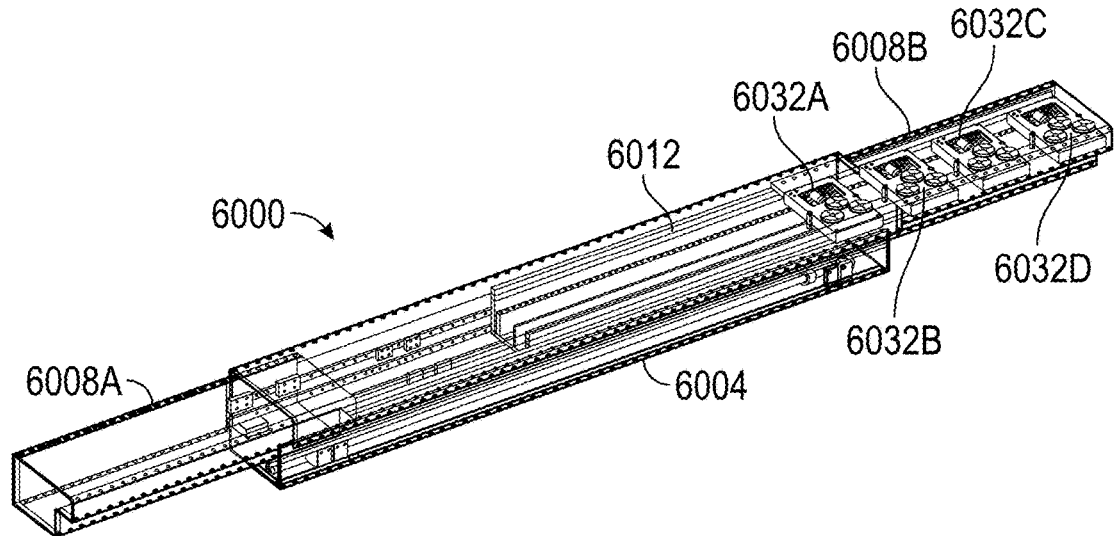

FIGS. 60C-60D illustrate the telescoping drive table 6000 in a deployed configuration in which the arms 6008A and 6008B are extended out of the main body 6004 and showing internal features of the telescoping drive table 6000.

As shown in FIGS. 60C-60D, the telescoping drive table 6000 can one or more hub adapters. The one or more hub adapters can include a first hub adapter 6032A, a second hub adapter 6032B, a third hub adapter 6032C, and a fourth hub adapter 6032D.

In certain embodiments, the telescoping drive table 6000 can include a shuttle 6012.

The one or more hub adapters 6032A-D can be sequentially placed along the shuttle 6012. In some embodiments, the first hub adapter 6032A can be positioned at a distal end of the shuttle 6012 and the fourth hub adapter 6032D can be positioned at a proximal end, or vice versa.

In certain embodiments, one or more linear actuator assemblies can be configured to move the telescoping members 6008A and 6008B, the shuttle 6012, and/or the hub adapters 6032A-D. For example, in some embodiments, one or more first linear actuator assemblies may translate the shuttle 6012 within the main body 6004 and the one or more telescoping members 6008A and 6008B. In some embodiments, one or more second linear actuator assemblies may translate the hub adapters 6032A-6032B along the shuttle 6012. In some embodiments, one or more third linear actuator assemblies can translate one or more of the telescoping members 6008A and 6008B between a collapsed state and a deployed state.

In some embodiments, the one or more telescoping members 6008A and 6008B can be configured to be deployed to extend from the main body 6004 at the time of setup of the drive table 6000 for a surgical procedure (in response to one or more user inputs). In some embodiments, telescoping member 6008A can be configured to deploy to allow further distal movement of the shuttle 6012. For example, if distal movement of the shuttle 6012 beyond a distal end of the main body 6004 is instructed (e.g., to facilitate distal movement of one or more interventional devices coupled to the hub adapters 6032A-D beyond a distal end of the main body 6004), the telescoping member 6008A can extend distally from the main body 6008A. In some embodiments, telescoping member 6008B can be configured to deploy to allow further proximal movement of the shuttle 6012. For example, if proximal movement of the shuttle 6012 beyond a proximal end of the main body 6004 is instructed (e.g., to facilitate proximal movement of one or more interventional devices coupled to the hub adapters 6032A-D beyond a proximal end of the main body 6004), the telescoping member 6008B can extend proximally from the main body 6008A.

As described herein, the shuttle 6012 can move axially along the length of the telescoping drive table 6000 (e.g., by a first linear actuator assembly). The shuttle 6012 can translate between the ends of the one or more telescoping members 6008A, 6008B. As shown in FIG. 60C, the shuttle 6012 can translate to be positioned at least partially in the first telescoping member 6008A. As shown in FIG. 60D, the shuttle 6012 can translated to be positioned at least partially in the second telescoping member 6008B.

In some embodiments, the length of the shuttle 6012 may be limited to the length of the main body 6004. The shuttle 6012 may be configured to extend along a full length of the telescoping drive table 6000 when one or more the telescoping members 6008A and 6008B are fully extended (e.g., the combined length of the main body 6004 and one or more of the telescoping members 6008A, 6008B).

In some embodiments, the shuttle 6012 can be translated within the main body 6004 and/or one or more telescoping members 6008A and 6008B to advantageously provide a full range of motion for the one or more hub adapters 6032A-D along the combined length of the main body 6004 and the one or more telescoping members 6008A, 6008B. In some embodiments, the shuttle 6012 can position the hub adapters 6032A-D in a general position.

As described above, the one or more hub adapters 6032A-D can translate along the length of the shuttle 6012 (e.g., by a second linear actuator assembly). In some embodiments, each of the one or more hub adapters 6032A-D can translate along the shuttle 6012 to a local position. Accordingly, each of the one or more hub adapters 6032A-D can be precisely positioned within the general position provided by the shuttle 6012. As shown in FIG. 60C, at least some of the hub adapters 6032A-D are positioned within the telescoping member 6008A at positions distal to a distal end of the main body 6004. As shown in FIG. 60D, at least some of the hub adapters 6032A-D are positioned within the telescoping member 6008B at positions proximal to a proximal end of the main body 6004.

In some embodiments, the shuttle 6012 may move to a general position along the length of the telescoping drive table 6000 before the one or more hub adapters 6032A-D move to a local position along the length of the shuttle 6012. Additionally and/or alternatively, the one or more hub adapters 6032A-D can move relative to the shuttle 6012 simultaneously with the shuttle 6012, as the shuttle 6012 translates along the length of the telescoping drive table 6000. In some embodiments, the shuttle 6012 can move to adjust an axial position of at least one of the hub adapters 6032A-D to a desired axial position (for example, to adjust the position of a coupled interventional device to a desired axial position), either while the at least one of the hub adapters 6032A-D is maintained at a fixed position along the shuttle 6012 or while the at least one of the hub adapters 6032A-D moves along the shuttle 6012.

In certain embodiments, the telescoping drive table 6000 can be configured to maintain at least one of the one or more hub adapters 6032A-D in a fixed position relative to a reference point when the shuttle 6012 is moved in a first axial direction relative to the reference point by moving the at least one of the one or more hub adapters 6032A in a second axial direction relative to the shuttle 6012 that is opposite to the first axial direction as the shuttle 6012 is moved in the first axial direction. The reference point can be a position along the main body 6004 and/or a designated location on the patient (e.g., a femoral access point). Similarly, the telescoping drive table 6000 can be configured to maintain additional hub adapters 6032A-D in a fixed position relative to a reference point when the shuttle 6012 is moved. For example, as the shuttle 6012 is moved, such as to move the first hub adapter 6032A (and corresponding interventional device), the position of the second hub adapter 6032B (and corresponding interventional device) relative to a reference point can be maintained or fixed by moving the second hub adapter 6032B along the shuttle 6012 by an equal magnitude or speed as compared to a movement of the shuttle 6012 in an opposite direction (e.g., if movement of the shuttle 6012 is not intended to cause axial movement of the interventional device coupled to the hub adapter 6032B). The third hub adapter 6032C and/or the fourth hub adapter 6032D (and/or any other additional hub adapters) can similarly be maintained in a fixed position relative to a patient reference point when the shuttle 6012 is moved relative to the reference point (e.g., if movement of the shuttle 6012 is not intended to cause axial movement of the interventional devices coupled to the hub adapters 6032C and/or 6032D).

In some embodiments, in response to user operation of controls to move the one or more hub adapters 6032A-D, the telescoping drive table 6000 can cause the one or more hub adapters 6032A-D to adjust their positions relative to one another to correspond to the positions they would be in if each of the one or more hub adapters 6032A-D were independently movable along an entirety of the length of the telescoping drive table 6000 in the absence of a shuttle 6012. For example, in response to a user control operation (e.g., manipulation of a first control) to move the interventional device coupled to the first hub adapter 6032A in a distal direction by moving the shuttle 6012 in the distal direction, the telescoping drive table 6000 can adjust the positions of the remaining hub adapters (e.g., the second hub adapter 6032B, the third hub adapter 6032C, and/or the fourth hub adapter 6032D) so that they move along the shuttle 6012 in the in the proximal direction by an equal magnitude or speed.

In response to control operations to axially move the first hub adapter 6032A (via movement of the shuttle 6012) and also axially move one or more of the other hub adapters 6032, the telescoping drive table 6000 can move the other hub adapters 6032 to the same position relative to a reference point or relative to the first hub adapter 6032A that they would be moved to in the absence of movement of the shuttle 6012. For example, if a user performs a control operation to move the first hub adapter 6032A and the second hub adapter 6032B distally by 5 mm, the telescoping drive table 6000 may move the shuttle 6012 distally by 5 mm without moving the first hub adapter 6032A or the second hub adapter 6032B relative to the shuttle 6012. If a user performs a control operation to move the first hub adapter 6032A distally by 5 mm and the second hub adapter 6032B distally by 6 mm, the telescoping drive table 6000 may move the shuttle 6012 distally by 5 mm and move the second hub adapter 6032B distally along the shuttle 6012 by 1 mm so that the second hub adapter 6032B has moved a total of 6 mm distally relative to the reference point. Alternatively, the telescoping drive table 6000 may move the shuttle 6012 by 4 mm, move the first hub adapter 6032A by 1 mm and the second hub adapter 6032B by 2 mm, or any other suitable combination of shuttle 6012 movement and hub adapter movement to translate the hub adapters 6032A and 6032B to the appropriate positions.

In certain embodiments, the telescoping drive table 6000 can be configured to adjust the positions of the hub adapters 6032A-D along the shuttle 6012 to maintain desired relative positions of interventional devices coupled to the hub adapters 6032 while the shuttle 6012 translates axially. For example, if the shuttle 6012 is translated in a first direction to cause a desired axial translation of an interventional device coupled to the hub adapter 6032A in the first direction relative to the interventional devices coupled to the hub adapters 6032B-D, the hub adapters 6032B-D may translate along the shuttle 6012 in a second direction opposite of the first direction to maintain the desired relative positioning of the interventional devices coupled to the hub adapters 6032B-D relative to the interventional device coupled to the hub adapter 6032A.

In certain embodiments, movement of two or more interventional devices, two or more hubs, and/or two or more hub adapters may be linked when controlled movements of one or more of the interventional devices, hubs, and/or hub adapters would result in relative positions between the interventional devices, interventional device hubs, and/or hub adapters at distances greater than a total available separation distance (e.g., due to the length of the drive surface of the drive table or due to a length of a shuttle along which hub adapters translate).

In some embodiments, linked interventional devices, hubs, and/or hub adapters can include a primary device, hub, and/or hub adapter and one or more secondary devices, hubs, and/or hub adapters. Movement of the primary device, hub, and/or hub adapter can cause movement of the secondary device, hub, and/or hub adapter in the same direction by the same magnitude and/or velocity. Movement of a control to move the secondary device, hub, and/or hub adapter, but not the primary device, hub, and/or hub adapter may not cause the primary device to move. In some embodiments, movement of a control to move the secondary device, hub, and/or hub adapter, but not the primary device, hub and/or hub adapter, in a direction that would increase a separation distance between the primary device, hub, and/or hub adapter and the secondary device, hub, and/or hub adapter may result in no movement of either the primary device, hub, and/or hub adapter or the secondary device, hub, and/or hub adapter. In some embodiments, movement of a control to move the secondary device, hub, and/or hub adapter, but not the primary device, hub, and/or hub adapter, in a direction that would decrease the separation distance between the primary device, hub, and/or hub adapter and the secondary device, hub, and/or hub adapter may cause the secondary device to move without movement of the primary device, hub, and/or hub adapter and/or may unlink the secondary device, hub, and/or hub adapter from the primary device, hub, and/or hub adapter.

During some procedures, a user may perform a control operation intended to cause the distal most interventional device (e.g., a guide catheter) coupled with the first hub adapter 6032A to move distally relative to the proximal most interventional device (e.g., a guidewire) coupled to the fourth hub adapter 6032D by a distance that would result in a distance between the first hub adapter 6032A and the fourth hub adapter 6032D greater than the total length of the shuttle 6012. As described above, if a user performs a control operation to move the shuttle 6012 and the first hub adapter 6032A distally, the telescoping drive table 6000 may adjust the position of the fourth hub adapter 6032D by moving the fourth hub adapter 6032D in the proximal direction, preferably by an equal magnitude or speed. In some procedures, the shuttle 6012 may be able to move in a distal direction by a greater magnitude than the fourth hub adapter 6032D can move proximally. In other words, while adjusting in response to movement of the shuttle 6012, the fourth hub adapter 6032D may reach a proximal most position along the shuttle 6012 and be prevented from further movement while the shuttle 6012 continues to move in the distal direction. In response, the telescoping drive table 6000 may compensate by temporarily linking the movement of the fourth hub adapter 6032D with the movement of the first hub adapter 6032A so that the fourth hub adapter 6032D moves in unison with the first hub adapter 6032A.

For example, when linked, if the first hub adapter 6032A is moved distally by way of the shuttle 6012 moving distally, the fourth hub adapter 6032D can move distally by the same magnitude and/or at the same speed. In this situation, the fourth hub adapter 6032D can move distally by the same magnitude and/or at the same speed as the first hub adapter 6032A by maintaining its position on the shuttle 6012 while the shuttle 6012 moves distally. Similarly, if the first hub adapter 6032A is moved proximally by way of the shuttle 6012 moving proximally, the fourth hub adapter 6032D can move proximally by the same magnitude and/or at the same speed. In this situation, the fourth hub adapter 6032D can move proximally by the same magnitude and/or at the same speed as the first hub adapter 6032A by maintaining its position on the shuttle 6012 while the shuttle 6012 moves proximally.

In some embodiments, the fourth hub adapter 6032D can be unlinked from the first hub adapter 6032A (e.g., such that it adjusts in response to movements of the first hub adapter 6032A) in response to user manipulation of a control for the fourth hub adapter 6032D causing it to move independently or in response to another user input. In certain embodiments, while the first hub adapter 6032A and fourth hub adapter 6032D are linked, the telescoping drive table 6000 can track the desired relative position of the fourth hub adapter 6032D relative to the first hub adapter 6032A and/or relative to a reference point and adjust the fourth hub adapter 6032D to the desired position once sufficient space is available along the shuttle 6012.

Linking of the distal most hub adapter (e.g., the first hub adapter 6032A) and the proximal most hub adapter (e.g., the fourth hub adapter 6032D) may allow for a shorter shuttle 6012. As an example, in certain embodiments, a length of the shuttle 6012 may be about 130 cm long. A distal most interventional device (e.g., a guide catheter) may have a length of about 127 cm. A length of a section of the distal most interventional device that overlaps the drive shuttle 6012 (e.g., when coupled to a hub coupled to the distal most hub adapter (e.g., the first hub adapter 6032A)) may be about 3 cm. A proximal most interventional device (e.g., a guidewire) can have a length of about 265 cm. A section of the proximal most interventional device may extend proximally from a proximal end of a proximal most hub coupled to a proximal most hub adapter (e.g., the fourth hub adapter 6032D) in some embodiments. For example, in certain embodiments, the section of the proximal most interventional device may extend between about 2 cm and about 20 cm, between about 5 cm and about 15 cm, or about 10 cm from the proximal end of the proximal most hub. In some embodiments, the proximal most hub may extend proximally from a proximal end of the shuttle 6012 by about 2.5 cm in its proximal most position. In certain embodiments, a proximal most end of the proximal most interventional device may be positioned proximally from a proximal end of the shuttle 6012 by a distance of between about 4.5 cm and about 22.5 cm, between about 7.5 cm and about 17.5 cm, or about 12.5 cm, when the proximal most hub adapter is in its proximal most position. In an initial configuration a distal most end of the proximal most interventional device may be proximal to a distal most end of the distal most interventional device.

While linking of hub adapters is described herein, one of skill in the art would understand that the corresponding hubs and/or corresponding interventional devices may also be linked. As described herein with respect to the hub adapters, linked hubs and/or linked interventional devices may move in the same direction by the same magnitude and/or speed.

As described herein, the telescoping drive table 6000 can be configured such that each of the hub adapters 6032A-D is independently controllable and movable relative to the other hub adapters. For example and without limitation, each of the hub adapters 6032A-D on the shuttle 6012 can have an independently controllable motor 6054 or other actuator configured to independently move the hub adapter 6032A-D relative to the shuttle 6012.

Alternatively, in some embodiments, the position of one of the hub adapters (e.g., the first hub adapter 6032A can be fixed relative to the shuttle 6012). For example, in an embodiment having a first hub adapter 6032A, a second hub adapter 6032B, a third hub adapter 6032C, and a fourth hub adapter 6032D, the first hub adapter 6032A can be fixed to the shuttle 6012 and the second hub adapter 6032B, the third hub adapter 6032C, and the fourth hub adapter 6032D can each have an independently controllable motor or actuator configured to independently move the second hub adapter 6032B, the third hub adapter 6032C, and the fourth hub adapter 6032D relative to the shuttle 6012 and the first hub adapter 6032A.

As mentioned, in some embodiments, one or more of the first hub adapter 6032A, the second hub adapter 6032B, third hub adapter 6032C, and fourth hub adapter 6032D can each be configured to move in the axial direction relative to the shuttle 6012 in response to an input provided by a user of the telescoping drive table 6000.

In some embodiments, one or more of the first hub adapter 6032A, the second hub adapter 6032B, the third hub adapter 6032C, and the fourth hub adapter 6032D can be configured to move in the axial direction relative to the shuttle 6012 via a linear actuator (e.g., a rack and pinion linear actuator) in response to an input provided by a user of the telescoping drive table 6000. The rack and pinion arrangement can have a rack (or straight gear) and a pinion gear (e.g., an output gear) coupled to a shaft of the motor. For example and without limitations, the second hub adapter 6032B can have a motor and an output gear that can engage the rack. The third hub adapter 6032C can have a motor and an output gear that can also engage the rack. Similarly, the fourth hub adapter 6032D can have a motor and an output gear that can also engage the rack. Each hub adapter 6032A-D can have its own unique motor and output gear to allow for independent movement of each hub adapter 6032A-D.

In certain embodiments, the drive table 6000 may be configured to cause the shuttle 6012 to move in particular situations instead of or in addition to moving one or more of the hub adapters 6032A-D. For example, movement of the shuttle 6012 and the hub adapters 6032A-D may be controlled by a control system as described herein (e.g., operating using one or more algorithms to control movement of the shuttle 6012 and the hub adapters 6032A-D), for example, in response to actuation of one or more controls by a user. For example, in certain embodiments, the shuttle 6012 may be configured to move distally when the distal most hub adapter 6032A reaches a distal most position along the shuttle 6012 and further distal movement of the hub adapter 6032A is instructed (e.g., to cause further distal movement of the interventional device coupled to the hub adapter 6032A). In some embodiments, the shuttle 6012 may be configured to move proximally when the proximal most hub adapter 6032D reaches a proximal most position along the shuttle 6012 and further proximal movement of the hub adapter 6032D is instructed (e.g., to cause further proximal movement of the interventional device coupled to the hub adapter 6032D). In some embodiments, as described herein, the shuttle 6012 may not move proximally in response to the proximal most hub adapter 6032D reaching the proximal most position along the shuttle 6012 when further proximal movement of the hub adapter 6032D is instructed if such proximal movement of the shuttle 6012 would cause an undesired proximal movement of the distal most hub adapter 6032A (e.g., if the distal most hub adapter 6032A is at the distal most position along the shuttle 6012). Instead, the proximal most hub adapter 6032D may be temporarily linked with the distal most hub adapter 6032A as described herein.

In some embodiments, the shuttle 6012 may configured to move in a particular direction in response to an instruction (e.g., a control signal) instructing a plurality or a majority of the hub adapters 6032A-D coupled to the shuttle 6012 to move in the particular direction.

In certain embodiments, as shown in FIGS. 60C-60D, a top surface of the one or more telescoping members 6008A, 6008B can be vertically offset from a top surface of the main body 6004. A sterile barrier can extend from the top surface of the main body 6004 to the ends of the one or more telescoping members 6008A, 6008B. The sterile barrier may form the support surface 6006.

In some embodiments, the sterile barrier may provide a transition between the one or more telescoping members 6008A, 6008B and the main body 6004 to provide a continuous surface for one or more hubs magnetically coupled to the hub adapters to translate along. The sterile barrier can prevent the one or more driven hubs from being stuck on the one or more telescoping members 6008A, 6008B or being dislodged or displaced. In some embodiments, ends of the sterile barrier may be coupled respective ends of the telescoping members 6008A, 6008B. In such embodiments, the sterile barrier may be extended as the telescoping members 6008A, 6008B are deployed. In some embodiments, the sterile barrier may be coupled to the ends of the telescoping members 6008A, 6008B via adhesive strips, double sided tape, magnets, and/or other fastening means. The sterile barrier can be retractable.

In some embodiments, devices (e.g., hubs, hub adapters, interventional devices, and/or trays) described herein may be used during a robotically driven procedure. For example, in a robotically driven procedure, one or more of the interventional devices may be driven through vasculature and to a procedure site. Robotically driving such devices may include engaging electromechanical components that are controlled by user input. In some implementations, users may provide the input at a control system that interfaces with one or more hubs and hub adapters.

In some embodiments, the hubs, hub adapters, interventional devices, and trays described herein may be used during a non-robotic (e.g., manually driven) procedure. Manually driving such devices may include engaging manually with the hubs to affect movement of the interventional devices.

In some embodiments, the devices described herein may be used to carry out a method of performing an intracranial procedure at an intracranial site. The method of performing the intracranial procedure may include any of the same steps as described herein for performing a neurovascular procedure. The procedure may be robotically performed, manually performed, or a hybridized combination of both.

While the foregoing describes magnetic coupling of hubs to drive magnets, in other embodiments, any of the interventional devices and/or hubs may be mechanically coupled to a drive system. Any of the methods described herein may include steps of mechanically coupling one or more interventional devices (e.g., the guidewire 2907, the access catheter 2902, the procedure catheter 2904, and/or the guide catheter 2906) and/or one or more hubs (e.g., the guidewire hub 2909, the access catheter hub 2910, the procedure catheter hub 2912, and/or the guide catheter hub 2914) with one or more drive mechanisms.

Figure 62:
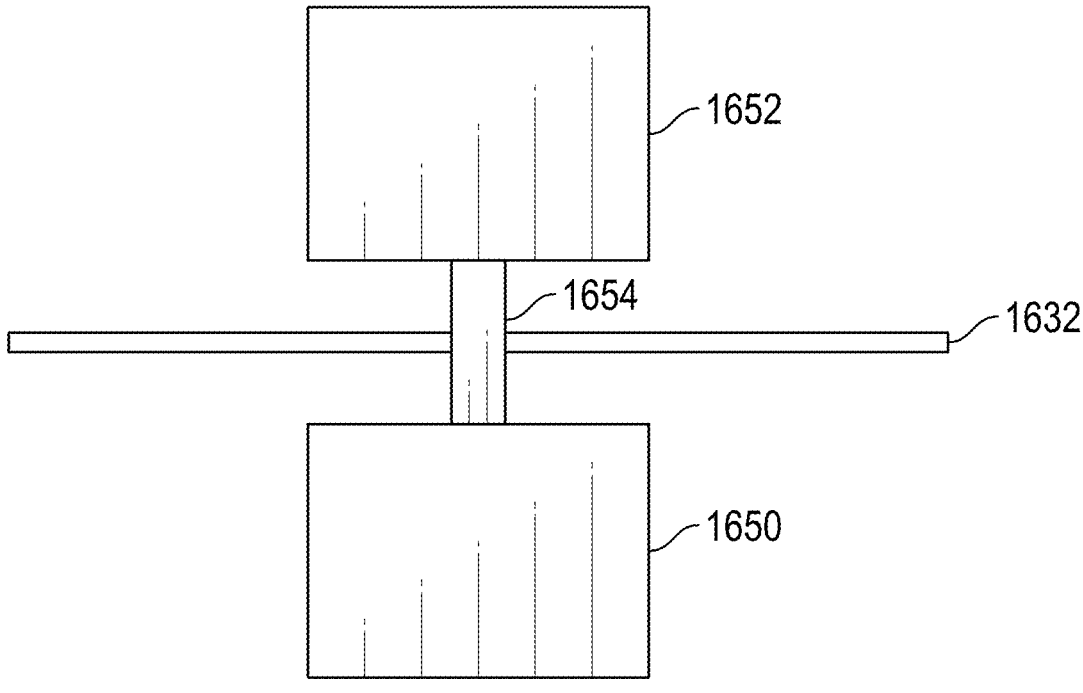
FIG. 62 schematically illustrates an embodiment of a mechanical coupling between a drive mechanism and a driven mechanism.

FIG. 62 illustrates a mechanical coupling mechanism 1654 between a drive mechanism 1650 and a driven mechanism 1652. Drive mechanism 1650 and driven mechanism 1652 may have any of the same or similar features or functions as the drive magnet 67 and driven magnet 69, respectively, except as otherwise described herein. The drive mechanism 1650 may be part of or coupled to a hub adapter (e.g., the hub adapter 48). The driven mechanism 1652 may be part of or coupled to a hub (e.g., the hub 36, the guidewire hub 2909, the access catheter hub 2910, the procedure catheter hub 2912, or the guide catheter hub 2914). In some instances, the mechanical coupling mechanism 1654 may comprise a structural support (e.g., a support rod or support strut) extending transversely through a seal in a sterile barrier 1632. The seal may permit the structural support to be advanced along a length of the sterile barrier 1632, while still maintaining a seal with the structural support to maintain the sterile field, as the drive mechanism 1650 and driven mechanism 1652 are advanced and/or retracted as described herein. For example, the seal may comprise a tongue and groove closure mechanism along the sterile barrier 1632 that is configured to close on either side of the structural support while permitting passage of the structural support through the sterile barrier 1632 and maintaining a seal against the structural support as the structural support is advanced along the length of the sterile barrier 1632.

In some embodiments, the structural support can extend through an elongate self closing seal between two adjacent coaptive edges of flexible material (e.g., similar in shape to a duckbill valve) that extends along an axis. As the structural support advances along the axis between the copative edges, the coaptive edges may permit the structural support to advance, and then may be biased back into a sealing engagement with each other as the structural support passes any given point along the axis.

In some embodiments, the drive mechanism may be a splined drive shaft (e.g., a non-sterile splined drive shaft). The coupling mechanism 1654 can include a pulley within a plate that serves as the sterile barrier 1632 and a sterile splined shaft configured to couple to the driven mechanism 1652. The driven mechanism 1652 can be a sterile pulley that receives the sterile splined shaft from the sterile barrier. In some embodiments, one or more splined drive shafts can engage and turn corresponding pulleys in the plate that serves as the sterile barrier. Each hub can have a sterile pulley that is configured to receive a sterile splined shaft from the sterile barrier plate. Rotation of the splined drive shaft can turn the pulley in the sterile barrier plate which can in turn turn the sterile pulley in the hub via the sterile splined shaft.

It will be understood by one having skill in the art that any embodiment as described herein may be modified to incorporate a mechanical coupling mechanism, for example, as shown in FIG. 62.

While the foregoing describes robotically driven interventional devices and manually driven interventional devices, the devices may be manually driven, robotically driven, or any combination of manually and robotically driven interventional devices, as will be appreciated by those of skill in the art in view of the disclosure herein.

The foregoing represents one specific implementation of a robotic control system. A wide variety of different robotic control system constructions can be made, for supporting and axially advancing and retracting two or three or four or more assemblies to robotically drive interventional devices, as will be appreciated by those of skill in the art in view of the disclosure herein.

Various systems and methods are described herein primarily in the context of a neurovascular access or procedure (e.g., neurothrombectomy). However, the catheters, systems (e.g., drive systems), and methods disclosed herein can be readily adapted for any of a wide variety of other diagnostic and therapeutic applications throughout the body, including particularly intravascular procedures such as in the peripheral vasculature (e.g., deep venous thrombosis), central vasculature (pulmonary embolism), and coronary vasculature, as well as procedures in other hollow organs or tubular structures in the body.

What is claimed is:

1. A robotic interventional device control system comprising:

an interventional device comprising a longitudinal axis and configured to rotate about the longitudinal axis;

a controller configured to control rotational movement of the interventional device about the longitudinal axis;

at least one sensor configured to detect rotational movement of the interventional device about the longitudinal axis;

one or more hardware processors configured to receive motion data from the at least one sensor, the motion data indicative of whether the interventional device is rotating about the longitudinal axis;

wherein the one or more hardware processors are further configured to, based on the motion data, generate a user interface comprising an instrument window, the instrument window comprising, a representation of the interventional device;

an interventional device marker associated with the representation of the interventional device, the interventional device marker comprising a radial progress indicator configured to provide a visual indication of a degree of rotation relative to a threshold of the interventional device about the longitudinal axis;

wherein the controller is further configured to control axial movement of the interventional device along a drive table, and wherein the representation of the interventional device is configured to transition from a first configuration to a second configuration along a central longitudinal axis when the interventional device is moving axially along the drive table.

2. The robotic interventional device control system of claim 1, wherein the radial progress indicator comprises a ring shaped progress bar configured to fill in at least one of a clockwise direction and a counterclockwise direction, wherein the radial progress indicator filling in the clockwise direction provides a visual indication that the interventional device is rotating in the clockwise direction, and wherein the radial progress indicator filling in the counterclockwise direction provides a visual indication that the interventional device is rotating in the counterclockwise direction.

3. The robotic interventional device control system of claim 1, wherein in the first configuration, the representation of the interventional device is in a first position, and wherein in the second configuration, the representation of the interventional device is in a second position.

4. The robotic interventional device control system of claim 3, wherein the first position is closer to a bottom end of the central longitudinal axis than the second position.

5. The robotic interventional device control system of claim 3, wherein the first position is closer to a top end of the central longitudinal axis than the second position.

6. The robotic interventional device control system of claim 1, wherein the interventional device marker is configured to transition from a first animation state to a second animation state upon an occurrence of an interventional device event.

7. The robotic interventional device control system of claim 6, wherein the interventional device event comprises one of aspiration being available at the interventional device, aspiration being unavailable at the interventional device, aspiration being active at the interventional device, contrast injection being available at the interventional device, or contrast injection being unavailable at the interventional device.

8. The robotic interventional device control system of claim 1, wherein the controller is configured to control rotational movement of the interventional device about the longitudinal axis responsive to a user input.

9. The robotic interventional device control system of claim 1, wherein the representation of the interventional device extends along the central longitudinal axis.

10. A robotic interventional device control system comprising:

an interventional device comprising a longitudinal axis and configured to rotate about the longitudinal axis;

a controller configured to control rotational movement of the interventional device about the longitudinal axis;

at least one sensor configured to detect rotational movement of the interventional device about the longitudinal axis;

one or more hardware processors configured to receive motion data from the at least one sensor, the motion data indicative of whether the interventional device is rotating about the longitudinal axis;

wherein the one or more hardware processors are further configured to, based on the motion data, generate a user interface comprising an instrument window, the instrument window comprising, a representation of the interventional device;

an interventional device marker associated with the representation of the interventional device, the interventional device marker comprising a radial progress indicator configured to provide a visual indication of a degree of rotation relative to a threshold of the interventional device about the longitudinal axis;

wherein the threshold represents a maximum rotation of the interventional device.

11. A robotic interventional device control system comprising:

an interventional device comprising a longitudinal axis and configured to rotate about the longitudinal axis;

a controller configured to control rotational movement of the interventional device about the longitudinal axis;

at least one sensor configured to detect rotational movement of the interventional device about the longitudinal axis;

one or more hardware processors configured to receive motion data from the at least one sensor, the motion data indicative of whether the interventional device is rotating about the longitudinal axis;

wherein the one or more hardware processors are further configured to, based on the motion data, generate a user interface comprising an instrument window, the instrument window comprising, a representation of the interventional device;

an interventional device marker associated with the representation of the interventional device, the interventional device marker comprising a radial progress indicator configured to provide a visual indication of a degree of rotation relative to a threshold of the interventional device about the longitudinal axis; and wherein the radial progress indicator comprises a ring shaped progress bar configured to fill up, wherein the ring shaped progress bar is further configured to be empty when the interventional device is not rotating, and wherein the ring shaped progress bar is further configured to be full when the interventional device completes a full revolution about the longitudinal axis.

12. A robotic interventional device control system comprising:

an interventional device comprising a longitudinal axis and configured to rotate about the longitudinal axis;

a controller configured to control rotational movement of the interventional device about the longitudinal axis;

at least one sensor configured to detect rotational movement of the interventional device about the longitudinal axis;

one or more hardware processors configured to receive motion data from the at least one sensor, the motion data indicative of whether the interventional device is rotating about the longitudinal axis;

wherein the one or more hardware processors are further configured to, based on the motion data, generate a user interface comprising an instrument window, the instrument window comprising, a representation of the interventional device, wherein the representation of the interventional device extends along a central longitudinal axis;

an interventional device marker associated with the representation of the interventional device, the interventional device marker comprising a radial progress indicator configured to provide a visual indication of a degree of rotation relative to a threshold of the interventional device about the longitudinal axis.

13. The robotic interventional device control system of claim 12, wherein the radial progress indicator comprises a ring shaped progress bar configured to fill in at least one of a clockwise direction and a counterclockwise direction, wherein the radial progress indicator filling in the clockwise direction provides a visual indication that the interventional device is rotating in the clockwise direction, and wherein the radial progress indicator filling in the counterclockwise direction provides a visual indication that the interventional device is rotating in the counterclockwise direction.

14. The robotic interventional device control system of claim 12, wherein the interventional device marker is configured to transition from a first animation state to a second animation state upon an occurrence of an interventional device event, wherein the interventional device event comprises one of: aspiration being available at the interventional device, aspiration being unavailable at the interventional device, aspiration being active at the interventional device, contrast injection being available at the interventional device, and contrast injection being unavailable at the interventional device.

15. The robotic interventional device control system of claim 12, wherein the controller is configured to control rotational movement of the interventional device about the longitudinal axis responsive to a user input.

16. A robotic interventional device control system comprising:

an interventional device comprising a longitudinal axis and configured to rotate about the longitudinal axis;

a controller configured to control rotational movement of the interventional device about the longitudinal axis;

at least one sensor configured to detect rotational movement of the interventional device about the longitudinal axis;

one or more hardware processors configured to receive motion data from the at least one sensor, the motion data indicative of whether the interventional device is rotating about the longitudinal axis;

wherein the one or more hardware processors are further configured to, based on the motion data, generate a user interface comprising an instrument window, the instrument window comprising, a representation of the interventional device;

an interventional device marker associated with the representation of the interventional device, the interventional device marker comprising a radial progress indicator configured to provide a visual indication of a degree of rotation relative to a threshold of the interventional device about the longitudinal axis;

wherein the interventional device marker comprises a first animation state and a second animation state, wherein the interventional device marker is configured to transition from the first animation state to the second animation state upon an occurrence of an interventional device event; and wherein the interventional device event comprises aspiration being available at the interventional device.

17. A robotic interventional device control system comprising:

an interventional device comprising a longitudinal axis and configured to rotate about the longitudinal axis;

a controller configured to control rotational movement of the interventional device about the longitudinal axis;

at least one sensor configured to detect rotational movement of the interventional device about the longitudinal axis;

one or more hardware processors configured to receive motion data from the at least one sensor, the motion data indicative of whether the interventional device is rotating about the longitudinal axis;

wherein the one or more hardware processors are further configured to, based on the motion data, generate a user interface comprising an instrument window, the instrument window comprising, a representation of the interventional device;

an interventional device marker associated with the representation of the interventional device, the interventional device marker comprising a radial progress indicator configured to provide a visual indication of a degree of rotation relative to a threshold of the interventional device about the longitudinal axis;

wherein the interventional device marker comprises a first animation state and a second animation state, wherein the interventional device marker is configured to transition from the first animation state to the second animation state upon an occurrence of an interventional device event; and wherein the interventional device event comprises aspiration being unavailable at the interventional device.

18. A robotic interventional device control system comprising:

an interventional device comprising a longitudinal axis and configured to rotate about the longitudinal axis;

a controller configured to control rotational movement of the interventional device about the longitudinal axis;

at least one sensor configured to detect rotational movement of the interventional device about the longitudinal axis;

one or more hardware processors configured to receive motion data from the at least one sensor, the motion data indicative of whether the interventional device is rotating about the longitudinal axis;

wherein the one or more hardware processors are further configured to, based on the motion data, generate a user interface comprising an instrument window, the instrument window comprising, a representation of the interventional device;

an interventional device marker associated with the representation of the interventional device, the interventional device marker comprising a radial progress indicator configured to provide a visual indication of a degree of rotation relative to a threshold of the interventional device about the longitudinal axis;

wherein the interventional device marker comprises a first animation state and a second animation state, wherein the interventional device marker is configured to transition from the first animation state to the second animation state upon an occurrence of an interventional device event; and wherein the interventional device event comprises aspiration being active at the interventional device.

19. A robotic interventional device control system comprising:

an interventional device comprising a longitudinal axis and configured to rotate about the longitudinal axis;

a controller configured to control rotational movement of the interventional device about the longitudinal axis;

at least one sensor configured to detect rotational movement of the interventional device about the longitudinal axis;

one or more hardware processors configured to receive motion data from the at least one sensor, the motion data indicative of whether the interventional device is rotating about the longitudinal axis;

wherein the one or more hardware processors are further configured to, based on the motion data, generate a user interface comprising an instrument window, the instrument window comprising, a representation of the interventional device;

an interventional device marker associated with the representation of the interventional device, the interventional device marker comprising a radial progress indicator configured to provide a visual indication of a degree of rotation relative to a threshold of the interventional device about the longitudinal axis;

wherein the interventional device marker comprises a first animation state and a second animation state, wherein the interventional device marker is configured to transition from the first animation state to the second animation state upon an occurrence of an interventional device event; and wherein the interventional device event comprises contrast injection being available at the interventional device.

20. A robotic interventional device control system comprising:

an interventional device comprising a longitudinal axis and configured to rotate about the longitudinal axis;

a controller configured to control rotational movement of the interventional device about the longitudinal axis;

at least one sensor configured to detect rotational movement of the interventional device about the longitudinal axis;

one or more hardware processors configured to receive motion data from the at least one sensor, the motion data indicative of whether the interventional device is rotating about the longitudinal axis;

wherein the one or more hardware processors are further configured to, based on the motion data, generate a user interface comprising an instrument window, the instrument window comprising, a representation of the interventional device;

an interventional device marker associated with the representation of the interventional device, the interventional device marker comprising a radial progress indicator configured to provide a visual indication of a degree of rotation relative to a threshold of the interventional device about the longitudinal axis;

wherein the interventional device marker comprises a first animation state and a second animation state, wherein the interventional device marker is configured to transition from the first animation state to the second animation state upon an occurrence of an interventional device event; and wherein the interventional device event comprises contrast injection being unavailable at the interventional device.

\* \* \* \* \*